(12) United States Patent
Crew et al.

(10) Patent No.: US 9,133,224 B2
(45) Date of Patent: Sep. 15, 2015

(54) MACROCYCLIC KINASE INHIBITORS

(75) Inventors: Andrew P. Crew, N. Babylon, NY (US); Hanqing Dong, Syosset, NY (US); Caterina Ferraro, Fresh Meadows, NY (US); Dan Sherman, New York, NY (US); Kam W. Siu, Farmingdale, NY (US)

(73) Assignee: OSI Pharmaceuticals, LLC, Northbrook, IL (US)

( * ) Notice: Subject to any disclaimer, the term of this patent is extended or adjusted under 35 U.S.C. 154(b) by 0 days.

(21) Appl. No.: 13/990,045

(22) PCT Filed: Nov. 29, 2011

(86) PCT No.: PCT/US2011/062290
§ 371 (c)(1),
(2), (4) Date: May 29, 2013

(87) PCT Pub. No.: WO2012/074951
PCT Pub. Date: Jun. 7, 2012

(65) Prior Publication Data
US 2013/0261086 A1    Oct. 3, 2013

Related U.S. Application Data

(60) Provisional application No. 61/417,601, filed on Nov. 29, 2010.

(51) Int. Cl.
*A61K 31/675* (2006.01)
*C07F 9/6584* (2006.01)

(52) U.S. Cl.
CPC .............. *C07F 9/6584* (2013.01); *A61K 31/675* (2013.01)

(58) Field of Classification Search
CPC ........................... C07F 9/6584; A61K 31/675
USPC ...................................... 514/79, 86; 544/243
See application file for complete search history.

(56) References Cited

U.S. PATENT DOCUMENTS

| | | | |
|---|---|---|---|
| 6,649,608 B2 | 11/2003 | Pease | |
| 6,878,697 B2 | 4/2005 | Metcalf | |
| 7,109,335 B2 | 9/2006 | Kath | |
| 7,109,337 B2 | 9/2006 | Kath | |
| 7,122,670 B2 | 10/2006 | Kath | |
| 7,230,098 B2 | 6/2007 | Cui | |
| 7,351,712 B2 | 4/2008 | Kath | |
| 7,514,446 B2 | 4/2009 | Davis-Ward | |
| 7,521,457 B2 | 4/2009 | Stadtmueller | |
| 8,399,433 B2 | 3/2013 | Appari | |
| 2004/0220177 A1 | 11/2004 | Kath | |
| 2005/0124637 A1 | 6/2005 | Cheng | |
| 2005/0203114 A1 | 9/2005 | Armistead | |
| 2005/0256144 A1 | 11/2005 | Kath | |
| 2005/0256145 A1 | 11/2005 | Kath | |
| 2006/0247241 A1 | 11/2006 | Garcia-Echeverria | |
| 2006/0252748 A1 | 11/2006 | Lindenthal | |
| 2007/0015207 A1 | 1/2007 | Ludovici | |
| 2007/0203161 A1 | 8/2007 | Argade | |
| 2008/0039447 A1 | 2/2008 | Brumby | |
| 2008/0132504 A1 | 6/2008 | Garcia-Echeverria | |
| 2008/0176881 A1 | 7/2008 | Michellys | |
| 2008/0182840 A1 | 7/2008 | Kath | |
| 2008/0293708 A1 | 11/2008 | Kawahara | |
| 2009/0054395 A1 | 2/2009 | Luzzio | |
| 2009/0149438 A1 | 6/2009 | Stadtmueller | |
| 2009/0221555 A1 | 9/2009 | Ahmed | |
| 2012/0202776 A1 | 8/2012 | Wang | |
| 2012/0316135 A1 | 12/2012 | Dalgarno | |

FOREIGN PATENT DOCUMENTS

| | | |
|---|---|---|
| WO | 0012485 A1 | 3/2000 |
| WO | 0164654 A1 | 9/2001 |
| WO | 0170741 A1 | 9/2001 |
| WO | 03030909 A1 | 4/2003 |
| WO | 2006021454 A2 | 3/2006 |
| WO | 2007021937 A2 | 2/2007 |

(Continued)

OTHER PUBLICATIONS

Annex to Form PCT/ISA/206 Communication Relating to the Results of the Partial International Search PCT/US2014/015925 mailed Apr. 24, 2014.
Communication Pursuant to Rule 62 EPC, the supplementary European search report (Art. 153(7) EPC) and the European search opinion European Patent App. No. 10783892.2 dated Nov. 19, 2012.
Database Reaxys [online] Reed Elsevier Properties SA; 1998 Geies A.A. XP002721918 Database accession No. RX-ID 5031443 the whole document.
International Preliminary Report on Patentability in PCT/US2010/036808, date of issuance Dec. 6, 2011.

(Continued)

*Primary Examiner* — Erich A Leeser
(74) *Attorney, Agent, or Firm* — Brinks Gilson & Lione

(57) ABSTRACT

Compounds of Formula (I): wherein variables are defined herein, and pharmaceutically acceptable salts, synthesis, intermediates, formulations, and methods of disease treatment therewith, including cancers for which FAK inhibition is beneficial.

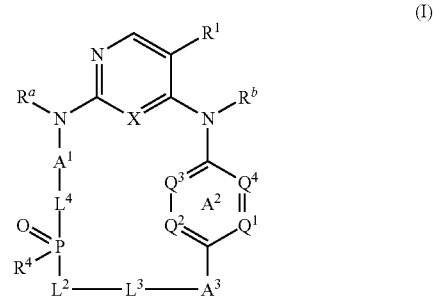

25 Claims, No Drawings

(56) References Cited

FOREIGN PATENT DOCUMENTS

| WO | 2007072158 A2 | 6/2007 | | |
|----|---------------|--------|---|---|
| WO | 2008079073 A1 | 7/2008 | | |
| WO | 2008094602 A2 | 8/2008 | | |
| WO | 2008094737 A2 | 8/2008 | | |
| WO | 2008116139 A2 | 9/2008 | | |
| WO | 2009020990 A1 | 2/2009 | | |
| WO | 2009071535 A1 | 6/2009 | | |
| WO | 2009105498 A1 | 8/2009 | | |
| WO | 2009132202 A2 | 10/2009 | | |
| WO | 2009143389 A1 | 11/2009 | | |
| WO | 2010028116 A1 | 3/2010 | | |
| WO | WO 2010/028116 | * | 3/2010 | ........... A61K 31/529 |
| WO | 2012074951 A1 | 6/2012 | | |
| WO | 2012168817 A1 | 12/2012 | | |

OTHER PUBLICATIONS

International Search Report and Written Opinion of the International Search Authority in PCT/US2010/036808, mailed Feb. 28, 2011.
International Search Report and Written Opinion of the International Search Authority in PCT/US2011/062290 mailed Mar. 5, 2012.
Notice of the Result of Substantive Examination of a Patent Application; Patents Office of the Cooperation Council for the Arab States of the Gulf GCC; Application No. 15970, dated Jul. 20, 2013 English Translation.
Cary, L.A. et al., J. Cell Sci., 109:1787-94 (1996).
Chamberlain, S.D. et al., J. Org. Chem. 73:9511-9514 (2008).
Chamberlain, S.D. et al., Bioorganic & Medical Chemistry Letters 19:373-377 (2009).
Cicchini, C. et al. Exp. Cell Res., 314, 143-52 (2008).
Dyatkina, N. et al., Nucleosides, Nucleotides & Nucleic Acids 19(3), pp. 585-591 (2000).
Golubev, O. et al. Helvetica Chimica Acta vol. 96, No. 9 pp. 1658-1669 (2013).
Maung, K. et al., Oncogene, 18:6824-28 (1999).
Owens, L.V. et al., Cancer Res., 55:2752-55 (1995).
Roberts, W.G.et al., Cancer Res., 68(6), 1935-1944 (2008).
Wang, D. et al., J. Cell Sci., 113:4221-30 (2000).
Weiner, T.M. et al., Lancet, 342(8878):1024-25 (1993).
Xu, Yao-Zhong et al., J. Org. Chem. vol. 57, pp. 3839-3845 (1992).
International Search Report and Written Opinion in PCT/US2014/015925, mailed Jul. 22, 2014.

* cited by examiner

MACROCYCLIC KINASE INHIBITORS

This application claims the benefit of U.S. Appl. No. 61/417,601, filed Nov. 29, 2010, which is incorporated herein in its entirety by this reference.

FIELD AND BACKGROUND

The present invention pertains in large part to cancer treatment, targeted therapies, tyrosine kinase inhibitors, certain chemical compounds, chemical syntheses, compositions, and methods of treating, e.g., tumors and other cancers with the compounds, including conditions in which FAK plays a significant role or FAK inhibition can be beneficial.

Focal adhesion kinase (FAK) is a cytoplasmic tyrosine kinase which plays a major role in the transduction of the signal transmitted by integrins, a family of heterodimeric receptors for cell adhesion. FAK and integrins are colocalized in perimembrane structures called adhesion plaques.

FAK signaling through ERK, PI3K, and p130cas is important in cancer cell proliferation, survival, and migration. pFAK and/or FAK overexpression has been reported in many cancer tumors. An increase in the proliferation of tumor cells in vivo has been observed after induction of the expression of FAK in human astrocytoma cells. Cary et al., *J. Cell Sci.*, 109:1787-94 (1996). FAK is overexpressed in prostate, breast, thyroid, colon, melanoma, brain and lung cancers, the level of FAK expression being directly correlated with tumors exhibiting the most aggressive phenotype. Weiner et al., *Lancet*, 342(8878):1024-25 (1993); Owens et al., *Cancer Res.*, 55:2752-55 (1995); Maung et al., *Oncogene*, 18:6824-28 (1999); Wang et al., *J. Cell Sci.*, 113:4221-30 (2000). FAK is highly active in human epithelial and mesenchymal tumors such as melanoma, lymphoma, and multiple myeloma. Increased FAK correlates with increased invasiveness and increased ability of cancer to metastasize.

Inhibition of FAK signaling in vitro induces cell growth arrest, reduces motility, and can cause cell death. KD-FAK and DN-FAK have been shown to inhibit tumor growth in vivo. FAK is also known as PTK2.

In hepatocytes, TGFβ induces a Src-dependent activation of FAK; and there is evidence that FAK signaling is required for transcriptional up-regulation of mesenchymal and invasiveness markers and for delocalization of membrane-bound E-cadherin. *Exp. Cell Res.*, 314, 143-52 (2008).

A number of publications and documents disclose compounds said to possess FAK or other kinase inhibiting activity, e.g., *Cancer Res.*, 68(6), 1935-1944 (2008), U.S. application Ser. No. 12/791,047 (Jun. 1, 2010), U.S. Pat. No. 6,649,608, U.S. Pat. No. 6,878,697, U.S. Pat. No. 7,109,335, U.S. Pat. No. 7,109,337, U.S. Pat. No. 7,122,670, U.S. Pat. No. 7,230,098, U.S. Pat. No. 7,351,712, U.S. Pat. No. 7,514,446, U.S. Pat. No. 7,521,457, US2004/0220177, US2005/0124637, US2005/0203114, US2005/0256144, US2005/0256145, US2006/0252748, US2007/0015207, US2007/0203161, US2008/0039447, US2008/0132504, US2008/0176881, US2008/0182840, US2008/0293708, US2009/0054395, US2009/0149438, US2009/0286778; WO2001/64655, WO2001/070741, WO02/096888, WO2006/021544, WO2007/021937, WO2008/051547, WO2008/094602, WO2008/094737, WO2008/129380, WO2009/020990, WO2009/071535, WO2009/105498, WO2009/143389, WO2010/028116.

There remains a need for new kinase inhibitors, including FAK inhibitors, having the potential to reach the clinic and regulatory approval for treating disease such as cancer, among others.

SUMMARY

In some aspects, the present invention concerns compounds of Formula I, as shown below:

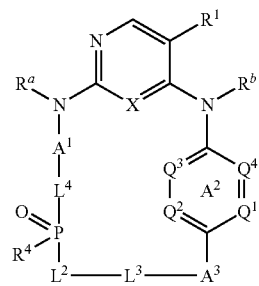

I wherein:
X is N or CH;
$A^1$ is optionally substituted phenylene or optionally substituted $_{5-6}$heteroaryl;
$A^3$ is optionally substituted $_{5-6}$heterocyclic;
$L^2$ is —O— or a bond;
$L^3$ is optionally substituted $C_{2-6}$aliphatic;
$L^4$ is optionally substituted $C_{1-2}$aliphatic;
$Q^1$ to $Q^4$ are independently N,N-oxide, or optionally substituted CH;
when $Q^1$ and $Q^4$ are independently CH or N, an optionally substituted $_{5-6}$cyclic containing one or more heteroatoms is optionally fused to Ring $A^2$ at $Q^1$ and $Q^4$;
$R^1$, $R^a$, and $R^b$ are each independently H or an optional substituent; and
$R^4$ is OH, $C_{1-4}$aliphatic, —$OC_{1-3}$aliphatic, $_{3-6}$-carbocyclic, or $_{4-6}$heterocyclic;
or a pharmaceutically acceptable salt thereof.

In some aspects, compounds of the invention are inhibitors of kinases, including FAK. In some aspects, compounds of the invention are selective inhibitors of FAK.

In some aspects, the invention includes methods treating proliferative disease, particularly cancers, including cancers mediated or driven at least in part by FAK, or for which FAK inhibition may be beneficially, alone or in combination regimens with other agents. In some embodiments FAK overexpression or pFAK may be implicated.

The invention includes the compounds and salts thereof, any physical forms thereof including solvates and hydrates, preparation of the compounds, intermediates, and pharmaceutical compositions and formulations thereof.

DETAILED DESCRIPTION

Compounds

In some aspects, the invention includes the compounds and salts thereof of Formula I, above, wherein (Subgenus 1):
$A^1$ is phenylene or $_{5-6}$heteroaryl either of which is optionally substituted by one or more independent $R^5$;
$A^3$ is $_{5-6}$heterocyclic optionally substituted by one or more independent $R^6$;
$L^3$ is $C_{2-6}$aliphatic optionally substituted by one or more independent $R^9$;
$L^4$ is $C_{1-3}$aliphatic optionally substituted by one or more independent $R^8$;
$Q^1$ to $Q^3$ are independently N,N-oxide, or $CR^2$;
$Q^4$ is N,N-oxide, or $CR^3$;

when $Q^1$ and $Q^4$ are independently CH or N, an optionally substituted $_{5-6}$cyclic containing one or more heteroatoms is optionally fused to Ring $A^2$ at $Q^1$ and $Q^4$;

$R^a$ and $R^b$ are each independently selected from H, $C_{1-6}$aliphatic, $C_{3-6}$carbocyclic, or $_{4-6}$heterocyclic, any of which can be substituted by one or more independent $R^{aa}$;

each $R^{aa}$ and $R^8$ is independently selected from H, oxo, halogen, $C_{1-6}$aliphatic, $C_{3-6}$cycloaliphatic, —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$;

$R^1$ is selected from H, halogen, —CN, $C_{1-3}$aliphatic (optionally substituted by one or more halogen), $C_{3-6}$carbocyclic, —$NO_2$, —$NR^{10}R^{11}$, —$SO_{0-2}R^{12}$, —$C(O)OR^{13}$, —$C(O)R^{13}$, or —$C(O)NR^{10}R^{11}$;

each $R^2$, $R^3$, $R^5$, and $R^6$ is independently selected from H, —$P(O)(OR^{22})_2$, halogen, —$CF_3$, —CN, —$NO_2$, —$NR^{20}R^{21}$, —$NR^{20}C(NR^{20}R^{21})(=CR^{22})$, —$CR^{20}(NR^{20}R^{21})(=NR^{20})$, —$NR^{20}C(NR^{20}R^{21})(=NR^{20})$, —$NR^{20}C(O)R^{22}$, —$C(O)NR^{20}R^{21}$, —$C(O)R^{22}$, —$C(O)C(O)R^{22}$, —$C(O)OR^{23}$, —$OC(O)R^{22}$, —$OR^{23}$, —$OC(O)OR^{23}$, —$S(O)_{0-2}R^{11}$, —$S(O)(=NR^{20})R^{21}$, $C_{1-6}$aliphatic, or $_{3-10}$cyclic; wherein any of the foregoing $R^2$, $R^3$, $R^5$, and $R^6$ is optionally substituted by one or more independent $R^7$ groups;

$R^4$ is OH, $C_{1-4}$aliphatic, or —$OC_{1-3}$aliphatic;

each $R^7$ is independently selected from H, —$P(O)(OR^{24})_2$, —$OR^{24}$, —$C(O)R^{24}$, —$C(O)OR^{24}$, —$OC(O)R^{24}$, —$OC(O)OR^{24}$, —$C(O)NR^{24}R^{25}$, —$NR^{24}C(O)NR^{24}R^{25}$, —$NR^{24}R^{25}$, —$NR^{24}C(NR^{24}R^{25})(=NR^{24})$, —$NR^{24}C(NR^{24}R^{25})(=N—C(O)R^{24})$, —$NR^{24}C(O)R^{25}$, —$NR^{24}S(O)_{0-2}R^{24}$, —$S(O)_{0-2}R^{24}$, —$CF_3$, —CN, $C_{1-6}$aliphatic, or $_{3-10}$cyclic; wherein any of the foregoing is optionally substituted by one or more independent -halo, —$CF_3$, —CN, —$NO_2$, —OH, —$O(C_{1-6}$aliphatic), —$C(O)R^{26}$, —$C(O)NR^{26}R^{27}$, —$S(O)_{0-2}R^{26}$, —$S(O)_{0-2}NR^{26}R^{27}$, $_{3-10}$cyclic, —SH, —$S(C_{1-6}$aliphatic), —$NH_2$, —$NH(C_{1-6}$aliphatic), or —$N(C_{1-6}$aliphatic$)_2$ groups;

each $R^9$ is independently selected from H, oxo, halogen $C_{1-6}$aliphatic, $C_{3-6}$cycloaliphatic, $_{3-6}$spirocyclic (optionally substituted by one or more independent $R^{26}$), —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$;

$R^{10}$, $R^{11}$, $R^{12}$, and $R^{13}$ are independently selected from H, $C_{1-6}$aliphatic, or $C_{3-6}$cycloaliphatic, wherein $R^{10}$ and $R^{11}$ attached to the same atom can be taken together with the atoms to which they are attached to form a ring containing one or more heteroatoms;

$R^{20}$ and $R^{21}$ are independently selected from H, —$OR^{23}$, —$S(O)_{0-2}R^{28}$, —$NO_2$, $C_{1-6}$aliphatic, or $_{3-10}$cyclic; wherein any of the foregoing is optionally substituted by one or more independent $R^7$ groups;

each $R^{22}$ is independently selected from H, halo, —$NR^{24}R^{25}$, $C_{1-6}$aliphatic, or $_{3-10}$cyclic; wherein any of the foregoing is optionally substituted by one or more independent $R^7$ groups;

each $R^{23}$ is independently selected from H, $C_{1-6}$aliphatic, or $_{3-10}$cyclic; wherein any of the foregoing is optionally substituted by one or more independent $R^7$ groups;

$R^{24}$ and $R^{25}$ are each independently selected from H, —$NR^{26}C(O)R^{27}$, —$CF_3$, —CN, —$S(O)_{0-2}$, $R^{26}$, $C_{1-6}$aliphatic, or $_{3-10}$cyclic; wherein any of the foregoing is optionally substituted by one or more independent halo, —$CF_3$, —CN, —$NO_2$, —OH, —$O(C_{1-6}$aliphatic), —$C(O)R^{26}$, —$C(O)NR^{26}R^{27}$, —$S(O)_{0-2}R^{26}$, —$S(O)_{0-2}NR^{26}R^{27}$, $_{3-10}$cyclic, —SH, —$S(C_{1-6}$aliphatic), —$NH_2$, —$NH(C_{1-6}$aliphatic), or —$N(C_{1-6}$aliphatic$)_2$ groups;

$R^{26}$ and $R^{27}$ are each independently selected from the group consisting of —H, $C_{1-6}$aliphatic, or $_{3-10}$cyclic; wherein any of the foregoing is optionally substituted by one or more independent halo, —$CF_3$, —CN, —$NO_2$, —OH, —$O(C_{1-6}$aliphatic), —$C(O)C_{1-6}$aliphatic, $_{3-10}$cyclic, —SH, —$S(C_{1-6}$aliphatic), —$NH_2$, —$NH(C_{1-6}$aliphatic), or —$N(C_{1-6}$aliphatic$)_2$ groups;

each $R^{28}$ is independently selected from H, —$NR^{24}R^{25}$, —$C(O)R^{24}$, —$CF_3$, $C_{1-6}$aliphatic, or $_{3-10}$cyclic; wherein any of the foregoing is optionally substituted by one or more independent $R^7$ groups;

wherein one or two carbon ring atoms in each of the aforementioned cyclic groups is optionally and independently replaced with C(O) or C(S);

wherein two groups attached to the same tetravalent carbon atom in each of the aforementioned cyclic and aliphatic groups are optionally joined to form a ring system.

In some aspects, the invention includes the compounds of Formula I and salts thereof, above, wherein (Subgenus 2):

X is N or CH;

$A^1$ is phenylene or $_{5-6}$heteroaryl either of which is optionally substituted by one or more independent $R^5$;

$A^3$ is $_{5-6}$heterocyclic optionally substituted by one or more independent $R^6$;

$L^2$ is —O— or a bond;

$L^3$ is $C_{2-6}$aliphatic optionally substituted by one or more independent $R^9$;

$L^4$ is $C_{1-3}$aliphatic optionally substituted by one or more independent $R^8$;

$Q^1$ to $Q^3$ are independently N, N-oxide, or $CR^2$;

$Q^4$ is N, N-oxide, or $CR^3$;

wherein an optionally substituted $_{5-6}$cyclic optionally containing one or more heteroatoms is optionally fused to Ring $A^2$ at $Q^1$ and $Q^4$;

$R^a$ and $R^b$ are each independently selected from H, $C_{1-6}$aliphatic, including $C_{3-6}$-carbocyclic, or $_{4-6}$heterocyclic, any of which can be substituted by one or more independent $R^{aa}$;

each $R^{aa}$ and $R^8$ is independently selected from H, oxo, halo, $C_{1-6}$aliphatic, $C_{3-6}$-carbocyclic, —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$;

$R^1$ is selected from H, halo, —CN, $C_{1-3}$aliphatic (optionally substituted by one or more halo), $C_{3-6}$carbocyclic, —$NO_2$, —$NR^{10}R^{11}$, —$SO_{0-2}R^{12}$, —$C(O)OR^{13}$, —$C(O)R^{12}$, or —$C(O)NR^{10}R^{11}$;

each $R^2$, $R^3$, $R^5$, and $R^6$ is independently selected from H, —$P(O)(OR^{23})_2$, halo, —$CF_3$, —CN, —$NO_2$, —$NR^{20}R^{21}$, —$C(NR^{20}R^{21})=NR^{20}$, —$C(R^{22})=NR^{20}$, —$NR^{20}C(NR^{20}R^{21})=NR^{20}$, —$NR^{20}C(NR^{20}R^{21})=N—C(O)R^{22}$, —$NR^{20}C(NR^{20}R^{21})=CR^{20}R^{21}$, —$NR^{20}C(O)R^{22}$, —$C(O)NR^{20}R^{21}$, —$C(O)R^{22}$, —$C(O)C(O)R^{22}$, —$C(O)OR^{23}$, —$OC(O)R^{22}$, —$OR^{23}$, —$OC(O)OR^{23}$, —$S(O)_{0-2}R^{22}$, —$S(O)(=NR^{20})R^{21}$, $C_{1-6}$aliphatic, or $_{3-10}$cyclic; wherein any substituted or unsubstituted $R^2$, $R^3$, $R^5$, or $R^6$ is optionally substituted by one or more independent $R^7$ groups;

$R^4$ is OH, $C_{1-4}$aliphatic, or —$OC_{1-3}$aliphatic;

each $R^7$ is independently selected from H, —$P(O)(OR^{23})_2$, —$OR^{23}$, —$C(O)R^{24}$, —$C(O)OR^{23}$, —$OC(O)R^{24}$, —$OC(O)OR^{23}$, —$C(O)NR^{24}R^{25}$, —$NR^{24}C(O)NR^{24}R^{25}$, —$NR^{24}R^{25}$, —$NR^{24}C(NR^{24}R^{25})(=NR^{24})$, —$NR^{24}C(NR^{24}R^{25})=N—C(O)R^{24}$, —$NR^{24}C(O)R^{25}$, —$NR^{24}S(O)_{0-2}R^{24}$, —$S(O)_{0-2}R^{24}$, —$CF_3$, —CN, $C_{1-6}$aliphatic, or $_{3-10}$cyclic; wherein any of the foregoing $R^7$ is optionally substituted by one or more independent -halo, —$CF_3$, —CN, —$NO_2$, —OH, —$O(C_{1-6}$aliphatic), —$C(O)R^{26}$, —$C(O)NR^{26}R^{27}$, —$S(O)_{0-2}R^{26}$, —$S(O)_{0-2}NR^{26}R^{27}$, $_{3-10}$cyclic, —SH, —$S(C_{1-6}$aliphatic), —$NH_2$, —$NH(C_{1-6}$aliphatic), or —$N(C_{1-6}$aliphatic$)_2$ groups;

each $R^9$ is independently selected from H, oxo, halo $C_{1-6}$aliphatic, $C_{3-6}$carbocyclic, $_{3-6}$-spirocyclic (optionally substituted by one or more independent $R^{26}$), —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$;

each $R^{10}$, $R^{11}$, $R^{12}$, and $R^{13}$ is independently selected from H, $C_{1-6}$aliphatic, including $C_{3-6}$-carbocyclic, wherein $R^{10}$ and $R^{11}$ attached to the same atom can be taken together to form a ring containing one or more heteroatoms;

each $R^{20}$ and $R^{21}$ is independently selected from H, —$OR^{23}$, —$S(O)_{0-2}R^{28}$, —$NO_2$, $C_{1-6}$aliphatic, or $_{3-10}$cyclic;

each $R^{22}$ is independently selected from H, halo, —$NR^{24}R^{25}$, $C_{1-6}$aliphatic, or $_{3-10}$cyclic;

each $R^{23}$ is independently selected from H, $C_{1-6}$aliphatic, or $_{3-10}$cyclic;

$R^{24}$ and $R^{25}$ are each independently selected from H, —$NR^{26}C(O)R^{27}$, —$CF_3$, —$CN$, —$S(O)_{0-2}R^\sim$, $C_{1-6}$aliphatic, or $_{3-10}$cyclic; wherein any of the foregoing is optionally substituted by one or more independent halo, —$CF_3$, —$CN$, —$NO_2$, —$OH$, —$O(C_{1-6}$aliphatic), —$C(O)R^{26}$, —$C(O)NR^{26}R^{27}$, —$S(O)_{0-2}R^{26}$, —$S(O)_{0-2}NR^{26}R^{27}$, $_{3-10}$cyclic, —$SH$, —$S(C_{1-6}$aliphatic), —$NH_2$, —$NH(C_{1-6}$aliphatic), or —$N(C_{1-6}$aliphatic)$_2$ groups;

$R^{26}$ and $R^{27}$ are each independently selected from the group consisting of —H, $C_{1-6}$aliphatic, or $_{3-10}$cyclic; wherein any of the foregoing is optionally substituted by one or more independent halo, —$CF_3$, —$CN$, —$NO_2$, —$OH$, —$O(C_{1-6}$aliphatic), —$C(O)C_{1-6}$aliphatic, $_{3-10}$cyclic, —$SH$, —$S(C_{1-6}$aliphatic), —$NH_2$, —$NH(C_{1-6}$aliphatic), or —$N(C_{1-6}$aliphatic)$_2$ groups;

each $R^{28}$ is independently selected from H, —$NR^{24}R^{25}$, —$C(O)R^{24}$, —$CF_3$, $C_{1-6}$aliphatic, or $_{3-10}$cyclic;

wherein one or two carbon ring atoms in each of the aforementioned cyclic groups is optionally and independently replaced with C(O) or C(S);

wherein two groups attached to the same tetravalent carbon atom in each of the aforementioned cyclic and aliphatic groups are optionally joined to form a ring system.

In some aspects, the invention includes the compounds and salts thereof of Formula I, above, wherein (Subgenus 3):

X is N or CH;

$A^1$ is phenylene or $_{5-6}$heteroaryl either of which is optionally substituted by one or more independent $R^5$;

$A^3$ is $_{5-6}$heterocyclic optionally substituted by one or more independent $R^6$;

$L^2$ is —O— or a bond;

$L^3$ is $C_{2-6}$aliphatic optionally substituted by one or more independent $R^9$;

$L^4$ is $C_{1-3}$aliphatic optionally substituted by one or more independent $R^8$;

$Q^1$ to $Q^3$ are independently N, N-oxide, or $CR^2$;

$Q^4$ is N, N-oxide, or $CR^3$;

an optionally substituted $_{5-6}$cyclic containing one or more heteroatoms is optionally fused to Ring $A^2$ at $Q^1$ and $Q^4$;

$R^a$ and $R^b$ are each independently selected from H, $C_{1-6}$aliphatic, $C_{3-6}$carbocyclic, or $_{4-6}$heterocyclic, any of which can be substituted by one or more independent halo or $C_{1-6}$aliphatic;

$R^1$ is selected from H, halo, —CN, $C_{1-3}$aliphatic (optionally substituted by one or more halo), $C_{3-6}$carbocyclic, —$NR^{10}R^{11}$, —$SO_{0-2}R^{12}$, —$C(O)OR^{13}$, —$C(O)R^{12}$, or —$C(O)NR^{10}R^{11}$;

each $R^2$, $R^3$, and $R^5$ is independently selected from H, —$P(O)(OR^{22})_2$, halo, —$CF_3$, —$CN$, —$NR^{20}R^{21}$, —$NR^{20}C(O)R^{22}$, —$C(O)NR^{20}R^{21}$, —$C(O)R^{22}$, —$C(O)C(O)R^{22}$, —$C(O)OR^{22}$, —$OC(O)R^{22}$, —$OR^{22}$, —$OC(O)OR^{22}$, —$S(O)_{0-2}R^{20}$, —$S(O)(=NR^{20})R^{21}$, $C_{1-6}$aliphatic, or $_{3-10}$cyclic;

$R^4$ is OH, $C_{1-4}$aliphatic, or —$OC_{1-3}$aliphatic;

each $R^6$, $R^{10}$, $R^{11}$, $R^{12}$, $R^{13}$, $R^{20}$, $R^{21}$, and $R^{22}$ is independently selected from H, $C_{1-6}$aliphatic, or $C_{3-6}$carbocyclic, wherein $R^{10}$ and $R^{11}$ or $R^{20}$ and $R^{21}$ attached to the same atom can be taken together to form a ring containing one or more heteroatoms;

each $R^8$ is independently selected from oxo, halo, $C_{1-6}$aliphatic, —$OC_{0-6}$aliphatic, —$NR^{10}R^{11}$, —$S(O)_{0-2}R^{12}$, —$S(O)_2$ $NR^{10}R^{11}$, —$C(O)NR^{10}R^{11}$, —$C(O)OR^{13}$, or —$NR^{10}S(O)_{0-2}R^{12}$; and each $R^9$ is independently selected from H, oxo, halo $C_{1-6}$aliphatic, $C_{3-6}$carbocyclic, $_{3-6}$spirocyclic, —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$.

In some aspects, the invention includes the compounds and salts thereof of Formula I or of any of Subgenera 1-3, above, wherein (Subgenus 4): X is N.

In some aspects, the invention includes the compounds and salts thereof of Formula I or of any of Subgenera 1-4, above, wherein (Subgenus 5): $R^1$ is selected from Cl, —CN, —$NO_2$, or —$CF_3$.

In some aspects, the invention includes the compounds and salts thereof of Formula I or of any of Subgenera 1-4, above, wherein (Subgenus 6): $R^1$ is —$CF_3$.

In some aspects, the invention includes the compounds and salts thereof of Formula I or of any of Subgenera 1-6, above, wherein (Subgenus 7): $R^a$ and $R^b$ are independently selected from H or $C_{1-3}$aliphatic.

In some aspects, the invention includes the compounds and salts thereof of Formula I or of any of Subgenera 1-7, above, wherein (Subgenus 8): $R^4$ is selected from —OH, $C_{1-4}$aliphatic, or —$OC_{1-3}$aliphatic.

In some aspects, the invention includes the compounds and salts thereof of Formula I or of any of Subgenera 1-8, above, wherein (Subgenus 9): $A^3$ is a 5-membered heteroaryl ring that is optionally substituted by one or more independent halo, —$CF_3$, —$CN$, —$NO_2$, —$OH$, —$O(C_{1-6}$aliphatic), —$C(O)R^{26}$, —$C(o)NR^{26}R^{27}$, —$S(O)_{0-2}R^{26}$, —$S(O)_{0-2}NR^{26}R^{27}$, $_{3-10}$cyclic, —$SH$, —$S(C_{1-6}$aliphatic), —$NH_2$, —$NH(C_{1-6}$aliphatic), or —$N(C_{1-6}$aliphatic)$_2$ groups.

In some aspects, the invention includes the compounds and salts thereof of Formula I or of any of Subgenera 1-8, above, wherein (Subgenus 10): $A^3$ is a 5-membered heteroaryl ring that is optionally substituted by one or more $C_{1-3}$aliphatic.

In some aspects, the invention includes the compounds and salts thereof of any of Subgenera 1-10, above, wherein (Subgenus 11): $L^3$ is $C_{2-4}$aliphatic that is optionally interrupted by one or more heteroatoms and is optionally substituted by one or more oxo, $C_{1-6}$aliphatic, $C_{3-6}$-carbocyclic, —$OC_{0-6}$aliphatic, —$S(O)_2R^{12}$, —$S(O)_2NR^{10}R^{11}$, —$C(O)NR^{10}R^{11}$, —$C(O)OR^{13}$; —$NR^{10}S(O)_2R^{12}$, or —$NR^{10}R^{11}$.

In some aspects, the invention includes the compounds and salts thereof of any of Subgenera 1-10, above, wherein (Subgenus 12): $L^3$ is $C_{3-4}$aliphatic that is optionally substituted by one or more oxo, —$C_{1-6}$aliphatic, $C_{3-6}$carbocyclic, —$OC_{0-6}$aliphatic, —$S(O)_2R^{12}$, —$S(O)_2NR^{10}R^{11}$, —$C(O)NR^{10}R^{11}$, —$C(O)OR^{13}$; —$NR^{10}S(O)_2R^{12}$, or —$NR^{10}R^{11}$.

In some aspects, the invention includes the compounds and salts thereof of Formula I or of any of Subgenera 1-12, above, wherein (Subgenus 13): $L^4$ is $C_{1-2}$aliphatic.

In some aspects, the invention includes the compounds and salts thereof of Formula I or of any of Subgenera 1-13, above, wherein (Subgenus 14): $A^1$ is phenylene optionally substituted by one or more halo, $C_{1-3}$aliphatic, or —$OC_{1-3}$aliphatic, either of which is optionally substituted by one or more halo.

In some aspects, the invention includes the compounds and salts thereof of any of Subgenera 1-14, above, wherein (Subgenus 15): each $R^2$ is independently selected from H, halo, $C_{1-2}$aliphatic or —$OC_{1-2}$aliphatic.

In some aspects, the invention includes the compounds and salts thereof of any of Subgenera 1-14, above, wherein (Subgenus 16):

$Q^4$ is $CR^3$;

$R^3$ is selected from halo, —$OR^{12}$, $R^{12}$, $_{3-6}$cyclic, —$NR^{10}R^{11}$, —$NR^{10}SO_2R^{13}$, —$OSO_2(R^{13})$, —$SO_2(R^{13})$, —$SO_2CF_3$, —$SO_2NR^{10}R^{11}$, —$C(O)NR^{10}R^{11}$, —$C(O)R^{12}$, —$C(O)O(R^{12})$, —$C(O)(R^{12})$—$O(R^{12})$, —$C(O)CF_3$, —$C(O)(_{3-6}$cyclic), or —$C(O)O(_{3-6}$cyclic); wherein any of the foregoing is optionally substituted with one or more, halo, —OH, —$CF_3$, —$NO_2$, —CN, —$C_{1-6}$aliphatic, —$OC_{1-6}$aliphatic, —C=N—OH, —C=N—$OR^{12}$, —$NR^{10}R^{11}$, —$SR^{13}$, —$SOR^{13}$, —$SO_2R^{13}$, —$CO_2R^{12}$, —$CONR^{10}R^{11}$, —$SO_2NR^{10}R^{11}$, —$NHCOR^{12}$, —$NR^{10}CONR^{10}R^{11}$, and —$NR^{10}SO_2R^{13}$, or —$P(O)(OR^{10})_2$;

when $R^3$ is —$C(O)NR^{10}R^{11}$, $R^{10}$ may be taken with $R^2$ to form a ring containing one or more heteroatoms and fused to Ring $A^2$.

In some aspects, the invention includes the compounds and salts thereof of any of Subgenera 1-15, above, wherein (Subgenus 17):

$Q^4$ is $CR^3$;

$R^3$ is selected from H, —$S(O)_2R^{13}$, —$S(O)_2NR^{10}R^{11}$, —$C(O)NR^{10}R^{11}$, —$C(O)R^{10}$, —$C(O)OR^{10}$; —$NR^{10}S(O)_2R^{13}$, or —$NR^{10}R^{11}$.

In some aspects, the invention includes the compounds and salts thereof of any of Subgenera 1-2, above, wherein (Subgenus 18):

$A^1$ is phenylene optionally substituted by halo, —$C_{1-3}$aliphatic, or —$OC_{1-3}$aliphatic, either of which is optionally substituted by one or more halo or —$OCF_3$;

$A^3$ is a 5-membered heteroaryl ring that is optionally substituted by one or more $C_{1-3}$aliphatic;

$L^2$ is —O— or a bond;

$L^3$ is $C_{2-4}$aliphatic optionally substituted by one or more $C_{1-6}$aliphatic or $C_{3-6}$carbocyclic;

$L^4$ is —$CH_2$— or —$CH_2CH_2$—;

$Q^1$ to $Q^3$ are independently N or $CR^2$;

$Q^4$ is $CR^3$;

$R^a$ and $R^b$ are independently H or $C_{1-3}$aliphatic;

$R^1$ is selected from H, halo, —CN, $C_{1-3}$aliphatic (optionally substituted by 1 to 3 halo), $C_{3-6}$-carbocyclic, —$NO_2$, —$N(C_{0-3}$aliphatic$)_2$, —$SO_{0-2}(C_{1-3}$aliphatic), —C(O)O($C_{1-3}$aliphatic), —$C(O)C_{0-3}$aliphatic, or —$C(O)N(C_{0-3}$aliphatic$)_2$;

each $R^2$ is independently H, halo, —$OC_{1-3}$aliphatic, or —$C_{1-3}$aliphatic;

wherein $R^2$ and $R^3$ are optionally taken together to define an optionally substituted $_{5-6}$cyclic fused at $Q^1$ and $Q^4$ to Ring $A^2$ and containing one or more heteroatoms;

$R^3$ is selected from halo, —$OR^{12}$, $R^{12}$, $_{3-6}$cyclic, —$NR^{10}R^{11}$, —$NR^{10}SO_2R^{13}$, —$OSO_2(R^{13})$, —$SO_2(R^{13})$, —$SO_2CF_3$, —$SO_2NR^{10}R^{11}$, —$C(O)NR^{10}R^{11}$, —$C(O)R^{12}$, —$C(O)O(R^{12})$, —$C(O)(R^{12})$—$O(R^{12})$, —$C(O)CF_3$, —$C(O)(_{3-6}$cyclic), or —$C(O)O(_{3-6}$cyclic); wherein any of the foregoing is optionally substituted with one or more, halo, —OH, —$CF_3$, —$NO_2$, —CN, —$C_{1-6}$aliphatic, —$OC_{1-6}$aliphatic, —C=N—OH, —C=N—$OR^{12}$, —$NR^{10}R^{11}$, —$SR^{13}$, —$SOR^{13}$, —$SO_2R^{13}$, —$CO_2R^{12}$, —$CONR^{10}R^{11}$, —$SO_2NR^{10}R^{11}$, —$NHCOR^{12}$, —$NR^{10}CONR^{10}R^{11}$, —$NR^{10}SO_2R^{13}$, or —$P(O)(OR^{10})_2$;

$R^4$ is OH, $C_{1-4}$aliphatic, or —$OC_{1-3}$aliphatic;

$R^{10}$, $R^{11}$, $R^{12}$, and $R^{13}$ are independently H, $C_{1-6}$aliphatic, or $C_{3-6}$carbocyclic, or $R^{10}$ and $R^{11}$ attached to the same atom can be taken together with the atoms to which they are attached to form a ring containing one or more heteroatoms.

In some aspects, the invention includes the compounds and salts thereof of Subgenus 18, above, wherein (Subgenus 19):

$A^1$ is phenylene optionally substituted by halo, methyl, ethyl, or methoxy;

$L^3$ is $C_{3-4}$aliphatic optionally substituted by one or more of $C_{1-2}$aliphatic, —OH, or —$OCH_3$;

$R^1$ is H, halo, $CF_3$, or CN;

$R^3$ is H, $C_{1-6}$aliphatic, —$S(O)_2R^{10}$, —$S(O)_2NR^{10}R^{11}$, —$C(O)NR^{10}R^{11}$, —$C(O)R^{10}$, —$C(O)OR^{10}$; —$NR^{10}S(O)_2R^{11}$, or —$NR^{10}R^{11}$;

$R^{10}$ and $R^{11}$ are independently $C_{0-6}$aliphatic, which $R^{10}$ and $R^{11}$ of a given substituent can be taken together at any of their atoms to form a ring containing one or more heteroatoms;

or alternatively $R^3$ and $Q^1$ define any optionally substituted $_{5-6}$cyclic containing one or more heteroatoms.

In some aspects, the invention includes the compounds and salts thereof of Subgenera 1 or 2, above, having the Formula II, wherein (Subgenus 20):

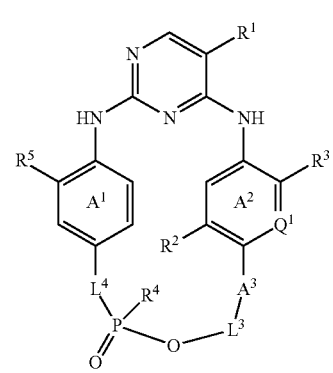

II $A^3$ is selected from one of:

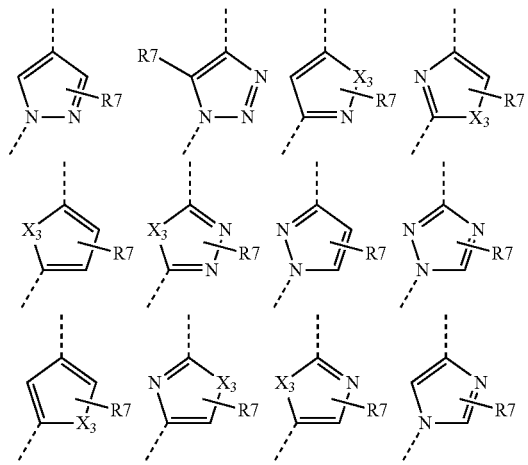

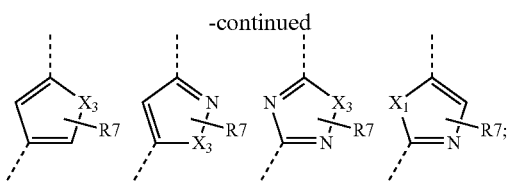

wherein the upper dotted line is a bond to $A^2$ and the lower dotted line is a bond to $L^3$, and each $X_3$ is independently selected from N, O, or S;

$L^3$ is $C_{2-4}$aliphatic that is optionally substituted by one or more $C_{1-2}$aliphatic;

$L^4$ is a bond, —$CH_2$—, or —$CH_2CH_2$—;

$Q^1$ is N or $CR^2$;

$R^1$ is halo, —$CF_3$, or —CCH;

each $R^2$ is independently H, halo, $C_{1-2}$aliphatic, or —$OC_{1-2}$aliphatic;

$R^3$ is H, $C_{1-6}$aliphatic, —$C(O)R^{10}$, —$S(O)_{0-2}NR^{10}R^{11}$ or —$C(O)NR^{10}R^{11}$;

and $Q^1$ and $R^3$ optionally define a $_{5-6}$cyclic fused to ring $A^2$ and optionally containing one or more heteroatoms of which each N atom is optionally substituted with an independent $C_{1-2}$aliphatic;

$R^4$ is OH, —$OC_{1-3}$aliphatic, or $C_{1-3}$aliphatic;

$R^5$ is H, halo, $C_{1-2}$aliphatic, or —$OCH_3$;

each R7 is independently H or $C_{1-3}$aliphatic;

each $R^{10}$ and $R^{11}$ is independently H, —$OCH_3$, or $C_{1-3}$aliphatic, and $R^{10}$ and $R^{11}$ can be taken together to form a ring optionally containing one or more additional heteroatoms.

In some aspects, the invention includes the compounds and salts thereof of Subgenera 1 or 2, above, having the Formula III, wherein (Subgenus 21):

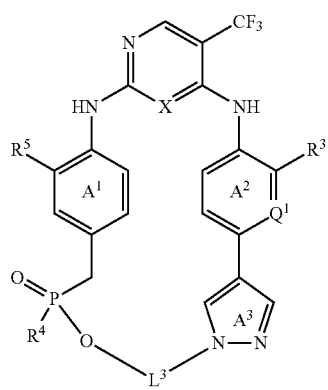

III $Q^1$ is N or $CR^2$;

$L^3$ is $C_{2-4}$alkylene optionally substituted by 1-2 independent halo or $C_{1-2}$alkyl;

$R^2$ is H, halo, $C_{1-2}$aliphatic, or —$OC_{1-2}$aliphatic;

$R^3$ is —$C(O)R^{10}$, —$S(O)_2NR^{10}R^{11}$, or —$C(O)NR^{10}R^{11}$;

$R^4$ is OH or —$OC_{1-3}$aliphatic;

$R^5$ is H or —$OCH_3$;

each $R^{10}$ and $R^{11}$ are independently H, —$OCH_3$, or $C_{1-3}$aliphatic, and $R^{10}$ and $R^{11}$ can be taken together to form a ring optionally containing one or more additional heteroatoms.

In some aspects, the invention includes the compounds and salts thereof of Subgenera 20 or 21, above, having the following formula (Subgenus 22):

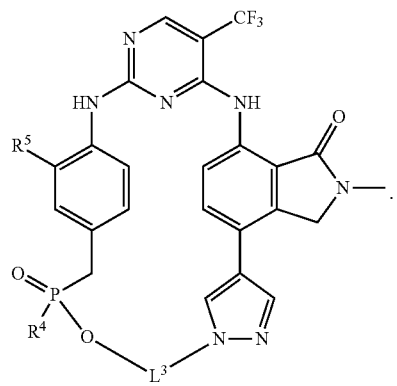

In some aspects, the invention includes the compounds and salts thereof of Subgenera 20 or 21, above, wherein (Subgenus 23):

$R^3$ is —$C(O)NR^{10}R^{11}$;

$Q^1$ is CH, N, or N-oxide;

each $R^{10}$ and $R^{11}$ is independently H, —$OCH_3$, or $C_{1-2}$aliphatic.

In some aspects, the invention includes the compounds and salts thereof of Subgenera 20-23, above, wherein (Subgenus 24): $Q^1$ is N.

In some aspects, the invention includes the compounds and salts thereof of any of the foregoing recitations, which exhibits inhibition of FAK in a cellular assay with an $IC_{50}$ of about 100 nM or less.

In some aspects, the invention includes the compounds of Formula I selected from any one of the examples herein or a pharmaceutically acceptable salt thereof.

In some aspects, the invention includes the compounds of Formula I, which is present as a material in substantially enantiomerically pure form.

In some aspects, the invention includes the compounds of Formula I, which is present as a material in substantially pure form.

Each variable definition above includes any subset thereof and the compounds of Formula I include any combination of such variables or variable subsets.

In some aspects, the invention includes any of the compound examples herein and pharmaceutically acceptable salts thereof.

In some embodiments, the compound is selected from any one of the examples herein or a pharmaceutically acceptable salt thereof.

The invention includes the compounds and salts thereof, and their physical forms, preparation of the compounds, useful intermediates, and pharmaceutical compositions and formulations thereof.

The invention includes the isomers of the compounds. Compounds may have one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

Included within the scope of the invention are all stereoisomers, geometric isomers and tautomeric forms of the inventive compounds, including compounds exhibiting more than one type of isomerism, and mixtures of one or more thereof.

When a tautomer of the compound of Formula (I) exists, the compound of formula (I) of the present invention includes any possible tautomers and pharmaceutically acceptable salts thereof, and mixtures thereof, except where specifically stated otherwise.

The compounds of the invention are not limited to those containing all of their atoms in their natural isotopic abundance. The present invention includes compounds wherein one or more hydrogen, carbon or other atoms are replaced by different isotopes thereof. Such compounds can be useful as research and diagnostic tools in metabolism pharmacokinetic studies and in binding assays. A recitation of a compound or an atom within a compound includes isotopologs, i.e., species wherein an atom or compound varies only with respect to isotopic enrichment and/or in the position of isotopic enrichment. For nonlimiting example, in some cases it may be desirable to enrich one or more hydrogen atoms with deuterium (D) or to enrich carbon with $^{13}C$. Other examples of isotopes suitable for inclusion in the compounds of the invention include isotopes of hydrogen, chlorine, fluorine, iodine, nitrogen, oxygen, phosphorus, and sulfur. Certain isotopically-labeled compounds of the invention may be useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Substitution with positron emitting isotopes may be useful in Positron Emission Topography (PET) studies for examining substrate receptor occupancy.

Further, the compounds may be amorphous or may exist or be prepared in various crystal forms or polymorphs, including solvates and hydrates. The invention includes any such forms provided herein, at any purity level. A recitation of a compound per se means the compound regardless of any unspecified stereochemistry, physical form and whether or not associated with solvent or water.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g., $D_2O$, d6-acetone, d 6-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized.

The invention includes prodrugs of compounds of the invention which may, when administered to a patient, be converted into the inventive compounds, for example, by hydrolytic cleavage. Prodrugs in accordance with the invention can, for example, be produced by replacing appropriate functionalities present in the inventive compounds with certain moieties known to those skilled in the art as 'pro-moieties' as known in the art. Particularly favored derivatives and prodrugs of the invention are those that increase the bioavailability of the compounds when such compounds are administered to a patient, enhance delivery of the parent compound to a given biological compartment, increase solubility to allow administration by injection, alter metabolism or alter rate of excretion.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Compounds that are basic are capable of forming a wide variety of salts with various inorganic and organic acids. The acids that can be used to prepare pharmaceutically acceptable acid addition salts of such basic compounds are those that form acceptable acid addition salts. When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Other salts are aspartate, besylate, bicarbonate/carbonate, bisulphate/sulfate, borate, camsylate, edisylate, gluceptate, glucuronate, hexafluorophosphate, hibenzate, hydrobromide/bromide, hydroiodide/iodide, malonate, methylsulfate, naphthylate, 2-napsylate, nicotinate, orotate, oxalate, palmitate, phosphate/hydrogen, phosphate/dihydrogen, phosphate, saccharate, stearate, tartrate, tosylate, and trifluoroacetate.

When the compound of the present invention is acidic, its corresponding salt can be conveniently prepared from pharmaceutically acceptable bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic bases include salts of primary, secondary, and tertiary amines, as well as cyclic amines and substituted amines such as naturally occurring and synthesized substituted amines. Other pharmaceutically acceptable organic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Other examples include benzathine, diolamine, glycine, meglumine, and olamine.

Synthesis

The invention includes the examples, compounds, intermediates, and synthetic methods described herein. Compounds according to the invention may be prepared according to the skill in the art and known literature in connection with the teachings herein of the examples and the following general synthetic schemes. Variables herein are not necessarily defined exactly according to Formula I herein, but are applicable thereto as is apparent in context, or can be further modified or derivatized as appropriate.

phinate (Reaction 1) using NaI, TMSBr, or the like, in a solvent such as pyridine, and heating if necessary. The resulting salt can be isolated and cyclized (Reaction 2) by a coupling reaction to form an ester bond using an agent such as PyBOP, DCC, or the like, and base (e.g., DIPEA or the like) in a solvent such as DCE, pyridine, DMF, or the like, and heating if necessary.

SCHEME 1:

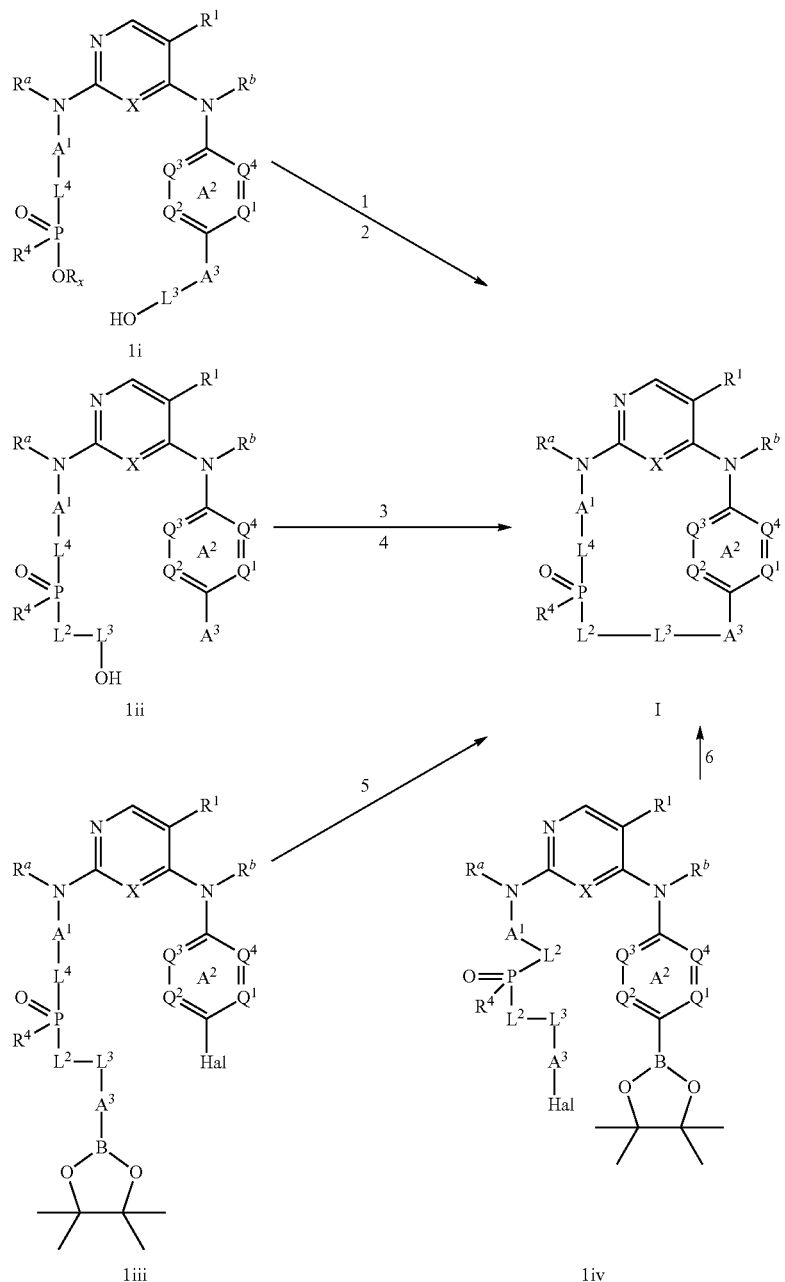

Macrocycles of the invention (Formula I) can be prepared as in Scheme 1, e.g., by intramolecular cyclization from a starting material comprising an appropriate phosphinate or phosphonate and OH-substituted $L^3$ group.

A Compound 1i can be converted to Formula I by a two-step process involving dealkylation of a phosphonate or phos- Alternatively, a Compound 1ii can be converted to Formula I by converting the terminal OH group to a leaving group such as a tosylate or mesylate (Reaction 3), and allowing the intramolecular displacement of the newly installed leaving group by a nucleophilic moiety on $A^3$, such as a de-protonated pyrrole nitrogen, to occur (Reaction 4). These conditions will require a base such as NaH or $Na_2CO_3$, or $Cs_2CO_3$ and a solvent such as DMF or DMSO. Heating may be required. Alternatively, if A3 is a suitably acidic nucleophile, cyclization to a compound of Formula I may be achieved by using the Mitsunobu reaction with triphenylphosphine and a dialkyl azodicarboxylate in a suitable solvent such as THF or DCM.

Furthermore, Compounds of Formula I can be prepared from Compounds 1iii or 1iv via the Suzuki reaction. There are numerous Pd catalyst and ligand systems, bases and solvent combinations favorable for this transformation. These conditions can provide access to compounds wherein $L^2$ is a bond.

SCHEME 2:

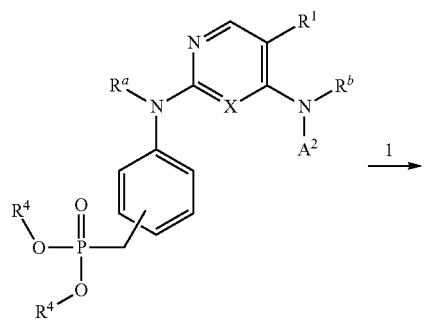

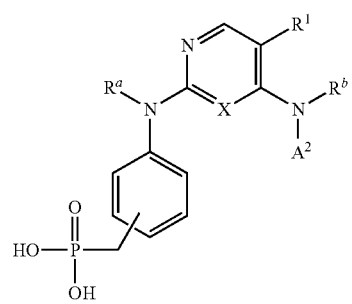

For example, as shown below, alkyl hydrogen phosphonates and phosphonic acids may be synthesized from the corresponding diethyl phosphonates by hydrolysis with concentrated hydrochloric acid. Stopping the reaction before complete hydrolysis occurs allows the isolation of both the alkyl hydrogen phosphonate and the phosphonic acid through chromatographic techniques such as preparative HPLC. Either of the resulting products can be isolated and cyclized according to the invention.

SCHEME 3:

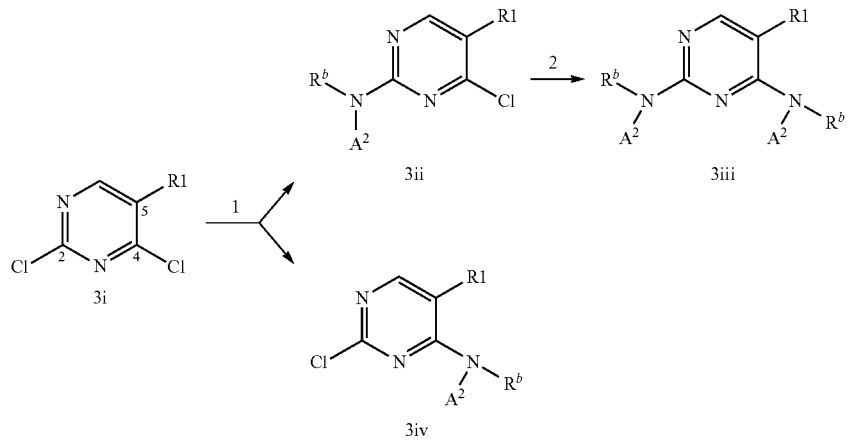

-continued

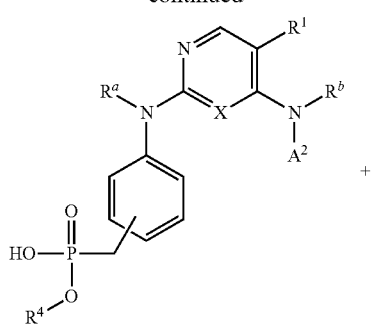

2,4-Di-aminopyrimidines may be synthesized through various approaches to afford target molecules. Below are non-limiting examples that the skilled artisan could utilize to realize target molecules and examples.

As in Scheme 3, commercially available or customized (See, e.g., Schemes 5-7) 5-substituted-2,4-dichloropyrimidines may be reacted directly with anilines or amines in SNAr reactions to afford mixtures of mono-substitution products (Scheme 3, 3ii/3iv). Depending on the conditions used and the nature of the aniline/amine and $R^1$ group, a predominant isomer may be formed. In these situations or under conditions of minimal regioselectivity, the isomers may be separated (fully or partially) through the use of chromatography and/or crystallization. Assignment of structure to each pure isomer may be made through NMR experiments, in particular through the use of HMBC experiments which may disclose a 3 bond H—C correlation between the C4-NH and the C5-C in the case of the 4-substituted product, which is not evident in the C2-NH isomer. Assignment of structure may be made by comparison of spectral data to those isomers made by the previous method described above or directly through NMR experimentation.

In addition to the SNAr displacements of the 2- and 4-chloro groups as indicated above, those skilled in the art will recognize that other groups may also serve as good leaving groups that may be displaced by amines and anilines under the appropriate conditions. Examples of displaceable groups include, but are not limited to alkylthio, alkylsulfonyl, bromo, trichloromethyl, fluoro, sulfonyloxy and N-benzotriazolyloxy, and in each case the 2- and 4-leaving groups may the same or different. Indeed in certain circumstances it may be preferred that the 2- and 4-displaceable groups are different as this offers the opportunity to take advantage of different leaving group potentials and so control the regiochemistry of the SNAr reaction.

SCHEME 4:

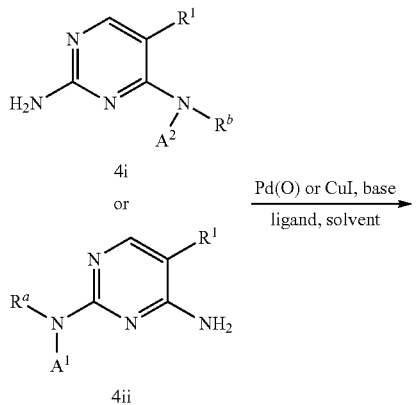

Another approach to access 2-anilino, 4-anilino or 2,4-dianilino-pyrimidines involves transition metal catalyzed arylation of an aminopyrimidine, as in Scheme 4. In a typical procedure, the 2- or 4-aminopyrimidine is heated with an aryl or heteroaryl bromide or iodide in the presence of copper (I) iodide, ethylenediamine ligand and potassium carbonate base in dioxane. Other commonly used reagents are $Ph_2$-pentadienone-Pd, NaOPh and XantPhos. Depending on the nature of the $R^1$ group at the 5-position, such reactions may be conducted on 2,4-diaminopyrimidines and some preference for one or other amino group observed. Further modification of $R^1$ may also be carried out.

SCHEME 5:

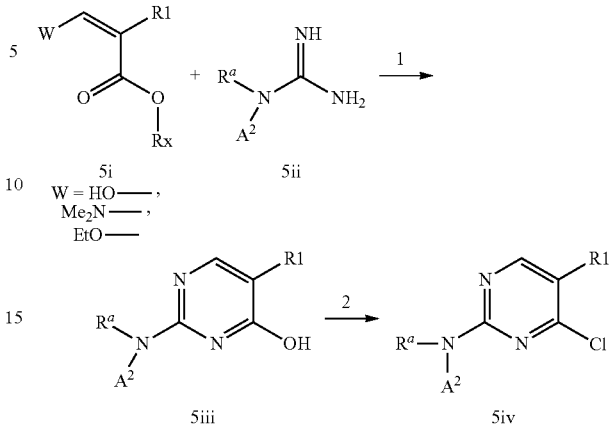

In addition to refunctionalizing an activated pyrimidine system, one may also access desired derivatives through construction of the pyrimidine ring itself, as in the following:

Reaction of an appropriately substituted guanidine with an appropriately substituted β-formyl ester, β-(dimethylamino) propenoate or β-(alkoxy)propenoate yields a hydroxy pyrimidine as indicated in the above scheme. Such hydroxypyrimidines may be chlorinated using reagents such as $POCl_3$ to form intermediates analogous to those described in Scheme 3. The $R^1$ substitution in the reactants could be the same as the final $R^1$ group, or different as necessary to allow for the cyclization and/or halogenation chemistry to be successful. Where $R^1$ is different from the final $R^1$, the interconversion to $R^1$ may be undertaken by the multiple methods known to the skilled artisan, a non-limiting list of which are described herein.

SCHEME 6a:

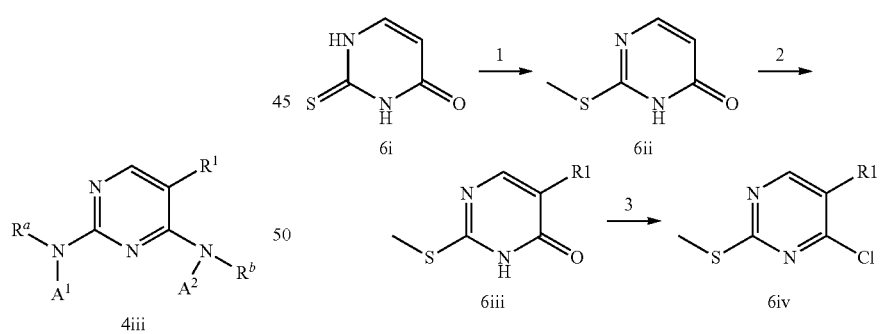

Other methods of accessing suitably functionalized pyrimidine derivatives include modification of commercially available uracil or thiouracil. For example, S-methylation of thiouracil using iodomethane and base affords an intermediate that may be functionalized at the C5 position to introduce $R^1$, or the precursor to $R^1$, such as Br or I. An example of such C5-functionalization is halogenation using bromine in acetic acid, N-iodosuccinimide in DMF or N-chlorosuccinimide in acetic acid, which introduces a C5 bromo-, iodo or chloro group, respectively. Groups such as $CF_3$ may be introduced through reaction with $CF_3I$ in the presence of $FeSO_4$, $H_2O_2$ and DMSO.

SCHEME 6b:

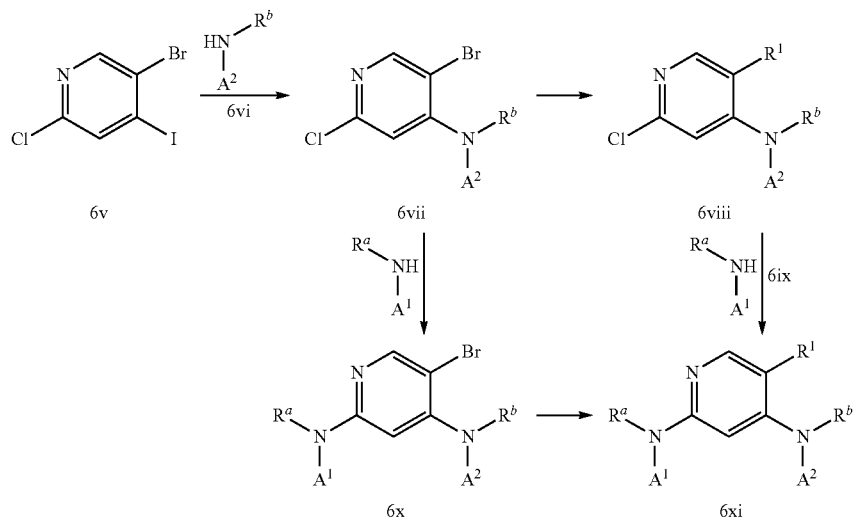

Also in the case of pyridines, as in Scheme 6b, modification of intermediates from this invention can provide access to a range of R¹ groups.

For example, the commercially available pyridine 6v can be subjected to a Buchwald Hartwig coupling with aniline 6vi to provide the intermediate 6vii. R¹ groups such as alkyl and cycloalkyl can be introduced by Suzuki or Negishi coupling to afford compounds of Formula 6viii. The aniline 6ix can then be installed via a second Buchwald-Hartwig reaction to afford a compound 6xi.

It may be preferable to install 6ix before introducing a new R¹ group as the chloro functionality of 6vii may be sensitive to those potential reaction conditions. Heating 6ix and 6vii in a polar, protic solvent with acid will give a compound 6x which can be converted to 6xi. For example, a methyl sulfone may be introduced through the L-proline-promoted CuI-catalyzed coupling of a methyl sulfinic acid salt.

SCHEME 7:

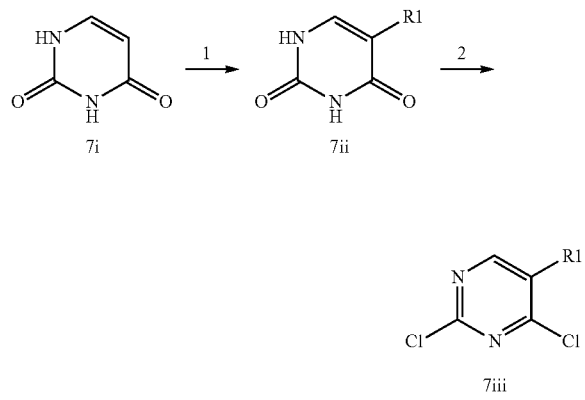

C5 chemistries may also be used on uracil itself and the derivatives converted to the 4-chloro (for the thiouracil derivative) or 2,4-dichloropyrimidine derivatives through reaction with reagents such as POCl₃.

SCHEME 8a:

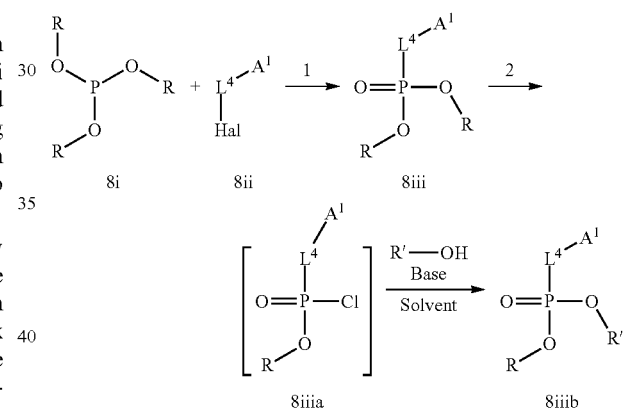

Dialkylphosphonates may be prepared according to the method of Michaelis-Arbuzov as shown whereby alkyl halides or sulfonates (e.g., Hal=Br, I, Cl, OMs) are heated with trialkylphosphites. Additionally, phosphonates 8iii can be trans-esterified by first transforming them into the corresponding phosphonochloridates 8iiia by heating 8iii in SOCl₂ and catalytic DMF. Stirring 8iiia with a base such as DIPEA or TEA, an alcohol such as butanol or isopropanol in a solvent such as THF or DCM affords transesterified phosphonate 8iiib.

SCHEME 8b:

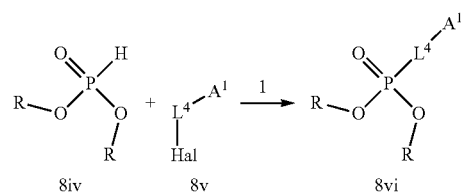

Phosphonates bearing a P-hydrogen may be reacted with alkyl halides or sulfonates (e.g., Hal=Cl, Br, I, OMs) in the presence of bases, including but not limited to $Na_2CO_3$, $K_2CO_3$, NaOH, $Cs_2CO_3$, $Et_3N$, DIPEA and DBU, and in suitable solvents, e.g., acetonitrile, DMF, dioxane, DMA to afford P-substituted products via SN2-type chemistries.

SCHEME 8c:

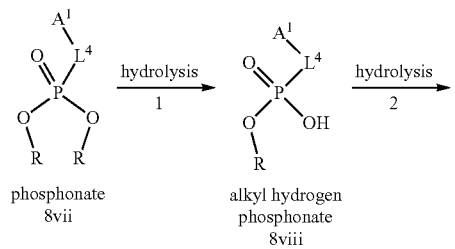

phosphonate
8vii alkyl hydrogen
phosphonate
8viii

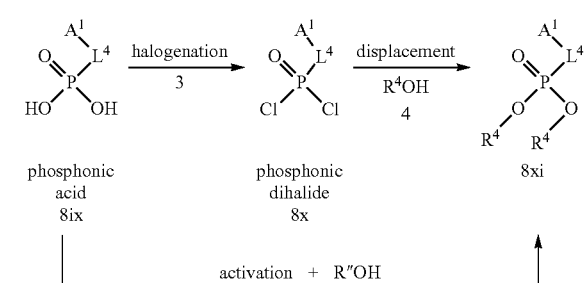

phosphonic
acid
8ix phosphonic
dihalide
8x

SCHEME 8d:

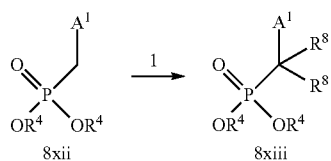

Phosphonates may be alkylated on an alpha carbon by deprotonation with strong base of which tBuOK, nBuLi, NaH and LDA are non-limiting examples, then treatment with carbon electrophiles, e.g., MeI, DMF and chloroformates (Scheme 8d) ($R^8$ and/or the other $R^8$ may be methyl). Control of the stoichiometry of the reaction components may afford mono- or dialkylated products. Additionally, sequential use of base, electrophile #1, base and electrophile #2 is another means to effectively control dialkylation.

For example, as shown below, dialkyl benzylphosphonates such as diethyl (4-nitrobenzyl)phosphonate I, may be monoalkylated at the benzylic carbon by reaction with strong base, of which LDA is a non-limiting example, followed by introduction of a suitable alkyl halide such as iodomethane. The monoalkylated product thus formed may be alkylated a second time at the benzylic carbon through deprotonation with sodium hydride and reaction with an alkyl halide such as iodomethane to yield the dialkylated material. In the instance shown below, the nitro-derived products may be reduced to the corresponding anilines via methods such as catalytic hydrogenation.

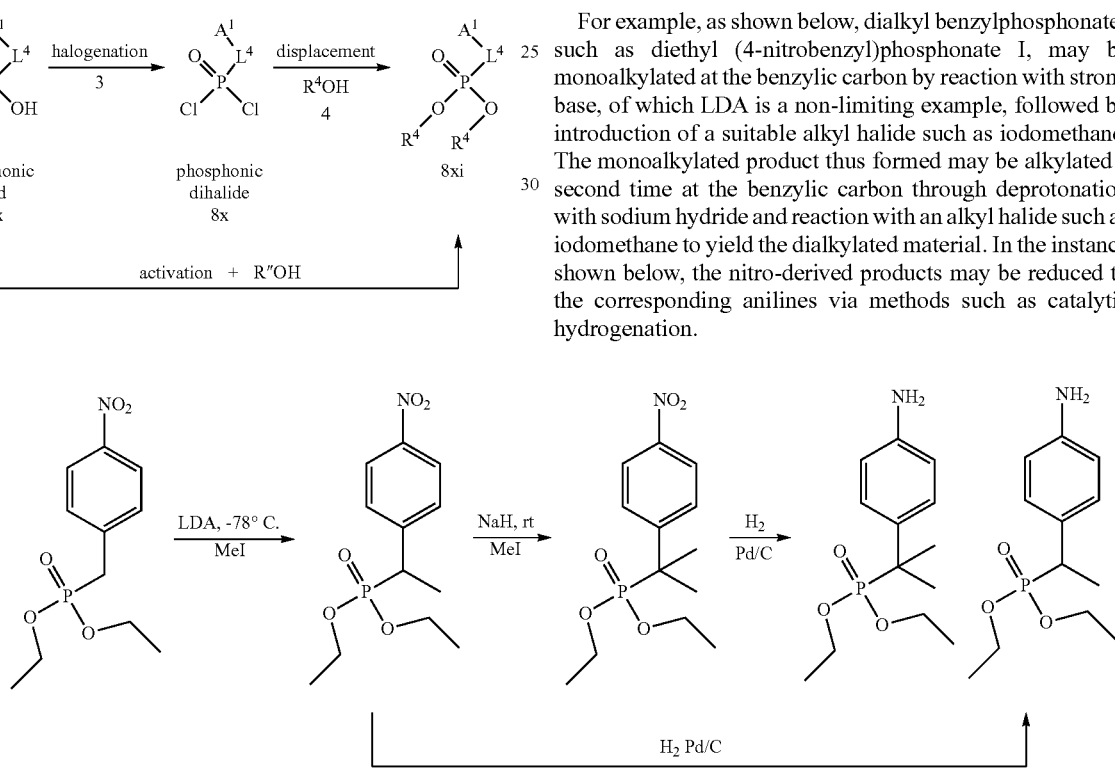

Preparation of dialkylphosphonates may be achieved via multiple approaches. For example, one dialkyl phosphonate may be converted into another, different dialkyl phosphonate. Hydrolysis of a dialkylphosphonate under acidic conditions such as concentrated hydrochloric acid affords the corresponding phosphonic acid. Other acid reagents may be used to effect this transformation including, but not limited to, HBr and HBr/HOAc. The transformation may also be achieved using basic conditions, e.g., by treatment with NaOH/MeOH or through the use of reagents such as, but not limited to, TMSI, TMSBr, TMSCl/NaI and NaI in solvents such as acetone, acetonitrile, DCM, chloroform and dioxane.

SCHEME 8e:

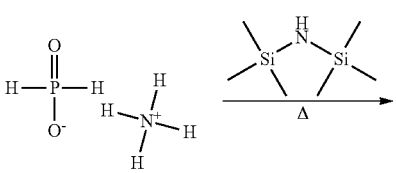

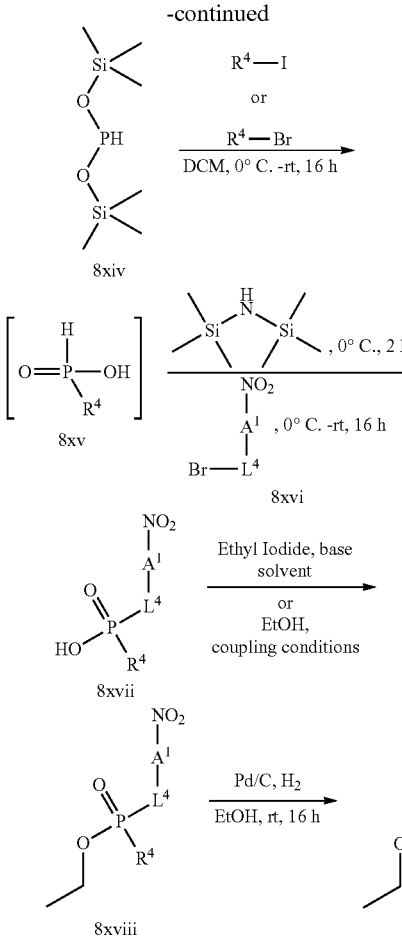

Phosphinates 8xviv can be obtained using the procedure shown in Scheme 8e. A protected phosphonite 8xiv, made from commercially available ammonium phosphinate and hexamethyldisilazide, can be alkylated with an alkyl halide to provide, in situ, the phosphinic acid 8xv. Alkyl bromide or iodides can be obtained commercially or prepared using techniques known to one skilled in the art. Compound 8xv can be alkylated with 8xvi, itself either obtained commercially or prepared using established methods, to form 8xvii. A third alkylation or coupling reaction is performed on 8xvii to form the phosphinate ester. A standard catalytic hydrogenation gives the aniline 8xviv which can be used in the chemistry, e.g., as described in Schemes 3 and 4.

Should 8xviii bear a functionality adversely affected by catalytic hydrogenation (such as chloro or bromo), alternative reduction conditions should be used. Non-limiting examples of these conditions are Fe/HCl, Fe/HOAc and $SnCl_2$/EtOH.

Solvents appropriate for the final alkylation include polar, aprotic solvents such as DMF or NMP. Suitable bases include $Na_2CO_3$, $K_2CO_3$, or the like; coupling conditions include EDC or PYBOP, in the former case it may be advantageous to use an accelerant such as DMAP. If coupling conditions are employed the same solvents may be used or it may be preferable to use an inert solvent such as DCM or THF.

SCHEME 8f:

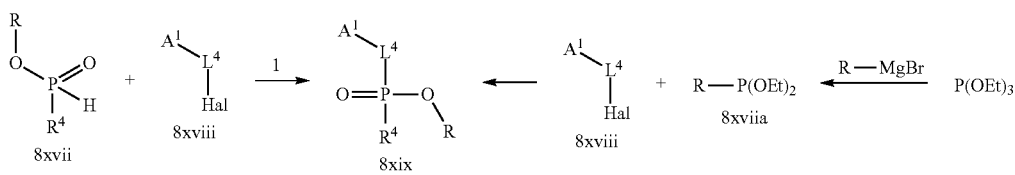

Similarly, the reaction of phosphinates bearing a P-hydrogen with alkyl halides or sulfonates (e.g., Hal=Cl, Br, I, OTf) in the presence of base also proceeds via SN2 chemistry as with phosphonates. Additionally, phosphinates 8xix can be prepared by treating the alkyl halide or sulfonate 8xviii with an alkyl phosphonite such as 8xviia, itself prepared by treating triethyl phosphite with a Grignard reagent according to the procedure of Petnehazy, et al in Synthetic Communications, 2003, 33, 1665-1674.

SCHEME 8g:

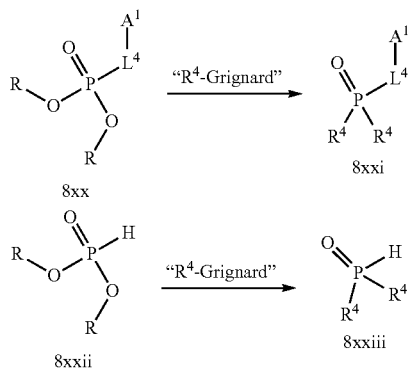

There may also be a desire to prepare phosphine oxides, such as via a number of methods including through the reaction of dialkyl phosphonates with carbon nucleophiles including, but not limited to, Grignard reagents.

SCHEME 8h:

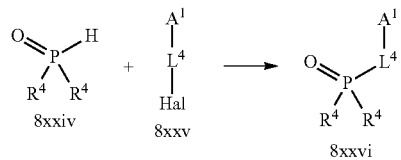

As in the case of phosphonates and phosphinates, dialkyl phosphine oxides bearing a P-hydrogen may be reacted with alkyl halides or sulfonates (e.g., Hal=Br, I, Cl, OMs) under basic conditions or aryl halides (e.g., Hal=Br, I, Cl, OTf) under transition metal catalysis to form the P-substituted derivatives.

SCHEME 8i:

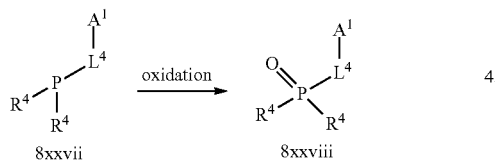

Other methods to access phosphine oxides include the oxidation of phosphines with oxidants such as, but not limited to, hydrogen peroxide.

SCHEME 8j:

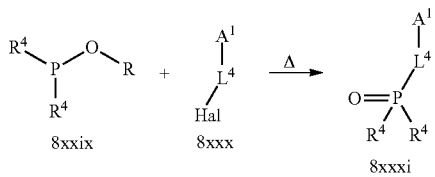

Additionally, dialkyl alkoxyphosphines may be reacted with alkyl halides or sulfonates (e.g., Hal=Br, I, Cl, OMs) to form phosphine oxides via Michaelis-Arbuzov chemistry.

Scheme 9: Functional Group Interconversion

Of general applicability, the various functionalities appearing in target molecules and examples (e.g., X at the 5-position of the pyrimidine system, or on the pendant N-aryl or N-benzyl groups), may be introduced through appropriate choice of starting materials, or where the final functionality is not available directly through this process, or where such functionality may be compromised during the subsequent chemistry to build the final molecule, alternative functionalities may be used and subsequently transformed into the final desired functionality by methods, and at points in the sequence, readily determined by one skilled in the art.

For example, a non-exhaustive list of such transformations includes the conversions: Ar/HetAr—OMe→Ar/HetAr—OH (BBr$_3$), Ar/HetAr—NH$_2$→Ar/HetAr—Cl (NaNO$_2$, CuCl), Ar/HetAr—Br→Ar/HetAr—CN (Pd$_2$(dba)$_3$, Zn(CN)$_2$, DPPF), Me→CO$_2$H (KMnO$_4$), CO$_2$H→CO$_2$Me (MeOH, H$_2$SO$_4$), OH→OAlkyl (Alkyl halide, base), CO$_2$H→CONR'R" (EDC, HOAt, DIPEA, HNR'R"), Ar/HetAr—Br→Ar/HetAr—CO$_2$Me (Pd$_2$(dba)$_3$, DPPF, CO(g), MeOH), Br→CO$_2$H ($^t$BuLi, CO$_2$), Ar/HetAr—H→Ar/HetAr—Br (NBS), CN→CO$_2$H (conc. H$_2$SO$_4$), Ar/HetAr—Br→Ar/HetAr—NR'R" (Pd$_2$(dba)$_3$, DPPF, HNR'R"), Ar/HetAr—I/Br→Ar/HetAr—CF$_3$ (CF$_3$CO$_2$Na, CuI, NMP). Other functional group interconversion (FGI) examples relating to the generation of aniline and benzylamine synthons used for SNAr chemistry with 2,4-dichloropyrimidines, pyrimidines, or pyridines with displaceable groups at the 2- or 4-positions, with other displaceable leaving groups, are shown below.

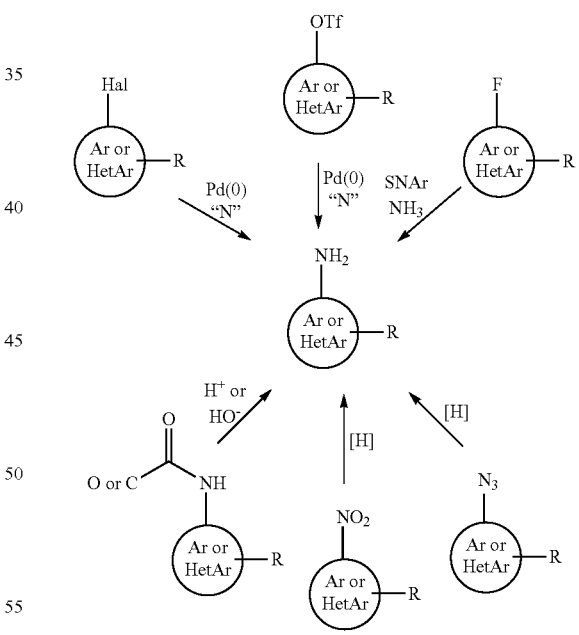

As shown in Scheme 9, nitro- or azidobenzenes may be reduced to the desired aniline compound under a range of conditions. Typically hydrogenation in the presence of a Pd/C catalyst in solvents such as methanol, ethanol, ethyl acetate will yield the desired product. In the case of the azide reduction, Staudinger conditions with Ph$_3$P may be effectively used. Many aniline precursors are commercially available for conversion to the aniline itself. N-acyl derivatives such as amides may be hydrolyzed under acidic or basic conditions to provide the aniline. In the case of carbamates, e.g., tert-butoxycarbonyl (BOC) protected anilines, the acyl group may be removed with HCl in solvents such as dioxane or through use of TFA in DCM. FMOC protected anilines require basic conditions, typically piperidine in DMF to remove the acyl moiety.

When R is an electron withdrawing group and/or when the aromatic system is a π-deficient heterocycle, a fluoro (or other halogen or triflate), ideally conjugated to said fluoro, may be displaced under SNAr conditions with ammonia itself or an ammonia equivalent or precursor.

Aryl or heteroaryl halides and triflates may also be reacted under transition metal catalysis with ammonia equivalents or precursors to allow the introduction of nitrogen functionality. One skilled in the art will appreciate the large number of catalysts, ligands, bases and solvents cited in the extensive literature and which are commercially available for this conversion.

SCHEME 10a:

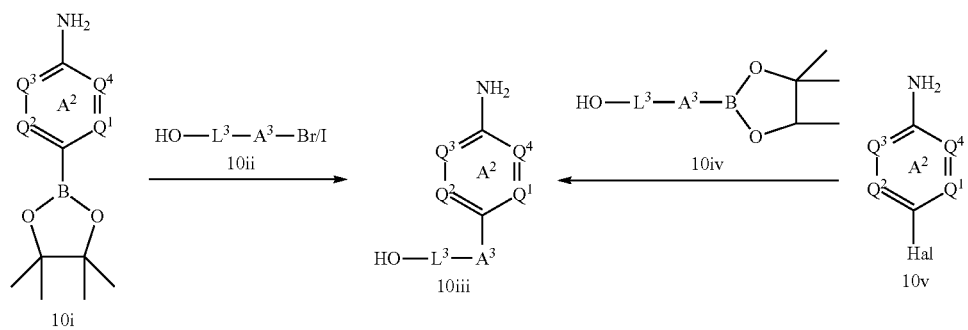

Intermediates of Formula 10iii can be prepared using a Suzuki coupling between an aryl or heteroaryl boronic acid of either formula 10i or 10iv and a corresponding aryl or heteroaryl halide of either formula 10ii or 10v.

Compounds of formula 10vii can be prepared from compounds of formula 10vi by Pd catalyzed installation of the boronic ester, involving the use an aryl halide, a Pd catalyst, KOAc, bis-pinacolatodiboron and an inert solvent such as dioxane or THF, typically heated.

SCHEME 10b:

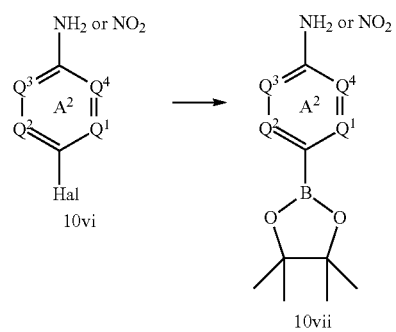

SCHEME 10c:

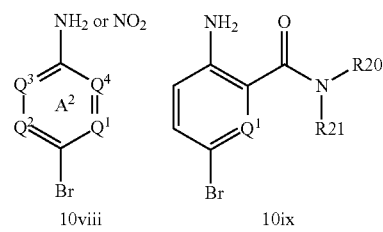

Intermediates of Formula 10ix are non-limiting examples of compounds of Formula 10viii.

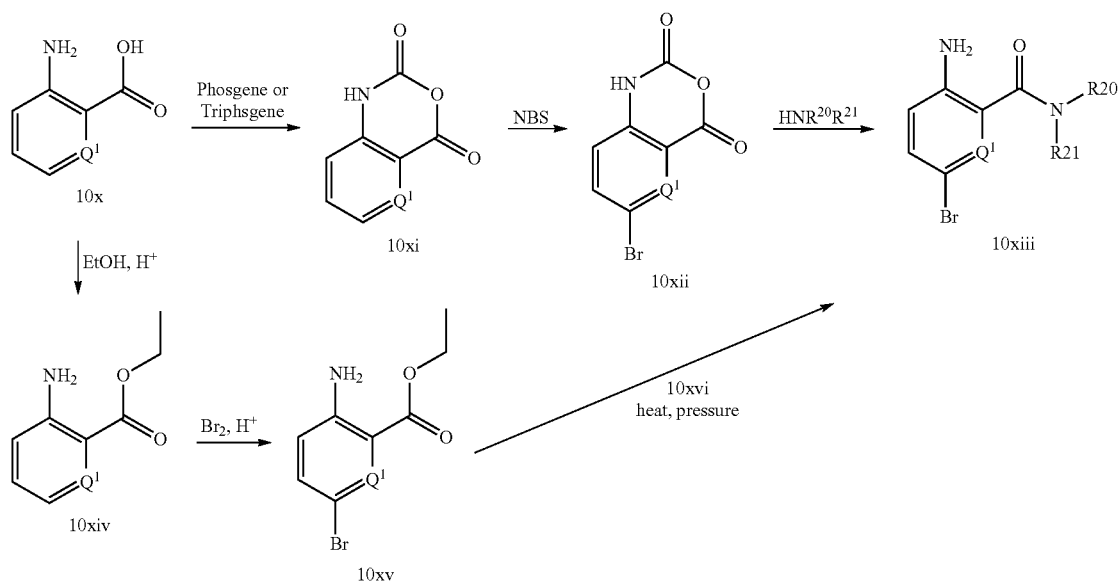

10viii (10ix) can be prepared starting with a commercially available intermediate of Formula 10x and by forming a benzoxazine-dione of Formula 10xi, performing a bromination with an agent such as NBS to give a compound of Formula 10xii. This can be transformed to the amide 10xiii by a reaction with the amine $HNR^{20}R^{21}$.

Alternatively, 10x can be esterified to form a compound of Formula 10xiv and brominated to form a compound of Formula 10xv. The amide 10xiii can be formed from 10xv by heating it, under pressure, with the amine $HNR^{20}R^{21}$ in a solvent mixture such as water/methanol.

Amines of Formula 10xvi are generally commercially available or readily prepared using techniques known in the art.

SCHEME 10d:

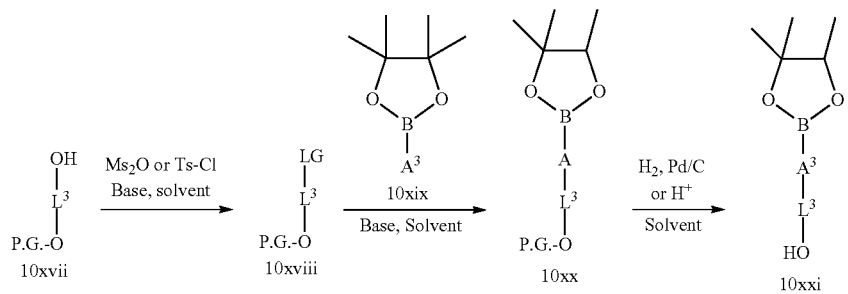

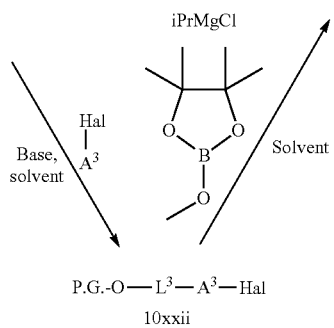

Intermediates of Formula 10ii and 10iv (Scheme 10A) can be prepared from compounds of Formula 10xvii or 10xviii which are either commercially available or readily prepared by one skilled in the art, as shown in the first step of Scheme 10d, above.

The P.G. in Formula 10xviii refers to a protecting group, either a benzyl or THP in most cases, similarly, the LG in Formula 10xviii refers to either a user installed leaving group such as mesylate or tosylate, or other leaving group, e.g., bromine or iodine from a commercial material. The LG can be displaced by a nucleophilic moiety on the heterocycle $A^3$ in the presence of a base and in an appropriate solvent to form compounds of the Formula 10xx. Bases can be $K_2CO3$ or $CS_2CO_3$, examples of an appropriate solvent is DMF or NMP. Heat may be required.

In cases where $A^3$ is not commercially available as its boronic ester, one can use a commercially available $A^3$ that has a halogen substituted on the appropriate position to prepare compounds of Formula 10xxii. Compounds 10xxii can be converted to compounds of Formula 10xx by a metal halogen exchange using a Grignard reagent (as shown) or other organometallic base such as a butyllithium species and quenching the resulting anion with a an appropriately substituted borate species.

Standard catalytic hydrogenation or an acid such as bit not limited to TsOH will remove the respective benzyl or THP protecting groups to provide 10xxi.

PREPARATIONS AND EXAMPLES

Unless otherwise noted, all materials/reagents were obtained from commercial suppliers and used without further purification. $^1$H NMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +(CH or $CH_3$), —($CH_2$), $C_{quart}$(C). Reactions were monitored by thin layer chromatography (TLC) on silica gel 60 $F_{254}$ (0.2 mm) precoated aluminum foil and visualized using UV light. Flash chromatography was performed with silica gel (400-230 mesh). Preparatory TLC was performed on Whatman LK6F Silica Gel 60 Å size 20×20 cm plates with a thickness of 1000 μm. Hydromatrix (=diatomaceous earth) was purchased from Varian.

Preparative HPLC purifications was performed on a Waters® Mass—Directed Purification System equipped with 2525 Binary Gradient Module, 2767 Sample Manager, a Column Fluidics Organizer (CFO), 2996 Photodiode Array Detector, a 515 pump for column regeneration, a reagent manager for the makeup flow, a 515 pump for at-column-dilution, ZQ™ single-quadrupole Mass Detector equipped with a Z-spray electrospray interface, controlled by MassLynx™ Version 4.1 with FractionLynx™ software. All purification work was completed using a parallel dual-column Luna C18(2) 21×150 mm, 5 μm LC/MS system and ARW (accelerated retention window). The mobile phases were water (0.1% TFA) and acetonitrile (0.1% TFA); all reagents used were of HPLC grade. The flow rate was 30 mL/min. After the columns, a 1:1000 LC packings flow splitter allowed transfer of a small portion of the eluent into the UV detector and, subsequently, a 10% portion into the ZQ MS. The electrospray source was set at 3.0 kV capillary voltage, 30 V cone voltage, 110° C. source temperature, 350° C. desolvation temperature, 600 L/h desolvation gas flow, and 60 L/h cone gas flow. For the analyzer, the multiplier was set at 550 for preparative tune method.

Analytical LC-MS data was collected on three instruments designated as follows: ZQ3, UPLC-TOF, and UPLC-SQD. ZQ3 is an Agilent 1100 HPLC equipped with an HP Series 1100 auto injector and Waters Micromass ZQ2000 for ionization. The system uses an XBridge C18, 3.5μ particle size, 4.6×50 mm column with a mobile phase of Acetonitrile (A) and 0.01% Formic Acid in HPLC water (B) and the flow rate is 1 mL/min. The methods used on this instrument are distinguished by either 4 or 5 minute run times the gradient profiles are as follows: 0.00 min 5% A, 2.00 min 90% A, 2.50 min 90% A, 3.00 min 5% A, 4.00 min 5% A for the polar_4 min method; 0.00 min 1% A, 3.00 min 90% A, 3.50 min 90% A, 4.00 min 1% A, 5.00 min 1% A for the vvpolar_5 min method; 0.00 min 5% A, 3.00 min 90% A, 3.50 min 90% A, 4.00 min 5% A, 5.00 min 5% A for the polar_5 min method; and 0.00 min 25% A, 3.00 min 99% A, 3.50 min 99% A, 4.00 min 25% A, 5.00 min 25% A for nonpolar_5 min method. The Waters Micromass ZQ2000 instrument utilizes electrospray ionization in positive (ES+) or negative (ES−) mode and may also utilize atmospheric pressure chemical ionization in positive (AP+) or negative (AP−) mode. UPLC-TOF is a Waters UPLC-LCT Premier system consisting of an ACQUITY UPLC equipped with an ACQUITY Sample Manager and LCT Premier XE MS for ionization. It uses an ACQUITY UPLC BEH® C18 2.1×50 mm 1.7 μm column with a mobile phase of Acetonitrile (A) and 0.01% formic acid in water (B). The flow rate is 0.6 mL/min, run time is 3 min, and the gradient profile is 0.00 min 5% A, 0.2 min 5% A, 1.50 min 90% A, 2 min 90% A, 2.2 min 5% A, 5 min 5% A for the polar_3 min method; Additionally, the flow rate is 0.7 mL/min, run time is 2 min, and the gradient profile is 0.00 min 10% A, 1 min 90% A, 1.50 min 90% A, 1.6 min 10% A, 2 min 10% A, for the polar_2 min method. The LCT Premier XE MS utilized electrospray ionization in positive (ES+) or negative (ES−), as well positive (AP+) or negative (AP−) in W mode. The Waters UPLC-SQD system consists of an ACQUITY sample manager attached to ACQUITY SQ MS and ACQUITY PDA detectors. It uses an ACQUITY UPLC BEH® C18 2.1×50 mm 1.7 μm column with a mobile phase of 0.1% formic acid in water (A) and 0.1% formic acid in acetonitrile (B). The flow rate is 1.0 mL/min, run time is 2 min, and the gradient profile is 0.00 min 85% A, 1.50 min 1% A, 1.80 min 1% A, 2.0 min 60% A for the analytical_2 min method; the flow rate is 0.8 mL/min, run time is 2 min, and the gradient profile is 0.00 min 60% A, 1.00 min 1% A, 1.85 min 1% A, 2.0 min 85% A for the nonpolar_2 min method; and the flow rate is 0.8 mL/min, run time is 2 min, and the gradient profile is 0.00 min 30% A, 1.00 min 1% A, 1.85 min 1% A, 2.0 min 30% A for the verynonpolar_2 min method. UV detection is at 254 nm, and the MS utilizes electrospray ionization in positive mode (ES+). All melting points were determined with a MeI-Temp II apparatus and are uncorrected. Elemental analyses were obtained by Atlantic Microlab, Inc., Norcross, Ga.

33

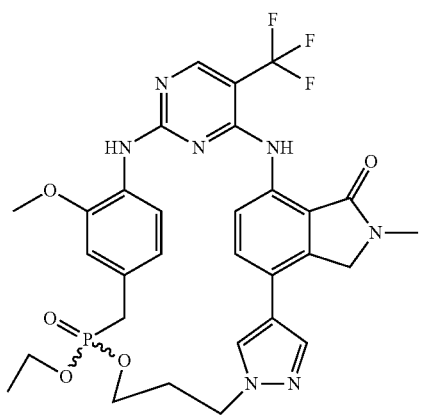

Example 1

(10S)-10-ethoxy-14-methoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide and (10S)-10-Ethoxy-14-methoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14, 17(31),18,20,23,29,32-undecaen-25-one 10-oxide A stirring suspension of sodium ethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate (Compound 1A, 50.0 mg, 0.07 mmol) and PYBOP (191.7 mg, 0.3684 mmol) in 1,2-dichloroethane (50 mL) and DMF (10 mL) was charged with DIPEA (0.07 mL, 0.4 mmol) and stirred for 3 d. The reaction mixture was concentrated in vacuo. The residue was dissolved in EtOAc and washed twice with brine. The combined organic layers were dried over anhydrous Na$_2$SO$_4$, filtered, concentrated in vacuo, and purified on a Teledyne ISCO CombiFlash® Rf system (eluting with 1-10% MeOH:CH$_2$Cl$_2$). The isolated material was purified a second time, using a SFC [Thar; Chromegabond Pyridyl Amide (5μ, 120 Å, 15 cm×20 mm); 0.2% isopropylamine in IPA, 40% isocratic gradient] to give the desired product as 6.5 mg as a light yellow solid. $^1$H NMR (400 MHz, DMSO-d$_6$) δ 9.66 (s, 1H), 8.82 (s, 1H), 8.52 (s, 1H), 8.38 (s, 1H), 7.74-7.87 (m, 2H), 7.65 (d, J=8.6 Hz, 1H), 7.24 (d, J=8.1 Hz, 1H), 7.05 (t, J=1.77 Hz, 1H), 6.74 (td, J=2, 7.9 Hz, 1H), 4.61 (d, J=2.3 Hz, 2H), 4.34 (t, J=5.7 Hz, 2H), 3.70-3.83 (m, 4H), 3.54-3.70 (m, 3H), 3.34-3.44 (m, 2H), 3.05 (s, 3H), 2.06-2.30 (m, 2H), 0.89 (t, J=7.1 Hz, 3H). MS (ESI): m/z 658.20 [M+H]$^+$. UPLC: t$_R$=1.32 min (UPLC-TOF: polar_3 min).

34

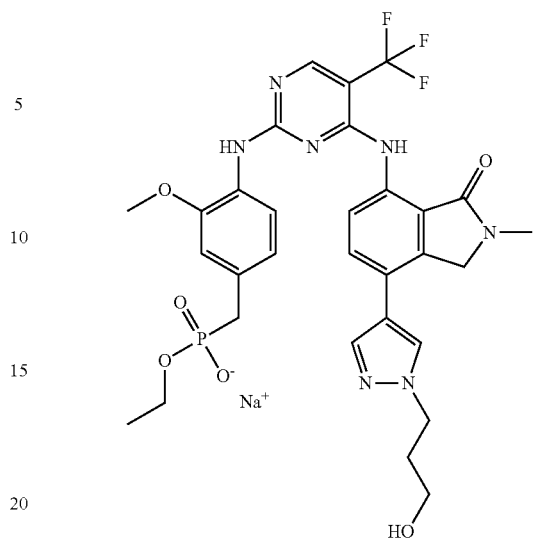

Compound 1A: Sodium ethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl) phosphonate A suspension of diethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate (Compound 1B, 255 mg, 0.36 mmol) and sodium iodide (606 mg, 4.04 mmol) in 2-butanone (5 mL) was subjected to 7 hours of microwave irradiation at 120° C. A solid precipitated, which filtered off, rinsed several times with ice cold acetone, and dried thoroughly to afford the desired compound as 277 mg as a light yellow solid. $^1$H NMR (400 MHz, DMSO-d$_6$) δ 10.64 (s, 1H), 9.26 (br s, 1H), 9.08 (s, 1H), 8.34 (s, 1H), 8.15 (br s, 2H), 7.71 (s, 1H), 7.13 (d, J=7.6 Hz, 1H), 7.08 (s, 1H), 6.89 (d, J=7.8 Hz, 1H), 6.45 (br s, 1H), 4.60 (s, 2H), 4.19 (t, J=6.1 Hz, 2H), 3.68 (s, 3H), 3.60-3.67 (m, 2H), 3.45 (q, J=5.9 Hz, 2H), 3.09 (s, 3H), 2.77 (d, J=19.7 Hz, 2H), 1.94 (quin, J=5.9 Hz, 2H), 0.94 (t, J=7.1 Hz, 3H). MS (ESI): m/z 676.30 [M+H]$^+$. UPLC: t$_R$=1.06 min (UPLC-SQD: analytical_2 min).

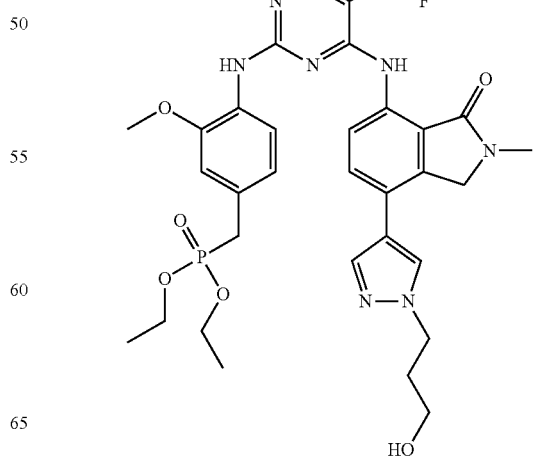

Compound 1B: Diethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate A solution of diethyl (4-{[4-chloro-5-(trifluoromethyl)pyrimidin-2-yl]amino}-3-methoxybenzyl)phosphonate (Compound 1E, 897 mg, 1.98 mmol) and 7-amino-4-[1-(3-hydroxypropyl)-1H-pyrazol-4-yl]-2-methyl-2,3-dihydro-1H-isoindol-1-one (Compound 1C, 634 mg, 2.21 mmol) in TFE (12 mL) was charged with TFA (654 mg, 5.74 mmol) and irradiated in a microwave reactor for 1 h at 105° C. The reaction mixture was transferred to a round bottom flask and concentrated in vacuo. The residue, dissolved in MeOH and cooled to 0° C., was charged with 7.0 M of $NH_3$ in MeOH (5 mL) and then warmed to rt over 2 h. The suspension was concentrated in vacuo and purified using a Teledyne ISCO CombiFlash® Rf system (eluting with 0-10% MeOH:$CH_2Cl_2$) to isolate the desired compound as 1.10 g of a white solid. $^1$H NMR (400 MHz, DMSO-$d_6$) δ 10.72 (s, 1H), 9.12 (s, 1H), 8.38 (s, 1H), 8.27 (s, 1H), 8.06-8.63 (m, 1H), 7.96 (s, 1H), 7.70 (d, J=8.8 Hz, 1H), 7.41 (d, J=7.1 Hz, 1H), 7.10 (br. t, J=2.0 Hz, 1H), 6.96 (brtd, J=2.3, 8.0 Hz, 1H), 4.53-4.67 (m, 3H), 4.21 (t, J=7.20 Hz, 2H), 4.00 (qd, J=7.1, 8.1 Hz, 4H), 3.74 (s, 3H), 3.43 (q, J=6.1 Hz, 2H), 3.36 (d, J=20 Hz, 2H), 3.11 (s, 3H), 1.97 (quin, J=6.6 Hz, 2H), 1.17 (t, J=7 Hz, 6H). MS (ESI): m/z 704.23 (100) [M+H]$^+$. HPLC: $t_R$=3.73 min (ZQ3: polar__5 min).

Compound 1C: 7-Amino-4-[1-(3-hydroxypropyl)-1H-pyrazol-4-yl]-2-methyl-2,3-dihydro-1H-isoindol-1-one A suspension of 4-[1-(3-hydroxypropyl)-1H-pyrazol-4-yl]-2-methyl-7-nitro-2,3-dihydro-1H-isoindol-1-one (Compound 1D, 920 mg, 2.91 mmol) and 10% Pd/C (50% $H_2O$) (1.41 g, 0.66 mmol) in EtOH (85 mL) was hydrogenated at rt for 2 h. The crude mixture was filtered through a pad of Celite, rinsed thoroughly with MeOH and EtOAc, concentrated in vacuo, and purified using a Teledyne ISCO CombiFlash® Rf system (eluting with 0-5% MeOH:$CH_2Cl_2$) to isolate the desired compound as 634 mg as a light brown solid. $^1$H NMR (400 MHz, DMSO-$d_6$) δ 7.93 (d, J=0.5 Hz, 1H), 7.71 (d, J=0.8 Hz, 1H), 7.43 (d, J=8.3 Hz, 1H), 6.61 (d, J=8.3 Hz, 1H), 6.05 (s, 2H), 4.59 (t, J=5.1 Hz, 1H), 4.45 (s, 2H), 4.17 (t, J=7 Hz, 2H), 3.41 (q, J=6.1 Hz, 2H), 3.03 (s, 3H), 1.94 (quin, J=6.1 Hz, 2H). MS (ESI): m/z 287.13 [M+H]$^+$. UPLC: $t_R$=0.89 min (UPLC-TOF: polar__3 min).

Compound 1D: 4-[1-(3-Hydroxypropyl)-1H-pyrazol-4-yl]-2-methyl-7-nitro-2,3-dihydro-1H-isoindol-1-one A suspension of 2-methyl-7-nitro-4-(4,4,5,5-tetramethyl-1,3,2-dioxaborolan-2-yl)-2,3-dihydro-1H-isoindol-1-one (Compound 1I, 1.825 g, 5.736 mmol), 3-(4-bromo-1H-pyrazol-1-yl)propan-1-ol (1.45 g, 7.07 mmol), [1,1'-bis(diphenylphosphino)ferrocene]dichloropalladium(II), complex with dichloromethane (1:1) (510 mg, 0.62 mmol), and potassium carbonate (2.4 g, 17.3 mmol) in dioxane (20 mL) and $H_2O$ (5 mL) was irradiated in a microwave reactor for 45 min at 100° C. The reaction mixture was poured into water and extracted with $CH_2Cl_2$ three times. The combined organic layers were washed with brine, dried over anhydrous $Na_2SO_4$, filtered, concentrated in vacuo, and purified using a Teledyne ISCO CombiFlash® Rf system (eluting with 0-15% MeOH:$CH_2Cl_2$) to isolate the desired compound as 920 mg as a yellow solid. $^1$H NMR (400 MHz, DMSO-$d_6$) δ 8.35 (s, 1H), 8.05 (s, 1H), 7.99 (d, J=8.3 Hz, 1H), 7.88 (d, J=8.3 Hz, 1H), 4.72 (s, 2H), 4.63 (t, J=5.1 Hz, 1H), 4.25 (t, J=7.1 Hz, 2H), 3.43 (q, J=6.1 Hz, 2H), 3.11 (s, 3H), 1.98 (quin, J=6.6 Hz, 2H). HRMS (ESI): m/z 317.11 [M+H]$^+$. UPLC: $t_R$=0.91 min (UPLC-TOF: polar__3 min).

Compound 1E: Diethyl (4-{[4-chloro-5-(trifluoromethyl)pyrimidin-2-yl]amino}-3-methoxybenzyl)phosphonate 1.0 M Zinc dichloride in ether (4.07 mL, 4.07 mmol) was added to a solution of the commercially available 2,4-dichloro-5-trifluoromethylpyrimidine (0.8 g, 3.70 mmol) in 1,2-dichloroethane (6.7 mL) and t-BuOH (6.7 mL). After 30 minutes diethyl (4-amino-3-methoxybenzyl)phosphonate (Compound 1F, 1.01 g, 3.70 mmol) was added followed by triethylamine (0.567 mL, 4.07 mmol) while keeping the temperature at ~25° C. The reaction mixture was allowed to stir at rt overnight before quenching with sat. aq. $NaHCO_3$ (10 mL). The resulting mixture was extracted with EtOAc (15 mL) and the organic layer was washed with brine (10 mL), dried over anhydrous $NaSO_4$, filtered, and concentrated under reduced pressure to afford a yellow oil. This crude material was initially purified using a Teledyne ISCO CombiFlash® Rf system eluting with 0-5% MeOH in DCM followed by preparative HPLC (MDP) to afford 1.09 g of the title compound (70%). $^1$H NMR ($CD_3OD$, 400 MHz): δ 1.28 (t, J=7.1 Hz, 6H), 3.23-3.29 (m, 2H), 3.90-3.95 (m, 3H), 4.01-4.13 (m, 4H), 6.90-6.96 (m, 1H), 7.03 (m, J=2.0 Hz, 1H), 8.02 (d, J=8.3 Hz, 1H), 8.62 (s, 1H).

Compound 1F: Diethyl (4-amino-3-methoxybenzyl)phosphonate

A solution of diethyl (3-methoxy-4-nitrobenzyl)phosphonate (Compound 1G, 1.07 g, 3.54 mmol) in ethanol (10.0 mL) was charged with palladium 10% wt on activated carbon (0.38 g). The reaction mixture was evacuated and purged with hydrogen gas (3×) and allowed to stir under hydrogen for 16 h. The reaction mixture was filtered through a pad of celite. The filtrate was concentrated under reduced pressure to afford the title compound as 0.78 g of an orange oil (80%). This material was used in successive reactions without further purification. MS (ESI): m/z 274.01 [M+H]$^+$.

Compound 1G: Diethyl (3-methoxy-4-nitrobenzyl)phosphonate

A mixture of 4-(chloromethyl)-2-methoxy-1-nitrobenzene (Compound 1H, 1.1 g, 5.46 mmol) and triethyl phosphite (1.09 g, 6.55 mmol) were heated at 100° C. for 16 h in a sealed tube. The reaction mixture was concentrated under reduced pressure to yield a black oil. The crude material was purified by silica gel chromatography on a Teledyne ISCO CombiFlash® Rf system using DCM/MeOH (100:0→95:5) as eluent to afford the title compound as 1.08 g of an orange oil (65%). MS (ESI): m/z 304.0902 [M+H]$^+$.

Compound 1H: 4-(Chloromethyl)-2-methoxy-1-nitrobenzene

A mixture of (3-methoxy-4-nitrophenyl)methanol (0.5 g, 2.73 mmol) and thionyl chloride (0.3 mL, 4.09 mmol) was heated at reflux for 12 h. The reaction mixture was concentrated under reduced pressure to afford the title compound as a tan solid, 0.55 g (100% yield). This material was used in successive reactions without further purification. $^1$H NMR ($CD_3OD$, 400 MHz): δ 4.00 (s, 3H), 4.60 (s, 2H), 7.05 (dd, J=8.3, 1.8 Hz, 1H), 7.14 (d, J=1.5 Hz, 1H), 7.86 (d, J=8.3 Hz, 1H). MS (ESI): m/z 202.03 [M+H]$^+$ (UPLC-TOF: polar__3 min).

Compound 1I: 2-Methyl-7-nitro-4-(4,4,5,5-tetramethyl-1,3,2-dioxaborolan-2-yl)-2,3-dihydro-1H-isoindol-1-one A mixture of Pd$_2$(dba)$_3$ (2.02 g, 2.21 mmol) and tricyclohexylphosphine (2.48 g, 8.85 mmol) in nitrogen degassed dioxane (375 mL) was stirred for 30 minutes and subsequently treated with 4-bromo-2-methyl-7-nitro-2,3-dihydro-isoindol-1-one (Compound 1L, 20.0 g, 73.8 mmol), bis(pinacolato)diboron (24.4 g, 96 mmol) and KOAc (11.58 g, 118.1 mmol) and heated to reflux for 6 h. The cooled reaction mixture was filtered and evaporated to dryness. The residue was triturated with diisopropyl ether (100 mL) and filtered to give 2-methyl-7-nitro-4-(4,4,5,5-tetramethyl-[1,3,2]dioxaborolan-2-yl)-2,3-dihydro-isoindol-1-one (3) as a yellow solid (16.0 g, 68%). $^1$H NMR (CDCl$_3$, 500 MHz) δ 1.34 (s, 12H), 3.24 (s, 3H), 4.58 (s, 2H), 7.68 (d, J=7.5 Hz, 1H), 8.06 (d, J=7.5 Hz, 1H).

Compound 1L: 4-Bromo-2-methyl-7-nitro-2,3-dihydro-1H-isoindol-1-one

An 8M solution of methylamine in ethanol (10 mL, 80 mmol) was added to a solution of methyl 3-Bromo-2-(bromomethyl)benzoate in THF (30 mL) and allowed to stir for 2 h. The reaction mixture was concentrated to dryness and the residue was triturated with water. The solids produced were collected by filtration and dried to afford 4-bromo-2-methyl-2,3-dihydroisoindol-1-one which used immediately in the next step. To a cold suspension of 4-bromo-2-methyl-2,3-dihydroisoindol-1-one (60 g, 265 mmol) in concentrated sulfuric acid (60 mL) was added pre-cooled mixture of conc. nitric acid (12.5 mL, 265 mmol) and conc. sulfuric acid (60 mL) over 20 min. The reaction mixture was stirred for 30 min at 0° C. and 2 h at room temperature. The reaction mixture was poured into an ice-water mixture (300 mL) and the precipitate that formed was collected by filtration and washed with water (3×100 mL). The solids were suspended in isopropanol (200 mL) and heated on a steam bath for 10 minutes. The mixture was cooled and the solid was collected by filtration and air dried to afford 53 g of the title compound (74%). $^1$H NMR (CDCl$_3$, 300 MHz) δ 3.22 (s, 3H), 4.36 (s, 2H), 7.67 (d, J=8.4 Hz, 1H), 7.78 (d, J=8.4 Hz, 1H).

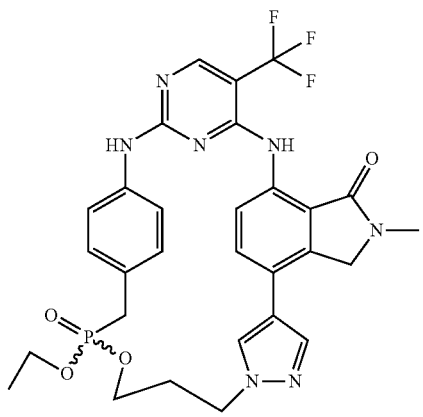

Example 2

(10S)-10-Ethoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide and (10R)-10-Ethoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide This material was prepared analogously to Example 1 using sodium ethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate (Compound 2A). $^1$H NMR (400 MHz, DMSO-d$_6$) δ 9.75 (s, 1H), 9.27 (s, 1H), 8.48 (s, 1H), 8.40 (d, J=0.50 Hz, 1H), 7.88 (s, 1H), 7.83 (d, J=8.3 Hz, 1H), 7.67 (d, J=8.3 Hz, 1H), 7.24 (d, J=8.1 Hz, 2H), 6.96 (dd, J=2.3, 8.6 Hz, 2H), 4.63 (s, 2H), 4.38 (t, J=5.8 Hz, 2H), 3.80-3.93 (m, 2H), 3.68 (tt, J=5.4, 10.4 Hz, 1H), 3.44-3.56 (m, 1H), 3.11-3.27 (m, 2H), 3.03 (s, 3H), 2.05-2.24 (m, 2H), 1.07 (t, J=7.1 Hz, 3H). MS (ESI): m/z 628.17 [M+H]$^+$. HPLC: t$_R$=1.30 min (ZQ3: polar_5 min).

Compound 2A: Sodium ethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate Prepared analogously to Compound 1A using diethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate (Compound 2B). $^1$H NMR (400 MHz, DMSO-d$_6$) δ 10.66 (br s, 1H), 9.74 (s, 1H), 8.46-9.05 (m, 2H), 8.41 (s, 1H), 8.00 (br s, 1H), 7.82 (s, 1H), 7.10-7.53 (m, 4H), 4.62 (s, 2H), 4.20 (t, J=6.4 Hz, 2H), 3.70 (quin, J=7 Hz, 2H), 3.45 (t, J=6.1 Hz, 2H), 3.11 (s, 3H), 2.84 (d, J=20.2 Hz, 2H), 1.96 (quin, J=6.3 Hz, 2H), 1.01 (t, J=6.7 Hz, 3H) [OH proton obscured]. HRMS (ESI): m/z 646.14 [M+H]$^+$. UPLC: t$_R$=1.16 min (UPLC-TOF: polar_3 min).

Compound 2B: Diethyl (4-{[4-({7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}benzyl)phosphonate This compound was prepared analogously to Compound 1B using diethyl (4-{[4-chloro-5-(trifluoromethyl)pyrimidin-2-yl]amino}benzyl)phosphonate (Compound 2C) and 7-amino-4-[1-(3-hydroxypropyl)-1H-pyrazol-4-yl]-2-methyl-2,3-dihydro-1H-isoindol-1-one (Compound 1C) $^1$H NMR (400 MHz, CD$_3$OD) δ 8.69 (br s, 1H), 8.32 (s, 1H), 8.04 (s, 1H), 7.89 (s, 1H), 7.68 (d, J=8.59 Hz, 1H), 7.57 (d, J=7.8 Hz, 2H), 7.34 (dd, J=2.4, 8.5 Hz, 2H), 4.55 (s, 2H), 4.31 (t, J=6.8 Hz, 2H), 4.01-4.12 (m, 4H), 3.57 (t, J=6.1 Hz, 2H), 3.29 (d, J=20.7 Hz, 2H), 3.17 (s, 3H), 2.10 (quin, J=6.5 Hz, 2H), 1.26 (t, J=7.1 Hz, 6H). MS (ES+): m/z 674.21 [M+H]$^+$. UPLC: t$_R$=1.33 min (UPLC-TOF: polar_3 min).

Compound 2C: diethyl (4-{[4-chloro-5-(trifluoromethyl)pyrimidin-2-yl]amino}benzyl) phosphonate Prepared analogously to Compound 1E replacing Compound 1F with diethyl-4-aminobenzyl phosphonate. $^1$H NMR (400 MHz, CD$_3$OD) δ 1.22-1.32 (m, 6H), 3.17-3.28 (m, 2H), 3.98-4.10 (m, 4H), 7.30 (dd, J=8.7, 2.7 Hz, 2H), 7.65 (d, J=7.8 Hz, 2H), 8.63 (s, 1H).

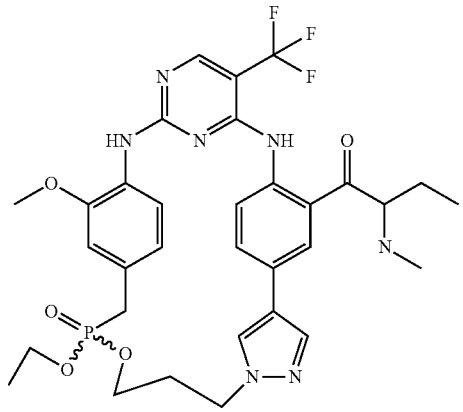

Example 3

(10S)-10-Ethoxy-N,N-diethyl-14-methoxy-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-N,N-diethyl-14-methoxy-20-(trifluoromethyl)-9-oxa-4,5,16,18,22,28-hexaaza-10-phosphapentacyclo[21.2.2.2$^{12,15}$.1$^{2,5}$.1$^{17,21}$] hentriaconta-1(25),2(31),3,12,14,17(28),18,20,23,26, 29-undecaene-24-carboxamide 10-oxide To a stirring suspension of ethyl hydrogen (4-{[4-({2-(diethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate (Compound 3A, 167.1 mg, 0.237 mmol) and (benzotriazol-1-yloxy)tripyrrolidino-phosphonium hexafluorophosphate (739.4 mg, 1.42 mmol) in 1,2-dichloroethane (200 mL) and DMF (30 mL), DIPEA (0.2 mL, 1 mmol) were added and the reaction was stirred at rt over 24 hrs. The reaction mixture was concentrated in vacuo and the residue was dissolved in EtOAc, washed with a semi-saturated sodium bicarbonate solution (1×) and then with brine (2×). The aqueous layers were back-extracted with EtOAc and the combined organic layers were dried over sodium sulfate, filtered and concentrated in vacuo to a solid. The crude mixture was purified using a Teledyne ISCO Combiflash® Rf system [0→10% MeOH in DCM] to yield the desired product (69.7 mg, 43%). $^1$H NMR (400 MHz, CD$_3$OD) δ 8.24 (s, 1H), 8.23 (d, J=1 Hz, 1H), 8.02 (d, J=1 Hz, 1H), 7.81 (dd, J=2.2, 8.2 Hz, 1H), 7.58 (d, J=1.8 Hz, 1H), 7.44 (d, J=8.3 Hz, 1H), 7.32 (d, J=8.3 Hz, 1H), 6.77 (t, J=1.9 Hz, 1H), 6.18 (td, J=2.3, 8.3 Hz, 1H), 4.44 (t, J=5.9 Hz, 2H), 3.96-4.07 (m, 2H), 3.76-3.87 (m, 5H), 3.36-3.46 (m, 2H), 2.98-3.13 (m, 4H), 2.29 (quin, J=5.8 Hz, 2H), 1.24 (t, J=7.1 Hz, 3H), 1.04 (t, J=7.1 Hz, 3H), 0.72 (t, J=7.1 Hz, 3H). MS (ESI): m/z 688.81 [M+H]$^+$. UPLC: t$_R$=1.14 min (UPLC-SQD: analytical_2 min).

Compound 3A: Ethyl hydrogen (4-{[4-({2-(diethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate A mixture of diethyl (4-{[4-({2-(diethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl) phosphonate (Compound 3B, 228 mg, 311 μmol), sodium iodide (158 mg, 1.06 mmol) in pyridine (3.52 ml) was stirred at reflux for 16 hrs then concentrated in vacuo to a solid which was purified by a Teledyne ISCO Combiflash® Rf system [elution gradient: 5%→95% MeOH in water over 25 CV using a C-18 RP column] to yield the desired product (167 mg, 76%). $^1$H NMR (400 MHz, CD$_3$OD) δ 8.25 (s, 1H), 8.18 (s, 1H), 7.93 (s, 1H), 7.74 (d, J=1.01 Hz, 2H), 7.69 (d, J=7.07 Hz, 1H), 7.55 (s, 1H), 6.99 (br. s., 1H), 6.52 (br. s., 1H), 4.32 (t, J=6.69 Hz, 2H), 3.88 (s, 3H), 3.71-3.80 (m, 2H), 3.59 (t, J=6.06 Hz, 2H), 3.47 (d, J=6.32 Hz, 2H), 3.14-3.23 (m, 2H), 2.85 (d, J=19.96 Hz, 2H), 2.07-2.16 (m, 2H), 1.11 (t, J=6.82 Hz, 6H), 0.90 (br. s., 3H). MS (ESI): m/z 706.80 [M+H]$^+$. UPLC: t$_R$=1.07 min (UPLC-SQD: analytical_2 min).

Compound 3B: Diethyl (4-{[4-({2-(diethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate Prepared analogously to Compound 1B using diethyl (4-{[4-chloro-5-(trifluoromethyl)pyrimidin-2-yl]amino}-3-methoxybenzyl)phosphonate (Compound 1 E, 282.1 mg, 0.62 mmol) and 2-amino-N,N-diethyl-5-[1-(3-hydroxypropyl)-1H-pyrazol-4-yl]benzamide (Compound 3C, 196.7 mg, 0.62 mmol) to afford 228 mg of the title compound (50%). $^1$H NMR (400 MHz, CD$_3$OD) δ 8.33 (br. s., 1H), 8.18 (s, 1H), 7.97 (s, 1H), 7.77 (dd, J=2.02, 8.34 Hz, 1H), 7.59-7.67 (m, 2H), 7.57 (d, J=8.08 Hz, 1H), 6.97 (br. s., 1H), 6.57 (br. s., 1H), 4.32 (t, J=6.95 Hz, 2H), 3.99 (quin, J=7.14 Hz, 4H), 3.89 (s, 3H), 3.59 (t, J=6.06 Hz, 2H), 3.43-3.52 (m, 2H), 3.08-3.22 (m, 4H), 2.11 (quin, J=6.57 Hz, 2H), 1.22 (t, J=7.07 Hz, 6H), 1.11 (t, J=6.95 Hz, 3H), 0.97 (br. s., 3H). MS (ESI): m/z 734.85 [M+H]$^+$. UPLC: t$_R$=1.22 min (UPLC-SQD: analytical_2 min).

Compound 3C: 2-Amino-N,N-diethyl-5-[1-(3-hydroxypropyl)-1H-pyrazol-4-yl]benzamide A suspension of 2-amino-5-bromo-N,N-diethylbenzamide (Compound 3D, 326 mg, 1.20 mmol), 3-[4-(4,4,5,5-tetramethyl-1,3,2-dioxaborolan-2-yl)-1H-pyrazol-1-yl]propan-1-ol (Compound 3E, 0.33 g, 1.32 mmol), [1,1'-bis(diphenylphosphino)ferrocene]dichloropalladium(II) complex with dichloromethane (1:1) (106.8 mg, 0.13 mmol) and potassium carbonate (0.50 g, 3.64 mmol) in 1,4-dioxane (4 mL, 50 mmol) to H$_2$O (1 mL, 60 mmol) was evacuated and charged with argon (3×). The sample was irradiated in a microwave reactor for 30 min at 100° C. The crude product was concentrated in vacuo to a solid and purified using a Teledyne ISCO Combiflash® Rf system [0→5% MeOH in DCM] to yield the desired product (197 mg, 52%). $^1$H NMR (400 MHz, CD$_3$OD) δ 7.86 (d, J=0.51 Hz, 1H), 7.71 (d, J=0.76 Hz, 1H), 7.36 (dd, J=2.02, 8.34 Hz, 1H), 7.22 (d, J=2.02 Hz, 1H), 6.81 (d, J=8.34 Hz, 1H), 4.24 (t, J=6.82 Hz, 2H), 3.33-3.60 (m, 6H), 2.05 (quin, J=6.57 Hz, 2H), 1.04-1.35 (m, 6H). MS (ESI): m/z 317.59 [M+H]$^+$. UPLC: t$_R$=0.74 min (UPLC-SQD: analytical_2 min).

Compound 3D: 2-amino-5-bromo-N,N-diethylbenzamide

A solution of 5-Bromoisatoic anhydride (2.00 g, 8.26 mmol) in THF (53.62 mL, 661.1 mmol) was treated with diethylamine (1.28 mL, 12.40 mmol) and allowed to stir overnight at rt. The mixture was concentrated in vacuo and purified using a Teledyne ISCO Combiflash® Rf system [0→4% MeOH in DCM] to afford 326 mg of the title compound (15%). $^1$H NMR (400 MHz, CD$_3$OD) δ 7.24 (dd, J=2.27, 8.84 Hz, 1H), 7.13 (d, J=2.27 Hz, 1H), 6.71 (d, J=8.59 Hz, 1H), 3.43 (br. s., 4H), 1.18 (br. s., 6H). MS (ESI): m/z 271.41 [M+H]$^+$. UPLC: t$_R$=1.09 min (UPLC-SQD: analytical_2 min).

Compound 3E: 3-[4-(4,4,5,5-Tetramethyl-1,3,2-dioxaborolan-2-yl)-1H-pyrazol-1-yl]propan-1-ol A deoxygenated mixture of 1-[3-(benzyloxy)propyl]-4-(4,4,5,5-tetramethyl-1,3,2-dioxaborolan-2-yl)-1H-pyrazole (Compound 3F, 505 mg, 1.48 mmol) and 10% Pd—C (100 mg) in EtOH (15 mL) was stirred under an atmosphere of hydrogen overnight. The reaction mixture was filtered through a pad of celite and evaporated under reduced pressure to give the desired product as 370 mg of a light-yellow oil (99%). $^1$H NMR (CDCl$_3$, 400 MHz): δ=7.80 (s, 1H), 7.71 (s, 1H), 4.32 (t, J=6.3 Hz, 2H), 3.63 (t, J=5.8 Hz, 2H), 2.06 (m, 3H), 1.33 (s, 12H).

Compound 3F: 1-[3-(Benzyloxy)propyl]-4-(4,4,5,5-tetramethyl-1,3,2-dioxaborolan-2-yl)-1H-pyrazole A mixture of 4-(4,4,5,5-tetramethyl[1,3,2]dioxaborolan-2-yl)-1H-pyrazole (5.0 g, 26 mmol), potassium carbonate (4.27 g, 30.9 mmol) and 1-bromo-3-benzyloxypropane (6.20 g, 27.0 mmol) in DMF (20 mL) was stirred at 80° C. overnight, quenched with water (20 mL) and extracted with EtOAc (100 mL). The organic layer was washed with water (2×30 mL), brine (30 mL), dried over anhydrous sodium sulfate, filtered, and concentrated under reduced pressure. The residue was purified by silica gel chromatography (ISCO system: EtOAc/Heptane=30-70%) to afford 7.67 g of the title compound as a light-yellow oil (87%). $^1$H NMR (CDCl$_3$, 400 MHz): δ=7.80 (s, 1H), 7.66 (s, 1H), 7.30-7.36 (m, 5H), 4.48 (s, 2H), 4.28 (t, J=6.8 Hz, 2H), 3.43 (t, J=5.8 Hz, 2H), 2.17 (m, 2H), 1.33 (s, 12H). MS (ES+): m/z=343.36 [MH$^+$]. HPLC: t$_R$=4.20 min (ZQ3: polar_5 min).

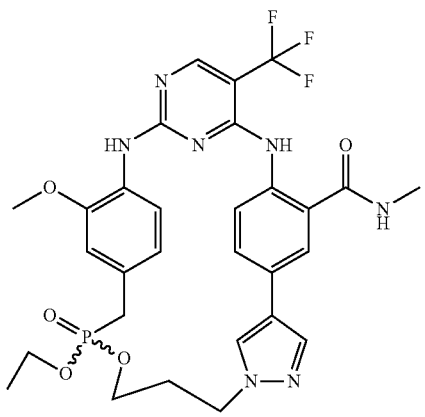

Example 4

(10S)-10-ethoxy-14-methoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-14-methoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide This material was prepared analogously to Example 3 using ethyl hydrogen (4-{[4-({4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl) phosphonate (Compound 4A, 173 mg, 260 mmol) to afford 70 mg of the desired product (41%). $^1$H NMR (400 MHz, CD$_3$OD) δ 8.26 (s, 2H), 8.02 (s, 1H), 7.90 (d, J=2.02 Hz, 1H), 7.77 (dd, J=2.15, 8.46 Hz, 1H), 7.57 (dd, J=6.57, 8.34 Hz, 2H), 6.81 (t, J=1.77 Hz, 1H), 6.41 (td, J=2.27, 8.34 Hz, 1H), 4.45 (t, J=5.94 Hz, 2H), 3.94-4.06 (m, 2H), 3.86 (s, 3H), 3.62-3.80 (m, 2H), 3.11-3.28 (m, 2H), 2.84 (s, 3H), 2.19-2.31 (m, 2H), 1.19 (t, J=7.07 Hz, 3H). MS (ESI): m/z 646.69 [M+H]$^+$. UPLC: t$_R$=1.10 min (UPLC-TOF: polar_3 min).

Compound 4A: Ethyl hydrogen (4-{[4-({4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate Prepared analogously to Compound 3A with diethyl (4-{[4-({4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate (234 mg, 338 μmol) to yield 156 mg of the desired product (70%). $^1$H NMR (400 MHz, CD$_3$OD) δ 8.30-8.36 (m, 1H), 8.26 (s, 1H), 8.14 (s, 1H), 7.92 (s, 1H), 7.86 (d, J=8.08 Hz, 1H), 7.83 (d, J=2.02 Hz, 1H), 7.63 (dd, J=2.02, 8.59 Hz, 1H), 7.04 (s, 1H), 6.80 (s, 1H), 4.30 (t, J=6.82 Hz, 2H), 3.88 (s, 3H), 3.84 (t, J=6.95 Hz, 2H), 3.58 (t, J=6.19 Hz, 2H), 2.92-3.02 (d, J=21.9 Hz, 2H), 2.91 (s, 3H), 2.10 (t, J=6.44 Hz, 2H), 1.15 (t, J=6.95 Hz, 3H). MS (ESI): m/z 664.21 [M+H]$^+$. UPLC: t$_R$=1.13 min (UPLC-TOF: polar_3 min).

Compound 4B: Diethyl (4-{[4-({4-[1-(3-hydroxypropyl)-1H-pyrazol-4-yl]-2-(methylcarbamoyl)-phenyl}amino)-5-(trifluoromethyl)pyrimidin-2-yl]amino}-3-methoxybenzyl)-phosphonate Prepared analogously to compound 1B replacing Compound 1C with 2-amino-5-[1-(3-hydroxypropyl)-1H-pyrazol-4-yl]-N-methylbenzamide (Compound 4C, 330 mg, 1.2 mmol) to give the title compound as a light-yellow solid. MS (ESI): m/z=692.59 [M+H]$^+$. UPLC: t$_R$=1.11 min (UPLC-SQD: analytical_2 min).

Compound 4C: 2-Amino-5-[1-(3-hydroxypropyl)-1H-pyrazol-4-yl]-N-methylbenzamide

Prepared analogously to Compound 3C replacing Compound 3D with 2-amino-5-bromo-N-methyl-benzamide (920 mg, 4.0 mmol) to give the title compound as 0.35 g of a white solid (32%, over two steps). $^1$H NMR (CDCl$_3$+CD$_3$OD, 400 MHz): δ=7.65 (s, 1H), 7.64 (s, 1H), 7.47 (d, J=2.0 Hz, 1H), 7.28 (dd, J=8.4, 2.0 Hz, 1H), 6.69 (d, J=8.4 Hz, 1H), 4.21 (t, J=6.6 Hz, 2H), 3.53 (t, J=5.6 Hz, 2H), 2.90 (s, 3H), 2.00 (m, 2H). MS (ESI): m/z=275.29 [M+H]⁺. HPLC: $t_R$=2.50 min (ZQ3: polar_5 min).

Compound 4D: 2-Amino-5-bromo-N-methyl-benzamide

To a solution of 5-bromoisatoic anhydride (4.84 g, 20.0 mmol) in THF (20 mL) was added 2M MeNH$_2$/THF (15 mL, 30 mmol). The resulting mixture was stirred at rt overnight. The solvent was evaporated under reduced pressure and the crude material was used in next step without further purification. MS (ESI): m/z=229.03/231.06 [M+H]⁺. HPLC: $t_R$=3.14 min (ZQ3: polar_5 min).

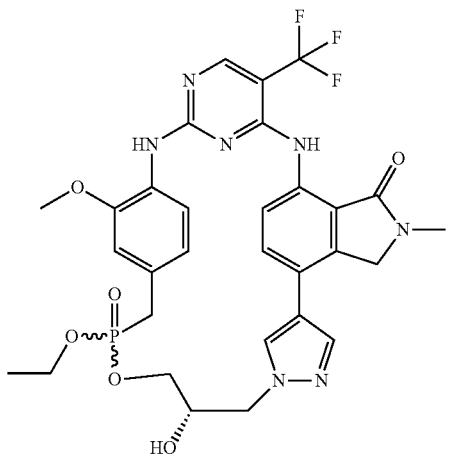

Example 5

(7S,10S)-10-Ethoxy-7-hydroxy-14-methoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide and (7S,10R)-10-Ethoxy-7-hydroxy-14-methoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide This material was prepared analogously to Example 3 using ethyl hydrogen [4-({4-[(7-{1-[(2S)-2,3-dihydroxypropyl]-1H-pyrazol-4-yl}-2-methyl-3-oxo-2,3-dihydro-1H-isoindol-4-yl)amino]-5-(trifluoromethyl)pyrimidin-2-yl}amino)-3-methoxybenzyl]phosphonate (Compound 5A, 180 mg, 260 mmol) to yield 2.8 mg of the desired product (1.6%). ¹H NMR (400 MHz, CD$_3$OD) δ 8.30 (br. s., 1H), 8.27 (s, 1H), 7.90 (s, 1H), 7.77-7.81 (m, 1H), 7.70-7.75 (m, 1H), 7.41 (d, J=8.3 Hz, 1H), 6.91 (t, J=1.9 Hz, 1H), 6.50 (td, J=2.3, 8.3 Hz, 1H), 4.64-4.71 (m, 1H), 4.57-4.62 (m, 1H), 4.37-4.55 (m, 2H), 4.26 (d, J=7.1 Hz, 1H), 3.83-3.94 (m, 5H), 3.72 (ddd, J=7.1, 8.3, 10.1 Hz, 1H), 3.37-3.64 (m, 2H), 3.09-3.22 (m, 4H), 0.94 (t, J=7.1 Hz, 3H). MS (ESI): m/z 674.63 [M+H]⁺. UPLC: $t_R$=1.05 min (UPLC-TOF: polar_3 min).

Compound 5A: Ethyl hydrogen [4-({4-[(7-{1-[(2S)-2,3-dihydroxypropyl]-1H-pyrazol-4-yl}-2-methyl-3-oxo-2,3-dihydro-1H-isoindol-4-yl)amino]-5-(trifluoromethyl)pyrimidin-2-yl}amino)-3-methoxybenzyl] phosphonate This material was prepared analogously to Compound 3A using diethyl[4-({4-[(7-{1-[(2S)-2,3-dihydroxypropyl]-1H-pyrazol-4-yl}-2-methyl-3-oxo-2,3-dihydro-1H-isoindol-4-yl)amino]-5-(trifluoromethyl) pyrimidin-2-yl}amino)-3-methoxybenzyl]phosphonate (Compound 5B, 254 mg, 353 μmol) to yield 184 mg of the desired product (75%). ¹H NMR (400 MHz, CD$_3$OD) δ 8.42 (br. s., 1H), 8.20 (br. s., 1H), 8.08-8.16 (m, 1H), 8.06 (br. s., 1H), 7.80 (s, 1H), 7.57 (d, J=8.6 Hz, 1H), 7.09 (br. s., 1H), 6.95 (d, J=7.8 Hz, 1H), 4.37 (dd, J=4.17, 14 Hz, 3H), 4.16-4.26 (m, 1H), 4.07 (dd, J=4.6, 7.3 Hz, 1H), 3.88-3.97 (m, 2H), 3.87 (s, 3H), 3.58 (d, J=5.3 Hz, 2H), 3.10 (br. s., 3H), 3.01-3.08 (m, 2H), 1.21 (t, J=7 Hz, 3H). MS (ESI): m/z 692.21 [M+H]⁺. UPLC: $t_R$=1.10 min (UPLC-TOF: polar_3 min).

Compound 5B: Diethyl[4-({4-[(7-{1-[(2S)-2,3-dihydroxypropyl]-1H-pyrazol-4-yl}-2-methyl-3-oxo-2,3-dihydro-1H-isoindol-4-yl)amino]-5-(trifluoromethyl) pyrimidin-2-yl}amino)-3-methoxy benzyl] phosphonate Prepared analogously to Compound 1B replacing Compound 1C with 7-amino-4-(1-{[(4S)-2,2-dimethyl-1,3-dioxolan-4-yl]methyl}-1H-pyrazol-4-yl)-2-methyl-2,3-dihydro-1H-isoindol-1-one (Compound 5C, 337 mg, 742 μmol) to afford 254 mg of the desired product (48%). ¹H NMR (400 MHz, CD$_3$OD) δ 8.49 (br. s., 1H), 8.34 (s, 1H), 8.09 (s, 1H), 7.96 (s, 1H), 7.67-7.77 (m, 2H), 7.11 (s, 1H), 7.00 (d, J=8.1 Hz, 1H), 4.61 (s, 2H), 4.37 (dd, J=4.3, 13.9 Hz, 1H), 4.15-4.24 (m, 1H), 4.00-4.14 (m, 5H), 3.90 (s, 3H), 3.52-3.56 (m, 2H), 3.35 (d, J=7.1 Hz, 2H), 3.21 (s, 3H), 1.26 (dt, J=2.7, 7 Hz, 6H). MS (ESI): m/z 720.23 [M+H]⁺. UPLC: $t_R$=1.12 min (UPLC-TOF: polar_3 min).

Compound 5C: 7-amino-4-(1-{[(4S)-2,2-dimethyl-1,3-dioxolan-4-yl]methyl}-1H-pyrazol-4-yl)-2-methyl-2,3-dihydro-1H-isoindol-1-one Prepared analogously to Compound 1C replacing Compound 1D with 4-(1-{[(4S)-2,2-dimethyl-1,3-dioxolan-4-yl]methyl}-1H-pyrazol-4-yl)-2-methyl-7-nitro-2,3-dihydro-1H-isoindol-1-one (Compound 5D, 1.96 g) to afford 1.03 g of the desired product (90%). ¹H NMR (400 MHz, DMSO-d$_6$) δ 7.96 (d, J=0.5 Hz, 1H), 7.75 (d, J=0.8 Hz, 1H), 7.43 (d, J=8.3 Hz, 1H), 6.62 (d, J=8.3 Hz, 1H), 6.07 (s, 2H), 4.38-4.47 (m, 3H), 4.24 (dd, J=1.4, 5.7 Hz, 2H), 4.01 (dd, J=6.3, 8.6 Hz, 1H), 3.78 (dd, J=5.7, 8.5 Hz, 1H), 3.03 (s, 3H), 1.24-1.35 (m, 6H). MS (ESI): m/z 343.15 [M+H]⁺. UPLC: $t_R$=1.09 min (UPLC-TOF: polar_3 min).

Compound 5D: 4-(1-{[(4S)-2,2-dimethyl-1,3-dioxolan-4-yl]methyl}-1H-pyrazol-4-yl)-2-methyl-7-nitro-2,3-dihydro-1H-isoindol-1-one Prepared analogously to Compound 3C replacing Compound 3D with Compound 1L and Compound 3E with 1-{[(4S)-2,2-dimethyl-1,3-dioxolan-4-yl]methyl}-4-(4,4,5,5-tetramethyl-1,3,2-dioxaborolan-2-yl)-1H-pyrazole (Compound 5E) to afford 1.96 g of the desired product (99%). ¹H NMR (400 MHz, CDCl$_3$) δ 7.79-7.85 (m, 2H), 7.74-7.80 (m, 1H), 7.65-7.73 (m, 1H), 4.46-4.58 (m, 3H), 4.36 (dd, J=5.05, 13.39 Hz, 2H), 4.14 (dd, J=6.44, 8.72 Hz, 1H), 3.83 (dd, J=6.06, 8.59 Hz, 1H), 3.24 (s, 3H), 1.34-1.44 (m, 6H). MS (ESI): m/z 373.16 [M+H]⁺. UPLC: $t_R$=1.16 min (UPLC-TOF: polar_3 min).

Compound 5E: 1-{[(4S)-2,2-Dimethyl-1,3-dioxolan-4-yl]methyl}-4-(4,4,5,5-tetramethyl-1,3,2-dioxaborolan-2-yl)-1H-pyrazole Isopropylmagnesium chloride in THF (2.0 M, 6.91 mL, 13.82 mmol) was added to a solution of 1-{[(4S)-2,2-dimethyl-1,3-dioxolan-4-yl]methyl}-4-iodo-1H-pyrazole (Compound 5F, 2.13 g, 6.91 mmol) in THF (60 mL, 800 mmol) at rt. After 10 minutes, the mixture was treated with 2-Methoxy-4,4,5,5-tetramethyl-1,3,2-dioxaborolane (3.40 mL, 20.74 mmol) and stirred for an additional 20 minutes at rt. The reaction was then quenched with sat. NH₄Cl and the mixture was concentrated in vacuo to a solid. The crude product was dissolved in DCM, washed with water (2×), dried with sodium sulfate, filtered and concentrated in vacuo to a clear oil. The crude material was purified using a Teledyne ISCO Combiflash® Rf system [20% EtOAc/hexanes] to afford 1.12 g of the title compound (53%). ¹H NMR (400 MHz, CD₃OD) δ 7.74 (s, 1H), 7.50 (s, 1H), 4.36-4.44 (m, 1H), 4.21-4.34 (m, 2H), 4.05 (dd, J=6.3, 8.6 Hz, 1H), 3.73 (dd, J=5.9, 8.7 Hz, 1H), 1.31 (d, J=8.6 Hz, 6H), 1.25 (s, 12H). MS (ESI): m/z 309.00 [M+H]⁺. UPLC: $t_R$=1.42 min (UPLC-TOF: polar_3 min).

Compound 5F: 1-{[(4S)-2,2-Dimethyl-1,3-dioxolan-4-yl]methyl}-4-iodo-1H-pyrazole

A mixture of 4-iodopyrazole (1.40 g, 7.21 mmol), (R)-(−)-(2,2-dimethyl-1,3-dioxolan-4-yl)methyl p-toluenesulfonate (2.27 g, 7.93 mmol), Cs₂CO₃ (3.52 g, 10.8 mmol) and DMF (10 mL, 100 mmol) was heated to 100° C. for 16 hrs. The reaction mixture was diluted with EtOAc, washed with water (2×), dried with sodium sulfate, filtered and concentrated in vacuo to a solid which was purified using a Teledyne ISCO Combiflash® Rf system [0→20% EtOAc/Heptane] to afford 2.13 g of the title compound (96%). ¹H NMR (400 MHz, CDCl₃) d 7.55 (s, 1H), 7.52 (s, 1H), 4.43 (dd, J=4.8, 6.1 Hz, 1H), 4.24-4.28 (m, 2H), 4.08 (dd, J=6.3, 8.8 Hz, 1H), 3.76 (dd, J=6.1, 8.6 Hz, 1H), 1.39 (s, 3H), 1.34-1.37 (m, 3H). MS (ESI): m/z 309.01 [M+H]⁺. UPLC: $t_R$=1.26 min (UPLC-TOF: polar_3 min).

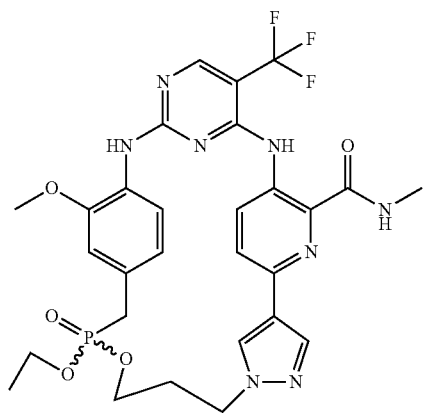

Example 6

(10S)-10-Ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14, 17(28),18,20,23, 26,29-undecaene-24-carboxamide 10-oxide This material was prepared analogously to Example 3 using ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 6A, 227 mg, 0.342 mmol). This compound required additional purification using ion exchange chromatography (SCX column, eluting first with 3 column volumes of MeOH followed by 3 column volumes of NH₃/MeOH) to isolate the title compound as 84 mg a white solid (30%). ¹H NMR (400 MHz, CDCl₃) d 10.84 (s, 1H), 8.36 (s, 1H), 8.30 (q, J=5 Hz, 1H), 8.19 (s, 1H), 8.17 (s, 1H), 8.13 (d, J=8.6 Hz, 1H), 7.80 (d, J=8.3 Hz, 1H), 7.68 (s, 1H), 7.59 (d, J=8.6 Hz, 1H), 6.67 (s, 1H), 6.43 (td, J=2.2, 8.3 Hz, 1H), 4.38-4.53 (m, 2H), 4.04-4.15 (m, 2H), 3.87 (s, 3H), 3.69-3.83 (m, 2H), 3.14 (d, J=21 Hz, 1H), 3.15 (d, J=21 Hz, 1H), 3.08 (d, J=5.1 Hz, 3H), 2.21-2.35 (m, 2H), 1.28 (t, J=7.1 Hz, 3H). MS (ESI): m/z 647.73 [M+H]⁺. UPLC: $t_R$=1.19 min (UPLC-SQD: analytical_2 min).

Compound 6A: Ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to compound 3A using diethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 6B, 0.330 g, 0.476 mmol) to isolate 227 mg of the title compound (72%). ¹H NMR (400 MHz, DMSO-d₆) δ 12.47 (s, 1H), 9.43 (br. s., 1H), 8.79 (d, J=9.6 Hz, 1H), 8.34 (s, 1H), 8.32 (s, 1H), 8.27 (d, J=9.1 Hz, 1H), 8.16 (t, J=7 Hz, 1H), 7.04-7.12 (m, 2H), 6.86 (d, J=7.8 Hz, 1H), 6.38 (br. s., 1H), 4.14-4.21 (m, 2H), 3.67-3.69 (m, 3H), 3.61-3.67 (m, 2H), 3.43-3.49 (m, 2H), 2.85 (d, J=5.1 Hz, 3H), 2.76 (d, J=19.7 Hz, 2H), 1.92 (quin, J=5.9 Hz, 2H), 1.54 (t, J=7.2 Hz, 1H), 0.94 (t, J=7.1 Hz, 3H). MS (ESI): m/z 665.72 [M+1]⁺; UPLC: $t_R$=1.11 min (UPLC-SQD: analytical_2 min).

Compound 6B: Diethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B replacing Compound 1C with 3-amino-6-[1-(3-hydroxypropyl)-1H-pyrazol-4-yl]-N-methylpyridine-2-carboxamide (Compound 6C, 220.0 mg, 0.7991 mmol) to afford 337 mg of the title compound (68%). ¹H NMR (400 MHz, CDCl₃) δ 12.19 (s, 1H), 9.04 (d, J=9.1 Hz, 1H), 8.36-8.44 (m, 2H), 8.21 (s, 1H), 8.08 (s, 1H), 8.04 (br. s., 1H), 7.63 (d, J=8.8 Hz, 1H), 7.52 (s, 1H), 6.95 (td, J=2.3, 8 Hz, 1H), 6.86 (t, J=1.9 Hz, 1H), 4.40 (t, J=6.2 Hz, 2H), 3.97-4.11 (m, 4H), 3.91 (s, 3H), 3.65 (q, J=5.3 Hz, 2H), 3.18 (d, J=21.1 Hz, 2H), 3.09 (d, J=5.1 Hz, 3H), 2.11

(quin, J=5.9 Hz, 2H), 1.26 (t, J=7.1 Hz, 6H) [OH proton obscured]. MS (ES+): m/z 693.75 [M+H]+. UPLC: $t_R$=1.24 min (UPLC-SQD: analytical_2 min).

Compound 6C: 3-amino-6-[1-(3-hydroxypropyl)-1H-pyrazol-4-yl]-N-methylpyridine-2-carboxamide Prepared analogously to Compound 3C replacing Compound 3D 3-amino-6-bromo-N-methylpyridine-2-carboxamide (Compound 6D 700 mg, 3 mmol) to isolate 386 mg of the title compound as a hygroscopic foam (46%). $^1$H NMR (400 MHz, CDCl$_3$) δ 8.11 (br. s., 1H), 7.88 (s, 1H), 7.82 (s, 1H), 7.36 (d, J=8.3 Hz, 1H), 7.03 (d, J=8.3 Hz, 1H), 5.95 (br. s., 2H), 4.34 (t, J=6.4 Hz, 2H), 3.68 (q, J=5.8 Hz, 2H), 3.02 (d, J=5.01 Hz, 3H), 2.58 (t, J=5.7 Hz, 1H), 2.11 (td, J=6, 12.3 Hz, 2H).

Compound 6D: 3-Amino-6-bromo-N-methylpyridine-2-carboxamide

A 10M solution of Methylamine in H$_2$O (30.0 mL, 386 mmol) was added to a stainless steel reactor containing 3-amino-6-bromopyridine-2-carboxylic acid ethyl ester (Compound 6E, 7.614 g, 31.07 mmol) in MeOH (20.0 mL). The reactor was sealed and heated to 100° C. for 16 hours. The cooled reaction mixture was transferred to a round bottom flask and concentrated in vacuo forming a yellow precipitate which was collected by filtration. Further precipitate formed in the filtrate which was also collected. The combined precipitates were dried in vacuo to afford the title compound as 6.18 g of a yellow solid. $^1$H NMR (400 MHz, CDCl$_3$) δ 7.80 (br. s., 1H), 7.27 (d, J=8.6 Hz, 1H), 6.91 (d, J=8.6 Hz, 1H), 6.02 (br. s., 2H), 2.97 (d, J=5.1 Hz, 3H).

Compound 6E: 3-Amino-6-bromopyridine-2-carboxylic acid ethyl ester

A suspension of ethyl 3-aminopicolinate (Compound 6F, 4.15 g, 25.0 mmol) in H$_2$O (30.0 mL) was treated with enough sulfuric acid to enable dissolution (~1 mL). 2 mL of the total 10.7 mL of acetic acid to be used in this reaction was added in order to make the reaction mixture mostly homogeneous. A solution of bromine (1.29 mL, 25.0 mmol) in the remaining AcOH (8.7 mL) was added drop-wise to the vigorously stirring reaction mixture forming an orange precipitate. The mixture was allowed to stir for 15 min. The resulting thick yellow-orange suspension was filtered to collect a yellow precipitate. The filtrate was neutralized with saturated aqueous K$_2$CO$_3$ and the additional precipitate that formed was collected by filtration and combined with the previously collected precipitate. The combined precipitates were dried and re-crystallized in EtOH (overnight in the dark) to isolate 4.24 g of pale orange crystals. The mother liquor was purified on an ISCO Combiflash system eluting with 0-5% MeOH/DCM. To isolate a further 0.58 g of the desired product for a total of 4.82 g (79%). $^1$H NMR (400 MHz, DMSO-d$_6$) δ 1.30 (t, J=7.1 Hz, 3H), 4.29 (q, J=7.1 Hz, 2H), 6.90 (br. s., 2H), 7.21 (d, J=8.6 Hz, 1H), 7.44 (d, J=8.8 Hz, 1H). MS (ESI): m/z 244.94 (100), 246.92 (100) [M+H]+. HPLC: $t_R$=3.45 min (ZQ3: polar_5 min).

Compound 6F: Ethyl 3-aminopicolinate

A solution of 3-aminopicolinic acid (5.00 g, 36.2 mmol) in EtOH (70 mL) and concentrated sulfuric acid (6.0 mL, 110 mmol) was heated to 100° C. and stirred for 5 days. The cooled mixture was concentrated to ~20 mL and poured over ice. This mixture was treated with aqueous ammonia (NH$_4$OH, conc) until pH>7. This was extracted twice with 100 mL EtOAc. The basified aqueous layer was saturated with salt and extracted again with 100 mL EtOAc (2×). The combined organic layers were washed with brine, dried over Na$_2$SO$_4$, filtered and concentrated to 4.15 g of an off white solid (69%). $^1$H NMR (400 MHz, DMSO-d$_6$) δ 1.30 (t, J=7.1 Hz, 3H), 4.27 (q, J=7.1 Hz, 2H), 6.67 (br. s., 2H), 7.17-7.22 (m, 1H), 7.24-7.29 (m, 1H), 7.84 (dd, J=4, 1.5 Hz, 1H). MS (ESI): m/z=167.06 [M+H]+. HPLC: $t_R$=2.76 min (ZQ3: vvpolar_5 min).

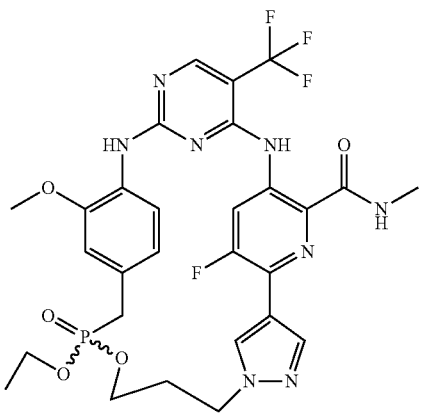

Example 7

(10S)-10-Ethoxy-26-fluoro-14-methoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-26-fluoro-14-methoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25), 2(31),3,12,14,17(28),18,20,23, 26,29-undecaene-24-carboxamide 10-oxide This material was prepared analogously to Example 3 using ethyl hydrogen (4-{[4-({5-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate (Compound 7A, 50.0 mg, 0.0734 mmol) to afford 7.4 mg of the title compound (15% yield). $^1$H NMR (CD$_3$OD, 400 MHz): δ 8.32 (d, J=2.8 Hz, 1H), 8.31 (s, 1H), 8.10 (s, 1H), 8.03 (d, J=8.1 Hz, 1H), 7.60 (d, J=8.3 Hz, 1H), 7.47 (d, J=12.4 Hz, 1H), 6.85 (t, J=1.9 Hz, 1H), 6.50-6.54 (m, 1H), 4.48 (t, J=6.1 Hz, 2H), 3.88-3.97 (m, 2H), 3.87 (s, 3H), 3.70-3.79 (m, 1H), 3.59-3.69 (m, 1H), 3.25 (d, J=21.5 Hz, 1H), 3.23 (d, J=21.5 Hz, 1H), 2.85 (s, 3H), 2.26 (quin, J=6 Hz, 2H), 1.12 (t, J=7 Hz, 3H). MS (ESI): m/z 664.18 [M+H]+. UPLC: $t_R$=1.39 min (UPLC-TOF: polar_3 min).

Compound 7A: Ethyl hydrogen (4-{[4-({5-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate Prepared analogously to Example 3A using diethyl (4-({5-fluoro-4-[1-(3-hydroxypropyl)-1H-pyrazol-4-yl]-2-

(methylcarbamoyl)phenyl}amino)-5-(trifluoromethyl)pyrimidin-2-yl]amino}-3-methoxybenzyl)phosphonate (Compound 7B) to afford the title compound. $^1$H NMR (CD$_3$OD, 400 MHz): δ 8.36 (d, J=13.6 Hz, 1H), 8.31 (s, 1H), 8.11 (d, J=1.8 Hz, 1H), 7.94-8.00 (m, 2H), 7.81 (d, J=8.1 Hz, 1H), 7.10 (s, 1H), 6.86 (d, J=8.1 Hz, 1H), 4.33 (t, J=7 Hz, 2H), 3.91 (s, 3H), 3.83 (quin, J=7 Hz, 2H), 3.58 (t, J=6.1 Hz, 2H), 2.94-3.04 (m, 2H), 2.92 (s, 3H), 2.10 (quin, J=6.5 Hz, 2H), 1.15 (t, J=7.1 Hz, 3H). MS (ESI): m/z 682.21 [M+H]$^+$. UPLC: $t_R$=1.16 min (UPLC-TOF: polar__3 min).

Compound 7B: Diethyl (4-{[4-({5-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate A suspension of diethyl (4-{[4-{[4-bromo-5-fluoro-2-(methylcarbamoyl)phenyl]amino}-5-(trifluoromethyl)pyrimidin-2-yl]amino}-3-methoxybenzyl)phosphonate (Compound 7C, 400 mg, 0.60 mmol), 3-[4-(4,4,5,5-tetramethyl-1,3,2-dioxaborolan-2-yl)-1H-pyrazol-1-yl]propan-1-ol (Compound 3E 258 mg, 1.02 mmol), [1,1-Bis(diphenylphosphino)ferrocene]dichloropalladium(II), complex with dichloromethane (1:1) (49.17 mg, 0.06 mmol), and potassium carbonate (252 mg, 1.82 mmol) in 1,4-Dioxane (2 mL) and H$_2$O (0.5 mL) was evacuated and purged with nitrogen (3×). The sample was irradiated in the microwave at 100° C. for 1.5 hours. The reaction mixture was filtered. The filtrate was quenched with water (10 mL) and extracted with EtOAc (20 mL). The organic layer was washed with brine (15 mL), dried over anhydrous Na$_2$SO$_4$, filtered, and concentrated under reduced pressure to a brown oil. The crude material was purified on a Teledyne ISCO Combiflash® Rf system using DCM/MeOH (100:0→85:15) to afford the title compound as 345 mg of a yellow solid (81%). $^1$H NMR (DMSO-d$_6$, 400 MHz): δ=11.84 (s, 1H), 8.94 (s, 1H), 8.80 (d, J=4.8 Hz, 1H), 8.45 (s, 1H), 8.39 (s, 1H), 8.16 (d, J=1.5 Hz, 1H), 8.04 (d, J=8.6 Hz, 1H), 7.94 (s, 1H), 7.53 (d, J=7.8 Hz, 1H), 7.02 (s, 1H), 6.86 (ddd, J=1.8, 2.2, 8.4 Hz, 1H), 4.62 (t, J=5.1 Hz, 1H), 4.23 (t, J=7 Hz, 2H), 3.91-4.00 (m, 4H), 3.78 (s, 3H), 3.39-3.45 (m, 2H), 3.19-3.27 (m, 2H), 2.81 (d, J=4.6 Hz, 3H), 1.96 (quin, J=6.6 Hz, 2H), 1.16 (t, J=7.1 Hz, 6H). MS (ESI): m/z 710.22 [M+H]$^+$. UPLC: $t_R$=1.42 min (UPLC-TOF: polar__3 min).

Compound 7C: Diethyl (4-{[4-{[4-bromo-5-fluoro-2-(methylcarbamoyl)phenyl]amino}-5-(trifluoromethyl)pyrimidin-2-yl]amino}-3-methoxybenzyl)phosphonate Prepared analogously to Compound 1B replacing Compound 1C with 2-amino-5-bromo-4-fluoro-N-methylbenzamide (Compound 7D, 0.327 g, 1.32 mmol) to afford the title compound as 642 mg of a white solid (88% yield). $^1$H NMR (DMSO-d$_6$, 400 MHz): δ 11.94 (br. s., 1H), 9.15 (br. s., 1H), 8.88 (d, J=4.6 Hz, 1H), 8.53 (br. s., 1H), 8.42 (s, 1H), 8.08 (d, J=7.8 Hz, 1H), 7.47 (d, J=7.6 Hz, 1H), 7.02 (s, 1H), 6.82-6.90 (m, 1H), 3.93-4.02 (m, 4H), 3.77 (s, 3H), 3.18-3.27 (m, 2H), 2.77 (d, J=4.3 Hz, 3H), 1.19 (t, J=7.1 Hz, 6H). MS (ESI): m/z 664.09 [M+H]$^+$. UPLC: $t_R$=1.60 min (UPLC-TOF: polar__3 min).

Compound 7D: 2-amino-5-bromo-4-fluoro-N-methylbenzamide

A solution of 2-amino-5-bromo-4-fluorobenzoic acid (2.00 g, 8.55 mmol), methylamine hydrochloride (0.692 g, 10.2 mmol), TBTU (2.74 g, 8.55 mmol), and DIPEA (4.46 mL, 25.6 mmol) in DCM (15.0 mL) was stirred at rt for 30 minutes. The reaction was quenched with sat. aq. NaHCO$_3$ (10 mL) and extracted with DCM (15 mL). The organic layer was washed with brine (10 mL), dried over anhydrous Na$_2$SO$_4$, filtered and concentrated under reduced pressure to a yellow oil. The crude material was purified on a Teledyne ISCO Combiflash® Rf system using DCM/MeOH (100:0→95:5) as eluent to afford the title compound as 2.54 g of a white solid. $^1$H NMR (CDCl$_3$, 400 MHz): δ 7.48 (d, J=7.3 Hz, 1H), 6.44 (d, J=10.4 Hz, 1H), 6.11 (br. s., 1H), 5.66 (br. s., 2H), 2.96 (d, J=4.8 Hz, 3H). MS (ESI): m/z 248.91 [M+H]$^+$. UPLC: $t_R$=3.26 min (ZQ3: polar__5 min).

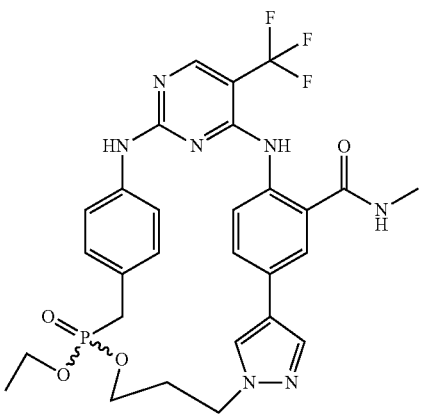

Example 8

(10S)-10-Ethoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({4-[1-(3-hydroxypropyl)-1H-pyrazol-4-yl]-2-(methylcarbamoyl)phenyl}amino)-5-(trifluoromethyl)pyrimidin-2-yl]amino}benzyl)phosphonate (Compound 8A, 447 mg, 705 mmol) to afford 182 mg of the title compound (42%). $^1$H NMR (400 MHz, CD$_3$OD) δ 8.28 (s, 1H), 8.26 (s, 1H), 8.02 (s, 1H), 7.90 (d, J=2 Hz, 1H), 7.79 (dd, J=2.2, 8.5 Hz, 1H), 7.60 (d, J=8.3 Hz, 1H), 7.27 (d, J=8.3 Hz, 2H), 6.93 (dd, J=2.4, 8.7 Hz, 2H), 4.45 (t, J=5.8 Hz, 2H), 3.89-4.01 (m, 2H), 3.65-3.78 (m, 2H), 3.15-3.25 (m, 2H), 2.85 (s, 3H), 2.21-2.30 (m, 2H), 1.16 (t, J=7.1 Hz, 3H). MS (ESI): m/z 616.68 [M+H]$^+$. UPLC: $t_R$=1.03 min (UPLC-SQD: analytical__2 min).

Compound 8A: Ethyl hydrogen (4-{[4-({4-[1-(3-hydroxypropyl)-1H-pyrazol-4-yl]-2-(methylcarbamoyl)phenyl}amino)-5-(trifluoromethyl)pyrimidin-2-yl]amino}benzyl)phosphonate This compound was prepared using the procedure Example 3A with diethyl (4-{[4-({4-[1-(3-hydroxypropyl)-1H-pyrazol-4-yl]-2-(methylcarbamoyl)phenyl}amino)-5-

(trifluoromethyl)pyrimidin-2-yl]amino}benzyl)phosphonate (Compound 8B, 550 mg, 831 µmol) to afford 447 mg of the title compound (85%). $^1$H NMR (400 MHz, CD$_3$OD) δ 8.46 (d, J=7.6 Hz, 1H), 8.28 (s, 1H), 8.17 (s, 1H), 7.92 (s, 1H), 7.83 (d, J=2.3 Hz, 1H), 7.68 (dd, J=2.2, 8.7 Hz, 1H), 7.46 (d, J=8.34 Hz, 2H), 7.20-7.30 (m, 2H), 4.31 (t, J=6.8 Hz, 2H), 3.81 (t, J=7.1 Hz, 2H), 3.58 (t, J=6.1 Hz, 2H), 2.98 (s, 1H), 2.90-2.94 (m, 4H), 2.10 (t, J=6.4 Hz, 2H), 1.12 (t, J=7 Hz, 3H). MS (ESI): m/z 634.66 [M+H]$^+$. UPLC: $t_R$=0.96 min (UPLC-SQD: analytical_2 min).

Compound 8B: Diethyl (4-{[4-({4-[1-(3-hydroxypropyl)-1H-pyrazol-4-yl]-2-(methylcarbamoyl)phenyl}amino)-5-(trifluoromethyl)pyrimidin-2-yl]amino}benzyl)phosphonate Prepared analogously to Compound 1B replacing Compound 1E with Compound 2C and replacing Compound 1C with 2-amino-5-[1-(3-hydroxypropyl)-1H-pyrazol-4-yl]-N-methylbenzamide (Compound 8C, 517 mg, 1.22 mmol) to afford 550 mg of the title compound (68%). $^1$H NMR (400 MHz, CD$_3$OD) δ 8.36 (br. s., 1H), 8.32 (s, 1H), 8.18 (s, 1H), 8.00 (s, 1H), 7.91 (d, J=2.0 Hz, 1H), 7.69 (dd, J=2.0, 8.8 Hz, 1H), 7.47 (d, J=8.1 Hz, 2H), 7.35 (dd, J=2.4, 8.5 Hz, 2H), 4.31 (t, J=6.9 Hz, 2H), 3.98-4.10 (m, 4H), 3.57 (t, J=6.1 Hz, 2H), 3.26 (s, 2H), 2.92 (s, 3H), 2.10 (t, J=6.4 Hz, 2H), 1.23 (t, J=7.1 Hz, 6H). MS (ESI): m/z: 662.74 [M+H]$^+$. UPLC: $t_R$=1.11 min (UPLC-SQD: analytical_2 min).

Compound 8C: 2-amino-5-[1-(3-hydroxypropyl)-1H-pyrazol-4-yl]-N-methylbenzamide

Prepared analogously to Compound 1D using 2-amino-5-bromo-n-methyl-benzamide (Compound 87D, 600 mg, 2.62 mmol) to afford 335 mg of the title compound (47%). $^1$H NMR (400 MHz, CD$_3$OD) δ 7.86 (s, 1H), 7.76 (s, 1H), 7.62 (d, J=2.0 Hz, 1H), 7.38 (dd, J=2.0, 8.3 Hz, 1H), 6.77 (d, J=8.3 Hz, 1H), 4.25 (t, J=6.8 Hz, 2H), 3.54 (t, J=6.2 Hz, 2H), 2.89 (s, 3H), 2.06 (quin, J=6.5 Hz, 2H). MS (ESI): m/z 275.57 [M+H]$^+$. UPLC: $t_R$=0.55 min (UPLC-SQD: analytical_2 min).

Example 8D:
2-Amino-5-bromo-N-methylbenzamide

2-Amino-5-bromobenzoic acid (80 g, 0.37 mol) was dissolved in MeOH (600 mL) and conc. H$_2$SO$_4$ (50 mL) was slowly added. The reaction mixture was refluxed for 72 h, then concentrated. NaOH solution was added to adjust the pH to 10-11. The mixture was extracted with EtOAc (3×500 mL). The combined organic layer was dried over MgSO$_4$, concentrated to afford the desired compound (65 g, yield: 76%) as a colorless oil, which is used directly in the next step without purification. A mixture of methyl 2-amino-5-bromobenzoate and CH$_3$NH$_2$.H$_2$O (1000 mL) was stirred at 80° C. overnight in a pressure tube. The mixture was diluted with H$_2$O (1000 mL) and extracted with EtOAc (3×500 mL). The combined organic layers were dried over MgSO$_4$, concentrated to afford the title compound (55 g, yield: 87%) as a gray solid. $^1$H NMR (CDCl$_3$, 400 MHz): δ 2.93 (d, J=5.2 Hz, 3H), 5.48 (s, br, 2H), 6.04 (s, br, 1H), 6.54 (d, J=8.4 Hz, 1H), 7.24 (dd, J=2.0, 8.4 Hz, 1H), 7.38 (d, J=2.0 Hz, 1H).

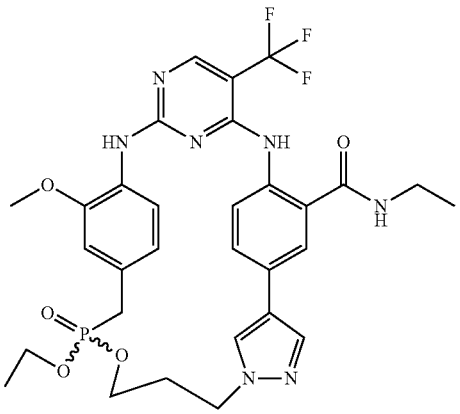

Example 9

(10S)-10-Ethoxy-N-ethyl-14-methoxy-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-N-ethyl-14-methoxy-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate (Compound 9A, 349 mg, 0.52 mmol) to afford 107 mg of the title compound (31%). $^1$H NMR (400 MHz, CD$_3$OD) δ 8.27 (d, J=2.5 Hz, 2H), 8.04 (s, 1H), 7.89 (d, J=2.0 Hz, 1H), 7.78 (dd, J=8.3, 2.0 Hz, 1H), 7.54 (dd, J=8.2, 6.7 Hz, 2H), 6.81 (s, 1H), 6.39 (d, J=8.3 Hz, 1H), 4.45 (t, J=5.9 Hz, 2H), 3.96-4.06 (m, 2H), 3.86 (s, 3H), 3.64-3.78 (m, 2H), 3.31 (m, 2H, obscured), 3.16-3.27 (m, 2H), 2.19-2.29 (m, 2H), 1.21 (t, J=7.1 Hz, 3H), 1.11 (t, J=7.3 Hz, 3H). MS (ESI): m/z 660.75 [M+H]$^+$. UPLC: $t_R$=1.16 min (UPLC-SQD: analytical_2 min).

Compound 9A: Ethyl hydrogen (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate Prepared analogously to Compound 3A using diethyl (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate (Compound 9B, 570 mg, 808 µmol) to afford the title compound as 349 mg of a white solid (65%). $^1$H NMR (400 MHz, CD$_3$OD) δ 8.30 (d, J=8.6 Hz, 1H), 8.27 (s, 1H), 8.16 (s, 1H), 7.93 (s, 1H), 7.85 (d, J=8.1 Hz, 1H), 7.82 (d, J=2.0 Hz, 1H), 7.66 (dd, J=2.0, 8.6 Hz, 1H), 7.05 (s, 1H), 6.80 (d, J=8.3 Hz, 1H), 4.31 (t, J=6.8 Hz, 2H), 3.89 (s, 3H), 3.83 (quin, J=6.9 Hz, 2H), 3.58 (t, J=6.1 Hz, 2H), 3.40 (q, J=7.2 Hz, 2H), 2.91-3.01 (m, 2H), 2.10 (quin, J=6.4 Hz, 2H), 1.22 (t, J=7.2 Hz, 3H), 1.12-1.17 (m, 3H). MS (ESI): m/z 678.74 [M+H]$^+$. UPLC: $t_R$=1.07 min (UPLC-SQD: analytical_2 min).

Compound 9B: Diethyl (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate Prepared analogously to Compound 1B using diethyl (4-{[4-chloro-5-(trifluoromethyl)pyrimidin-2-yl]amino}-3-methoxybenzyl)phosphonate (Compound 9C, 455 mg, 1.00 mmol) and 2-amino-N-ethyl-5-[1-(3-hydroxypropyl)-1H-pyrazol-4-yl]benzamide (364 mg, 884 μmol) to afford the title compound as 570 mg of a solid (570 mg, 91%). $^1$H NMR (400 MHz, CD$_3$OD) δ 8.27-8.32 (m, 2H), 8.12 (s, 1H), 7.90-7.98 (m, 2H), 7.83 (d, J=2.0 Hz, 1H), 7.65 (dd, J=2.1, 8.7 Hz, 1H), 6.98 (t, J=2.0 Hz, 1H), 6.80 (td, J=2.1, 8.2 Hz, 1H), 4.30 (t, J=6.9 Hz, 2H), 3.98-4.07 (m, 4H), 3.89 (s, 3H), 3.57 (t, J=6.1 Hz, 2H), 3.40 (q, J=7.2 Hz, 2H), 3.17-3.27 (m, 2H), 2.10 (quin, J=6.5 Hz, 2H), 1.19-1.27 (m, 9H). MS (ESI): m/z 706.82 [M+H]$^+$. UPLC: $t_R$=1.24 min (UPLC-SQD: analytical_2 min).

Compound 9C: 2-amino-N-ethyl-5-[1-(3-hydroxypropyl)-1H-pyrazol-4-yl]benzamide

Prepared analogously to Compound 3C replacing Compound 3D with 2-amino-5-bromo-N-ethylbenzamide (Compound 9D, 1.40 g, 5.77 mmol) to afford 729 mg of the title compound (37%). $^1$H NMR (400 MHz, CD$_3$OD) δ 7.87 (s, 1H), 7.76 (d, J=0.5 Hz, 1H), 7.63 (d, J=2.0 Hz, 1H), 7.34-7.41 (m, 1H), 6.77 (d, J=8.3 Hz, 1H), 4.25 (t, J=6.9 Hz, 2H), 3.54 (t, J=6.2 Hz, 2H), 3.38 (q, J=7.2 Hz, 2H), 2.06 (quin, J=6.6 Hz, 2H), 1.23 (t, J=7.2 Hz, 3H). MS (ESI): m/z 289.32 [M+H]$^+$. UPLC: $t_R$=0.63 min (UPLC-SQD: analytical_2 min).

Compound 9D: 2-amino-5-bromo-N-ethylbenzamide

Prepared analogously to Compound 3D replacing diethylamine with ethylamine to afford 1.41 g of the title product (70%). $^1$H NMR (400 MHz, CD$_3$OD) δ 7.55 (d, J=2.3 Hz, 1H), 7.25 (dd, J=2.4, 8.7 Hz, 1H), 6.67 (d, J=8.8 Hz, 1H), 3.32-3.38 (m, 2H), 1.20 (t, J=7.3 Hz, 3H). MS (ESI): m/z 243.33 [M+H]$^+$. UPLC: $t_R$=0.98 min (UPLC-SQD: analytical_2 min).

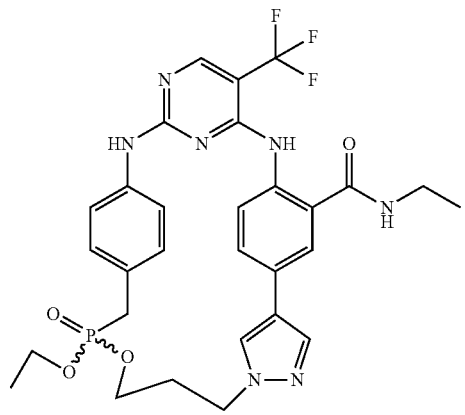

Example 10

(10S)-10-ethoxy-N-ethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-N-ethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}benzyl)phosphonate (Compound 10A, 296 mg, 0.46 mmol) to yield the desired product (40 mg, 14%). $^1$H NMR (400 MHz, CD$_3$OD) δ 8.29 (s, 1H), 8.25 (s, 1H), 8.03 (s, 1H), 7.89 (d, J=2.3 Hz, 1H), 7.79 (dd, J=2.0, 8.3 Hz, 1H), 7.56 (d, J=8.3 Hz, 1H), 7.26 (s, 1H), 7.23 (s, 1H), 6.91 (dd, J=2.5, 8.6 Hz, 2H), 4.45 (t, J=5.9 Hz, 2H), 3.92-4.02 (m, 2H), 3.64-3.80 (m, 2H), 3.34-3.50 (m, 2H), 3.15-3.25 (m, 2H), 2.21-2.30 (m, 2H), 1.18 (t, J=7.1 Hz, 3H), 1.12 (t, J=7.2 Hz, 3H). MS (ESI): m/z 630.74 [M+H]$^+$. UPLC: $t_R$=1.08 min (UPLC-SQD: analytical_2 min).

Compound 10A: Ethyl hydrogen (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}benzyl)phosphonate Prepared analogously to Compound 3A using diethyl (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}benzyl)phosphonate (Compound 10B, 589 mg, 872 μmol) to afford 296 mg of the title compound (53%). $^1$H NMR (400 MHz, CD$_3$OD) δ 8.41 (br. s., 1H), 8.27 (s, 1H), 8.16 (s, 1H), 7.93 (s, 1H), 7.82 (d, J=1.5 Hz, 1H), 7.67 (d, J=8.6 Hz, 1H), 7.46 (d, J=8.1 Hz, 2H), 7.24 (d, J=7.6 Hz, 2H), 4.31 (t, J=6.8 Hz, 2H), 3.84 (t, J=6.9 Hz, 2H), 3.58 (t, J=6.1 Hz, 2H), 3.40 (q, J=7.1 Hz, 2H), 2.90-3.03 (m, 2H), 2.10 (t, J=6.3 Hz, 2H), 1.22 (t, J=7.2 Hz, 3H), 1.14 (t, J=6.9 Hz, 3H). MS (ESI): m/z 648.70 [M+H]$^+$. UPLC: $t_R$=1.04 min (UPLC-SQD: analytical_2 min).

Compound 10B: Diethyl (4-{[4-({2-(ethylcarbamoyl)-4-[1-(3-hydroxypropyl)-1H-pyrazol-4-yl]phenyl}amino)-5-(trifluoromethyl)pyrimidin-2-yl]amino}benzyl)phosphonate Prepared analogously to Compound 1B replacing Compound 1C with 2-amino-N-ethyl-5-[1-(3-hydroxypropyl)-1H-pyrazol-4-yl]benzamide (Compound 9C, 455 mg, 1.07 mmol) to afford 589 mg of the title compound (81%). $^1$H NMR (400 MHz, CD$_3$OD) δ 8.42 (d, J=8.8 Hz, 1H), 8.31 (s, 1H), 8.13 (s, 1H), 7.96 (s, 1H), 7.84 (d, J=2.0 Hz, 1H), 7.68 (dd, J=2.2, 8.7 Hz, 1H), 7.55 (d, J=8.3 Hz, 2H), 7.23 (dd, J=2.6, 8.7 Hz, 2H), 4.31 (d, J=13.6 Hz, 2H), 3.97-4.08 (m, 4H), 3.57 (t, J=6.2 Hz, 2H), 3.38-3.42 (m, 2H), 3.18-3.25 (m, 2H), 2.10 (quin, J=6.5 Hz, 2H), 1.17-1.26 (m, 9H). MS (ESI): m/z 676.78 [M+H]$^+$. UPLC: $t_R$=1.18 min (UPLC-SQD: analytical_2 min).

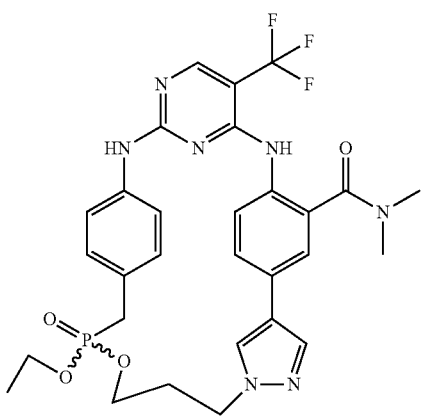

Example 11

(10S)-10-Ethoxy-N,N-dimethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-N,N-dimethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}benzyl)phosphonate (Compound 11A, 119 mg, 0.18 mmol) to afford 88 mg of the title compounds (76%). $^1$H NMR (400 MHz, CD$_3$OD) δ 8.28 (s, 1H), 8.21 (s, 1H), 8.01 (s, 1H), 7.81 (dd, J=2.0, 8.3 Hz, 1H), 7.61 (d, J=2.0 Hz, 1H), 7.44 (d, J=8.3 Hz, 1H), 7.15 (d, J=8.3 Hz, 2H), 6.80 (dd, J=2.4, 8.7 Hz, 2H), 4.44 (t, J=5.9 Hz, 2H), 3.95 (quin, J=7.2 Hz, 2H), 3.82 (ddd, J=5.4, 11.2, 14.5 Hz, 2H), 3.03-3.12 (m, 2H), 2.97 (s, 3H), 2.70 (s, 3H), 2.29 (quin, J=5.7 Hz, 2H), 1.19 (t, J=6.9 Hz, 3H). MS (ESI): m/z 630.74 [M+H]$^+$. UPLC: t$_R$=0.96 min (UPLC-SQD: analytical_2 min).

Compound 11A: Ethyl hydrogen (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}benzyl) phosphonate Prepared analogously to Compound 3A using diethyl (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}benzyl)phosphonate (Compound 11B, 177 mg, 262 μmol) to afford 119 mg of the title compound (70%). $^1$H NMR (400 MHz, CD$_3$OD) δ 8.25 (s, 1H), 8.17 (s, 1H), 7.92 (s, 1H), 7.89 (d, J=8.6 Hz, 1H), 7.72 (dd, J=2.2, 8.5 Hz, 1H), 7.58 (d, J=2.0 Hz, 1H), 7.38 (d, J=8.3 Hz, 2H), 7.13 (d, J=7.8 Hz, 2H), 4.32 (t, J=6.8 Hz, 2H), 3.70-3.81 (m, 2H), 3.58 (t, J=6.2 Hz, 2H), 3.04 (s, 3H), 2.81-2.95 (m, 5H), 2.10 (quin, J=6.4 Hz, 2H), 1.11 (t, J=7.1 Hz, 3H). MS (ESI): m/z 648.71 [M+H]$^+$. UPLC: t$_R$=0.89 min (UPLC-SQD: analytical_2 min).

Compound 11B: Diethyl (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}benzyl)phosphonate Prepared analogously to Compound 1B replacing Compound 1C with 2-Amino-5-[1-(3-hydroxypropyl)-1H-pyrazol-4-yl]-N,N-dimethylbenzamide (Compound 11C, 506 mg, 1.19 mmol) to afford 177 mg of the title compound (22%). $^1$H NMR (400 MHz, CD$_3$OD) δ 8.29 (s, 1H), 8.16 (s, 1H), 7.97 (s, 1H), 7.71-7.79 (m, 2H), 7.62 (d, J=1.8 Hz, 1H), 7.40 (d, J=7.8 Hz, 2H), 7.12 (d, J=5.6 Hz, 2H), 4.32 (t, J=6.9 Hz, 2H), 3.91-4.04 (m, 4H), 3.55-3.61 (m, 2H), 3.07-3.16 (d, J=21 Hz, 2H), 3.04 (s, 3H), 2.91 (s, 3H), 2.10 (t, J=6.4 Hz, 2H), 1.21 (t, J=7.1 Hz, 6H). MS (ESI): m/z 676.77 [M+H]$^+$. UPLC: t$_R$=1.07 min (UPLC-SQD: analytical_2 min).

Compound 11C: 2-Amino-5-[1-(3-hydroxypropyl)-1H-pyrazol-4-yl]-N,N-dimethylbenzamide Prepared analogously to Compound 3C replacing Compound 3D with 2-amino-5-bromo-N,N-dimethyl benzamide (Compound 11D, 1.47 g, 6.06 mmol) to afford 689 mg of the title compound (39%). $^1$H NMR (400 MHz, CD$_3$OD) δ 7.86 (d, J=0.5 Hz, 1H), 7.71 (d, J=0.8 Hz, 1H), 7.36 (dd, J=2.2, 8.5 Hz, 1H), 7.26 (d, J=2.0 Hz, 1H), 6.80 (d, J=8.3 Hz, 1H), 4.24 (t, J=6.8 Hz, 2H), 3.54 (t, J=6.1 Hz, 2H), 3.07 (br. s., 6H), 2.05 (quin, J=6.6 Hz, 2H). MS (ESI): m/z 289.56 [M+H]$^+$. UPLC: t$_R$=0.57 min (UPLC-SQD: analytical_2 min).

Compound 11D: 2-Amino-5-bromo-N,N dimethyl benzamide

Prepared analogously to Compound 3D replacing diethylamine with dimethylamine to afford 1.47 g of the title compound (73%). $^1$H NMR (400 MHz, CD$_3$OD) δ 7.24 (dd, J=2.4, 8.7 Hz, 1H), 7.18 (d, J=2.3 Hz, 1H), 6.70 (d, J=8.8 Hz, 1H), 3.04 (br. s., 6H). MS (ESI): m/z 243.33 [M+H]$^+$. UPLC: t$_R$=0.88 min (UPLC-SQD: analytical_2 min).

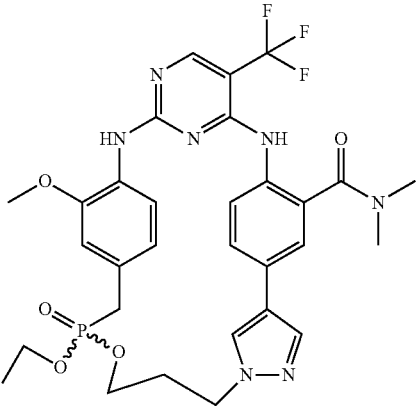

Example 12

(10S)-10-Ethoxy-14-methoxy-N,N-dimethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-14-methoxy-N,N-dimethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate (Compound 12A, 39 mg, 57.6 mmol) to afford 5.5 mg of the title compounds (15%). $^1$H NMR (400 MHz, CD$_3$OD) δ 8.26 (s, 1H), 8.23 (s, 1H), 8.02 (d, J=0.5 Hz, 1H), 7.81 (dd, J=2.2, 8.2 Hz, 1H), 7.62 (d, J=2.0 Hz, 1H), 7.44 (d, J=8.1 Hz, 1H), 7.40 (d, J=7.8 Hz, 1H), 6.76 (s, 1H), 6.19-6.28 (m, 1H), 4.44 (t, J=5.9 Hz, 2H), 3.96-4.05 (m, 2H), 3.85 (s, 3H), 3.06-3.22 (m, 4H), 2.97 (s, 3H), 2.74 (s, 3H), 2.22-2.31 (m, 2H), 1.23 (t, J=7.1 Hz, 3H). MS (ESI): m/z 660.73 [M+H]$^+$. UPLC: $t_R$=1.03 min (UPLC-SQD: analytical_2 min).

Compound 12A: Ethyl hydrogen (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate Prepared analogously to Compound 3A using diethyl (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl)phosphonate (Compound 12B, 72 mg, 102 μmol) to afford 39 mg of the title compound (56%). $^1$H NMR (400 MHz, CD$_3$OD) δ 8.26 (s, 1H), 8.18 (s, 1H), 7.93 (s, 1H), 7.79-7.86 (m, 1H), 7.70-7.79 (m, 2H), 7.59 (d, J=2.0 Hz, 1H), 7.01 (s, 1H), 6.61 (br. s., 1H), 4.32 (t, J=6.8 Hz, 2H), 3.88 (s, 3H), 3.76 (quin, J=6.9 Hz, 2H), 3.59 (t, J=6.1 Hz, 2H), 3.04 (s, 3H), 2.90 (d, J=3.8 Hz, 4H), 2.85 (s, 1H), 2.04-2.17 (m, 2H), 1.11 (t, J=7.1 Hz, 3H). MS (ESI): m/z 678.70 [M+H]$^+$. UPLC: $t_R$=0.95 min (UPLC-SQD: analytical_2 min).

Compound 12B: Diethyl (4-{[4-({2-(dimethylcarbamoyl)-4-[1-(3-hydroxypropyl)-1H-pyrazol-4-yl]phenyl}amino)-5-(trifluoromethyl)pyrimidin-2-yl]amino}-3-methoxybenzyl) phosphonate Prepared analogously to Compound 1B replacing 1C with 2-Amino-5-[1-(3-hydroxypropyl)-1H-pyrazol-4-yl]-N,N-dimethylbenzamide (Compound 11C, 554 mg, 1.22 mmol) to afford 72 mg of the title compound (8%). $^1$H NMR (400 MHz, CD$_3$OD) δ 8.27-8.32 (m, 1H), 8.13-8.18 (m, 1H), 7.95-7.98 (m, 1H), 7.73-7.81 (m, 3H), 7.60-7.64 (m, 1H), 6.92-6.96 (m, 1H), 6.58-6.65 (m, 1H), 4.27-4.35 (m, 2H), 3.95-4.05 (m, 4H), 3.88-3.89 (m, 3H), 3.55-3.60 (m, 2H), 3.12-3.18 (m, 2H), 3.02-3.05 (m, 3H), 2.89-2.95 (m, 3H), 2.06-2.15 (m, 2H), 1.18-1.25 (m, 6H). MS (ESI): m/z 706.81 [M+H]$^+$. UPLC: $t_R$=1.12 min (UPLC-SQD: analytical_2 min).

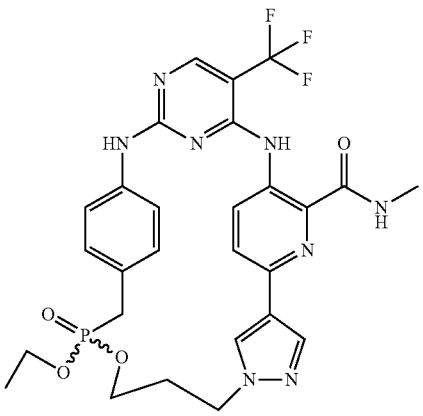

Example 13

(10S)-10-ethoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate (Compound 13A, 144 mg, 0.227 mmol) to afford 49 mg $^1$H NMR (400 MHz, DMSO-d$_6$) δ 10.77 (s, 1H), 9.86 (s, 1H), 9.05 (q, J=4.6 Hz, 1H), 8.66 (s, 1H), 8.45 (s, 1H), 8.41 (s, 1H), 8.18 (d, J=8.6 Hz, 1H), 7.84 (d, J=8.6 Hz, 1H), 7.32 (d, J=8.3 Hz, 2H), 7.03 (dd, J=2.0, 8.6 Hz, 2H), 4.36 (t, J=6.2 Hz, 2H), 3.76-3.91 (m, 2H), 3.59-3.69 (m, 1H), 3.34-3.42 (m, 1H), 3.11-3.29 (m, 2H), 2.84 (d, J=5.0 Hz, 3H), 2.02-2.23 (m, 2H), 1.05 (t, J=7.1 Hz, 3H). MS (ES+): m/z=617.70 [M+H]$^+$. UPLC: $t_R$=1.12 min (UPLC-SQD: analytical_2 min).

Compound 13A: Ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to compound 3A using diethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate (Compound 13B, 0.316 g, 0.476 mmol) to afford 144 mg of the title compound (48%). $^1$H NMR (400 MHz, DMSO-d$_6$) δ 12.43 (s, 1H), 9.66 (s, 1H), 9.40 (br. s., 1H), 9.12 (d, J=5.1 Hz, 1H), 9.01 (br. s., 1H), 8.39 (s, 1H), 8.33 (s, 1H), 7.16-7.31 (m, 4H), 6.32 (br. s., 1H), 4.18 (t, J=6.1 Hz, 2H), 3.61 (quin, J=7.1 Hz, 2H), 3.47 (q, J=5.7 Hz, 2H), 2.87 (d, J=5.1 Hz, 3H), 2.72 (d, J=20.2 Hz, 2H), 1.86-2.00 (m, 2H), 0.95 (t, J=6.9 Hz, 3H). MS (ES+): m/z=635.71 [M+H]$^+$. UPLC: $t_R$=1.08 min (analytical_2 min)

Compound 13B: Diethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to Compound 1B using 3-amino-6-[1-(3-hydroxypropyl)-1H-pyrazol-4-yl]-N-methylpyridine- 2-carboxamide (Compound 6C, 220 mg, 0.80 mmol) and diethyl (4-{[4-chloro-5-(trifluoromethyl)pyrimidin-2-yl] amino}benzyl)phosphonate (Compound 2C, 305 mg, 0.72 mmol) to afford 320 mg of the title compound (62%). $^1$H NMR (400 MHz, DMSO-$d_6$) δ 12.46 (s, 1H), 9.87 (s, 1H), 9.17 (d, J=5.1 Hz, 1H), 8.63 (s, 1H), 8.46 (s, 1H), 8.33 (s, 1H), 7.82 (d, J=9.1 Hz, 1H), 7.43-7.56 (m, 2H), 7.28 (dd, J=2.0, 8.3 Hz, 2H), 4.63 (t, J=4.9 Hz, 1H), 4.21 (t, J=7.2 Hz, 2H), 3.90-4.03 (m, 4H), 3.40-3.47 (m, 2H), 3.25 (d, J=21.2 Hz, 2H), 2.89 (d, J=5.1 Hz, 3H), 1.98 (quin, J=6.7 Hz, 2H), 1.16 (t, J=7.1 Hz, 6H). MS (ES+): m/z=663.73 [M+H]$^+$. UPLC: 1.21 min (UPLC-SQD: analytical_2 min).

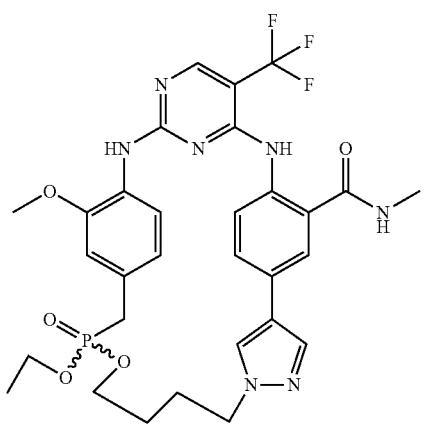

Example 14

(11S)-11-ethoxy-15-methoxy-N-methyl-21-(trifluoromethyl)-10-oxa-4,5,17,19,23,29-hexaaza-11-phosphapentacyclo[22.2.2.2$^{13,16}$.1$^{2,5}$.1$^{18,22}$]dotriaconta-1(26),2(32),3,13,15,18(29),19,21,24,27,30-undecaene-25-carboxamide 11-oxide and (11R)-11-ethoxy-15-methoxy-N-methyl-21-(trifluoromethyl)-10-oxa-4,5,17,19,23,29-hexaaza-11-phosphapentacyclo[22.2.2.2$^{13,16}$.1$^{2,5}$.1$^{18,22}$]dotriaconta-1(26),2(32),3,13,15,18(29),19,21,24,27,30-undecaene-25-carboxamide 11-oxide Prepared analogously to Example 3 using ethyl hydrogen (4-{[4-({4-[1-(4-hydroxybutyl)-1H-pyrazol-4-yl]-2-(methylcarbamoyl)phenyl}amino)-5-(trifluoromethyl)pyrimidin-2-yl]amino}-3-methoxybenzyl)phosphonate (Compound 14A, 58.9 mg, 86.9 μmol) to afford 18 mg of the title compound (31%). $^1$H NMR (400 MHz, CD$_3$OD) δ 8.31 (s, 1H), 8.28 (s, 1H), 7.98 (s, 1H), 7.89 (d, J=1.8 Hz, 1H), 7.76-7.81 (m, 1H), 7.71-7.75 (m, 1H), 7.66 (d, J=7.6 Hz, 1H), 6.86 (t, J=1.9 Hz, 1H), 6.50 (td, J=2.3, 8.3 Hz, 1H), 4.28-4.36 (m, 2H), 3.87-4.01 (m, 4H), 3.82-3.87 (m, 3H), 3.07-3.25 (m, 2H), 2.87 (s, 3H), 1.98-2.07 (m, 2H), 1.65 (dt, J=2.2, 7.0 Hz, 2H), 1.09-1.16 (m, 3H). MS (ESI): m/z 660.77 [M+H]$^+$. UPLC: $t_R$=1.15 min (UPLC-SQD: analytical_2 min).

Compound 14A: Ethyl hydrogen (4-{[4-({4-[1-(4-hydroxybutyl)-1H-pyrazol-4-yl]-2-(methylcarbamoyl)phenyl}amino)-5-(trifluoromethyl)pyrimidin-2-yl]amino}-3-methoxybenzyl)phosphonate Prepared analogously to Compound 3A using diethyl (4-{[4-({4-[1-(4-hydroxybutyl)-1H-pyrazol-4-yl]-2-(methylcarbamoyl)phenyl}amino)-5-(trifluoromethyl)pyrimidin-2-yl] amino}-3-methoxybenzyl)phosphonate (Compound 14B, 63.6 mg, 0.09 mmol) to afford 59 mg of the title compound (96%). $^1$H NMR (400 MHz, CD$_3$OD) δ 8.34 (d, J=8.6 Hz, 1H), 8.28 (s, 1H), 8.15 (s, 1H), 7.91 (d, J=0.5 Hz, 1H), 7.87 (d, J=8.1 Hz, 1H), 7.83 (d, J=2.3 Hz, 1H), 7.65 (dd, J=2.15, 8.72 Hz, 1H), 7.06 (t, J=1.9 Hz, 1H), 6.80 (dd, J=1.9, 8.2 Hz, 1H), 4.23 (t, J=6.9 Hz, 2H), 3.90 (s, 3H), 3.83 (quin, J=7.0 Hz, 2H), 3.56-3.62 (m, 2H), 2.93-3.00 (m, 2H), 2.91 (s, 3H), 1.92-2.02 (m, 2H), 1.50-1.60 (m, 2H), 1.14 (t, J=7.1 Hz, 3H). MS (ESI): m/z 678.79 [M+H]$^+$. UPLC: $t_R$=1.02 min (UPLC-SQD: analytical_2 min).

Compound 14B: Diethyl (4-{[4-({4-[1-(4-hydroxybutyl)-1H-pyrazol-4-yl]-2-(methyl carbamoyl) phenyl}amino)-5-(trifluoromethyl)pyrimidin-2-yl] amino}-3-methoxybenzyl) phosphonate Prepared analogously to Compound 1B replacing Compound 1C with 2-amino-5-[1-(4-hydroxybutyl)-1H-pyrazol-4-yl]-N-methylbenzamide (Compound 14B, 63 mg, 0.22 mmol) and to afford 64 mg of the title compound (41%). $^1$H NMR (400 MHz, CD$_3$OD) δ 8.32 (d, J=8.6 Hz, 1H), 8.28 (s, 1H), 8.09 (s, 1H), 7.95 (d, J=8.1 Hz, 1H), 7.92 (s, 1H), 7.83 (d, J=2.0 Hz, 1H), 7.62 (dd, J=2.0, 8.6 Hz, 1H), 6.96 (t, J=1.9 Hz, 1H), 6.79 (td, J=2.2, 8.2 Hz, 1H), 4.21 (t, J=7.1 Hz, 2H), 3.98-4.07 (m, 4H), 3.88 (s, 3H), 3.59 (t, J=6.4 Hz, 2H), 3.23 (s, 1H), 3.18 (s, 1H), 2.91 (s, 3H), 1.92-2.01 (m, 2H), 1.50-1.59 (m, 2H), 1.23 (t, J=7.1 Hz, 6H). MS (ESI): m/z 706.77 [M+H]$^+$. UPLC: $t_R$=1.18 min (UPLC-SQD: analytical_2 min).

Example 14B

2-Amino-5-[1-(4-hydroxybutyl)-1H-pyrazol-4-yl]-N-methylbenzamide

Prepared analogously to Compound 3C using 2-amino-5-bromo-n-methyl-benzamide (Compound 8D, 300 mg, 1.31 mmol) and 4-[4-(4,4,5,5-tetramethyl-1,3,2-dioxaborolan-2-yl)-1H-pyrazol-1-yl]butan-1-ol (Compound 14C, 383 mg, 1.44 mmol) to afford 64 mg of the title compound (17%). $^1$H NMR (400 MHz, CDCl$_3$) δ 7.67 (s, 1H), 7.54 (s, 1H), 7.40 (d, J=2.0 Hz, 1H), 7.32 (dd, J=2.0, 8.6 Hz, 1H), 6.71 (d, J=8.3 Hz, 1H), 6.13 (br. s., 1H), 5.43 (br. s., 2H), 4.20 (t, J=6.9 Hz, 2H), 3.65-3.72 (m, 2H), 3.01 (d, J=5.1 Hz, 3H), 2.01 (quin, J=7.3 Hz, 2H), 1.58-1.67 (m, 3H).

Compound 14C: 4-[4-(4,4,5,5-tetramethyl-1,3,2-dioxaborolan-2-yl)-1H-pyrazol-1-yl]butan-1-ol A mixture of 1-[4-(benzyloxy)butyl]-4-(4,4,5,5-tetramethyl-1,3,2-dioxaborolan-2-yl)-1H-pyrazole (Compound 14D, 12.2 g, 34.3 mmol) and 10% Palladium on carbon (50% water, 2.19 g, 1.03 mmol) in EtOH (50 mL) was evacuated and purged with nitrogen (3×). After a fourth evacuation, the mixture was allowed to stir under 1 atmosphere of hydrogen at RT overnight. The mixture was filtered and concentrated to afford the title product as 9.52 g of a clear colorless oil (100%). $^1$H NMR (400 MHz, CDCl$_3$) δ 7.79 (s, 1H), 7.69 (s, 1H), 4.19 (t, J=6.8 Hz, 2H), 3.69-3.78 (m, 1H), 3.61-3.69 (m, 2H), 1.92-2.02 (m, 2H), 1.56 (dd, J=6.2, 9.0 Hz, 2H), 1.33 (s, 12H).

Compound 14D: 1-[3-(benzyloxy)propyl]-4-(4,4,5,5-tetramethyl-1,3,2-dioxaborolan-2-yl)-1H-pyrazole A solution of 4-(4,4,5,5-Tetramethyl[1,3,2]dioxaborolan-2-yl)-1H-pyrazole (8.47 g, 43.6 mmol) in DMF (85 mL) was treated with 1-bromo-3-benzyloxypropane (10.0 g, 43.6 mmol) and $Cs_2CO_3$ (14.2 g, 43.6 mmol). This mixture was heated to 90° C. and allowed to stir under $N_2$ overnight. The reaction mixture was poured into water and extracted twice with EtOAc. The combined organic layers were washed with water 3 times, once with brine, dried over $Na_2SO_4$, filtered and concentrated to an orange oil which was purified on a Teledyne ISCO Combiflash® Rf system (0-30% EtOAc/DCM) to afford the title compound as 8.5 g of a clear oil (57%). $^1$H NMR (400 MHz, $CDCl_3$) δ 7.79 (s, 1H), 7.66 (s, 1H), 7.29-7.40 (m, 5H), 4.48 (s, 2H), 4.26 (t, J=6.8 Hz, 2H), 3.43 (t, J=5.9 Hz, 2H), 2.16 (quin, J=6.3 Hz, 2H), 1.60 (dd, J=6.6, 8.6 Hz, 2H), 1.33 (s, 12H).

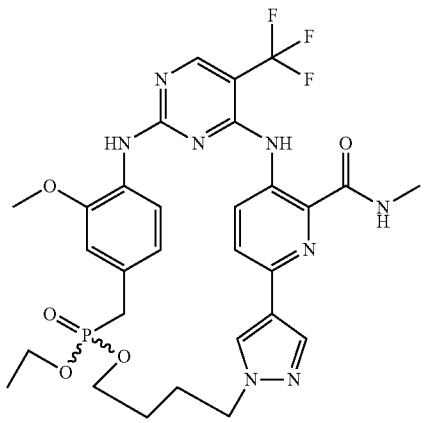

Example 15

(11S)-11-ethoxy-15-methoxy-N-methyl-21-(trifluoromethyl)-10-oxa-4,5,17,19,23,26,29-heptaaza-11-phosphapentacyclo[22.2.2.2$^{13,16}$.1$^{2,5}$.1$^{18,22}$]dotriaconta-1(26), 2(32),3,13,15,18(29),19,21,24,27,30-undecaene-25-carboxamide 11-oxide and (11R)-11-ethoxy-15-methoxy-N-methyl-21-(trifluoromethyl)-10-oxa-4,5,17,19,23,26,29-heptaaza-11-phosphapentacyclo[22.2.2.2$^{13,16}$.1$^{2,5}$.1$^{18,22}$]dotriaconta-1(26), 2(32),3,13,15,18(29),19,21,24,27, 30-undecaene-25-carboxamide 11-oxide Prepared analogously to Example 3 using ethyl hydrogen (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 15A, 106 mg, 157 μmol) to afford 27 mg of the title compound (26%). $^1$H NMR (400 MHz, $CD_3OD$) δ 8.51-8.56 (m, 1H), 8.35-8.38 (m, 1H), 8.33-8.35 (m, 1H), 8.31-8.32 (m, 1H), 7.71-7.77 (m, 1H), 7.55-7.62 (m, 1H), 6.93-6.97 (m, 1H), 6.66-6.75 (m, 1H), 4.30-4.36 (m, 2H), 3.98-4.15 (m, 2H), 3.85 (s, 3H), 3.10-3.17 (m, 2H), 2.97 (s, 3H), 2.02-2.11 (m, 2H), 1.75-1.90 (m, 2H), 1.59-1.69 (m, 2H), 0.98-1.06 (m, 3H). MS (ESI): m/z 661.70 [M+H]$^+$. UPLC: $t_R$=1.24 min (UPLC-SQD: analytical_2 min).

Compound 15A: Ethyl hydrogen (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 3A using diethyl (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 15B, 95 mg, 0.13 mmol) to afford 91 mg of the title compound (99%). $^1$H NMR (400 MHz, $CD_3OD$) δ 8.96 (d, J=6.1 Hz, 1H), 8.50 (s, 1H), 8.29 (s, 1H), 8.20 (s, 1H), 7.69 (d, J=9.1 Hz, 2H), 7.10 (s, 1H), 6.93 (dd, J=2.0, 8.1 Hz, 1H), 4.24 (t, J=6.9 Hz, 2H), 3.83-3.91 (m, 5H), 3.60 (t, J=6.4 Hz, 2H), 2.99-3.06 (m, 2H), 2.98 (s, 3H), 1.94-2.04 (m, 2H), 1.51-1.61 (m, 2H), 1.16 (t, J=7.1 Hz, 3H). MS (ESI): m/z 679.80 [M+H]$^+$. UPLC: $t_R$=1.11 min (UPLC-SQD: analytical_2 min).

Compound 15B: Diethyl (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using 3-amino-6-[1-(4-hydroxybutyl)-1H-pyrazol-4-yl]-N-methylpyridine-2-carboxamide (Compound 15C, 95 mg, 333 μmol) to afford 95 mg of the title compound (40%). $^1$H NMR (400 MHz, $CD_3OD$) δ 8.98 (d, J=8.3 Hz, 1H), 8.42 (s, 1H), 8.28 (s, 1H), 8.20 (s, 1H), 7.76 (d, J=6.1 Hz, 1H), 7.64 (d, J=8.8 Hz, 1H), 7.01 (d, J=1.8 Hz, 1H), 6.90 (td, J=2.2, 8.1 Hz, 1H), 4.22 (t, J=7.1 Hz, 2H), 4.01-4.11 (m, 4H), 3.87 (s, 3H), 3.59 (t, J=6.4 Hz, 2H), 3.28-3.29 (m, 1H), 3.24 (s, 1H), 2.96 (s, 3H), 1.92-2.04 (m, 2H), 1.51-1.60 (m, 2H), 1.25 (t, J=7.1 Hz, 6H). MS (ESI): m/z 707.71 [M+H]$^+$. UPLC: $t_R$=1.25 min (UPLC-SQD: analytical_2 min).

Compound 15C: 3-amino-6-[1-(4-hydroxybutyl)-1H-pyrazol-4-yl]-N-methylpyridine-2-carboxamide Prepared analogously to Compound 6D using ethyl 3-amino-6-[1-(4-hydroxybutyl)-1H-pyrazol-4-yl]pyridine-2-carboxylate (Compound 15D, 0.211 g, 0.69 mmol) to afford 196 mg of the title compound (98%). $^1$H NMR (400 MHz, $CDCl_3$) δ 8.12 (br. s., 1H), 7.87 (s, 1H), 7.81 (s, 1H), 7.36 (d, J=8.6 Hz, 1H), 7.03 (d, J=8.6 Hz, 1H), 5.94 (br. s., 2H), 4.23 (t, J=6.9 Hz, 2H), 3.70 (q, J=5.9 Hz, 2H), 3.03 (d, J=5.1 Hz, 3H), 2.03 (quin, J=7.3 Hz, 2H), 1.60-1.67 (m, 3H).

Compound 15D: Ethyl 3-amino-6-[1-(4-hydroxybutyl)-1H-pyrazol-4-yl]pyridine-2-carboxylate Prepared analogously to Compound 3C using 3-amino-6-bromopyridine-2-carboxylic acid ethyl ester (Compound 6E, 300 mg, 1.22 mmol) and 4-[4-(4,4,5,5-tetramethyl-1,3,2-dioxaborolan-2-yl)-1H-pyrazol-1-yl]butan-1-ol (Compound 14C, 358 mg, 1.35 mmol) to afford 196 mg of the title compound (55%). $^1$H NMR (400 MHz, $CDCl_3$) δ 8.12 (br. s., 1H), 7.87 (s, 1H), 7.81 (s, 1H), 7.36 (d, J=8.6 Hz, 1H), 7.03 (d, J=8.6 Hz, 1H), 5.94 (br. s., 2H), 4.23 (t, J=6.9 Hz, 2H), 3.70 (q, J=5.9 Hz, 2H), 3.03 (d, J=5.1 Hz, 3H), 2.03 (quin, J=7.3 Hz, 2H), 1.60-1.67 (m, 3H) [OH proton obscured].

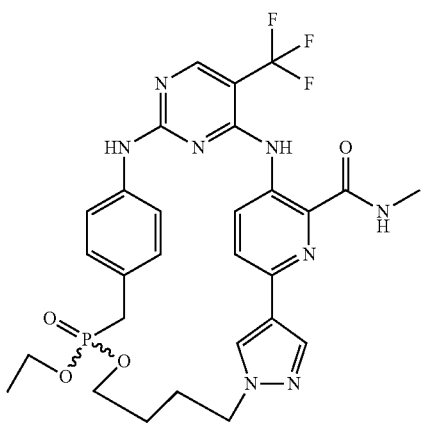

Example 16

11-ethoxy-N-methyl-21-(trifluoromethyl)-10-oxa-4, 5,17,19,23,26,29-heptaaza-11-phosphapentacyclo [22.2.2.2$^{13,16}$.1$^{2,5}$.1$^{18,22}$]dotriaconta-1(26),2(32),3, 13,15,18(29),19,21,24,27,30-undecaene-25-carboxamide 11-oxide Prepared analogously to Example 3 using ethyl hydrogen (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}benzyl)phosphonate (Compound 16A, 109 mg, 168 μmol) to afford 13 mg of the title compound (12%). $^1$H NMR (400 MHz, CD$_3$OD) δ 8.54-8.58 (m, 1H), 8.38-8.43 (m, 1H), 8.34 (s, 1H), 8.33 (s, 1H), 7.78 (d, J=8.8 Hz, 1H), 7.36 (d, J=7.8 Hz, 2H), 7.12 (dd, J=2.5, 8.6 Hz, 2H), 4.33 (s, 2H), 3.78-3.89 (m, 2H), 3.48 (td, J=1.6, 3.3 Hz, 2H), 3.25 (d, J=1.8 Hz, 2H), 2.97 (s, 3H), 2.07 (s, 2H), 1.61-1.74 (m, 2H), 1.03 (t, J=7.1 Hz, 3H). MS (ESI): m/z 631.71 [M+H]$^+$. UPLC: t$_R$=1.19 min (UPLC-SQD: analytical_2 min).

Compound 16A: Ethyl hydrogen (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 3A using (4-{[4-({6-[1-(4-hydroxybutyl)-1H-pyrazol-4-yl]-2-(methylcarbamoyl) pyridin-3-yl}amino)-5-(trifluoromethyl)pyrimidin-2-yl] amino}benzyl)phosphonate (Compound 16B, 127 mg, 188 μmol) to afford 109 mg of the title compound (90%). $^1$H NMR (400 MHz, CD$_3$OD) δ 9.16 (br. s., 1H), 8.44 (br. s., 1H), 8.28 (s, 1H), 8.15-8.19 (m, 1H), 7.67 (d, J=8.8 Hz, 1H), 7.44 (dd, J=2.6, 7.9 Hz, 2H), 7.33 (dd, J=1.9, 8.5 Hz, 2H), 4.22 (t, J=7.1 Hz, 2H), 3.86 (quin, J=7.0 Hz, 2H), 3.57-3.63 (m, 2H), 3.03 (s, 1H), 2.94-3.00 (m, 4H), 1.92-2.05 (m, 2H), 1.50-1.64 (m, 2H), 1.16 (t, J=7.1 Hz, 3H). MS (ESI): m/z 649.75 [M+H]$^+$. UPLC: t$_R$=1.10 min (UPLC-SQD: analytical_2 min).

Compound 16B: Diethyl (4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl] amino}benzyl) phosphonate Prepared analogously to Compound 1B replacing Compound 1C with 3-amino-6-[1-(4-hydroxybutyl)-1H-pyrazol-4-yl]-N-methylpyridine-2-carboxamide (Compound 15C, 96 mg, 333 μmol) and to afford 127 mg of the title compound (56%). $^1$H NMR (400 MHz, CD$_3$OD) δ 9.19 (br. s., 1H), 8.47 (s, 1H), 8.36 (s, 1H), 8.24 (s, 1H), 7.74 (d, J=9.1 Hz, 1H), 7.53 (d, J=7.8 Hz, 2H), 7.32 (dd, J=2.5, 8.6 Hz, 2H), 4.24 (t, J=6.9 Hz, 2H), 4.00-4.10 (m, 4H), 3.59 (t, J=6.6 Hz, 2H), 3.24 (s, 1H), 3.21 (s, 1H), 2.99 (s, 3H), 1.91-2.05 (m, 2H), 1.50-1.60 (m, 2H), 1.25 (t, J=7.1 Hz, 6H). MS (ESI): m/z 677.72 [M+H]$^+$. UPLC: t$_R$=1.22 min (UPLC-SQD: analytical_2 min).

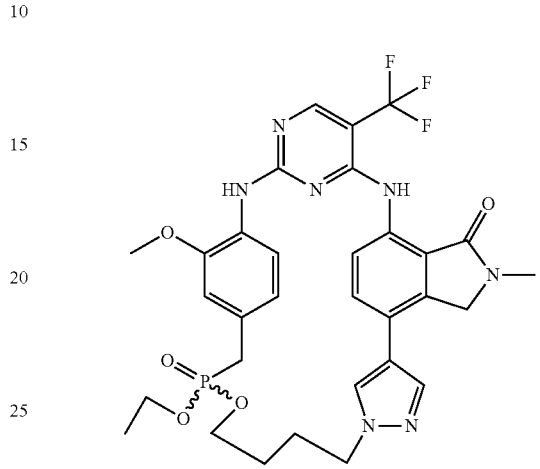

Example 17

(11S)-11-Ethoxy-15-methoxy-27-methyl-21-(trifluoromethyl)-10-oxa-4,5,17,19,23,27,32-heptaaza-11-phosphahexacyclo[22.5.2.2$^{13,16}$.1$^{2,5}$.1$^{18,22}$.0$^{25,29}$] pentatriaconta-1(29),2(35),3,13,15,18(32),19,21,24, 30,33-undecaen-26-one 11-oxide and (11S)-11-Ethoxy-15-methoxy-27-methyl-21-(trifluoromethyl)-10-oxa-4,5,17,19,23,27,32-heptaaza-11-phosphahexacyclo[22.5.2.2$^{13,16}$.1$^{2,5}$.1$^{18,22}$.0$^{25,29}$] pentatriaconta-1(29),2(35),3,13,15,18(32),19,21,24, 30,33-undecaen-26-one 11-oxide Prepared analogously to Example 3 using ethyl hydrogen (4-{[4-({7-[1-(4-hydroxybutyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate (Compound 17A, 91 mg, 131 μmol) to afford 19 mg of the title compound (21%). $^1$H NMR (400 MHz, CD$_3$OD) δ 8.38 (s, 1H), 8.32 (s, 1H), 8.13 (d, J=8.6 Hz, 1H), 7.80 (s, 1H), 7.71 (d, J=8.8 Hz, 1H), 7.53 (d, J=7.3 Hz, 1H), 7.03 (s, 1H), 6.83 (d, J=8.1 Hz, 1H), 4.65 (s, 2H), 4.33 (t, J=5.3 Hz, 2H), 4.09-4.19 (m, 2H), 3.85-3.98 (m, 2H), 3.83 (s, 3H), 3.39-3.49 (m, 2H), 3.18 (s, 3H), 2.01-2.13 (m, 2H), 1.72 (dd, J=7.3, 16.9 Hz, 2H), 1.05 (t, J=7.1 Hz, 3H). MS (ESI): m/z 672.77 [M+H]$^+$. UPLC: t$_R$=1.19 min (UPLC-SQD: analytical_2 min).

Compound 17A: Ethyl hydrogen (4-{[4-({7-[1-(4-hydroxybutyl)-1H-pyrazol-4-yl]-2-methyl-3-oxo-2, 3-dihydro-1H-isoindol-4-yl}amino)-5-(trifluoromethyl)pyrimidin-2-yl]amino}-3-methoxybenzyl) phosphonate Prepared analogously to Compound 3A using diethyl (4-{[4-({7-[1-(4-hydroxybutyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)

phosphonate (Compound 17B, 73 mg, 101 μmol) to afford 71 mg of the title compound (100%). $^1$H NMR (400 MHz, CD$_3$OD) δ 8.49 (d, J=6.57 Hz, 1H), 8.23 (s, 1H), 8.04 (br. s., 1H), 7.77 (s, 2H), 7.57 (d, J=8.84 Hz, 1H), 7.11 (s, 1H), 6.95 (d, J=8.08 Hz, 1H), 4.42 (s, 2H), 4.22 (t, J=7.07 Hz, 2H), 3.82-3.92 (m, 5H), 3.59 (t, J=6.44 Hz, 2H), 3.07-3.11 (m, 3H), 3.03 (d, J=21, 2H), 1.97 (quin, J=7.33 Hz, 2H), 1.51-1.60 (m, 2H), 1.17 (t, J=7.07 Hz, 3H). MS (ESI): m/z 690.80 [M+H]$^+$. UPLC: t$_R$=1.07 min (UPLC-SQD: analytical_2 min).

Compound 17B: Diethyl (4-{[4-({7-[1-(4-hydroxybutyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate Prepared analogously to Compound 1B replacing Compound 1C with 7-amino-4-[1-(4-hydroxybutyl)-1H-pyrazol-4-yl]-2-methyl-2,3-dihydro-1H-isoindol-1-one (Compound 17C, 80 mg, 265 μmol) and to afford 73 mg of the title compound (38%). $^1$H NMR (400 MHz, CD$_3$OD) δ 8.51 (d, J=8.3 Hz, 1H), 8.30 (s, 1H), 8.06 (s, 1H), 7.89 (s, 1H), 7.83 (s, J=4.8 Hz, 1H), 7.65 (d, J=8.6 Hz, 1H), 7.06 (s, 1H), 6.97 (d, J=8.1 Hz, 1H), 4.54 (s, 2H), 4.24 (t, J=7.1 Hz, 2H), 4.02-4.12 (m, 4H), 3.90 (s, 3H), 3.59 (t, J=6.4 Hz, 2H), 3.34 (d, J=3.5 Hz, 1H), 3.28 (s, 1H), 3.16 (s, 3H), 1.93-2.03 (m, 2H), 1.49-1.60 (m, 2H), 1.26 (t, J=7.1 Hz, 6H). MS (ESI): m/z 718.78 [M+H]$^+$. UPLC: t$_R$=1.20 min (UPLC-SQD: analytical_2 min).

Compound 17C: 7-amino-4-[1-(4-hydroxybutyl)-1H-pyrazol-4-yl]-2-methyl-2,3-dihydro-1H-isoindol-1-one Prepared analogously to Compound 3C using 7-amino-4-bromo-2-methyl-2,3-dihydro-1H-isoindol-1-one (Compound 17D, 300 mg, 1.24 mmol) and 4-[4-(4,4,5,5-tetramethyl-1,3,2-dioxaborolan-2-yl)-1H-pyrazol-1-yl]butan-1-ol (Compound 14C, 364 mg, 1.37 mmol) to afford 81 mg of the title compound (22%). $^1$H NMR (400 MHz, CDCl$_3$) d 7.65 (s, 1H), 7.50 (s, 1H), 7.36 (d, J=8.3 Hz, 1H), 6.63 (d, J=8.3 Hz, 1H), 5.25 (br. s., 2H), 4.38 (s, 2H), 4.23 (t, J=7.0 Hz, 2H), 3.70 (t, J=6.2 Hz, 2H), 3.18 (s, 3H), 1.98-2.08 (m, 2H), 1.60-1.66 (m, 2H) [OH obscured].

Compound 17D: 7-Amino-4-bromo-2-methyl-2,3-dihydro-1H-isoindol-1-one

NBS (2.3 g, 12.96) was added to a cold (−8° C. to −10° C.) solution of 7-amino-2-methyl-2,3-dihydro-1H-isoindol-1-one (Compound 17E, 2 g, 12.4 mmol) in DCM (40 mL) and the mixture stirred at −8° C. to −10° C. for 1 h. A solution of 10% aq. sodium thiosulfate (30 mL) was then added to the reaction mixture and stirring was continued for another 20 minutes. The layers were separated and the aqueous layer was extracted with DCM (2×20 mL). The combined organic extracts were washed with water (3×40 mL) and brine (30 mL), and the organic layer was dried (Na$_2$SO$_4$) and concentrated in vacuo to yield 3.2 g of crude product. This material was triturated with ethyl acetate (10 mL) to give 2.2 g of pure 7-amino-4-bromo-2-methyl-2,3-dihydro-1H-isoindol-1-one (yield: 74%). $^1$H NMR (CDCl$_3$ 400 MHz): δ 3.14 (s, 3H), 4.20 (s, 2H), 5.20 (bs, 2H), 5.49 (d, 1H, J=8.4 Hz), 5.79 (d, 1H, J=8.4 Hz).

Compound 17E: 7-Amino-2-methyl-2,3-dihydro-1H-isoindol-1-one

A solution of 2-methyl-7-nitro-2,3-dihydro-1H-isoindol-1-one (Compound 17F, 6.09 g, 31 mmol) in DCM:ethanol (8:2) was hydrogenated under 40 psi of H$_2$ in the presence of 5% Pd/C (500 mg) until cessation of H$_2$ uptake. The reaction mixture was filtered, and the filtrate dried (Na$_2$SO$_4$) and concentrated in vacuo to afford 4.45 g of 7-amino-2-methyl-2,3-dihydro-1H-isoindol-1-one (yield: 73%). $^1$H NMR (CDCl$_3$, 400 MHz): δ 3.11 (s, 3H), 4.27 (s, 2H), 5.19 (bs, 2H), 5.5 (d, 1H, J=7.8 Hz), 6.71 (d, 1H, J=7.2 Hz).

Compound 17F: 2-Methyl-7-nitro-2,3-dihydro-1H-isoindol-1-one

A solution of methylamine in ethanol (10 mL, 80 mmol, 8M solution in ethanol) was added to a solution of methyl 2-(bromomethyl)-6-nitrobenzoate (Compound 17G, 8.1 g, 29.6 mmol) in THF (30 mL). After stirring for 2 h the reaction mixture was concentrated to dryness and water (30 mL) was added with rapid stirring. The solids produced were isolated by filtration and dried to give 4.35 g of 2-methyl-7-nitro-2,3-dihydro-1H-isoindol-1-one (yield: 78%). $^1$H NMR (CDCl$_3$, 400 MHz): δ 3.21 (s, 3H), 4.44 (s, 2H), 7.64 (m, 2H), 7.73-7.74 (m, 1H).

Compound 17G: Methyl 2-(bromomethyl)-6-nitrobenzoate

A solution of methyl 2-methyl-6-nitrobenzoate (Tetrahedron Letters (1996) 37 5425; 15.6 g, 80 mmol), NBS (21.4 g, 120 mmol) and benzoyl peroxide (200 mg, 0.82 mmol) in 1,2-dichloroethane (250 mL) was heated at reflux for 8 h. The reaction mixture was concentrated to dryness and the crude mixture purified by chromatography over silica gel eluting with 2% ethyl acetate/hexanes to afford 10.5 g of methyl 2-(bromomethyl)-6-nitrobenzoate (yield: 65%). $^1$H NMR (CDCl3, 400 MHz): δ 3.98 (s, 3H), 4.57 (s, 2H), 7.59 (dd, 1H, J=7.8, 8.4 Hz), 7.78 (d, 1H, J=7.8 Hz), 8.1 (d, 1H, J=8.4 Hz).

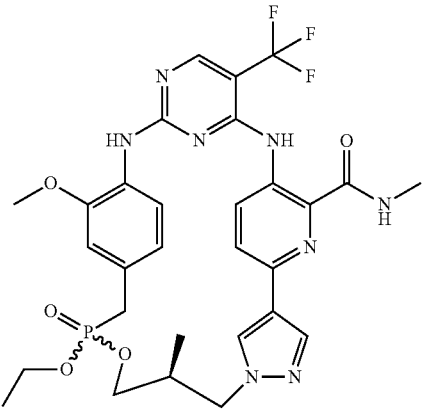

-continued

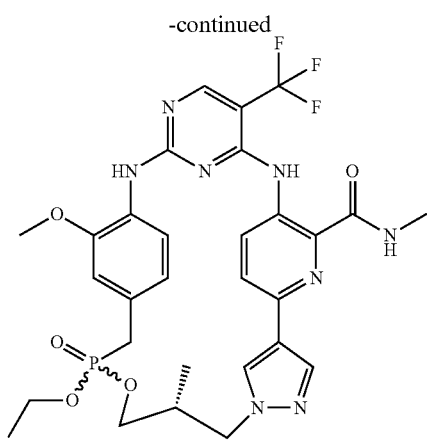

Example 18 and Example 19*

(7S,10S)-10-ethoxy-14-methoxy-N,7-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (7S,10R)-10-ethoxy-14-methoxy-N,7-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide; and (7R,10S)-10-ethoxy-14-methoxy-N,7-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (7R,10R)-10-ethoxy-14-methoxy-N,7-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 18A). Following the chromatography, the material was re-purified by mass directed purification. The fractions from the first eluting peak containing the product ion were combined and concentrated under reduced pressure to afford 4.8 mg of a white solid (7% yield).* $^1$H NMR (CD$_3$OD, 400 MHz): δ=8.40 (s, 1H) 8.32-8.39 (m, 2H) 8.17 (d, J=8.6 Hz, 1H) 7.77 (d, J=8.6 Hz, 1H) 7.55 (d, J=8.3 Hz, 1H) 6.92 (br. s., 1H) 6.65 (d, J=6.6 Hz, 1H) 4.38 (dd, J=13.5, 4.9 Hz, 1H) 4.14-4.25 (m, 1H) 3.87 (s, 3H) 3.68-3.81 (m, 2H) 3.51-3.63 (m, 1H) 3.41-3.51 (m, 1H) 3.33 (d, J=21.0 Hz, 2H, obscured) 2.94 (s, 3H) 2.48 (br. s., 1H) 1.19 (d, J=6.8 Hz, 3H) 0.81-0.88 (m, 3H). MS (ESI): m/z=661.73 [M+H]$^+$. UPLC: t$_R$=1.23 min (UPLC-SQD: analytical_2 min). The fractions from the second eluting peak containing product ion were combined and concentrated under reduced pressure to afford 4.1 mg of a white solid (6% yield).* $^1$H NMR (CD$_3$OD, 400 MHz): δ=8.44 (s, 1H) 8.33-8.37 (m, 2H) 8.10 (d, J=8.6 Hz, 1H) 7.76 (d, J=8.6 Hz, 1H) 7.61 (d, J=8.1 Hz, 1H) 6.88 (s, 1H) 6.56 (dt, J=8.3, 2.3 Hz, 1H) 4.41 (dd, J=13.9, 5.1 Hz, 1H) 4.18 (dd, J=14.0, 9.2 Hz, 1H) 3.99-4.09 (m, 2H) 3.87 (s, 3H) 3.70-3.79 (m, 1H) 3.41-3.50 (m, 1H) 3.20-3.40 (m, 2H) 2.95 (s, 3H) 2.42-2.55 (m, 1H) 1.17-1.25 (m, 6H). MS (ESI): m/z=661.72 [M+H]$^+$. UPLC: t$_R$=1.26 min (UPLC-SQD: analytical_2 min). *(Note—Tentatively assigned stereochemistry, racemic compounds).

Compound 18A: Ethyl hydrogen (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 3A using diethyl (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 18B). $^1$H NMR (CD$_3$OD, 400 MHz): δ=9.02 (br. s., 1H), 8.52 (s, 1H), 8.32 (s, 1H), 8.25 (s, 1H), 7.75 (d, J=8.8 Hz, 1H), 7.64 (br. s., 1H), 7.12 (s, 1H), 6.98-6.92 (m, 1H), 4.29 (dd, J=6.7, 13.5 Hz, 1H), 4.08 (dd, J=7.1, 13.6 Hz, 1H), 3.92-3.83 (m, 5H), 3.48 (d, J=5.8 Hz, 2H), 3.03 (d, J=21.0 Hz, 2H), 2.99 (s, 3H), 2.33-2.23 (m, 1H), 1.15 (t, J=7.1 Hz, 3H), 0.95 (d, J=7.1 Hz, 3H). MS (ESI): m/z=679.75 [M+H]$^+$. UPLC: t$_R$=1.16 min (UPLC-SQD: analytical_2 min).

Compound 18B: Diethyl (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using replacing compound 1C with 3-amino-6-[1-(3-hydroxy-2-methylpropyl)-1H-pyrazol-4-yl]-N-methylpyridine-2-carboxamide (Compound 18C). $^1$H NMR (CD$_3$OD, 400 MHz): δ=8.92 (br. s., 1H) 8.51 (s, 1H) 8.37 (br. s., 1H) 8.31 (s, 1H) 7.77 (d, J=8.8 Hz, 1H) 7.54 (d, J=7.8 Hz, 1H) 7.17 (s, 1H) 7.04 (d, J=7.8 Hz, 1H) 4.29 (dd, J=13.8, 6.44 Hz, 1H) 4.00-4.16 (m, 5H) 3.89 (s, 3H) 3.47 (d, J=5.6 Hz, 2H) 3.37 (d, J=21.7 Hz, 2H) 3.00 (s, 3H) 2.26 (dq, J=12.8, 6.4 Hz, 1H) 1.27 (t, J=7.1 Hz, 6H) 0.94 (d, J=6.8 Hz, 3H). MS (ESI): m/z=707.70 [M+H]$^+$. UPLC: t$_R$=1.29 min (UPLC-SQD: analytical_2 min).

Compound 18C: 3-amino-6-[1-(3-hydroxy-2-methylpropyl)-1H-pyrazol-4-yl]-N-methylpyridine-2-carboxamide Prepared analogously to Compound 3C replacing Compound 3D with Compound 6D and replacing compound 3E with Compound 18D. $^1$H NMR (CDCl$_3$, 400 MHz): δ=8.51 (br. s., 1H) 8.02 (br. s., 1H) 7.90 (s, 1H) 7.42 (d, J=8.3 Hz, 1H) 7.14 (d, J=8.3 Hz, 1H) 4.24-4.31 (m, 1H) 4.17-4.24 (m, 1H) 3.6 (dd, J=11.4, 4.04 Hz, 1H) 3.42 (dd, J=11.1, 6.32 Hz, 1H) 3.03 (d, J=4.8 Hz, 3H) 2.21-2.31 (m, 1H) 1.01 (d, J=6.8 Hz, 3H). MS (ESI): m/z=290.15 [M+H]$^+$. UPLC: t$_R$=0.98 min (UPLC-TOF: polar_3 min).

Compound 18D: 2-methyl-3-[4-(4,4,5,5-tetramethyl-1,3,2-dioxaborolan-2-yl)-1H-pyrazol-1-yl]propan-1-ol Prepared analogously to Compound 3E using 1-[3-(Benzyloxy)-2-methylpropyl]-4-(4,4,5,5-tetramethyl-1,3,2-dioxaborolan-2-yl)-1H-pyrazole to afford 376 mg of the title com pound (91%). ¹H NMR (CDCl₃, 400 MHz): δ=7.81 (s, 1H) 7.70 (s, 1H) 4.22-4.29 (m, 1H) 4.13-4.20 (m, 1H) 3.51-3.55 (m, 1H) 3.50 (s, 1H) 3.36 (dd, J=11.37, 6.57 Hz, 1H) 2.16-2.26 (m, 1H) 1.33 (s, 12H) 0.93 (d, J=6.82 Hz, 3H). MS (ESI): m/z=267.18 [M+H]⁺. UPLC: $t_R$=1.18 min (UPLC-TOF: polar_3 min).

Compound 18E: 1-[3-(Benzyloxy)-2-methylpropyl]-4-(4,4,5,5-tetramethyl-1,3,2-dioxaborolan-2-yl)-1H-pyrazole Potassium carbonate (0.855 g, 6.18 mmol) and 3-(benzyloxy)-2-methylpropyl methanesulfonate (Compound 18F, 1.46 g, 5.67 mmol) were added to a solution of 4-(4,4,5,5-tetramethyl[1,3,2]dioxaborolan-2-yl)-1H-pyrazole (1.0 g, 5.2 mmol) in DMF (4 mL) and the mixture was allowed to stir at 80° C. overnight. The reaction was quenched with water (20 mL) and extracted with EtOAc (50 mL). The organic layer was washed with water (2×30 mL), washed with brine (30 mL), dried over anhydrous sodium sulfate, filtered, and concentrated under reduced pressure. The residue was purified on a Teledyne ISCO Combiflash® Rf system using Heptane/EtOAc (70:30→30:70) as eluent to give the desired product as a light-yellow oil. ¹H NMR (CDCl₃, 400 MHz): δ=7.80 (s, 1H), 7.65 (s, 1H), 7.29-7.37 (m, 5H), 4.49 (s, 2H), 4.26, 4.04 (ABX, $J_{AB}$=13.4 Hz, $J_{AX}$=6.3 Hz, $J_{BX}$=7.1 Hz, 2H), 3.32 (d, J=5.6 Hz, 2H), 2.41 (m, 1H), 1.33 (s, 12H), 0.95 (d, J=6.8 Hz, 3H).

Compound 18F: 3-(Benzyloxy)-2-methylpropyl methanesulfonate

Triethylamine (5.6 g, 55 mmol) and methanesulfonyl chloride (3.8 g, 33 mmol) were added to a solution of 3-benzyloxy-2-methyl-1-propanol (5.0 g, 28 mmol) in DCM (30 mL) at 0° C. and the mixture was allowed to stir overnight while slowly warming to rt. The mixture was diluted with DCM (50 mL), washed with sat. aq. NaHCO₃ (2×30 mL), washed with brine (30 mL), and dried over anhydrous sodium sulfate. The solvent was evaporated under reduced pressure to give the desired product as a yellow oil, 7.2 g, 100% yield. The crude product was used in next step without further purification. ¹H NMR (CDCl₃, 400 MHz): δ=7.30-7.36 (m, 5H), 4.52 (s, 2H), 4.26, 4.20 (ABX, $J_{AB}$=9.6 Hz, $J_{AX}$=5.8 Hz, $J_{BX}$=5.8 Hz, 2H), 3.46, 3.40 (ABX, $J_{AB}$=9.4 Hz, $J_{AX}$=5.0 Hz, $J_{BX}$=7.1 Hz, 2H), 2.97 (s, 3H), 2.22 (m, 2H), 1.04 (d, J=6.8 Hz, 3H).

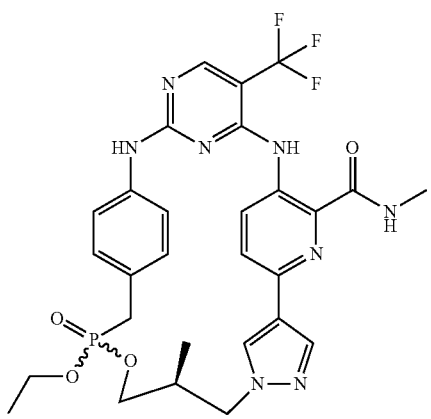

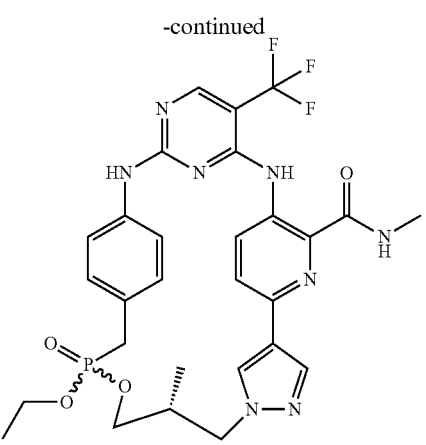

Example 20 and Example 21

(7S,10S)-10-ethoxy-N,7-dimethyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide and (7S,10R)-10-ethoxy-N,7-dimethyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide; and (7R,10R)-10-ethoxy-N,7-dimethyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide and (7R,10S)-10-ethoxy-N,7-dimethyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}benzyl)phosphonate (Compound 20A) to afford the first eluting isomer* ¹H NMR (CD₃OD, 400 MHz): δ=8.42 (s, 1H) 8.36 (s, 1H) 8.33 (s, 1H) 8.17 (d, J=8.3 Hz, 1H) 7.80 (d, J=8.6 Hz, 1H) 7.31 (d, J=8.3 Hz, 2H) 7.09 (d, J=8.3 Hz, 2H) 4.34-4.43 (m, 1H) 4.18 (dd, J=13.6, 10.36 Hz, 1H) 3.65-3.76 (m, 2H) 3.43-3.57 (m, 2H) 3.31 (d, J=21.0 Hz, 2H, obscured) 2.95 (s, 3H) 2.47 (br. s., 1H) 1.19 (d, J=6.8 Hz, 3H) 0.82 (t, J=7.0 Hz, 3H). MS (ESI): m/z=631.75 [M+H]⁺. UPLC: $t_R$=1.18 min (UPLC-SQD: analytical_2 min); and the later eluting isomer*. ¹H NMR (CD₃OD, 400 MHz): δ=8.46 (s, 1H) 8.36 (s, 1H) 8.34 (s, 1H) 8.12 (d, J=8.8 Hz, 1H) 7.78 (d, J=8.8 Hz, 1H) 7.32 (d, J=8.1 Hz, 2H) 7.03 (d, J=7.6 Hz, 2H) 4.41 (dd, J=13.9, 4.80 Hz, 1H) 4.18 (dd, J=14.0, 9.47 Hz, 1H) 4.03 (t, J=7.1 Hz, 2H) 3.76 (td, J=10.0, 4.55 Hz, 1H) 3.44-3.53 (m, 1H) 3.16-3.42 (m, 2H) 2.96 (s, 3H) 2.50 (br. s., 1H) 1.17-1.24 (m, 6H). MS (ESI): m/z=631.72 [M+H]⁺. UPLC: $t_R$=1.20 min (UPLC-SQD: analytical_2 min). *(Note—Tentatively assigned stereochemistry, racemic).

Compound 20A: ethyl hydrogen (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 3A using diethyl (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}benzyl)phosphonate (Compound 20B). $^1$H NMR (CD$_3$OD, 400 MHz): δ=9.20 (br. s., 1H), 8.51 (br. s., 1H), 8.34 (s, 1H), 8.25 (s, 1H), 7.78 (d, J=8.8 Hz, 1H), 7.42 (br. s., 2H), 7.35 (d, J=6.6 Hz, 2H), 4.29 (dd, J=6.6, 13.6 Hz, 1H), 4.15-4.04 (m, 1H), 3.85 (t, J=6.9 Hz, 2H), 3.48 (d, J=5.3 Hz, 2H), 3.05-2.91 (m, 5H), 2.33-2.22 (m, 1H), 1.14 (t, J=6.9 Hz, 3H), 0.95 (d, J=6.8 Hz, 3H). MS (ESI): m/z=649.70 [M+H]$^+$. UPLC: t$_R$=1.13 min (UPLC-SQD: analytical_2 min).

Compound 20B: Diethyl (4-{[4-({6-[1-(3-hydroxy-2-methylpropyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 1B replacing Compound 1C with 3-amino-6-[1-(3-hydroxy-2-methylpropyl)-1H-pyrazol-4-yl]-N-methylpyridine-2-carboxamide (Compound 18C) and Compound 1E with Compound 2C. $^1$H NMR (CD$_3$OD, 400 MHz): δ=9.20 (br. s., 1H) 8.45 (s, 1H) 8.36 (s, 1H) 8.25 (s, 1H) 7.75 (d, J=8.8 Hz, 1H) 7.54 (d, J=7.3 Hz, 2H) 7.32 (d, J=7.6 Hz, 2H) 4.29 (dd, J=13.6, 6.32 Hz, 1H) 4.06 (quin, J=7.1 Hz, 5H) 3.47 (d, J=5.3 Hz, 2H) 3.30 (d, J=21.0 Hz, 2H, obscured) 3.00 (s, 3H) 2.21-2.32 (m, 1H) 1.25 (t, J=7.1 Hz, 6H) 0.95 (d, J=6.8 Hz, 3H). MS (ESI): m/z=677.80 [M+H]$^+$. UPLC: t$_R$=1.26 min (UPLC-SQD: analytical_2 min).

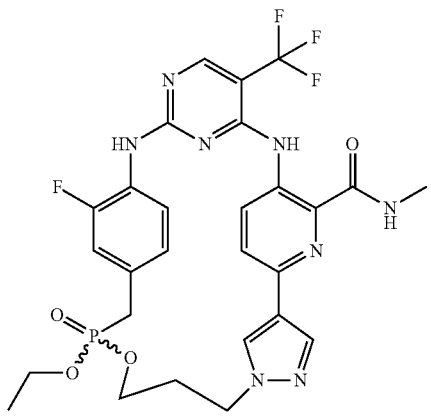

Example 22

(10S)-10-ethoxy-14-fluoro-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-14-fluoro-N-methyl-20-(trifluoromethyl)-9-oxa-4,5,16,18,22,25,28-heptaaza-10-phosphapentacyclo[21.2.2.2$^{12,15}$1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (3-fluoro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate (Compound 22A, 141 mg, 216 μmol) to 14.6 mg of the title compound (11%). $^1$H NMR (400 MHz, CD$_3$OD) δ=8.43 (s, 1H), 8.35 (d, J=4.0 Hz, 2H), 8.18 (d, J=8.8 Hz, 1H), 7.71 (d, J=8.6 Hz, 1H), 7.44 (t, J=8.3 Hz, 1H), 7.15 (td, J=2.0, 11.6 Hz, 1H), 6.92 (d, J=8.3 Hz, 1H), 4.39-4.49 (m, 2H), 3.79 (dd, J=6.6, 11.1 Hz, 1H), 3.68-3.75 (m, 1H), 3.55 (d, J=21.0 Hz, 2H), 3.35 (d, J=3.0 Hz, 2H), 2.92-2.97 (m, 3H), 2.24-2.30 (m, 2H), 0.83 (t, J=7.1 Hz, 3H). MS (ESI): m/z=635.66 [M+H]$^+$. UPLC: t$_R$=1.15 min (UPLC-SQD: analytical_2 min).

Compound 22A: Ethyl hydrogen (3-fluoro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 3A using diethyl (3-fluoro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate (Compound 22B, 156 mg, 230 μmol) to afford 141 mg of the title compound (94%). $^1$H NMR (400 MHz, CD$_3$OD) δ=9.05 (d, J=4.8 Hz, 1H), 8.55 (s, 1H), 8.32 (s, 1H), 8.23 (s, 1H), 7.71 (d, J=8.8 Hz, 1H), 7.50 (t, J=7.8 Hz, 1H), 7.26 (d, J=11.9 Hz, 1H), 7.17 (d, J=8.3 Hz, 1H), 4.31 (t, J=6.8 Hz, 2H), 3.88 (quin, J=7.0 Hz, 2H), 3.58 (t, J=6.1 Hz, 2H), 3.05 (d, J=21.0 Hz, 2H), 2.96-3.00 (m, 3H), 2.11 (quin, J=6.5 Hz, 2H), 1.13 (t, J=7.1 Hz, 3H). MS (ESI): m/z=653.66 [M+H]$^+$. UPLC: t$_R$=1.09 min (UPLC-SQD: analytical_2 min).

Compound 22B: Diethyl (3-fluoro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 1B replacing compound 1C with Compound 6C (278 mg, 1.01 mmol) and Compound 1 E with diethyl (4-{[4-chloro-5-(trifluoromethyl)pyrimidin-2-yl]amino}-3-fluorobenzyl)phosphonate (Compound 22C, 446 mg, 1.01 mmol) to afford 157 mg of the title compound (23%). $^1$H NMR (400 MHz, CD$_3$OD) δ=8.61-8.86 (m, 1H), 8.56 (s, 1H), 8.43 (br. s., 1H), 8.35 (s, 1H), 7.76 (d, J=8.8 Hz, 1H), 7.55 (t, J=8.0 Hz, 1H), 7.37 (dd, J=2.2, 11.0 Hz, 1H), 7.32 (d, J=8.3 Hz, 1H), 4.32 (t, J=7.0 Hz, 2H), 4.12 (quin, J=7.3 Hz, 4H), 3.57 (t, J=6.1 Hz, 2H), 3.42 (d, J=21.0 Hz, 2H), 3.00 (s, 3H), 2.11 (quin, J=6.5 Hz, 2H), 1.17-1.34 (m, 6H). MS (ESI): m/z=681.74 [M+H]$^+$. UPLC: t$_R$=1.20 min (UPLC-SQD: analytical_2 min).

Compound 22C: Diethyl (4-{[4-chloro-5-(trifluoromethyl)pyrimidin-2-yl]amino}-3-fluorobenzyl)phosphonate A solution of 2,6-Dichloro-5-trifluoromethylpyrimidine (4.76 gm, 22 mmol) in 20 mL of dichloroethane and t-butanol (1:1) was treated with a 1M solution of zinc chloride in ether (22 mL, 22 mmol) and allowed to stir at RT for 30 minutes. The mixture was subsequently cooled to 0° C. and treated with a solution of (4-amino-3-fluorobenzyl)phosphonic acid diethyl ester (Compound 22D, 3.3 g, 7.94 mmol) in dichloroethane and t-butanol (10 mL, 1:1) over 10 min through an addition funnel. After 1 hr, diisopropylethylamine (2.2 mL, 12.6 mmol) was added and the mixture was allowed to stir for 24 hours at RT. The solvents were evaporated and the residue was purified using flash column chromatography (9:1 DCM: EtOAc) to afford 3.9 g of the title compound (71%). $^1$H NMR (600 MHz, CDCl₃): δ=1.23-1.28 (m, 6H), 3.1 (d, J=22 Hz, 2H), 4.02-4.09 (m, 4H), 7.09-7.25 (m, 2H), 7.63 (s, 1H), 8.24-8.27 (m, 1H), 8.58 (s, 1H).

Compound 22D: Diethyl (4-amino-3-fluorobenzyl)phosphonate

Prepared starting with (3-fluoro-4-nitrophenyl)methanol and following the procedures used for Compounds 1H-1F. ¹H NMR (300 MHz, CDCl₃): δ=1.25 (t, J=7 Hz, 6H), 3.03 (d, J=21 Hz, 2H), 3.68 (br.s., 2H), 3.99-4.04 (m, 4H), 6.85 (dd, J=8.1 and 1.0 Hz, 1H), 6.84-6.85 (m, 1H), 6.87-6.98 (m, 1H).

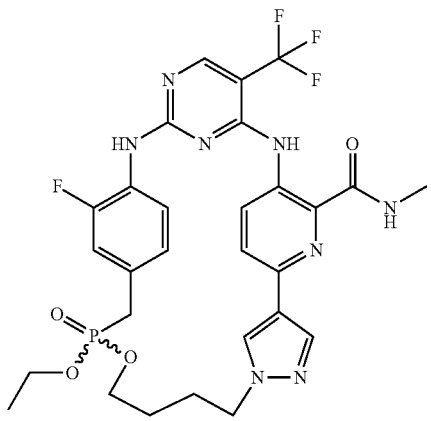

Example 23

(11S)-11-ethoxy-15-fluoro-N-methyl-21-(trifluoromethyl)-10-oxa-4,5,17,19,23,26,29-heptaaza-11-phosphapentacyclo[22.2.2.2¹³,¹⁶.1²,⁵.1¹⁸,²²]dotriaconta-1(26),2(32),3,13,15, 18(29),19,21,24,27,30-undecaene-25-carboxamide 11-oxide and (11R)-11-ethoxy-15-fluoro-N-methyl-21-(trifluoromethyl)-10-oxa-4,5,17,19,23,26,29-heptaaza-11-phosphapentacyclo[22.2.2.2¹³,¹⁶.1²,⁵.1¹⁸,²²]dotriaconta-1(26),2(32),3,13,15, 18(29),19,21,24,27,30-undecaene-25-carboxamide 11-oxide Prepared analogously to Example 3 using ethyl hydrogen (3-fluoro-4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}benzyl)phosphonate (Compound 23A, 115 mg, 172 μmol) to afford 29 mg of the title compound (20%). ¹H NMR (400 MHz, CD₃OD) δ=8.52 (s, 1H), 8.35-8.41 (m, 2H), 8.29 (s 1H), 7.68 (d, J=8.8 Hz, 1H), 7.45 (t, J=8.2 Hz, 1H), 7.17 (d, J=11.4 Hz, 1H), 7.02 (d, J=8.1 Hz, 1H), 4.28-4.34 (m, 2H), 4.01-4.21 (m, 2H), 3.64-3.86 (m, 2H), 3.20 (d, J=21.0 Hz, 2H), 2.96 (s, 3H), 2.08, (dd, J=7.0, 14.5 Hz, 2H), 1.55-1.75 (m, 2H), 0.92 (t, J=7.1 Hz, 3H). MS (ESI): m/z=649.66 [M+H]⁺. UPLC: $t_R$=1.22 min (UPLC-SQD: analytical_2 min).

Compound 23A: Ethyl hydrogen (3-fluoro-4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 3A using diethyl (3-fluoro-4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}benzyl)phosphonate (Compound 23B, 133 mg, 191 μmol) to afford 115 mg of the title compound (90%). ¹H NMR (400 MHz, CD₃OD) δ=8.98-9.08 (m, 1H), 8.56 (s, 1H), 8.32 (s, 1H), 8.23 (s, 1H), 7.71 (d, J=8.8 Hz, 1H), 7.51 (t, J=7.8 Hz, 1H), 7.26 (d, J=11.9 Hz, 1H), 7.18 (d, J=8.1 Hz, 1H), 4.24 (t, J=7.1 Hz, 2H), 3.88 (quin, J=7.0 Hz, 2H), 3.60 (t, J=6.4 Hz, 2H), 3.01-3.10 (m, 2H), 2.96-3.00 (m, 3H), 1.93-2.03 (m, 2H), 1.50-2.06 (m, 2H), 1.14 (t, J=7.07 Hz, 3H). MS (ESI): m/z=667.69 [M+H]⁺. UPLC: $t_R$=1.13 min (UPLC-SQD: analytical_2 min).

Compound 23B: Diethyl (3-fluoro-4-{[4-({6-[1-(4-hydroxybutyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to Compound 1B replacing Compound 1C with 3-amino-6-[1-(4-hydroxybutyl)-1H-pyrazol-4-yl]-n-methylpyridine-2-carboxamide (Compound 15C, 262 mg, 906 μmol) and replacing Compound 1E with diethyl (4-{[4-chloro-5-(trifluoromethyl)pyrimidin-2-yl]amino}-3-fluorobenzyl)phosphonate (Compound 22C, 400 mg, 906 μmol) and to afford the desired product (133 mg, 21%). ¹H NMR (400 MHz, CD₃OD) δ=8.99 (br. s., 1H), 8.49 (s, 1H), 8.36 (s, 1H), 8.27 (s, 1H), 7.70 (d, J=9.1 Hz, 1H), 7.62 (t, J=7.8 Hz, 1H), 7.25 (d, J=11.1 Hz, 1H), 7.20 (d, J=8.1 Hz, 1H), 4.23 (t, J=7.1 Hz, 2H), 4.09 (quin, J=7.3 Hz, 4H), 3.59 (t, J=6.4 Hz, 2H), 3.35 (d, J=21.0 Hz, 2H, obscured), 2.99 (s, 3H), 1.92-2.04 (m, 2H), 1.49-1.61 (m, 2H), 1.25 (t, J=7.1 Hz, 6H). MS (ESI): m/z=695.78 [M+H]⁺. UPLC: $t_R$=1.23 min (UPLC-SQD: analytical_2 min).

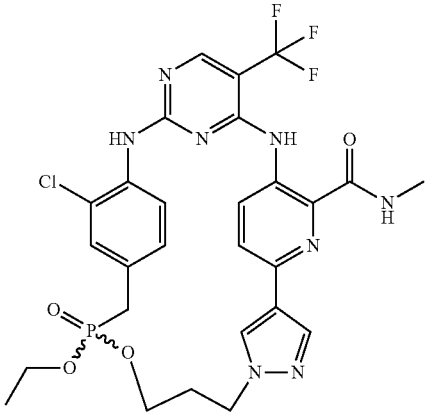

Example 24

(10S)-14-chloro-10-ethoxy-N-methyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14, 17(28),18,20,23,26,29-undecaene-24-carboxamide 10-oxide and (10R)-14-chloro-10-ethoxy-N-methyl-20-(trifluoromethyl)-9-oxa-4,5,16,18,22,25,28-heptaaza-10-phosphapentacyclo[21.2.2.2¹²,¹⁵.1²,⁵.1¹⁷,²¹] hentriaconta-1(25),2(31),3,12,14, 17(28),18,20,23, 26,29-undecaene-24-carboxamide 10-oxide Prepared analogously to Example 3 using ethyl hydrogen (3-chloro-4-{[4-({6-[1-(3-hydroxypropyl)-1H-pyrazol-4-yl]-2-(methylcarbamoyl)pyridin-3-yl}amino)-5-(trifluoromethyl) pyrimidin-2-yl]amino}benzyl)phosphonate (Compound 24A, 169 mg, 253 μmol) to afford 6 mg of the title compound (4%). $^1$H NMR (400 MHz, CD$_3$OD) δ=8.46 (d, J=0.5 Hz, 1H), 8.38 (d, J=0.5 Hz, 1H), 8.35 (d, J=0.5 Hz, 1H), 8.16 (d, J=8.6 Hz, 1H), 7.69 (d, J=8.8 Hz, 1H), 7.60 (d, J=8.1 Hz, 1H), 7.39 (t, J=2.2 Hz, 1H), 7.05 (td, J=2.3, 8.3 Hz, 1H), 4.41-4.47 (m, 2H), 3.75-3.84 (m, 2H), 3.60-3.71 (m, 2H), 3.31 (d, J=21.0 Hz, 2H), 2.94 (s, 3H), 2.25-2.31 (m, 2H), 0.92 (t, J=7.1 Hz, 3H). MS (ESI): m/z=651.64 [M+H]$^+$. UPLC: $t_R$=1.23 min (UPLC-SQD: analytical_2 min).

Compound 24A: Ethyl hydrogen (3-chloro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 3A using diethyl (3-chloro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate (Compound 24B, 176 mg, 253 μmol) to afford 169 mg of the title compound (100%). $^1$H NMR (400 MHz, CD$_3$OD) δ=8.85-8.93 (m, 1H), 8.55 (s, 1H), 8.32 (s, 1H), 8.23 (s, 1H), 7.68 (d, J=9.1 Hz, 1H), 7.52-7.59 (m, 2H), 7.34 (d, J=8.01 Hz, 1H), 4.31 (t, J=6.8 Hz, 2H), 3.88 (t, J=7.1 Hz, 2H), 3.58 (t, J=6.2 Hz, 2H), 3.04 (d, J=21.0 Hz, 2H), 2.98 (s, 3H), 2.11 (t, J=6.3 Hz, 2H), 1.14 (t, J=7.1 Hz, 3H). MS (ESI): m/z=669.66 [M+H]$^+$. UPLC: $t_R$=1.17 min (UPLC-SQD: analytical_2 min).

Compound 24B: Diethyl (3-chloro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate Prepared analogously to Compound 1B replacing Compound 1C with 3-amino-6-[1-(3-hydroxypropyl)-1H-pyrazol-4-yl]-n-methylpyridine-2-carboxamide (Compound 6C, 278 mg, 1.01 mmol) and Compound 1E with diethyl (3-chloro-4-{[4-chloro-5-(trifluoromethyl)pyrimidin-2-yl]amino}benzyl)phosphonate (Compound 24C, 463 mg, 1.01 mmol) to afford 176 mg of the title compound (25%). $^1$H NMR (400 MHz, CD$_3$OD) δ=8.64-8.79 (m, 1H), 8.55 (s, 1H), 8.44 (s, 1H), 8.35 (s, 1H), 7.73 (d, J=9.1 Hz, 1H), 7.65 (t, J=2.3 Hz, 1H), 7.60 (d, J=8.3 Hz, 1H), 7.44-7.49 (m, 1H), 4.28-4.35 (m, 2H), 4.08-4.18 (m, 4H), 3.56 (t, J=6.2 Hz, 2H), 3.42 (d, J=21.0 Hz, 2H), 3.00 (s, 3H), 2.11 (quin, J=6.5 Hz, 2H), 1.26 (t, J=7.1 Hz, 6H). MS (ESI): m/z=697.72 [M+H]$^+$. UPLC: $t_R$=1.28 min (UPLC-SQD: analytical_2 min).

Compound 24C: Diethyl (3-chloro-4-{[4-chloro-5-(trifluoromethyl)pyrimidin-2-yl]amino}benzyl)phosphonate Prepared analogously to Compound 22C using 2,6-Dichloro-5-trifluoromethylpyrimidine (2.2 g, 10.3 mmol) and (4-amino-3-chlorobenzyl)phosphonic acid diethyl ester (Compound 24D, 2.2 g, 7.94 mmol) to afford 1.1 g of the title compound (30%). $^1$H NMR (400 MHz, CDCl$_3$): δ=1.22-1.26 (m, 6H), 3.1 (d, J=22 Hz, 2H), 3.99-4.08 (m, 4H), 7.23 (d, J=8.4 Hz, 1H), 7.36 (s, 1H), 7.83 (brs, 1H), 8.3 (d, J=8.2 Hz, 1H), 8.57 (s, 1H).

Compound 24D: Diethyl (4-amino-3-chlorobenzyl)phosphonate

A solution of diethyl (3-chloro-4-nitrobenzyl)phosphonate (Compound 24E, 0.500 g, 1.62 mmol) in EtOH (10 mL) was charged with iron (0.454 g, 8.12 mmol) and heated to reflux. When the reaction mixture reached reflux, it was charged with 0.1 N aq HCl (0.500 mL, 0.08 mmol) and stirred for 10 min. The reaction mixture was filtered through a pad of celite and the filtrate was concentrated in vacuo. The compound was purified on an Teledyne Isco Combiflash® Rf system eluting with 40 to 90% EtOAc in heptane to afford the title compound. $^1$H NMR (400 MHz, chloroform-d) δ 7.19 (t, J=2.40 Hz, 1H), 7.01 (td, J=2.27, 8.08 Hz, 1H), 6.71 (dd, J=0.63, 8.21 Hz, 1H), 3.96-4.08 (m, 4H), 2.96-3.06 (m, 2H), 1.26 (t, J=7.07 Hz, 6H); MS (ES+): m/z: 278.06 [MH$^+$]. UPLC: $t_R$=1.18 min (UPLC-TOF: polar_3 min).

Compound 24E: Diethyl (3-chloro-4-nitrobenzyl)phosphonate

A solution of 4-(bromomethyl)-2-chloro-1-nitrobenzene (Compound 24F, 2.9 g, 12 mmol) in triethyl phosphite (2.6 mL, 15 mmol) was stirred at 120° C. for 16 h under nitrogen. The reaction mixture was concentrated in vacuo and the residue was purified on an Isco Combiflash eluting with 50 to 90% EtOAc in heptane to afford the title compound. MS (ES+): m/z: 308.04 [MH$^+$]. UPLC: $t_R$=1.33 min (UPLC-TOF: polar_3 min).

Compound 24F: 4-(bromomethyl)-2-chloro-1-nitrobenzene

A solution of 3-chloro-4-nitrotoluene (2.0 g, 12 mmol), NBS (2.62 g, 14.6 mmol) and 2,2'-azo-bis-isobutyronitrile (0.195 g, 1.16 mmol) in α,α,α-trifluorotoluene (200 mL) was heated at 80° C. under an atmosphere of nitrogen for 3 h. Solvent was removed in vacuo and the residue was partitioned between EtOAc and water and separated. The aqueous layer was extracted with EtOAc (3×) and the combined organic fractions were washed with brine, dried over sodium sulfate, filtered, and concentrated. The crude product was taken to the next step without purification.

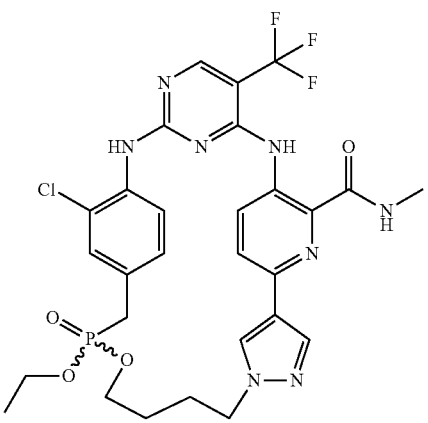

Example 25

(11S)-15-chloro-11-ethoxy-N-methyl-21-(trifluoromethyl)-10-oxa-4,5,17,19,23,26,29-heptaaza-11-phosphapentacyclo[22.2.2.2$^{13,16}$.1$^{2,5}$.1$^{18,22}$]dotriaconta-1(26),2(32),3,13,15,18(29), 19,21,24,27,30-undecaene-25-carboxamide 11-oxide and (11R)-15-chloro-11-ethoxy-N-methyl-21-(trifluoromethyl)-10-oxa-4,5,17,19,23,26,29-heptaaza-11-phosphapentacyclo[22.2.2.2$^{13,16}$.1$^{2,5}$.1$^{18,22}$]dotriaconta-1(26),2(32),3,13,15, 18(29), 19,21,24,27, 30-undecaene-25-carboxamide 11-oxide Prepared analogously to Example 3 using ethyl hydrogen (3-chloro-4-{[4-({6-[1-(4-hydroxybutyl)-1H-pyrazol-4-yl]-2-(methylcarbamoyl)pyridin-3-yl}amino)-5-(trifluoromethyl) pyrimidin-2-yl]amino}benzyl)phosphonate (Compound 25A, 280 mg, 410 μmol) to afford 52 mg of the title compound (19%). $^1$H NMR (400 MHz, CD$_3$OD) δ=8.54 (s, 1H), 8.38 (s, 1H), 8.36 (d, J=8.6 Hz, 1H), 8.29 (s, 1H), 7.66 (d, J=8.8 Hz, 1H), 7.57 (d, J=8.3 Hz, 1H), 7.46 (t, J=2.0 Hz, 1H), 7.16 (td, J=2.1, 8.3 Hz, 1H), 4.32 (t, J=5.8 Hz, 2H), 4.04-4.22 (m, 2H), 3.73-3.91 (m, 2H), 3.38-3.26 (m, 2H, obscured), 2.97 (s, 3H), 2.08 (d, J=4.0 Hz, 2H), 1.59-1.75 (m, 2H), 0.99 (t, J=7.1 Hz, 3H). MS (ESI): m/z=665.63 [M+H]$^+$. UPLC: t$_R$=1.30 min (UPLC-SQD: analytical_2 min).

Compound 25A: Ethyl hydrogen (3-chloro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to Compound 3A using diethyl (3-chloro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl)phosphonate (Compound 25B, 176 mg, 253 μmol) to afford 169 mg of the title compound (99.9%). $^1$H NMR (400 MHz, CD$_3$OD) δ=8.85-8.93 (m, 1H), 8.55 (s, 1H), 8.32 (s, 1H), 8.23 (s, 1H), 7.68 (d, J=9.1 Hz, 1H), 7.52-7.59 (m, 2H), 7.34 (d, J=8.1 Hz, 1H), 4.31 (t, J=6.8 Hz, 2H), 3.88 (t, J=7.1 Hz, 2H), 3.58 (t, J=6.2 Hz, 2H), 3.04 (d, J=21.0 Hz, 2H), 2.98 (s, 3H), 2.11 (t, J=6.3 Hz, 2H), 1.51-1.60 (m, 2H), 1.14 (t, J=7.1 Hz, 3H). MS (ESI): m/z=669.66 [M+H]$^+$. UPLC: t$_R$=1.17 min (UPLC-SQD: analytical_2 min).

Compound 25B: Diethyl (3-chloro-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to Compound 1B replacing Compound 1C with 3-amino-6-[1-(3-hydroxypropyl)-1H-pyrazol-4-yl]-n-methylpyridine-2-carboxamide (Compound 15C, 278 mg, 1.01 mmol) and Compound 1E with diethyl (3-chloro-4-{[4-chloro-5-(trifluoromethyl)pyrimidin-2-yl]amino}benzyl)phosphonate (Compound 24C, 463 mg, 1.01 mmol) and to afford 176 mg of the title compound (25%). $^1$H NMR (400 MHz, CD$_3$OD) δ=8.64-8.79 (m, 1H), 8.55 (s, 1H), 8.44 (s, 1H), 8.35 (s, 1H), 7.73 (d, J=9.1 Hz, 1H), 7.65 (t, J=2.3 Hz, 1H), 7.60 (d, J=8.3 Hz, 1H), 7.44-7.49 (m, 1H), 4.28-4.35 (m, 2H), 4.08-4.18 (m, 4H), 3.56 (t, J=6.2 Hz, 2H), 3.42 (d, J=21.0 Hz, 2H), 3.00 (s, 3H), 2.11 (quin, J=6.5 Hz, 2H), 1.93-2.04 (m, 2H), 1.26 (t, J=7.1 Hz, 6H). MS (ESI): m/z=697.72 [M+H]$^+$. UPLC: t$_R$=1.28 min (UPLC-SQD: analytical_2 min).

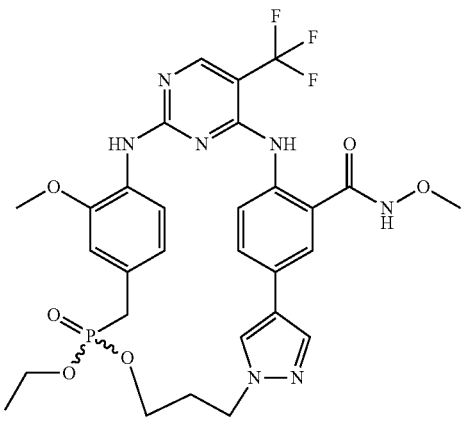

Example 26

(10S)-10-ethoxy-N,14-dimethoxy-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14, 17(28),18,20,23,26,29-undecaene-24-carboxamide 10-oxide and (10R)-10-ethoxy-N,14-dimethoxy-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3, 12,14, 17(28),18,20,23,26,29-undecaene-24-carboxamide 10-oxide Prepared analogously to Example 3 using ethyl hydrogen (4-{[4-({4-[1-(3-hydroxypropyl)-1H-pyrazol-4-yl]-2-(methoxycarbamoyl)phenyl}amino)-5-(trifluoromethyl)pyrimidin-2-yl]amino}-3-methoxybenzyl)phosphonate (Compound 26A, 26 mg, 38.2 μmol) to afford 12 mg of the title compound (47%). $^1$H NMR (400 MHz, CD$_3$OD) δ=8.27 (s, 2H), 8.02 (s, 1H), 7.83 (s, 2H), 7.58 (d, J=8.8 Hz, 1H), 7.51 (d, J=8.3 Hz, 1H), 6.82 (s, 1H), 6.34-6.41 (m, 1H), 4.45 (t, J=5.9 Hz, 2H), 4.02 (quin, J=7.3 Hz, 2H), 3.86 (s, 3H), 3.64-3.77 (m, 5H), 3.12-3.27 (m, 2H), 2.22-2.31 (m, 2H), 1.20-1.24 (m, 3H). MS (ESI): m/z=662.18 [M+H]$^+$. UPLC: t$_R$=1.28 min (UPLC-SQD: analytical_2 min).

Example 26A

Ethyl hydrogen (4-{[4-({4-[1-(3-hydroxypropyl)-1H-pyrazol-4-yl]-2-(methoxycarbamoyl)phenyl}amino)-5-(trifluoromethyl)pyrimidin-2-yl]amino}-3-methoxybenzyl)phosphonate Prepared analogously to Compound 3A using diethyl (4-{[4-({4-[1-(3-hydroxypropyl)-1H-pyrazol-4-yl]-2-(methoxycarbamoyl)phenyl}amino)-5-(trifluoromethyl)pyrimidin-2-yl]amino}-3-methoxybenzyl)phosphonate (Compound 26B, 114 mg, 161 μmol) to afford 108 mg of the title compound (99%). MS (ESI): m/z=680.75 [M+H]$^+$. UPLC: t$_R$=1.02 min (UPLC-SQD: analytical_2 min).

Example 26B

Diethyl (4-{[4-({4-[1-(3-hydroxypropyl)-1H-pyrazol-4-yl]-2-(methoxycarbamoyl)phenyl}amino)-5-(trifluoromethyl)pyrimidin-2-yl]amino}-3-methoxybenzyl)phosphonate Prepared analogously to Compound 1B replacing Compound 1C with 2-amino-5-[1-(3-hydroxypropyl)-1H-pyrazol-4-yl]-N-methoxybenzamide (Compound 26C, 169 mg, 583 µmol) to afford 114 mg of the title compound (28%). ¹H NMR (400 MHz, CD₃OD) δ=8.33 (s, 1H), 8.14 (s, 1H), 7.96 (d, J=0.5 Hz, 1H), 7.92 (d, J=8.1 Hz, 1H), 7.77 (d, J=2.0 Hz, 1H), 7.71 (dd, J=2.2, 8.7 Hz, 1H), 7.00 (t, J=2.2 Hz, 1H), 6.81 (d, J=8.3 Hz, 1H), 4.31 (t, J=7.0 Hz, 2H), 3.99-4.08 (m, 4H), 3.90 (s, 3H), 3.81 (s, 3H), 3.58 (t, J=6.1 Hz, 2H), 3.24 (d, J=21.0 Hz, 2H), 2.10 (quin. J=6.6 Hz, 2H), 1.24 (t, J=7.1 Hz, 6H). MS (ESI): m/z=708.72 [M+H]⁺. UPLC: $t_R$=1.13 min (UPLC-SQD: analytical_2 min).

Example 26C

2-Amino-5-[1-(3-hydroxypropyl)-1H-pyrazol-4-yl]-N-methoxybenzamide

Prepared analogously to Compound 3C replacing Compound 3D with 2-amino-5-bromo-N-methoxybenzamide (Compound 26D, 1 g, 4.08 mmol) to afford 169 mg of the title compound (14%). ¹H NMR (400 MHz, CD₃OD) δ=7.85 (d, J=0.5 Hz, 1H), 7.74 (d, J=0.8 Hz, 1H), 7.54 (d, J=2.0 Hz, 1H), 7.41 (dd, J=2.2, 8.5 Hz, 1H), 6.79 (d, J=8.6 Hz, 1H), 4.25 (t, J=7.0 Hz, 2H), 3.81 (s, 3H), 3.54 (t, J=6.2 Hz, 2H), 2.06 (t, J=6.4 Hz, 2H). MS (ESI): m/z=291.13 [MH]. UPLC: $t_R$=0.85 min (UPLC-TOF: polar_3 min).

Example 26D:
2-Amino-5-bromo-N-methoxybenzamide

Prepared analogously to Compound 3D replacing diethylamine with a mixture of methoxylamine hydrochloride (2.07 g, 24.8 mmol) and triethylamine (6.9 mL, 50 mmol) to afford 2.64 g of the title compound (65%). ¹H NMR (400 MHz, CD₃OD) δ=7.45 (d, J=2.3 Hz, 1H), 7.27 (dd, J=2.3, 8.8 Hz, 1H), 6.69 (d, J=8.8 Hz, 1H), 3.77 (s, 3H).

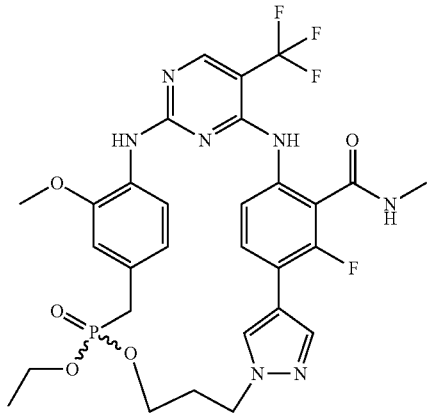

Example 27

(10S)-10-ethoxy-25-fluoro-14-methoxy-N-methyl-20-(trifluoromethyl)-9-oxa-4,5,16,18,22,28-hexaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide and (10S)-10-ethoxy-25-fluoro-14-methoxy-N-methyl-20-(trifluoromethyl)-9-oxa-4,5,16,18,22,28-hexaaza-10-phosphapentacyclo[21.2.2.2¹²,¹⁵.1²,⁵.1¹⁷,²¹] hentriaconta-1(25),2(31),3,12,14,17(28),18,20,23,26, 29-undecaene-24-carboxamide 10-oxide Prepared analogously to Example 3 using ethyl hydrogen (4-{[4-({3-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate (Compound 27A, 190 mg, 278 µmol) to afford 108 mg of the title compound (59%). ¹H NMR (400 MHz, CD₃OD) δ=8.32 (s, 1H), 8.27 (s, 1H), 8.02 (d, J=2.5 Hz, 1H), 7.83 (t, J=8.3 Hz, 1H), 7.51 (d, J=7.8 Hz, 1H), 7.33-7.38 (m, 1H), 6.81 (t, J=1.9 Hz, 1H), 6.37 (td, J=2.3, 8.5 Hz, 1H), 4.47 (t, J=5.9 Hz, 2H), 3.95-4.05 (m, 2H), 3.86 (s, 3H), 3.65-3.83 (m, 2H), 3.15-3.24 (m, 2H), 2.83 (s, 3H), 2.21-2.31 (m, 2H), 1.21 (t, J=7.07 Hz, 3H). MS (ESI): m/z=664.18 [M+H]⁺. UPLC: $t_R$=1.30 min (UPLC-TOF: polar_3 min).

Compound 27A: Ethyl hydrogen (4-{[4-({3-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate Prepared analogously to Compound 3A using diethyl (4-{[4-({3-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate (Compound 27B, 200 mg, 282 µmol) to afford 190 mg of the title compound (99%). ¹H NMR (400 MHz, CD₃OD) δ=8.31 (s, 1H), 8.20 (s, 1H), 7.93 (s, 1H), 7.86 (d, J=8.6 Hz, 1H), 7.77 (d, J=7.6 Hz, 1H), 7.67 (d, J=8.6 Hz, 1H), 7.04 (s, 1H), 6.69 (d, J=7.3 Hz, 1H), 4.37 (t, J=6.8 Hz, 2H), 3.91 (s, 3H), 3.81 (quin, J=7.0 Hz, 2H), 3.62 (t, J=6.1 Hz, 2H), 2.95 (s, 1H), 2.90 (s, 4H), 2.14 (quin, J=6.5 Hz, 2H), 1.15 (t, J=7.1 Hz, 3H). MS (ESI): m/z=682.19 [M+H]⁺. UPLC: $t_R$=1.11 min (UPLC-TOF: polar_3 min).

Compound 27B: Diethyl (4-{[4-({3-fluoro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxy benzyl)phosphonate Prepared analogously to Compound 1B replacing compound 1C with 6-amino-2-fluoro-3-[1-(3-hydroxypropyl)-1H-pyrazol-4-yl]-N-methylbenzamide (281 mg, 961 µmol) to afford 204 mg of the title compound (30%). ¹H NMR (400 MHz, CD₃OD) δ=8.32 (s, 1H), 8.15 (d, J=1.8 Hz, 1H), 7.94-8.01 (m, 2H), 7.89 (d, J=8.1 Hz, 1H), 7.73 (t, J=8.6 Hz, 1H), 6.98 (t, J=2.0 Hz, 1H), 6.77 (d, J=8.1 Hz, 1H), 4.32 (t, J=7.0 Hz, 2H), 3.97-4.07 (m, 4H), 3.89 (s, 3H), 3.55-3.60 (m, 2H), 3.24 (s, 1H), 3.19 (s, 1H), 2.91 (s, 3H), 2.10 (quin, J=6.5 Hz, 2H), 1.23 (t, J=7.1 Hz, 6H). MS (ESI): m/z=710.21 [M+H]⁺. UPLC: $t_R$=1.39 min (UPLC-TOF: polar_3 min).

Compound 27C: 6-amino-2-fluoro-3-[1-(3-hydroxypropyl)-1H-pyrazol-4-yl]-N-methylbenzamide Prepared analogously to Compound 3C replacing Compound 3D with 6-amino-3-bromo-2-fluoro-N-methylbenzamide (Compound 27D, 700 mg, 2.83 mmol) to afford 281 mg of the title compound (34%). ¹H NMR (400 MHz, CD₃OD) δ=7.88 (d, J=1.8 Hz, 1H), 7.76 (d, J=1.0 Hz, 1H), 7.38 (t, J=8.6 Hz, 1H), 6.59 (d, J=8.6 Hz, 1H), 4.26 (t, J=7.0 Hz, 2H), 3.54 (t, J=6.2 Hz, 2H), 2.92 (s, 3H), 1.98-2.13 (m, 2H). MS (ESI): m/z=293.87 [M+H]⁺. UPLC: $t_R$=0.60 min (UPLC-SQD: analytical_2 min).

Compound 27 D:
6-Amino-3-bromo-2-fluoro-N-methylbenzamide

NBS (9.42 g, 52.9 mmol) was added to a cold (0° C.) solution of 5-fluoro-1H-benzo[d][1,3]oxazine-2,4-dione (Compound 27E, 9.2 g, 50.8 mmol) in DCM and DMF (120 mL+60 mL) over the course of 40 min. The reaction mixture was stirred at 0° C. for 2 h then allowed to warm to RT. After 30 min, the DCM was removed in vacuo. The remaining reaction mixture was cooled −10° C., treated with a solution of 2M methyl amine in THF (50.8 mL, 101.6 mmol) and allowed to stir for overnight at room temperature. The reaction mixture was poured to water (240 mL) and the resulting suspension was extracted with ethyl acetate (3×100 mL). The combined ethyl acetate layer was washed with water (3×100 mL), dried (Na$_2$SO$_4$) and concentrated to give crude residue which was purified by column chromatography (20% ethyl acetate/hexanes) to afford 4 g of the title compound (32% over two steps). $^1$H NMR (CDCl$_3$, 500 MHz) δ=2.98 (d, J=4.5 Hz, 3H), 5.90 (brs, 2H), 6.38 (d, J=9.0 Hz, 1H), 6.55 (brs, 1H), 7.24-7.27 (m, 1H).

Compound 27 E:
5-fluoro-1H-benzo[d][1,3]oxazine-2,4-dione

To a solution of 2-amino-6-fluorobenzoic acid (8.0 g, 51.6 mmol) in THF (110 mL) was added triphosgene (7.6 g, 25.8 mmol). The resulting suspension was stirred at 50° C. for 12 h. The reaction mixture was cooled to RT and filtered to give 8.2 g of the title compound as a pink solid (87%). $^1$H NMR (DMSO-d$_6$, 500 MHz) δ=6.95 (d, J=8.5 Hz, 1H), 7.02-7.05 (m, 1H), 7.69-7.72 (m, 1H), 11.85 (brs, 1H).

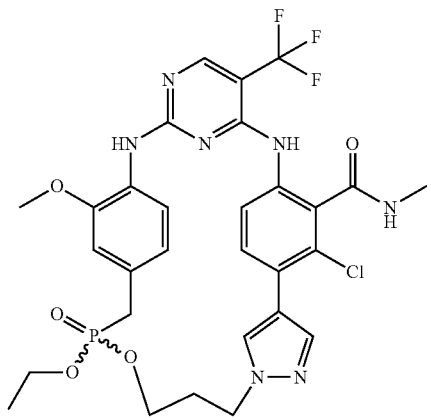

Example 28

(10S)-25-chloro-10-ethoxy-14-methoxy-N-methyl-20-(trifluoromethyl)-9-oxa-4,5,16,18,22,28-hexaaza-10-phosphapentacyclo[21.2.2.2$^{12,15}$1$^{2,5}$.1$^{17,21}$]hentriaconta-1(25),2 (31),3,12,14,17(28),18,20,23,26,29-undecaene-24-carboxamide 10-oxide and (10S)-25-chloro-10-ethoxy-14-methoxy-N-methyl-20-(trifluoromethyl)-9-oxa-4,5,16,18,22,28-hexaaza-10-phosphapentacyclo[21.2.2.2$^{12,15}$1$^{2,5}$.1$^{17,21}$]hentriaconta-1(25),2 (31),3,12,14,17(28),18,20,23,26,29-undecaene-24-carboxamide 10-oxide Prepared analogously to Example 3 using ethyl hydrogen (4-{[4-({3-chloro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate (Compound 28A, 17.4 mg, 24.9 μmol) to afford 17 mg of the title compounds (100%). $^1$H NMR (400 MHz, CD$_3$OD) δ=8.25 (s, 1H), 8.20 (d, J=0.5 Hz, 1H), 8.05 (d, J=0.5 Hz, 1H), 7.72 (d, J=8.3 Hz, 1H), 7.45 (d, J=8.1 Hz, 1H), 7.40 (d, J=8.3 Hz, 1H), 6.81 (t, J=2.0 Hz, 1H), 6.38 (td, J=2.5, 8.2 Hz, 1H), 4.48 (t, J=6.1 Hz, 2H), 3.99-4.10 (m, 2H), 3.87 (s, 3H), 3.64-3.81 (m, 2H), 3.16-3.25 (m, 2H), 2.79 (s, 3H), 2.19-2.29 (m, 2H), 1.25 (t, J=7.1 Hz, 3H). MS (ESI): m/z=680.15 [M+H]$^+$. UPLC: t$_R$=1.27 min (UPLC-TOF: polar_3 min).

Compound 28A: Ethyl hydrogen (4-{[4-({3-chloro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxy benzyl)phosphonate Prepared analogously to Compound 3A using diethyl (4-{[4-({3-chloro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxybenzyl)phosphonate (Compound 28B, 18 mg, 24.8 μmol) to afford 19.4 mg of the title compound. $^1$H NMR (400 MHz, CD$_3$OD) δ=8.29 (s, 1H), 8.21 (s, 1H), 7.99 (d, J=8.6 Hz, 1H), 7.95 (d, J=1.8 Hz, 1H), 7.81 (d, J=8.1 Hz, 1H), 7.74 (t, J=8.6 Hz, 1H), 7.05 (s, 1H), 6.76 (d, J=8.3 Hz, 1H), 4.33 (t, J=6.8 Hz, 2H), 3.89 (s, 3H), 3.82 (s, 2H), 3.58 (t, J=6.1 Hz, 2H), 2.96 (s, 1H), 2.92 (s, 4H), 2.10 (quin, J=6.51 Hz, 2H), 1.13 (t, J=6.95 Hz, 3H). MS (ESI): m/z=698.19 [M+H]$^+$. UPLC: t$_R$=1.06 min (UPLC-TOF: polar_3 min).

Compound 28B: Diethyl (4-{[4-({3-chloro-4-[1-(3-hydroxypropyl)-1H-pyrazol-4-yl]-2-(methylcarbamoyl)phenyl}amino)-5-(trifluoromethyl)pyrimidin-2-yl]amino}-3-methoxy benzyl)phosphonate Prepared analogously to Compound 1B replacing Compound 1C with 6-amino-2-chloro-3-[1-(3-hydroxypropyl)-1H-pyrazol-4-yl]-N-methylbenzamide (Compound 28C, 274 mg, 887 μmol) to afford 21 mg of the title compound (3%). $^1$H NMR (400 MHz, CD$_3$OD) δ=8.31 (s, 1H), 8.17 (s, 1H), 7.93 (s, 1H), 7.84 (d, J=7.8 Hz, 1H), 7.79 (d, J=8.6 Hz, 1H), 7.65 (d, J=8.6 Hz, 1H), 6.94 (t, J=2.0 Hz, 1H), 6.66 (d, J=7.8 Hz, 1H), 4.34 (t, J=6.8 Hz, 2H), 3.95-4.05 (m, 4H), 3.89 (s, 3H), 3.59 (t, J=6.2 Hz, 2H), 3.20 (s, 1H), 3.14 (s, 1H), 2.86 (s, 3H), 2.11 (quin, J=6.6 Hz, 2H), 1.22 (t, J=7.1 Hz, 6H). MS (ESI): m/z=726.19 [M+H]$^+$. UPLC: t$_R$=1.32 min (UPLC-TOF: polar_3 min).

Compound 28C: 6-Amino-2-chloro-3-[1-(3-hydroxypropyl)-1H-pyrazol-4-yl]-N-methyl benzamide Prepared analogously to Compound 3C replacing compound 3D with 6-amino-3-bromo-2-chloro-N-methylbenzamide (Compound 28D, 700 mg, 2.66 mmol) to and to afford 274 mg of the title compound (33%). $^1$H NMR (400 MHz, CD$_3$OD) δ=7.87 (s, 1H), 7.68 (s, 1H), 7.25 (d, J=8.6 Hz, 1H), 6.73 (d, J=8.6 Hz, 1H), 4.27 (t, J=7.0 Hz, 2H), 3.55 (t, J=6.2 Hz, 2H), 2.92 (s, 3H), 2.06 (quin, J=6.5 Hz, 2H). MS (ESI): m/z=309.10 [M+H]$^+$. UPLC: t$_R$=0.81 min (UPLC-TOF: polar_3 min).

Compound 28D:
6-Amino-3-bromo-2-chloro-N-methylbenzamide

Prepared analogously to Compound 27D replacing 5-fluoro-1H-benzo[d][1,3]oxazine-2,4-dione (Compound 27E) with 5-Chloro-1H-benzo[d][1,3]oxazine-2,4-dione (Compound 28E). $^1$H NMR (CDCl$_3$, 500 MHz) δ=2.95 (d, J=5.2 Hz, 3H), 6.02 (brs, 2H), 6.89 (d, J=8.8 Hz, 1H), 7.25 (d, J=8.8 Hz, 1H), 7.79 (brs, 1H).

Compound 28E:
5-Chloro-1H-benzo[d][1,3]oxazine-2,4-dione

Prepared analogously to Compound 27E replacing 2-amino-6-fluorobenzoic acid with 2-amino-6-chlorobenzoic acid. $^1$H NMR (DMSO-$d_6$, 400 MHz) δ=7.07 (dd, J=0.8, 8 Hz, 1H), 7.24-7.27 (m, 1H), 7.58-7.63 (m, 1H), 11.81 (brs, 1H).

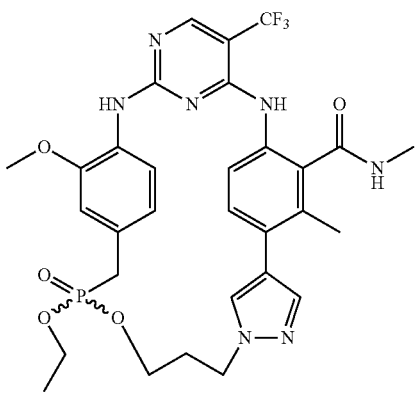

Example 29

(10S)-10-Ethoxy-14-methoxy-N,25-dimethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-14-methoxy-N,25-dimethyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({4-[1-(3-hydroxypropyl)-1H-pyrazol-4-yl]-3-methyl-2-(methylcarbamoyl)phenyl}amino)-5-(trifluoromethyl) pyrimidin-2-yl]amino}-3-methoxybenzyl)phosphonate (Compound 29A). $^1$H NMR (CD$_3$OD, 400 MHz): δ 8.25 (s, 1H), 8.01 (s, 1H), 7.84 (s, 1H), 7.57 (d, J=8.3 Hz, 1H), 7.46 (d, J=8.3 Hz, 1H), 7.29 (d, J=8.1 Hz, 1H), 6.82 (t, J=1.8 Hz, 1H), 6.34 (dt, J=8.6, 2.3 Hz, 1H), 4.50 (t, J=6.1 Hz, 2H), 4.08 (m, 2H), 3.89 (s, 3H), 3.65-3.85 (m, 2H), 3.13-3.35 (m, 2H), 2.81 (s, 3H), 2.42 (s, 3H), 2.26 (m, 2H), 1.29 (t, J=7.1 Hz, 3H). MS (ESI): m/z=660.20 [MH$^+$]. UPLC: $t_R$=1.27 min (UPLC-TOF: polar_3 min).

Compound 29A: Ethyl hydrogen (4-{[4-({4-[1-(3-hydroxypropyl)-1H-pyrazol-4-yl]-3-methyl-2-(methylcarbamoyl)phenyl}amino)-5-(trifluoromethyl)pyrimidin-2-yl]amino}-3-methoxybenzyl)phosphonate Prepared analogously to Compound 3A using diethyl (4-{[4-({4-[1-(3-hydroxypropyl)-1H-pyrazol-4-yl]-3-methyl-2-(methyl carbamoyl)phenyl}amino)-5-(trifluoromethyl) pyrimidin-2-yl]amino}-3-methoxybenzyl)phosphonate (Compound 29B). $^1$H NMR (CD$_3$OD, 400 MHz): δ 8.25 (s, 1H), 7.92 (s, 1H), 7.79 (d, J=8.1 Hz, 1H), 7.69 (s, 1H), 7.64 (d, J=8.3 Hz, 1H), 7.46 (d, J=8.4 Hz, 1H), 6.99 (s, 1H), 6.59 (d, J=6.8 Hz, 1H), 4.35 (t, J=6.8 Hz, 2H), 3.88 (s, 3H), 3.79 (m, 2H), 3.60 (t, J=6.1 Hz, 2H), 2.87 (d, J=21.5 Hz, 2H), 2.85 (s, 3H), 2.36 (s, 3H), 2.12 (m, 2H), 1.13 (t, J=7.1 Hz, 3H). MS (ESI): m/z=678.23 [M+H]$^+$. UPLC: $t_R$=1.03 min (UPLC-TOF: polar_3 min).

Compound 29B: Diethyl (4-{[4-({4-[1-(3-hydroxypropyl)-1H-pyrazol-4-yl]-3-methyl-2-(methyl carbamoyl)phenyl}amino)-5-(trifluoromethyl)pyrimidin-2-yl]amino}-3-methoxybenzyl)phosphonate Prepared analogously to Compound 1B replacing Compound C with 6-amino-3-[1-(3-hydroxypropyl)-1H-pyrazol-4-yl]-N,2-dimethyl benzamide (Compound 29C). $^1$H NMR (CD$_3$OD, 400 MHz): δ=8.28 (s, 1H), 7.92 (s, 1H), 7.89 (d, J=8.3 Hz, 1H), 7.72 (s, 1H), 7.63 (d, J=8.4 Hz, 1H), 7.48 (d, J=8.3 Hz, 1H), 6.92 (t, J=2.0 Hz, 1H), 6.60 (d, J=7.4 Hz, 1H), 4.35 (t, J=6.8 Hz, 2H), 4.00 (m, 4H), 3.89 (s, 3H), 3.60 (t, J=6.1 Hz, 2H), 3.16 (d, J=21.5 Hz, 2H), 2.85 (s, 3H), 2.37 (s, 3H), 2.12 (m, 2H), 1.22 (t, J=7.1 Hz, 6H). MS (ESI): m/z=706.58 [M+H]$^+$. HPLC: $t_R$=3.47 min (ZQ3: polar_5 min).

Compound 29C: 6-Amino-3-[1-(3-hydroxypropyl)-1H-pyrazol-4-yl]-N,2-dimethyl benzamide Prepared analogously to Compound 3C substituting 6-amino-3-bromo-2-methyl-N-methylbenzamide (Compound 29D) for 2-amino-5-bromo-N,N-diethylbenzamide (Compound 3D). MS (ESI): m/z=289.29 [M+H]$^+$. UPLC: $t_R$=2.33 min (ZQ3: polar_5 min).

Compound 29D:
6-Amino-3-bromo-2-methyl-N-methylbenzamide

Prepared analogously to Compound 27D replacing 5-fluoro-1H-benzo[d][1,3]oxazine-2,4-dione (Compound 27E) with 5-methyl-1H-benzo[d][1,3]oxazine-2,4-dione (Compound 29E). $^1$H NMR (CDCl$_3$, 500 MHz) δ 2.32 (s, 3H), 2.98 (d, J=4.8 Hz, 3H), 4.0 (br.s, 2H), 5.81 (br.s, 1H), 6.42 (d, J=8.8 Hz, 1H), 7.27 (d, J=8.8 Hz, 1H).

Compound 29E:
5-Methyl-1H-benzo[d][1,3]oxazine-2,4-dione

Prepared analogously to Compound 27E replacing 2-amino-6-fluorobenzoic acid with 2-amino-6-methylbenzoic acid. $^1$H NMR (DMSO-$d_6$, 500 MHz) δ 2.32 (s, 3H), 7.09 (m, 1H), 7.21-7.25 (m, 1H), 7.51-7.61 (m, 1H), 11.65 (br.s, 1H).

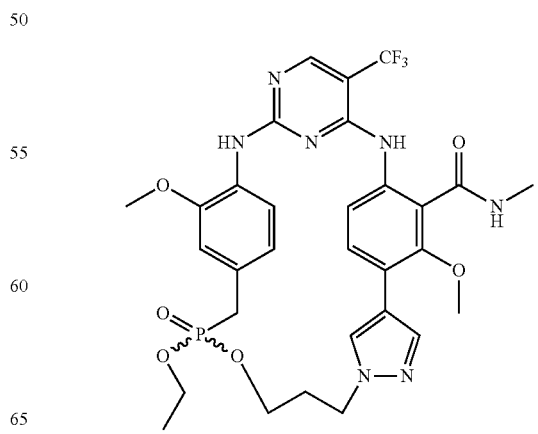

Example 30

(10S)-10-Ethoxy-14,25-dimethoxy-N-methyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-14,25-dimethoxy-N-methyl-20-(trifluoromethyl)-9-oxa-4,5,16,18,22,28-hexaaza-10-phosphapentacyclo[21.2.2.2$^{12,15}$1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({4-[1-(3-hydroxypropyl)-1H-pyrazol-4-yl]-3-methoxy-2-(methylcarbamoyl)phenyl}amino)-5-(trifluoromethyl)pyrimidin-2-yl]amino}-3-methoxybenzyl)phosphonate (Compound 30A). $^1$H NMR (CD$_3$OD, 400 MHz): δ 8.30 (s, 1H), 8.26 (s, 1H), 8.08 (s, 1H), 7.74 (dd, J=8.4, 1.5 Hz, 1H), 7.50 (d, J=8.4 Hz, 1H), 7.27 (dd, J=8.4, 1.3 Hz, 1H), 6.81 (s, 1H), 6.33 (d, J=8.4 Hz, 1H), 4.48 (t, J=5.6 Hz, 2H), 4.05 (m, 2H), 3.87 (s, 3H), 3.65-3.85 (m, 2H), 3.73 (s, 3H), 3.10-3.28 (m, 2H), 2.85 (s, 3H), 2.28 (m, 2H), 1.25 (t, J=7.1 Hz, 3H). MS (ESI): m/z=676.20 [M+H]$^+$. UPLC: t$_R$=1.29 min (UPLC-TOF: polar__3 min).

Compound 30A: Ethyl hydrogen (4-{[4-({4-[1-(3-hydroxypropyl)-1H-pyrazol-4-yl]-3-methoxy-2-(methylcarbamoyl)phenyl}amino)-5-(trifluoromethyl)pyrimidin-2-yl]amino}-3-methoxybenzyl)phosphonate Prepared analogously to Compound 3A using diethyl (4-{[4-({4-[1-(3-hydroxypropyl)-1H-pyrazol-4-yl]-3-methoxy-2-(methyl carbamoyl)phenyl}amino)-5-(trifluoromethyl)pyrimidin-2-yl]amino}-3-methoxy benzyl)phosphonate (Compound 30B). $^1$H NMR (CD$_3$OD, 400 MHz): δ 8.27 (s, 1H), 8.18 (s, 1H), 7.98 (s, 1H), 7.86 (d, J=8.3 Hz, 1H), 7.83 (d, J=7.8 Hz, 1H), 7.66 (d, J=8.8 Hz, 1H), 7.02 (s, 1H), 6.69 (d, J=8.1 Hz, 1H), 4.33 (t, J=6.8 Hz, 2H), 3.88 (s, 3H), 3.82 (m, 2H), 3.64 (s, 3H), 3.59 (t, J=6.1 Hz, 2H), 2.92 (s, 3H), 2.91 (d, J=20.2 Hz, 2H), 2.11 (m, 2H), 1.13 (t, J=7.1 Hz, 3H). MS (ESI): m/z=694.22 [M+H]$^+$. UPLC: t$_R$=1.09 min (UPLC-TOF: polar__3 min).

Compound 30B: Diethyl (4-{[4-({4-[1-(3-hydroxypropyl)-1H-pyrazol-4-yl]-3-methoxy-2-(methyl carbamoyl)phenyl}amino)-5-(trifluoromethyl)pyrimidin-2-yl]amino}-3-methoxy benzyl)phosphonate Prepared analogously to Compound 1B replacing Compound 1C with 6-amino-3-[1-(3-hydroxypropyl)-1H-pyrazol-4-yl]-2-methoxy-N-methyl benzamide (Compound 30C). $^1$H NMR (CD$_3$OD, 400 MHz): δ 8.31 (s, 1H), 8.17 (s, 1H), 8.00 (s, 1H), 7.92 (d, J=8.4 Hz, 1H), 7.84 (d, J=8.6 Hz, 1H), 7.67 (d, J=8.6 Hz, 1H), 6.96 (t, J=2.0 Hz, 1H), 6.70 (d, J=8.3 Hz, 1H), 4.33 (t, J=6.8 Hz, 2H), 3.99 (m, 4H), 3.90 (s, 3H), 3.66 (s, 3H), 3.58 (t, J=6.3 Hz, 2H), 3.19 (d, J=21.5 Hz, 2H), 2.92 (s, 3H), 2.11 (m, 2H), 1.22 (t, J=7.1 Hz, 6H). MS (ESI): m/z=722.53 [M+H]$^+$. HPLC: t$_R$=3.63 min (ZQ3: polar__5 min).

Compound 30C: 6-Amino-3-[1-(3-hydroxypropyl)-1H-pyrazol-4-yl]-2-methoxy-N-methyl benzamide Prepared analogously to Compound 3C substituting 6-amino-3-bromo-2-methoxy-N-methylbenzamide (Compound 30D) for 2-amino-5-bromo-N,N-diethylbenzamide (Compound 3D). MS (ESI): m/z=305.23 [M+H]$^+$. HPLC: t$_R$=2.48 min (ZQ3: polar__5 min).

Compound 30D: 6-Amino-3-bromo-2-methoxy-N-methylbenzamide

Prepared analogously to Compound 27D replacing 5-fluoro-1H-benzo[d][1,3]oxazine-2,4-dione (Compound 27E) with 5-methoxy-1H-benzo[d][1,3]oxazine-2,4-dione (Compound 30E). $^1$H NMR (CDCl$_3$, 500 MHz) δ 2.98 (d, J=4.5 Hz, 3H), 3.77 (s, 3H), 5.82 (br.s, 2H), 6.74 (d, J=9.0 Hz, 1H), 7.27 (d, J=9.0 Hz, 1H), 7.58 (br.s, 1H).

Compound 30E: 5-Methoxy-1H-benzo[d][1,3]oxazine-2,4-dione

Prepared analogously to Compound 27E replacing 2-amino-6-fluorobenzoic acid with 2-amino-6-methoxybenzoic acid. $^1$H NMR (DMSO-d$_6$, 500 MHz) δ 3.87 (s, 3H), 6.64 (d, J=8.6 Hz, 1H), 6.81 (d, J=8.6 Hz, 1H), 7.65 (m, 1H), 11.59 (br.s, 1H).

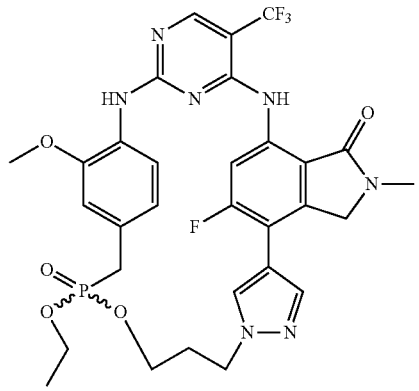

Example 31

(10S)-10-Ethoxy-29-fluoro-14-methoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide and (10R)-10-Ethoxy-29-fluoro-14-methoxy-26-methyl-20-(trifluoromethyl)-9-oxa-4,5,16,18,22,26,31-heptaaza-10-phosphahexacyclo[21.5.2.2$^{12,15}$.1$^{2,5}$.1$^{17,21}$.0$^{24,28}$]tetratriaconta-1(28),2(34),3,12,14,17(31),18,20,23,29,32-undecaen-25-one 10-oxide This compound was prepared analogously to Example 3 using ethyl hydrogen (4-{[4-({6-fluoro-7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate (Compound 31A). $^1$H NMR (CD$_3$OD, 400 MHz): δ 8.36 (d, J=3.0 Hz, 1H), 8.34 (d, J=0.5 Hz, 1H), 7.94 (s, 1H), 7.55 (d, J=13.1 Hz, 1H), 7.47 (d, J=7.6 Hz, 1H), 6.90 (s, 1H), 6.62 (d, J=8.3 Hz, 1H), 4.71-4.58 (m, 2H), 4.54-4.48 (m, 2H), 3.86 (s, 3H), 3.85-3.60 (m, 4H), 3.33 (d, J=4.8 Hz, 2H), 3.28 (d, J=4.8 Hz, 1H), 3.12 (s, 3H), 2.25 (quin, J=5.8 Hz, 2H), 0.96 (t, J=7.1 Hz, 3H). MS (ESI): m/z=676.18 [M+H]$^+$. UPLC: t$_R$=1.39 min (UPLC-TOF: polar__3 min).

Compound 31A: Ethyl hydrogen (4-{[4-({6-fluoro-7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate This compound was prepared analogously to Compound 3A using diethyl (4-{[4-({6-fluoro-7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate (Compound 31B). MS (ESI): m/z=694.21 [M+H]$^+$. UPLC: $t_R$=1.13 min (UPLC-TOF: polar_3 min).

Compound 31B: Diethyl (4-{[4-({6-fluoro-7-[1-(3-hydroxypropyl)-1H-pyrazol-4-yl]-2-methyl-3-oxo-2,3-dihydro-1H-isoindol-4-yl}amino)-5-(trifluoromethyl)pyrimidin-2-yl]amino}-3-methoxybenzyl)phosphonate This compound was prepared analogously to Compound 1B replacing Compound 1C with 7-amino-5-fluoro-4-[1-(3-hydroxypropyl)-1H-pyrazol-4-yl]-2-methyl-2,3-dihydro-1H-isoindol-1-one (Compound 31C). $^1$H NMR (CD$_3$OD, 400 MHz): δ 8.39 (d, J=13.9 Hz, 1H), 8.30 (s, 1H), 8.00 (s, 1H), 7.85 (d, J=7.3 Hz, 1H), 7.82 (d, J=1.3 Hz, 1H), 7.05 (s, 1H), 6.95 (d, J=8.3 Hz, 1H), 4.51 (s, 2H), 4.33 (t, J=6.9 Hz, 2H), 4.08 (quin, J=7.3 Hz, 4H), 3.91 (s, 3H), 3.58 (t, J=6.1 Hz, 2H), 3.28 (d, J=21 Hz, 2H, obscured), 3.12 (s, 3H), 2.10 (quin, J=6.5 Hz, 2H), 1.28 (t, J=7.1 Hz, 6H). MS (ESI): m/z=722.23 [M+H]$^+$. UPLC: $t_R$=1.43 min (UPLC-TOF: polar_3 min).

Compound 31C: 7-Amino-5-fluoro-4-[1-(3-hydroxypropyl)-1H-pyrazol-4-yl]-2-methyl-2,3-dihydro-1H-isoindol-1-one Prepared analogously to Compound 3C substituting 7-amino-4-bromo-5-fluoro-2-methyl-2,3-dihydro-1H-isoindol-1-one (Compound 31D) for 2-amino-5-bromo-N,N-diethylbenzamide (Compound 3D). $^1$H NMR (CDCl$_3$, 400 MHz): δ 7.75 (d, J=4.5 Hz, 2H), 6.41 (d, J=13.1 Hz, 1H), 4.46 (t, J=6.1 Hz, 2H), 4.39 (s, 2H), 3.70 (t, J=5.6 Hz, 2H), 3.17 (s, 3H), 2.20-2.09 (m, 3H). MS (ESI): m/z=305.14 [M+H]$^+$. UPLC: $t_R$=0.95 min (UPLC-TOF: polar_3 min).

Compound 31 D: 7-Amino-4-bromo-5-fluoro-2-methyl-2,3-dihydro-1H-isoindol-1-one A suspension of 4-bromo-5-fluoro-2-methyl-7-nitro-2,3-dihydro-1H-isoindol-1-one (Compound 31E, 490 mg, 1.70 mmol) in EtOH (10.0 mL) was charged with iron powder (473 mg, 8.48 mmol) and then heated to reflux. After 10 min of reflux, the reaction mixture was charged with 1 M of HCl in H$_2$O (2.03 mL, 2.03 mmol) and stirred at reflux for 10 min. The reaction mixture was filtered through a pad of celite. The filtrate was concentrated under reduced pressure. The residue was quenched with NaHCO$_3$ (10 mL) and extracted with DCM (15 mL). The organic layer was washed with brine, dried over Na$_2$SO$_4$, filtered and concentrated under reduced pressure to an orange solid. The crude material was purified using a Teledyne ISCO Combiflash® Rf system using DCM/MeOH (100:0→95:5) as eluent. The fractions containing product were combined and then concentrated under reduced pressure to yield a bright yellow solid (218 mg, 50%). $^1$H NMR (CDCl$_3$, 400 MHz): δ 6.38 (d, J=10.9 Hz, 1H) 5.29 (br. s., 2H) 4.22 (s, 2H) 3.14 (s, 3H). MS (ESI): m/z=260.99 [M+H]$^+$. UPLC: $t_R$=1.26 min (UPLC-TOF: polar_3 min).

Compound 31 E: 4-Bromo-5-fluoro-2-methyl-7-nitro-2,3-dihydro-1H-isoindol-1-one A solution of 4-bromo-5-fluoro-2-methyl-2,3-dihydro-1H-isoindol-1-one (Compound 31F, 1.5 g, 6.1 mmol) in sulfuric acid (3.0 mL, 56 mmol) was cooled in an ice bath to 0° C. and then charged with nitric acid (2.0 mL, 43 mmol). The reaction mixture was allowed to stir overnight while gradually warming to rt. The reaction mixture was quenched by adding the mixture dropwise into a separatory funnel containing ice and then extracted with DCM (15 mL). The organic layer was washed with brine (15 mL), dried over anhydrous Na$_2$SO$_4$, filtered and concentrated under reduced pressure to a yellow solid. The crude material was purified using a Teledyne ISCO Combiflash® Rf system using DCM/EtOAc (100:0→90:10) as eluent to afford the product compound as a yellow solid (493 mg, 28%). $^1$H NMR (CDCl$_3$, 400 MHz): δ 7.60 (d, J=7.6 Hz, 1H) 4.39 (s, 2H) 3.23 (s, 3H). MS (ESI): m/z=290.96 [M+H]$^+$. UPLC: $t_R$=1.23 min (UPLC-TOF: polar_3 min).

Compound 31F: Methyl 3-bromo-5-formyl-4-(methylamino)benzoate

The regio-isomeric mixture of Compound 31G and Compound 31H (2.02 g, 8.18 mmol) was taken up in carbon tetrachloride (40 mL) and treated with NBS (2.91 g, 16.4 mmol) and 2,2'-azo-bis-isobutyronitrile (3.12 mg, 0.019 mmol) and allowed to stir at 80° C. overnight. The reaction mixture was quenched with water (10 mL) and extracted with DCM (2×20 mL). The organic layer was washed with water (10 mL), brine (10 mL), and then dried over anhydrous sodium sulfate. The solvents were evaporated under reduced pressure to give a light-yellow oil. The product mixture was taken up in THF (15 mL) and then treated with a solution of 2.0 M of methylamine in THF (8.18 mL, 16.4 mmol) and DIPEA (2.85 mL). After stirring overnight at rt, the reaction mixture was evaporated under reduced pressure to afford a crude solid which was purified using a Teledyne ISCO Combiflash® Rf system [gradient eluent EtOAc/Heptane=50-100%) to give the desired product as 1.40 g of a white solid. $^1$H NMR (CDCl$_3$, 400 MHz): δ 7.77 (dd, J=8.3, 4.5 Hz, 1H), 7.24 (app t, J=8.6 Hz, 1H), 4.33 (s, 2H), 3.22 (s, 3H). MS (ESI): m/z=244.05/246.03 [M+H]$^+$. UPLC: $t_R$=3.33 min (ZQ3: polar_5 min).

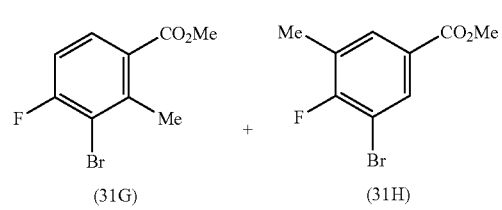 [SMILES: COC(=O)c1ccc(F)c(Br)c1C ; COC(=O)c1cc(C)c(F)c(Br)c1]

Compound 31G and Compound 31H: Methyl 3-bromo-4-fluoro-2-methylbenzoate and Methyl 3-bromo-4-fluoro-5-methylbenzoate n-BuLi (66.0 mmol, 41 mL of 1.6 M solution in hexanes) was added to a solution of 2,2,6,6-tetramethyl-piperidine (9.32 g, 66.0 mmol) in THF (80 mL) at −20° C. under an atmosphere of argon. The resulting mixture was stirred at this temperature for 30 min, cooled to −50° C. and then treated, drop-wise, with a solution of 3-bromo-4-fluorobenzoic acid (6.57 g, 30.0 mmol) in THF (20 mL). After 1 hour of stirring, a solution of methyl iodide (7.47 mL, 120 mmol) in THF (10 mL) was added. The mixture was slowly warmed to rt and then allowed to stir at rt overnight. The reaction was quenched with aq. NH$_4$Cl (20 mL) and then diluted with EtOAc (100 mL). The organic layer was washed with brine (30 mL) and then dried over anhydrous sodium sulfate. The solvents were evaporated under reduced pressure to give a mixture of 1- and 5-methyl-substituted benzoic acid. This mixture was taken up in DMF (30 mL) and then treated with potassium carbonate (8.29 g, 60.0 mmol) and methyl iodide (3.74 mL, 60.0 mmol). The resulting mixture was stirred at rt overnight. The mixture was diluted with EtOAc (100 mL), washed with water (3×30 mL), brine (30 mL), and then dried over anhydrous sodium sulfate. The residue was purified using a Teledyne ISCO Combiflash® Rf system [gradient eluent EtOAc/Heptane=0-20%) to afford a mixture of the desired compounds as 2.5 g of a light-yellow oil (ratio of Compound 31G to Compound 31H is 3:1). Compound 31G: $^1$H NMR (CDCl$_3$, 400 MHz) δ 7.82 (dd, J=8.6, 5.6 Hz, 1H), 7.02 (app t, J=8.1 Hz, 1H), 3.91 (s, 3H), 2.71 (s, 3H).

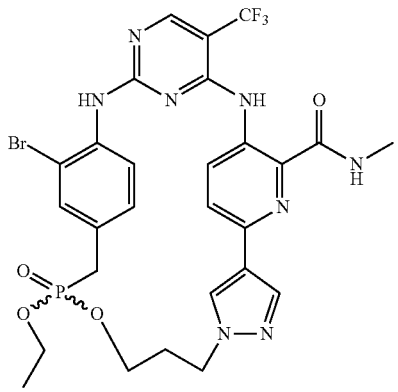

Example 32

(10S)-14-Bromo-10-ethoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-14-Bromo-10-ethoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (3-bromo-4-{[4-({6-[1-(3-hydroxypropyl)-1H-pyrazol-4-yl]-2-(methylcarbamoyl)pyridin-3-yl}amino)-5-(trifluoromethyl) pyrimidin-2-yl]amino}benzyl)phosphonate (Compound 32A, 332 mg, 465 µmol) to afford the desired products (31.3 mg, 10%). $^1$H NMR (400 MHz, DMSO-d$_6$) δ 11.24 (s, 1H), 9.36 (s, 1H), 8.63 (s, 1H), 8.45 (s, 1H), 8.33 (s, 1H), 8.18 (d, J=8.6 Hz, 2H), 7.54-7.64 (m, 2H), 7.45 (d, J=8.1 Hz, 1H), 7.32 (d, J=8.1 Hz, 1H), 4.32 (t, J=5.9 Hz, 2H), 3.61-3.72 (m, 1H), 3.48-3.60 (m, 3H), 3.29 (d, J=21.0 Hz 2H, obscured), 2.78-2.85 (m, 3H), 2.09-2.23 (m, 2H), 0.80 (t, J=7.1 Hz, 3H). MS (ESI): m/z=695.09 [M+H]$^+$. UPLC: t$_R$=1.43 min (UPLC-TOF: polar_3 min).

Compound 32A: Ethyl hydrogen (3-bromo-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to Compound 3A using diethyl (3-bromo-4-{[4-({6-[1-(3-hydroxypropyl)-1h-pyrazol-4-yl]-2-(methylcarbamoyl)pyridin-3-yl}amino)-5-(trifluoromethyl)pyrimidin-2-yl]amino}benzyl)phosphonate (Compound 32B, 339 mg, 457 µmol) to afford 332 mg of the title compound (99%). MS (ESI): m/z=713.10 [M+H]$^+$. UPLC: t$_R$=1.17 min (UPLC-TOF: polar_3 min).

Compound 32B: Diethyl (3-bromo-4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}benzyl) phosphonate Prepared analogously to Compound 1B replacing Compound 1C with 3-amino-6-[1-(3-hydroxypropyl)-1h-pyrazol-4-yl]-N-methylpyridine-2-carboxamide (Compound 6C, 229 mg, 832 µmol) and Compound 1E with diethyl (3-bromo-4-{[4-chloro-5-(trifluoromethyl)pyrimidin-2-yl]amino}benzyl)phosphonate (Compound 32C, 418 mg, 832 µmol) to afford 343 mg of the title compound (56%). $^1$H NMR (400 MHz, CD$_3$OD) δ 8.91 (d, J=8.8 Hz, 1H), 8.45 (s, 1H), 8.35 (s, 1H), 8.26 (s, 1H), 7.60-7.72 (m, 3H), 7.39 (td, J=2.3, 8.3 Hz, 1H), 4.31 (t, J=7.0 Hz, 2H), 4.05-4.16 (m, 4H), 3.56-3.61 (m, 2H), 3.34 (d, J=21.0 Hz, 2H, obscured), 2.99 (s, 3H), 2.12 (quin, J=6.5 Hz, 2H), 1.27 (t, J=7.0 Hz, 6H). MS (ESI): m/z=743.14 [M+H]$^+$. UPLC: t$_R$=1.48 min (UPLC-TOF: polar_3 min).

Compound 32C: Diethyl (3-bromo-4-{[4-chloro-5-(trifluoromethyl)pyrimidin-2-yl]amino}benzyl)phosphonate A 1M solution of zinc chloride in ether (18.7 mL, 18.7 mmol) was added to a solution of 2,6-dichloro-5-trifluoromethylpyrimidine (4 g, 18.72 mmol) in 20 mL of dichloroethane and t-butanol (1:1) under nitrogen atmosphere. The reaction mixture was stirred at rt for 30 min, cooled to 0° C. and then treated slowly over 10 min with a solution of diethyl (4-amino-3-bromobenzyl)phosphonate (Compound 32D, 3.35 gm, 10.4 mmol) in dichloroethane and t-butanol (10 mL, 1:1) through an addition funnel and stirred for 1 hr. Diisopropylethylamine (3.2 mL, 10.4 mmol) was added and the mixture was allowed to stir at rt for 3 days. The solvents were evaporated and the residue was purified using flash column chromatography (0-30% EtOAc/DCM) to afford 1.2 g of the title compound (23%). $^1$H NMR (400 MHz, CDCl$_3$): δ 1.23-1.25 (m, 6H), 3.10 (d, J=22.0 Hz, 2H), 3.99-4.06 (m, 4H), 7.28 (d, J=8.4 Hz, 1H), 7.52 (s, 1H), 7.8 (s, 1H), 8.26 (d, J=8.4 Hz, 1H), 8.57 (s, 1H).

Compound 32D: Diethyl (4-amino-3-bromobenzyl)phosphonate

Di-tert-butyl [2-bromo-4-(bromomethyl)phenyl]imidodicarbonate (Compound 32E, 6.0 g, 13 mmol) was taken up in triethyl phosphite (5.0 mL, 29 mmol) and stirred at 120° C. for 16 h. The reaction mixture was transferred to a microwave vial and was irradiated in the microwave for 4 h at 190° C. The reaction mixture was concentrated in vacuo. The compound was purified by flash column chromatography eluting with 10 to 100% EtOAc in heptane. The product was partitioned between EtOAc and water and separated. The aqueous was extracted with EtOAc (3×) and the combined organic fractions were washed with brine, dried over sodium sulfate, filtered, and concentrated to afford the title compound. $^1$H NMR (400 MHz, chloroform-d) δ 7.33 (t, J=2.3 Hz, 1H), 7.04 (ddd, J=2.3, 2.4, 8.2 Hz, 1H), 6.71 (dd, J=0.8, 8.1 Hz, 1H), 3.97-4.06 (m, 4H), 2.96-3.04 (m, 2H), 1.26 (t, J=7.1 Hz, 6H); MS (ESI): m/z: 322.00, 323.96 [M+H]$^+$. UPLC: $t_R$=2.83 min (UPLC-TOF: polar_3 min).

Compound 32E: Di-tert-butyl [2-bromo-4-(bromomethyl)phenyl]imido dicarbonate A solution of di-tert-butyl (2-bromo-4-methylphenyl)imidodicarbonate (Compound 32F, 5.0 g, 13 mmol), NBS (2.56 g, 14.2 mmol) and 2,2'-Azo-bis-isobutyronitrile (0.217 g, 1.29 mmol) in α,α,α-trifluorotoluene (16 mL) was heated at 80° C. under an atmosphere of nitrogen for 3 h. Solvent was removed in vacuo and the residue was partitioned between EtOAc and water and separated. The aqueous was extracted with EtOAc (3×) and the combined organic fractions were washed with brine, dried over sodium sulfate, filtered, and concentrated to afford the title compound. $^1$H NMR (400 MHz, chloroform-d) δ 7.64 (d, J=1.8 Hz, 1H), 7.34 (dd, J=2.0, 8.1 Hz, 1H), 7.19 (d, J=8.1 Hz, 1H), 4.44 (s, 2H), 1.41 (s, 18H); UPLC: $t_R$=1.83 min (UPLC-TOF: polar_3 min).

Compound 32F: Di-tert-butyl (2-bromo-4-methylphenyl)imidodicarbonate

A solution of 3-bromo-4-aminotoluene (4.0 g, 21 mmol) in THF (50 mL) was charged with di-tert-butyldicarbonate (4.7 g, 21 mmol) and stirred at reflux for 24 h. The reaction mixture was partitioned between EtOAc and water and separated. The aqueous layer was extracted with EtOAc (3×) and the combined organic fractions were washed with brine, dried over sodium sulfate, filtered, and concentrated. The compound was purified in two batches on an Isco Combiflash eluting with 0 to 10% EtOAc in heptane to afford the title compound. $^1$H NMR (400 MHz, chloroform-d) δ 7.40-7.44 (m, 1H), 7.08-7.10 (m, 2H), 2.35 (s, 3H), 1.41 (s, 18H).

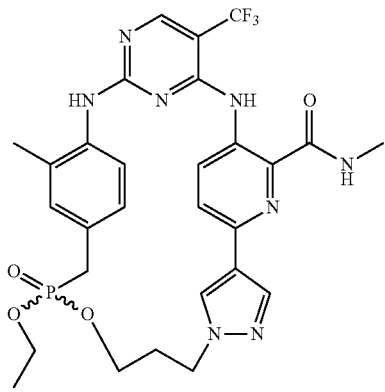

Example 33

(10S)-10-Ethoxy-N,14-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-N,14-dimethyl-20-(trifluoromethyl)-9-oxa-4,5,16,18,22,25,28-heptaaza-10-phosphapentacyclo [21.2.2.2$^{12,15}$.1$^{2,5}$.1$^{17,21}$]hentriaconta-1(25),2(31),3,12,14,17(28), 18,20,23,26,29-undecaene-24-carboxamide 10-oxide Prepared analogously to Example 3 using ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methylbenzyl)phosphonate (Compound 33A, 330 mg, 509 µmol) to afford 23 mg of the title compounds (7%). $^1$H NMR (400 MHz, CD$_3$OD) δ 8.42 (s, 1H), 8.30-8.35 (m, 2H), 8.13 (d, J=8.8 Hz, 1H), 7.61 (d, J=8.8 Hz, 1H), 7.37 (d, J=8.3 Hz, 1H), 7.14 (s, 1H), 7.09 (d, J=8.1 Hz, 1H), 4.40-4.47 (m, 2H), 3.83 (dd, J=6.1, 11.1 Hz, 1H), 3.69 (td, J=7.4, 10.3 Hz, 1H), 3.55-3.62 (m, J=5.8, 10.9 Hz, 1H), 3.46-3.52 (m, 1H), 3.36 (d, J=21.9, 2H, obscured), 2.94 (s, 3H), 2.24-2.31 (m, 2H), 2.20 (s, 3H), 0.79 (t, J=7.1 Hz, 3H). MS (ESI): m/z=631.70 [M+H]$^+$. UPLC: $t_R$=1.19 min (UPLC-SQD: analytical_2 min).

Compound 33A: Ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methylbenzyl)phosphonate Prepared analogously to Compound 3A using diethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methylbenzyl)phosphonate (Compound 33B, 345 mg, 510 µmol) to afford 330 mg of the title compound (99.8%). $^1$H NMR (400 MHz, CD$_3$OD) δ 8.71-8.96 (m, 1H), 8.60 (s, 1H), 8.28 (s, 1H), 8.23 (s, 1H), 7.63 (d, J=9.1 Hz, 1H), 7.34 (s, 1H), 7.22-7.28 (m, 2H), 4.32 (t, J=6.8 Hz, 2H), 3.88 (t, J=7.0 Hz, 2H), 3.59 (t, J=6.1 Hz, 2H), 3.06 (d, J=21.9 Hz, 2H), 2.98 (s, 3H), 2.23 (s, 3H), 2.11 (t, J=6.3 Hz, 2H), 1.12 (t, J=7.1 Hz, 3H). MS (ESI): m/z=649.65 [M+H]$^+$. UPLC: $t_R$=1.06 min (UPLC-SQD: analytical_2 min).

Compound 33B: diethyl (4-{[4-({6-[1-(3-hydroxypropyl)-1H-pyrazol-4-yl]-2-(methylcarbamoyl) pyridin-3-yl}amino)-5-(trifluoromethyl)pyrimidin-2-yl]amino}-3-methyl benzyl)phosphonate Prepared analogously to Compound 1B replacing Compound 1C with Compound 6C and Compound 1E with diethyl (4-{[[4-chloro-5-(trifluoromethyl)pyrimidin-2-yl]amino}-3-methylbenzyl)phosphonate (Compound 33C, 339 mg, 774 µmol) to afford 345 mg of the title compound (66%). $^1$H NMR (400 MHz, CD$_3$OD) δ 8.90 (br. s., 1H), 8.49 (s, 1H), 8.31 (d, J=10.1 Hz, 2H), 7.63 (d, J=9.1 Hz, 1H), 7.35-7.39 (m, 1H), 7.33 (s, 1H), 7.24-7.31 (m, 1H), 4.32 (t, J=7.0 Hz, 2H), 4.11 (quin, J=7.3 Hz, 4H), 3.56-3.61 (m, 2H), 3.33 (d, J=21.0 Hz, 2H), 3.00 (s, 3H), 2.28 (s, 3H), 2.12 (quin, J=6.5 Hz, 2H), 1.24-1.30 (m, 6H). MS (ESI): m/z=677.21 [M+H]$^+$. UPLC: $t_R$=1.42 min (UPLC-TOF: polar_3 min).

Compound 33C: Diethyl (4-{[4-chloro-5-(trifluoromethyl)pyrimidin-2-yl]amino}-3-methyl benzyl)phosphonate A 1M solution of zinc chloride in ether (12.8 mL, 12.8 mmol) was added to a solution of 2,6-dichloro-5-trifluoromethylpyrimidine (2.76 gm, 12.8 mmol) in 20 mL of dichloroethane and t-butanol (1:1) under an atmosphere of nitrogen. The reaction mixture was stirred at rt for 30 min, cooled to 0° C. and then treated with a solution of (4-amino-3-methylbenzyl)phosphonic acid diethyl ester (Compound 33D, 2.2 gm, 8.5 mmol) in dichloroethane and t-butanol (10 mL, 1:1) slowly over 10 min through an addition funnel. After 1 hour, diisopropylethylamine (2.2 mL, 12.6 mmol) was added and then reaction gradually warmed up to rt over 4 hrs. The reaction mixture was refrigerated overnight causing the desired product to precipitate out of solution. This was collected by filtration to afford 2.7 g of the title compound (73%). $^1$H NMR (300 MHz, CDCl$_3$): δ 1.21-1.26 (m, 6H), 2.3 (s, 3H), 3.15 (d, J=22.0 Hz, 2H), 3.99-4.09 (m, 4H), 7.17 (m, 3H), 7.72 (d, J=7.5 Hz, 1H), 8.52 (s, 1H).

Compound 33D: Diethyl (4-amino-3-methylbenzyl)phosphonate

Prepared starting with (3-methyl-4-nitrophenyl)methanol and following the procedures used to for Compounds 1H-1F. $^1$H NMR (300 MHz, CDCl$_3$): δ 1.24 (t, J=7.0 Hz, 6H), 2.14 (s, 3H), 3.17 (d, J=21.0 Hz, 2H), 3.56 (br.s, 3H), 3.94-4.05 (m, 4H), 6.65 (d, J=8.1 Hz, 1H), 6.93-6.97 (m, 2H).

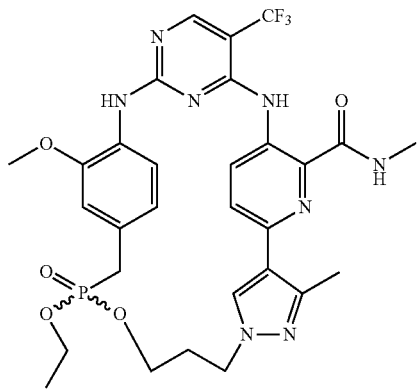

Example 34

(10S)-10-Ethoxy-14-methoxy-N,3-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-14-methoxy-N,3-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31), 3,12,14, 17(28),18,20,23,26,29-undecaene-24-carboxamide 10-oxide Prepared analogously to Example 3 using ethyl hydrogen (4-{[4-({6-[1-(3-hydroxypropyl)-3-methyl-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 34A, 533 mg, 785 µmol) to afford 89.6 mg of the racemic title compound (17%). $^1$H NMR (400 MHz, CD$_3$OD) δ 8.33-8.38 (m, 1H), 8.19 (d, J=8.6 Hz, 1H), 7.79 (d, J=8.6 Hz, 1H), 7.63 (d, J=8.8 Hz, 1H), 6.92 (m, 1H), 6.67 (d, J=8.3 Hz, 1H), 4.37-4.43 (m, 2H), 3.81-3.96 (m, 5H), 3.72 (d, J=8.3 Hz, 2H), 3.37 (d, J=21.0 Hz 2H), 2.97 (s, 3H), 2.67 (s, 3H), 2.23 (t, J=5.8 Hz, 2H), 1.07 (t, J=7.1 Hz, 3H). MS (ESI): m/z=661.67 [M+H]$^+$. UPLC: t$_R$=1.25 min (UPLC-SQD: analytical_2 min).

Compound 34A: Ethyl hydrogen (4-{[4-({6-[1-(3-hydroxypropyl)-3-methyl-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 3A using diethyl (4-{[4-({6-[1-(3-hydroxypropyl)-3-methyl-1H-pyrazol-4-yl]-2-(methylcarbamoyl)pyridin-3-yl}amino)-5-(trifluoromethyl)pyrimidin-2-yl]amino}-3-methoxybenzyl) phosphonate (Compound 34B, 582 mg, 824 µmol) to afford 533 mg of the title compound (95%). $^1$H NMR (400 MHz, CD$_3$OD) δ 8.95-9.04 (m, 1H), 8.41 (s, 1H), 8.30 (d, J=0.5 Hz, 1H), 7.64 (d, J=8.8 Hz, 2H), 7.11 (s, 1H), 6.87-6.96 (m, 1H), 4.24 (t, J=6.8 Hz, 2H), 3.80-3.92 (m, 5H), 3.58 (t, J=6.1 Hz, 2H), 3.02 (d, J=21.0 Hz, 2H), 2.98 (s, 3H), 2.56 (s, 3H), 2.09 (t, J=6.3 Hz, 2H), 1.14 (t, J=7.1 Hz, 3H). MS (ESI): m/z=679.67 [M+H]$^+$. UPLC: t$_R$=1.15 min (UPLC-TOF: polar_3 min).

Compound 34B: Diethyl (4-{[4-({6-[1-(3-hydroxypropyl)-3-methyl-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 1B replacing compound 1C with 3-Amino-6-[1-(3-hydroxypropyl)-3-methyl-1H-pyrazol-4-yl]-N-methylpyridine-2-carboxamide (Compound 34C, 343 mg, 1.19 mmol) to afford 582 mg of the title compound (69%). $^1$H NMR (400 MHz, CD$_3$OD) δ 8.99 (d, J=7.6 Hz, 1H), 8.28 (s, 2H), 7.82 (d, J=6.8 Hz, 1H), 7.55 (d, J=9.1 Hz, 1H), 7.01 (t, J=1.9 Hz, 1H), 6.88 (td, J=2.3, 8.1 Hz, 1H), 4.17-4.25 (m, 2H), 3.99-4.10 (m, 4H), 3.88 (s, 3H), 3.54-3.61 (m, 2H), 3.25 (d, J=21.9 Hz, 2H), 2.94 (br. s., 3H), 2.53 (s, 3H), 2.01-2.14 (m, 2H), 1.25 (d, J=13.9 Hz, 6H). MS (ESI): m/z=707.17 [M+H]$^+$. UPLC: t$_R$=3.91 min (ZQ3: polar_5 min).

Compound 34C: 3-Amino-6-[1-(3-hydroxypropyl)-3-methyl-1H-pyrazol-4-yl]-N-methylpyridine-2-carboxamide A mixture of 3-Amino-6-{1-[3-(benzyloxy)propyl]-3-methyl-1H-pyrazol-4-yl}-N-methylpyridine-2-carboxamide (Compound 34D, 639 mg, 1.68 mmol) in EtOH (18.0 mL) and palladium on carbon (10:90, Palladium 10% wt. on Calcium Carbonate:carbon black, 100.0 mg, 0.048 mmol) was evacuated and flushed with argon (3×). After a fourth evacuation, the mixture was flushed with H$_2$ and allowed to stir overnight at rt. The reaction mixture was filtered, concentrated in vacuo and purified using a Teledyne ISCO Combiflash® Rf system [elution gradient: 0→10% MeOH in DCM] to afford 342 mg of the title compound (70%). $^1$H NMR (400 MHz, CDCl$_3$) δ 8.01 (s, 1H), 7.42 (d, J=8.6 Hz, 1H), 7.16 (d, J=8.6 Hz, 1H), 4.19 (t, J=7.0 Hz, 2H), 3.55 (t, J=6.2 Hz, 2H), 2.94 (s, 3H), 2.48 (s, 3H), 2.05 (t, J=6.4 Hz, 2H). MS (ESI): m/z=290.58 [M+H]$^+$. UPLC: t$_R$=0.65 min (UPLC-SQD: analytical_2 min).

Compound 34D and 34E: 3-Amino-6-{1-[3-(benzyloxy)propyl]-3-methyl-1H-pyrazol-4-yl}-N-methylpyridine-2-carboxamide and 3-Amino-6-{1-[3-(benzyloxy)propyl]-5-methyl-1H-pyrazol-4-yl}-N-methylpyridine-2-carboxamide Prepared analogously to Compound 3C replacing Compound 3D with 3-amino-6-bromo-N-methylpyridine-2-carboxamide (Compound 6D, 1 g, 4.35 mmol) and replacing 3E with a mixture of 1-[3-(benzyloxy)propyl]-3-methyl-4-(4,4,5,5-tetramethyl-1,3,2-dioxaborolan-2-yl)-1H-pyrazole and 1-[3-(benzyloxy)propyl]-5-methyl-4-(4,4,5,5-tetramethyl-1,3,2-dioxaborolan-2-yl)-1H-pyrazole (Compound 34F and Compound 34G, 1 g, 4.35 mmol). Additional purification to isolate the individual regioisomers was achieved using SFC to afford 647 mg of 3-amino-6-{1-[3-(benzyloxy)propyl]-3-methyl-1H-pyrazol-4-yl}-N-methylpyridine-2-carboxamide (Compound 34D, 39%). $^1$H NMR (400 MHz, CD$_3$OD) δ 7.92 (s, 1H), 7.38 (d, J=8.6 Hz, 1H), 7.21-7.35 (m, 5H), 7.17 (d, J=8.6 Hz, 1H), 4.48 (s, 2H), 4.20 (t, J=6.8 Hz, 2H), 3.46 (t, J=5.9 Hz, 2H), 2.93 (s, 3H), 2.47 (s, 3H), 2.08-2.18 (m, J=6.1, 6.06 Hz, 2H). MS (ESI): m/z=380.18 [M+H]$^+$. UPLC: t$_R$=1.37 min (UPLC-TOF: polar_3 min) and 439 mg of 3-amino-6-{1-[3-(benzyloxy)propyl]-5-methyl-1H-pyrazol-4-yl}-N-methylpyridine-2-carboxamide (Compound 34E, 27%). $^1$H NMR (400 MHz, CD$_3$OD) δ 7.81 (s, 1H), 7.43 (d, J=8.8 Hz, 1H), 7.23-7.36 (m, 5H), 7.19 (d, J=8.8 Hz, 1H), 4.49 (s, 2H), 4.25 (t, J=6.8 Hz, 2H), 3.48 (t, J=5.8 Hz, 2H), 2.94 (s, 3H), 2.54 (s, 3H), 2.12 (quin, J=6.4 Hz, 2H). MS (ESI): m/z=380.18 [M+H]$^+$. UPLC: t$_R$=1.38 min (UPLC-TOF: polar_3 min).

Compound 34F and Compound 34G: 1-[3-(Benzyloxy)propyl]-3-methyl-4-(4,4,5,5-tetramethyl-1,3,2-dioxaborolan-2-yl)-1H-pyrazole and 1-[3-(Benzyloxy)propyl]-5-methyl-4-(4,4,5,5-tetramethyl-1,3,2-dioxaborolan-2-yl)-1H-pyrazole Prepared analogously to Compound 5E replacing Compound 5F with a mixture of 1-[3-(benzyloxy)propyl]-4-iodo-3-methyl-1H-pyrazole and 1-[3-(benzyloxy)propyl]-4-iodo-5-methyl-1H-pyrazole (Compound 34H and Compound 34I, 3.60 g, 10.1 mmol) to afford 5.8 g of the title compounds as a mixture of regioisomers (80%). MS (ESI): m/z=357.21 [M+H]$^+$. UPLC: t$_R$=1.67-1.69 min (UPLC-TOF: polar_3 min).

Compound 34H and Compound 34I: 1-[3-(Benzyloxy)propyl]-4-iodo-3-methyl-1H-pyrazole and 1-[3-(benzyloxy)propyl]-4-iodo-5-methyl-1H-pyrazole A mixture of 3-methyl-4-iodopyrazole (2.59 g, 12.5 mmol) and 1-bromo-3-benzyloxypropane (3.00 g, 13.1 mmol) in DMF (11.4 mL) was charged with potassium carbonate (2.07 g, 15.0 mmol). The reaction mixture was allowed to stir at rt for 16 hrs overnight. The reaction mixture was quenched with water and then extracted with EtOAc. The organic layer was washed with water, brine (2x), dried over sodium sulfate, filtered, and then concentrated in vacuo to yield an oil. The crude material was purified using a Teledyne ISCO Combiflash® Rf system [Heptane/EtOAc (100:0→0:100)] to afford the title products as a mixture of regioisomers (3.60 g, 41% combined yield). The reaction was carried onto the next step without any further purification. MS (ESI): m/z=357.02 [M+H]$^+$. UPLC: t$_R$=1.62 min (UPLC-TOF: polar_3 min).

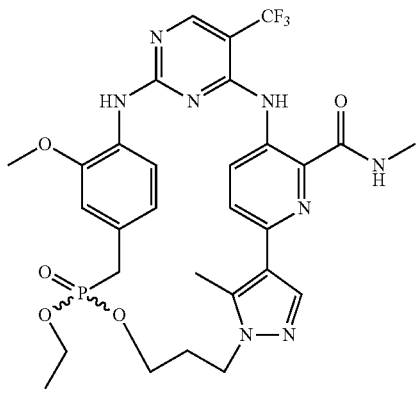

Example 35

(10S)-10-ethoxy-14-methoxy-N,31-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-14-methoxy-N,31-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(3-hydroxypropyl)-5-methyl-1H-pyrazol-4-yl]-2-(methylcarbamoyl)pyridin-3-yl}amino)-5-(trifluoromethyl) pyrimidin-2-yl]amino}-3-methoxybenzyl)phosphonate (Compound 35A, 278 mg, 410 μmol) to afford 3 mg of racemic Example 35 (1%). $^1$H NMR (400 MHz, CD$_3$OD) δ 8.32 (s, 1H), 8.19 (s, 1H), 7.89 (d, J=8.6 Hz, 1H), 7.68 (d, J=8.6 Hz, 1H), 7.26 (d, J=8.3 Hz, 1H), 6.77 (s, 1H), 6.16 (td, J=2.2, 8.2 Hz, 1H), 4.33-4.47 (m, 2H), 3.98 (quin, J=7.3 Hz, 2H), 3.81 (s, 3H), 3.07 (d, J=21.0 Hz, 2H), 2.91 (s, 3H), 2.66 (s, 3H), 2.30-2.38 (m, 2H), 1.29 (s, 2H), 1.19 (t, J=7.1 Hz, 3H). MS (ESI): m/z=661.67 [M+H]$^+$. UPLC: t$_R$=1.17 min (UPLC-SQD: analytical_2 min).

Compound 35A: Ethyl hydrogen (4-{[4-({6-[1-(3-hydroxypropyl)-5-methyl-1H-pyrazol-4-yl]-2-(methylcarbamoyl)pyridin-3-yl}amino)-5-(trifluoromethyl) pyrimidin-2-yl]amino}-3-methoxybenzyl) phosphonate Prepared analogously to Compound 3A using diethyl (4-{[4-({6-[1-(3-hydroxypropyl)-5-methyl-1H-pyrazol-4-yl]-2-(methylcarbamoyl)pyridin-3-yl}amino)-5-(trifluoromethyl) pyrimidin-2-yl]amino}-3-methoxybenzyl)phosphonate (Compound 35B, 270 mg, 382 μmol) to afford 278 mg of the title compound (100%). $^1$H NMR (400 MHz, CD$_3$OD) δ 8.95-9.04 (m, 1H), 8.26 (s, 1H), 7.96-8.01 (m, 1H), 7.71-7.80 (m, 1H), 7.51 (d, J=9.1 Hz, 1H), 7.08 (s, 1H), 6.83-6.90 (m, 1H), 4.25 (t, J=7.1 Hz, 2H), 3.81-3.92 (m, 5H), 3.55-3.60 (m, 2H), 2.97 (d, J=21.0 Hz, 2H), 2.92 (s, 1H), 2.61 (s, 3H), 2.03 (t, J=6.7 Hz, 2H), 1.17 (t, J=7.1 Hz, 3H). MS (ESI): m/z=679.67 [M+H]$^+$. UPLC: t$_R$=1.15 min (UPLC-SQD: analytical_2 min).

Compound 35B: Diethyl (4-{[4-({6-[1-(3-hydroxypropyl)-5-methyl-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B replacing Compound 1C with 3-Amino-6-[1-(3-hydroxypropyl)-5-methyl-1H-pyrazol-4-yl]-N-methylpyridine-2-carboxamide (Compound 35C, 177 mg, 644 µmol) to afford 270 mg of the title compound (59%). $^1$H NMR (400 MHz, CD$_3$OD) d 8.59-8.68 (m, 1H), 8.30 (s, 1H), 8.03 (s, 1H), 7.76-7.86 (m, 1H), 7.58 (d, J=9.1 Hz, 1H), 7.01 (s, 1H), 6.88 (d, J=8.1 Hz, 1H), 4.26 (t, J=7.1 Hz, 2H), 4.05 (quin, J=7.3 Hz, 4H), 3.88 (s, 3H), 3.53-3.60 (m, 2H), 3.25 (d, J=21.0 Hz, 2H), 2.92-2.98 (m, 3H), 2.63 (s, 3H), 2.04 (t, J=6.7 Hz, 2H), 1.25 (t, J=7.1 Hz, 6H). MS (ESI): m/z=677.21 [M+H]$^+$. UPLC: $t_R$=3.8 min (ZQ3: polar_5 min).

Compound 35C: 3-Amino-6-[1-(3-hydroxypropyl)-5-methyl-1H-pyrazol-4-yl]-N-methylpyridine-2-carboxamide Prepared analogously to Compound 34C replacing Compound 34D with 3-amino-6-{1-[3-(benzyloxy)propyl]-5-methyl-1H-pyrazol-4-yl}-N-methylpyridine-2-carboxamide (Compound 34E, 429 mg, 1.13 mmol) to afford 177 mg of the title compound (54%). $^1$H NMR (400 MHz, CD$_3$OD) δ 7.75 (s, 1H), 7.35 (d, J=8.8 Hz, 1H), 7.12 (d, J=8.6 Hz, 1H), 4.18 (t, J=7.1 Hz, 2H), 3.51 (t, J=6.2 Hz, 2H), 2.89 (s, 3H), 2.51 (s, 3H), 1.97 (quin, J=6.6 Hz, 2H). MS (ESI): m/z=290.57 [M+H]$^+$. UPLC: $t_R$=0.67 min (UPLC-SQD: analytical_2 min).

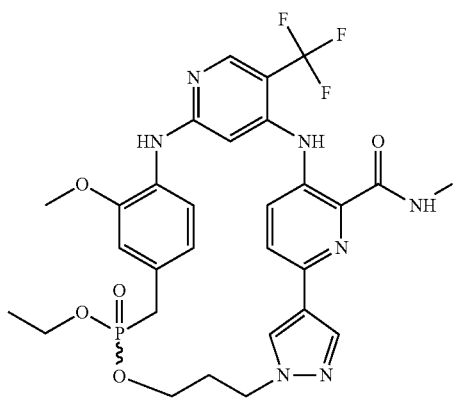 [SMILES: CCOP1(=O)Cc2ccc(c(OC)c2)Nc2cc(c(C(F)(F)F)cn2)Nc2ccc(nc2C(=O)NC)-c2cnn(c2)CCCO1]

Example 36

(10-S)-10-Ethoxy-14-methoxy-N-methyl-20-(trifluoromethyl)-9-oxa-4,5,16,18,22,25-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10-R)-10-Ethoxy-14-methoxy-N-methyl-20-(trifluoromethyl)-9-oxa-4,5,16,18,22,25-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyridin-2-yl]amino}-3-methoxybenzyl)phosphonate (Compound 36A) to afford the title compound. $^1$H NMR (400 MHz, CDCl$_3$) δ 10.07 (s, 1H), 8.29 (s, 1H), 8.15 (d, J=5.1 Hz, 1H), 8.09 (s, 1H), 7.87 (s, 1H), 7.79 (d, J=8.6 Hz, 1H), 7.52 (d, J=8.8 Hz, 1H), 7.06 (d, J=8.1 Hz, 1H), 6.79-6.88 (m, 2H), 6.72 (td, J=2.5, 8.1 Hz, 1H), 6.52 (s, 1H), 4.43 (t, J=5.9 Hz, 2H), 3.88-4.03 (m, 2H), 3.82 (s, 3H), 3.57-3.78 (m, 2H), 3.17 (d, J=21.2 Hz, 1H), 3.16 (d, J=21.2 Hz, 1H), 3.03 (d, J=5.1 Hz, 3H), 2.21 (quin, J=6 Hz, 2H), 1.12 (t, J=7.1 Hz, 3H). MS (ESI): m/z 646.19 [M+H]+. UPLC: $t_R$=1.33 min (UPLC-TOF: polar_3 min).

Compound 36A: Ethyl hydrogen (4-{[4-({6-[1-(3-hydroxypropyl)-1H-pyrazol-4-yl]-2-(methylcarbamoyl)pyridin-3-yl}amino)-5-(trifluoromethyl)pyridin-2-yl]amino}-3-methoxybenzyl)phosphonate Prepared analogously to Compound 3A using diethyl (4-{[4-({6-[1-(3-hydroxypropyl)-1H-pyrazol-4-yl]-2-(methylcarbamoyl)pyridin-3-yl}amino)-5-(trifluoromethyl)pyridin-2-yl]amino}-3-methoxybenzyl)phosphonate (Compound 36B). $^1$H NMR (400 MHz, CD$_3$OD) δ 8.39 (s, 1H), 8.20 (s, 1H), 8.17 (s, 1H), 7.92 (d, J=8.8 Hz, 1H), 7.72 (d, J=8.8 Hz, 1H), 7.46 (d, J=7.8 Hz, 1H), 7.08 (t, J=1.8 Hz, 1H), 6.88 (td, J=2.0, 8.1 Hz, 1H), 6.63 (s, 1H), 4.31 (t, J=6.8 Hz, 2H), 3.88 (s, 3H), 3.74 (quin, J=7 Hz, 2H), 3.57 (t, J=6.1 Hz, 2H), 2.89-2.98 (m, 5H), 2.10 (quin, J=6.5 Hz, 2H), 1.03 (t, J=7.1 Hz, 3H). MS (ESI): m/z 664.21 [M+H]+. UPLC: $t_R$=1.06 min (UPLC-TOF: polar_3 min).

Compound 36B: Diethyl (4-{[4-({6-[1-(3-hydroxypropyl)-1H-pyrazol-4-yl]-2-(methylcarbamoyl)pyridin-3-yl}amino)-5-(trifluoromethyl)pyridin-2-yl]amino}-3-methoxybenzyl)phosphonate A solution of 3-{[2-chloro-5-(trifluoromethyl)pyridin-4-yl]amino}-6-[1-(3-hydroxypropyl)-1H-pyrazol-4-yl]-N-methylpyridine-2-carboxamide (Compound 36C, 158 mg, 0.35 mmol) and diethyl (4-amino-3-methoxybenzyl)phosphonate (Compound 1F, 104 mg, 0.38 mmol) in 1,4-dioxane (4.0 mL) was treated with Pd(II)(OAc)$_2$ (3.90 mg, 0.017 mmol), Xantphos (20.1 mg, 0.035 mmol) and Cs$_2$CO$_3$ (226 mg, 0.70 mmol). The mixture was purged with N$_2$ for 2 minutes, sealed and irradiated in a microwave reactor for 40 minutes at 120° C. The cooled reaction mixture was poured into water and extracted twice with EtOAc. The combined organic layers were washed with brine, dried over Na$_2$SO$_4$, filtered and concentrated to a brown residue which was taken purified using a Teledyne ISCO Combiflash® system (0%-5%-10% MeOH/DCM) to afford 27 mg of a brown foam (11%). $^1$H NMR (400 MHz, CDCl$_3$) δ 10.91 (s, 1H), 8.38 (s, 1H), 8.23 (q, J=5.6 Hz, 1H), 7.98 (s, 1H), 7.98 (s, 1H), 7.86 (d, J=8.8 Hz, 1H), 7.76 (d, J=7.8 Hz, 1H), 7.51 (d, J=8.6 Hz, 1H), 6.86-6.94 (m, 3H), 6.70 (s, 1H), 4.38 (t, J=6.3 Hz, 2H), 3.93-4.05 (m, 4H), 3.88 (s, 3H), 3.66 (q, J=5.5 Hz, 2H), 3.12 (d, J=21.2 Hz, 2H), 3.06 (d, J=5.1 Hz, 3H), 2.79 (t, J=5.2 Hz, 1H), 2.13 (quin, J=6.1 Hz, 2H), 1.21 (t, J=7.0 Hz, 6H).

Compound 36C: 3-{[2-Chloro-5-(trifluoromethyl)pyridin-4-yl]amino}-6-[1-(3-hydroxypropyl-1H-pyrazol-4-yl]-N-methylpyridine-2-carboxamide A mixture of 2-chloro-5-(trifluoromethyl)-4-iodopyridine (200.0 mg, 0.65 mmol), 3-amino-6-[1-(3-hydroxypropyl)-1H-pyrazol-4-yl]-N-methylpyridine-2-carboxamide (Compound 6C, 179 mg, 0.65 mmol), Pd(II)(OAc)$_2$ (7.3 mg, 0.033 mmol), Xantphos (37.6 mg, 0.065 mmol), and Cs$_2$CO$_3$ (424 mg, 1.30 mmol) in anhydrous 1,4-dioxane (1.5 mL) was prepared in a sealable microwave tube and sparged with N$_2$ for 2 min. The tube was sealed and irradiated in a microwave reactor for 30 min at 80° C. Additional 2-chloro-5-(trifluoromethyl)-4-iodopyridine, catalyst, ligand and base were added followed by additional 30 min of irradiation at 80° C. The reagent addition and re-irradiation was performed a total of 4 times. The cooled reaction mixture was poured into water and extracted with EtOAc (2×). The combined organic layers were washed with brine, dried over Na$_2$SO$_4$, filtered and concentrated to a green residue. This was purified using a Teledyne ISCO Combiflash® system (0-5% MeOH/DCM) to isolate the desired product as 158 mg of a yellow foam (53%). $^1$H NMR (400 MHz, CDCl$_3$) δ 11.26 (s, 1H), 8.49 (s, 1H), 8.18-8.32 (m, J=4.5 Hz, 1H), 7.99 (s, 1H), 7.95 (s, 1H), 7.89 (d, J=8.8 Hz, 1H), 7.59 (d, J=8.6 Hz, 1H), 7.31 (s, 1H), 4.39 (t, J=6.4 Hz, 2H), 3.70 (t, J=5.4 Hz, 2H), 3.07 (d, J=5.1 Hz, 3H), 2.15 (quin, J=6.1 Hz, 2H). MS (ESI): m/z=455.10 [M+H]$^+$; UPLC: t$_R$=1.33 min (UPLC-TOF: polar_3 min).

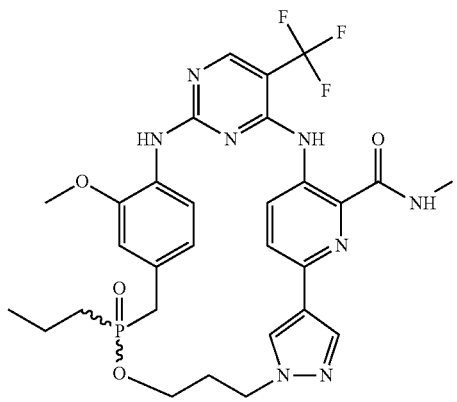

Example 37

(10S)-14-Methoxy-N-methyl-10-propyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-14-Methoxy-N-methyl-10-propyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide The reaction mixture from Compound 37A was charged with DCC (60.0 mg, 0.29 mmol) and heated at reflux for 5-6 hours. The reaction mixture was concentrated under reduced pressure to a brown solid. The crude material was purified on a Teledyne ISCO Combiflash® Rf system using DCM/MeOH (100:0→90:10) to afford the title compound as 5.1 mg of a white solid (55%). $^1$H NMR (CDCl$_3$, 400 MHz): δ 10.89 (br. s., 1H), 8.27-8.40 (m, 3H), 8.17 (s, 1H), 8.13 (d, J=8.6 Hz, 1H), 7.81 (d, J=8.3 Hz, 2H), 7.60 (d, J=8.6 Hz, 1H), 6.59 (s, 1H), 6.29-6.38 (m, 1H), 4.34-4.55 (m, 2H), 4.00-4.13 (m, 1H), 3.87 (s, 3H), 3.47-3.59 (m, 1H), 2.98-3.21 (m, 5H), 2.19-2.38 (m, 2H), 1.66-1.73 (m, 4H), 1.04 (t, J=5.8 Hz, 3H). MS (ESI): m/z 645.07 [M+H]$^+$. HPLC: t$_R$=3.11 min (polar_4 min).

Compound 37A: (4-{[4-({6-[1-(3-Hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)propylphosphinic acid A solution of ethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)propylphosphinate (Compound 37B, 10 mg, 0.015 mmol) in pyridine (1 mL) was charged with bromotrimethylsilane (0.012 mL, 0.087 mmol). The reaction was stirred at rt for 20 min. The material was not isolated. MS (ESI): m/z 663.23 [M+H]$^+$. UPLC: t$_R$=0.85 min (polar_2 min).

Compound 37B: Ethyl (4-{[4-({6-[1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)propylphosphinate Prepared analogously to Compound 1B replacing Compound 1E with ethyl (4-{[4-chloro-5-(trifluoromethyl)pyrimidin-2-yl]amino}-3-methoxybenzyl)propylphosphinate (Compound 37C, 0.680 g, 1.50 mmol) and Compound 1C with Compound 6F (0.420 g, 1.52 mmol) to isolate the title compound as 650 mg of a light yellow solid (63%). MS (ESI): m/z 691.25 [M+H]$^+$. UPLC: t$_R$=0.98 min (polar_2 min).

Compound 37C: Ethyl (4-{[4-chloro-5-(trifluoromethyl)pyrimidin-2-yl]amino}-3-methoxybenzyl)propylphosphinate Prepared analogously to Compound 1E replacing compound 1F with ethyl (4-amino-3-methoxybenzyl)propylphosphinate (Compound 37D, 0.971 g, 3.58 mmol). The crude material was purified on a Teledyne ISCO Combiflash® Rf system using DCM/MeOH (100:0→95:5) as eluent to afford the title compound as 1.08 g of a white foam (67%). MS (ESI): m/z 452.10 [M+H]$^+$. UPLC: t$_R$=1.10 min (polar_2 min).

Compound 37D: Ethyl (4-amino-3-methoxybenzyl)propylphosphinate

A solution of ethyl (3-methoxy-4-nitrobenzyl)prop-2-en-1-ylphosphinate (Compound 37E, 1.075 g, 3.59 mmol) in EtOH (20.0 mL) was charged with Palladium 10% wt on activated carbon (0.365 mg, 0.34 mmol). The reaction mixture was evacuated and purged with hydrogen gas (3×). The reaction mixture was allowed to stir under hydrogen at rt for 16 h. The reaction mixture was filtered through a pad of celite. The filtrate was concentrated under reduced pressure to a light purple oil, (0.97 g, 99%). This material was used in successive reactions without further purification. $^1$H NMR (CDCl$_3$, 400 MHz): δ=6.79 (t, J=1.8 Hz, 1H), 6.70-6.75 (m, 1H), 6.64-6.69 (m, 1H), 3.93-4.09 (m, 2H), 3.86 (s, 3H), 3.04 (d, J=16.2 Hz, 2H), 1.60 (dt, J=2.5, 4.9 Hz, 4H), 1.29 (t, J=7.1 Hz, 3H), 0.98 (dt, J=1.3, 7.1 Hz, 3H). MS (ESI): m/z 272.13 [M+H]$^+$. UPLC: t$_R$=0.98 min (UPLC-TOF: polar_3 min).

Compound 37E: Ethyl (3-methoxy-4-nitrobenzyl)prop-2-en-1-ylphosphinate

A mixture of (3-methoxy-4-nitrobenzyl)prop-2-en-1-ylphosphinic acid (Compound 37F, 1.28 g, 4.72 mmol) and iodoethane (1.47 g, 9.44 mmol) in DMF (5.0 mL) was charged with potassium carbonate (1.30 g, 9.44 mmol). The reaction mixture was allowed to stir at rt for 16 hours. The reaction mixture was quenched with water (15 mL) and extracted with EtOAc (25 mL). The organic layer was washed with water (10 mL), washed with brine (10 mL), dried over Na$_2$SO$_4$, filtered, concentrated under reduced pressure to yield a yellow oil. The crude material was purified on a Teledyne ISCO Combiflash® Rf system using DCM/MeOH (100:0→95:5) as eluent to afford the title compound as 1.08 g of a yellow oil (77%). $^1$H NMR (CDCl$_3$, 400 MHz): δ=7.84 (d, J=8.3 Hz, 1H), 7.11 (t, J=1.8 Hz, 1H), 6.92 (td, J=1.8, 8.3 Hz, 1H), 5.76-5.90 (m, 1H), 5.18-5.32 (m, 2H), 4.00-4.14 (m, 2H), 3.98 (s, 3H), 3.19 (d, J=16.4 Hz, 2H), 2.60 (dd, J=7.3, 17.7 Hz, 2H), 1.29 (t, J=7.1 Hz, 3H). MS (ESI): m/z 300.10 [M+H]$^+$. UPLC: $t_R$=1.22 min (UPLC-TOF: polar_3 min).

Compound 37F:
(3-methoxy-4-nitrobenzyl)prop-2-en-1-ylphosphinic acid

A mixture of ammonium phosphinate (1.00 g, 12.0 mmol) and Hexamethyldisilazane (1.94 g, 12.0 mmol) was heated to 110° C. under N$_2$ for approximately 1.5 hours. The reaction mixture was cooled to 0° C., charged with anhydrous DCM (10 mL) followed by Allyl bromide (1.46 g, 12.0 mmol) and allowed to stir at RT for 16 hours. The reaction mixture was then cooled to 0° C. and charged with more hexamethyldisilazane (1.94 g, 12.0 mmol). The reaction mixture was stirred at 0° C. for 2 hours then treated with 4-(bromomethyl)-2-methoxy-1-nitrobenzene (3.00 g, 12.2 mmol). The reaction mixture was allowed to stir for 16 hours at rt after which it was filtered. The filtrate was quenched with 1N HCl (10 mL) and extracted with DCM (20 mL). The organic layer was washed with brine (10 mL), dried over anhydrous Na$_2$SO$_4$, filtered and concentrated under reduced pressure to a yellow oil. The material was dissolved in DCM and extracted with aq. NaHCO$_3$. The aqueous layer was cooled to 0° C. and then acidified with 6 M HCl. The aqueous layer was saturated with solid NaCl then extracted with DCM. The organic layer was concentrated under reduced pressure to a yellow oil (1.29 g, 39%). This material was used in successive reactions without any further purification. $^1$H NMR (CDCl$_3$, 400 MHz): δ=9.81 (br. s., 1H), 7.81 (d, J=8.3 Hz, 1H), 7.01 (s, 1H), 6.89 (td, J=1.8, 8.3 Hz, 1H), 5.79-5.67 (m, 1H), 5.29-5.18 (m, 2H), 3.96 (s, 3H), 3.10 (d, J=15.9 Hz, 2H), 2.53-2.44 (m, 2H). MS (ESI): m/z 270.37 [M−H]$^+$. UPLC: $t_R$=0.76 min (UPLC-SQD: analytical_2 min).

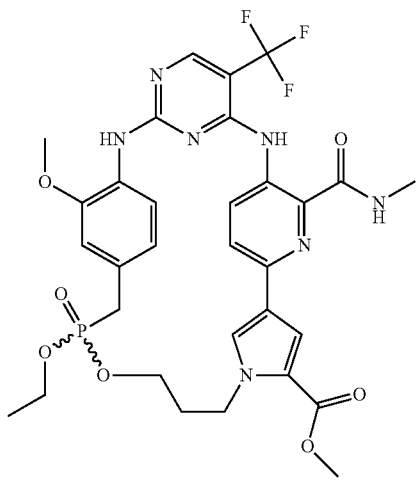

Example 38

Methyl (10S)-10-ethoxy-14-methoxy-24-(methylcarbamoyl)-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17 (28),18,20,23,26,29-undecaene-4-carboxylate 10-oxide and Methyl (10R)-10-ethoxy-14-methoxy-24-(methylcarbamoyl)-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17 (28),18,20,23,26,29-undecaene-4-carboxylate 10-oxide Prepared analogously to Example 3 by adding (benzotriazol-1-yloxy)tripyrrolidino-phosphonium hexafluorophosphate (1.43 g, 2.74 mmol) to a stirring suspension of methyl 4-[5-({2-[(4-{[ethoxy(hydroxy)phosphoryl]methyl}-2-methoxyphenyl)amino]-5-(trifluoromethyl)pyrimidin-4-yl}amino)-6-(methylcarbamoyl) pyridin-2-yl]-1-(3-hydroxypropyl)-1H-pyrrole-2-carboxylate (Compound 38, 330 mg, 0.46 mmol), and DIPEA (0.4 mL, 2 mmol) in 1,2-dichloroethane (300 mL) at rt over 24 hrs. The reaction mixture was diluted with EtOAc and washed with brine (2×), dried over sodium sulfate, filtered and concentrated in vacuo and purified using Teledyne ISCO Combiflash® Rf system [0→10% EtOH in DCM] to afford 186 mg of the title compound (58%). $^1$H NMR (400 MHz, CD$_3$OD) δ 8.35 (s, 1H), 8.21 (d, J=8.8 Hz, 1H), 7.81 (d, J=2.0 Hz, 1H), 7.76-7.80 (m, 2H), 7.68 (d, J=8.3 Hz, 1H), 6.92-6.96 (m, 1H), 6.71 (td, J=2.2, 8.3 Hz, 1H), 4.64-4.73 (m, 1H), 4.59 (d, J=6.8 Hz, 1H), 3.78-3.97 (m, 8H), 3.63-3.76 (m, 2H), 3.33-3.41 (m, 2H), 2.96 (s, 3H), 2.20 (t, J=5.3 Hz, 2H), 1.06 (t, J=6.9 Hz, 3H). MS (ESI): m/z 704.19 [M+H]$^+$. UPLC: $t_R$=1.59 min (UPLC-TOF: polar_3 min).

Compound 38A: Methyl 4-[5-({2-[(4-{[ethoxy(hydroxy)phosphoryl]methyl}-2-methoxyphenyl)amino]-5-(trifluoromethyl)pyrimidin-4-yl}amino)-6-(methylcarbamoyl)pyridin-2-yl]-1-(3-hydroxypropyl)-1H-pyrrole-2-carboxylate A mixture of methyl 1-[3-(benzyloxy)propyl]-4-[5-({2-[(4-{[ethoxy(hydroxy)phosphoryl]methyl}-2-methoxyphenyl)amino]-5-(trifluoromethyl)pyrimidin-4-yl}amino)-6-(methylcarbamoyl)pyridin-2-yl]-1H-pyrrole-2-carboxylate (Compound 38B, 582 mg, 0.717 mmol) and Palladium 10% wt. on Calcium Carbonate:Carbon black (63.4 mg, 0.031 mmol) in EtOH (11.4 mL), was evacuated and purged with d with H$_{2(g)}$ (3×) and left to stir overnight at rt for 16 hrs. The reaction mixture was filtered and concentrated in vacuo to a 330 mg of a solid which was used without further purification (64%). $^1$H NMR (400 MHz, CD$_3$OD) δ 8.88-9.02 (m, 1H), 8.27 (s, 1H), 7.89 (s, 1H), 7.72 (d, J=6.3 Hz, 1H), 7.56-7.62 (m, 1H), 7.52 (d, J=1.5 Hz, 1H), 7.09 (s, 1H), 6.91 (d, J=8.1 Hz, 1H), 4.47 (t, J=6.8 Hz, 2H), 3.85-3.92 (m, 5H), 3.85 (br. s., 3H), 3.54-3.61 (m, 2H), 3.03 (d, J=22.0 Hz, 2H), 2.95-2.99 (m, 3H), 1.97-2.06 (m, 2H), 1.17 (t, J=7.1 Hz, 3H). MS (ESI): m/z=722.60 [M+H]$^+$. UPLC: $t_R$=1.22 min (UPLC-TOF: polar_2 min).

Compound 38B: Methyl 1-[3-(benzyloxy)propyl]-4-[5-({2-[(4-{[ethoxy(hydroxy)phosphoryl]methyl}-2-methoxyphenyl)amino]-5-(trifluoromethyl)pyrimidin-4-yl}amino)-6-(methylcarbamoyl)pyridin-2-yl]-1H-pyrrole-2-carboxylate A mixture of [1,1'-Bis(diphenylphosphino)ferrocene]dichloropalladium(II), complex with dichloromethane (1:1)

(77.9 mg, 0.095 mmol), potassium carbonate (366 mg, 2.65 mmol), ethyl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 38C, 543 mg, 0.877 mmol) and methyl 1-[3-(benzyloxy)propyl]-4-(4,4,5,5-tetramethyl-1,3,2-dioxaborolan-2-yl)-1H-pyrrole-2-carboxylate (Compound 38E, 385 mg, 0.964 mmol) in 4:1 dioxane:H$_2$O (3.8 mL) was degassed with Argon and irradiated for 30 min at 100° C. in a CEM microwave reactor. The reaction was then concentrated in vacuo and purified using a Teledyne ISCO Combiflash® Rf system [5→100% MeOH in Water] to afford 586 mg of the title compound (82%). MS (ESI): m/z 812.60 [M+H]$^+$. UPLC: $t_R$=1.57 min (UPLC-TOF: polar_2 min).

Compound 38C: Ethyl hydrogen (4-{[4-{[6-bromo-2-(methylcarbamoyl)pyridin-3-yl]amino}-5-(trifluoromethyl)pyrimidin-2-yl]amino}-3-methoxybenzyl) phosphonate A solution of {4-[4-(6-bromo-2-methylcarbamoyl-pyridin-3-ylamino)-5-trifluoromethyl-pyrimidin-2-ylamino]-3-methoxy-benzyl}-phosphonic acid diethyl ester (Compound 38D, 610 mg, 0.94 mmol) in pyridine (9.57 mL) was treated with Sodium iodide (847 mg, 5.65 mmol) and heated at 120° C. for 16 hrs overnight. The reaction solution was concentrated in vacuo and purified using a Teledyne ISCO Combiflash® Rf system [5%→95% MeOH in Water over 25 CV] to afford 543 mg of the title compound (93%). $^1$H NMR (400 MHz, CD$_3$OD) 8.99 (br. s, 1H), 8.80 (d, J=4.6 Hz, 1H), 8.34 (s, 1H), 7.55 (d, J=9.1 Hz, 1H), 7.10 (s, 1H), 6.90 (d, J=8.1 Hz, 1H), 3.83-3.95 (m, 5H), 3.04 (s, 1H), 2.99 (s, 1H), 2.93 (d, J=5.1 Hz, 3H), 1.21 (t, J=7.0 Hz, 3H). MS (ESI): m/z 619.42/621.44 [M+H]$^+$. UPLC: $t_R$=1.24 min (UPLC-TOF: polar_2 min).

Compound 38D: {4-[4-(6-Bromo-2-methylcarbamoyl-pyridin-3-ylamino)-5-trifluoromethyl-pyrimidin-2-ylamino]-3-methoxy-benzyl}-phosphonic acid diethyl ester Prepared analogously to Compound 1B replacing Compound 10 with 3-amino-6-bromo-N-methylpyridine-2-carboxamide (Compound 6D, 279 mg, 1.21 mmol). The reaction mixture was concentrated in vacuo and purified using a Teledyne ISCO Combiflash® Rf system [0→5% MeOH in DCM] to afford 661 mg of the title compound (78%). $^1$H NMR (400 MHz, CD$_3$OD) δ 8.94-9.11 (m, 1H), 8.37 (s, 1H), 7.68 (d, J=7.1 Hz, 1H), 7.58 (d, J=9.1 Hz, 1H), 7.07 (t, J=2.0 Hz, 1H), 6.94 (td, J=2.4, 8.2 Hz, 1H), 4.04-4.16 (m, 4H), 3.88 (s, 3H), 3.33-3.34 (m, 1H), 3.28 (s, 1H), 2.94 (s, 3H), 1.29 (t, J=7.1 Hz, 6H). MS (ESI): m/z 647.53/649.53 [M+H]$^+$. UPLC: $t_R$=1.49 min (UPLC-TOF: polar_2 min).

Compound 38E: Methyl 1-[3-(benzyloxy)propyl]-4-(4,4,5,5-tetramethyl-1,3,2-dioxaborolan-2-yl)-1H-pyrrole-2-carboxylate A mixture of methyl 4-(4,4,5,5-tetramethyl-1,3,2-dioxaborolan-2-yl)-1H-pyrrole-2-carboxylate (Compound 38F, 600 mg, 2.39 mmol) and 1-bromo-3-benzyloxypropane (575 mg, 2.51 mmol) in DMF (2.19 mL) was charged with cesium carbonate (778 mg, 2.39 mmol). The reaction mixture was allowed to stir at 70° C. for 16 hrs. The reaction mixture was diluted with water and then extracted with EtOAc (2×). The organic layer was washed with water (2×), brine (1×), dried over Na$_2$SO$_4$, filtered, concentrated in vacuo and purified using a Teledyne ISCO Combiflash® Rf system [0→4% Ethanol in DCM] to afford 442 mg of the title compound (46%). $^1$H NMR (400 MHz, CD$_3$OD) δ 7.26-7.37 (m, 5H), 7.25 (d, J=1.8 Hz, 1H), 7.17 (d, J=1.8 Hz, 1H), 4.45 (s, 2H), 4.42 (t, J=6.8 Hz, 2H), 3.78 (s, 3H), 3.38 (t, J=5.9 Hz, 2H), 2.01 (t, J=6.2 Hz, 2H), 1.31 (s, 12H). MS (ESI): m/z 440.59 [M+H]$^+$. UPLC: $t_R$=1.60 min (UPLC-TOF: polar_2 min).

Compound 38F: Methyl 4-(4,4,5,5-tetramethyl-1,3, 2-dioxaborolan-2-yl)-1H-pyrrole-2-carboxylate 1-Boc-2-(methoxycarbonyl)pyrrole-4-boronic acid, pinacol ester (900 mg, 2.56 mmol) was heated at 180° C. for 18 min to afford 0.643 mg of the title compound which was used without further purification (99%). $^1$H NMR (400 MHz, CD$_3$OD) δ 7.27 (d, J=1.5 Hz, 1H), 7.10 (d, J=1.3 Hz, 1H), 3.82 (s, 3H), 1.31 (s, 12H). MS (ESI): m/z 252.13 [M+H]$^+$. HPLC: $t_R$=1.32 min (UPLC-TOF: polar_3 min).

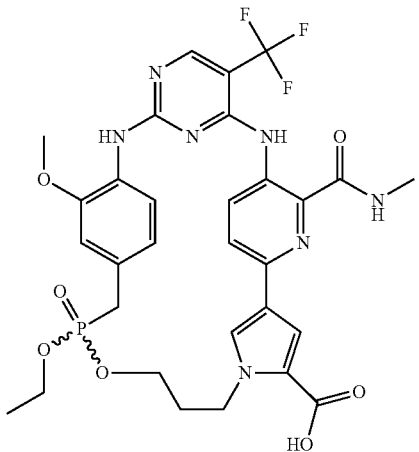

Example 39

(10S)-10-Ethoxy-14-methoxy-24-(methylcarbamoyl)-20-(trifluoromethyl)-9-oxa-5,16,18,22,25, 28-hexaaza-10-phosphapentacyclo[21.2.2. 2$^{12,15}$.1$^{2,5}$.1$^{17,21}$]hentriaconta-1(25),2(31),3,12,14,17 (28),18,20,23,26,29-undecaene-4-carboxylic acid 10-oxide and (10R)-10-ethoxy-14-methoxy-24-(methylcarbamoyl)-20-(trifluoromethyl)-9-oxa-5,16,18, 22,25,28-hexaaza-10-phosphapentacyclo[21.2.2. 2$^{12,15}$.1$^{2,5}$.1$^{17,21}$]hentriaconta-1(25),2(31),3,12,14,17 (28),18,20,23,26,29-undecaene-4-carboxylic acid 10-oxide Racemic Example 39 was prepared by adding a solution of lithium hydroxide, monohydrate (50.7 mg, 1.21 mmol) in H$_2$O (0.32 mL) to a stirring solution of methyl 10-ethoxy-14-methoxy-24-(methylcarbamoyl)-20-(trifluoromethyl)-9-oxa-5,16,18,22,25,28-hexaaza-10-phosphapentacyclo [21.2.2.2$^{12,15}$.1$^{2,5}$.1$^{17,21}$]hentriaconta-1(25),2(31),3,12,14, 17(28),18,20,23,26,29-undecaene-4-carboxylate 10-oxide (Example 38, 170 mg, 0.242 mmol) in THF (0.32 mL) and MeOH (0.32 mL) at rt for 30 hrs. The reaction was concentrated in vacuo and purified using a reverse phase chromatography (Teledyne ISCO Combiflash® Rf system, C-18 column [0→100% MeOH in Water]) to afford 137 mg of the title compound (82%). $^1$H NMR (400 MHz, CD$_3$OD) δ 8.35 (s, 1H), 8.19 (d, J=8.8 Hz, 1H), 7.78 (d, J=8.8 Hz, 1H), 7.66-7.74

(m, 3H), 6.94 (s, 1H), 6.68-6.74 (m, 1H), 4.67-4.75 (m, 1H), 4.54-4.63 (m, 1H), 3.82-4.00 (m, 5H), 3.68-3.77 (m, 2H), 3.44 (s, 2H), 2.96 (s, 3H), 2.17-2.28 (m, J=5.3 Hz, 2H), 1.09 (t, J=7.1 Hz, 3H). MS (ESI): m/z=690.61 [M+H]$^+$. HPLC: $t_R$=1.29 min (UPLC-TOF: polar_3 min).

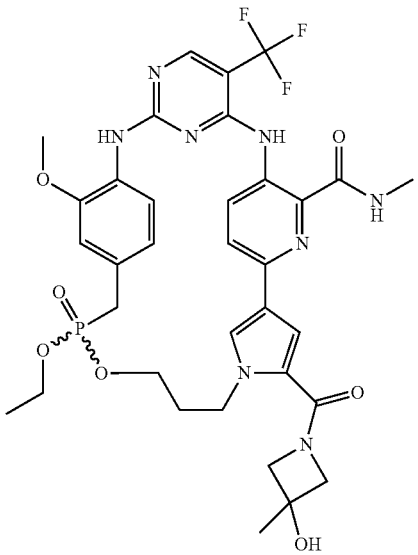

Example 40

(10S)-10-ethoxy-4-[(3-hydroxy-3-methylazetidin-1-yl)carbonyl]-14-methoxy-N-methyl-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-4-[(3-hydroxy-3-methylazetidin-1-yl)carbonyl]-14-methoxy-N-methyl-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Racemic Example 40 was prepared by adding 3-methyl-3-azetidinol (3.05 mg, 35.0 mmol) to a stirring solution of 10-ethoxy-14-methoxy-24-(methylcarbamoyl)-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-4-carboxylic acid 10-oxide (Example 39, mg, 21.8 mmol), TBTU (8.38 mg, 26.1 mmol) and DIPEA (30.3 ml 174 mmol) in DCM (836 ml) at 25° C. for 30 min. The reaction was diluted with water, extracted with EtOAc (3x), dried with sodium sulfate, filtered, concentrated in vacuo and purified using a Teledyne ISCO Combiflash® Rf system [elution gradient: 0→10% MeOH in DCM] to afford 16 mg of the title compound (97%). $^1$H NMR (400 MHz, CDCl$_3$): δ 8.34 (s, 1H), 8.18 (d, J=8.6 Hz, 1H), 7.66-7.77 (m, 3H), 7.39 (d, J=1.8 Hz, 1H), 6.92 (t, J=1.8 Hz, 1H), 6.67 (td, J=2.2, 8.3 Hz, 1H), 4.51-4.70 (m, 2H), 4.29-4.52 (m, 2H), 3.96-4.09 (m, 2H), 3.85-3.95 (m, 5H), 3.66-3.74 (m, 2H), 3.34-3.42 (m, 2H), 2.97 (s, 3H), 2.14-2.24 (m, 2H), 1.55 (s, 3H), 1.10 (t, J=7.1 Hz, 3H). MS (ESI): m/z=759.60 [M+H]$^+$. UPLC: $t_R$=1.31 min (UPLC-TOF: polar_2 min).

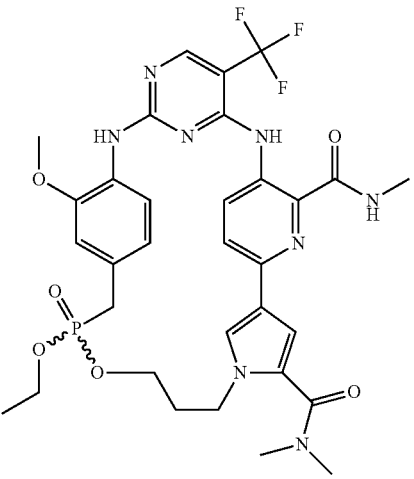

Example 41

(10S)-10-Ethoxy-14-methoxy-N$^4$,N$^4$,N$^{24}$-trimethyl-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-4,24-dicarboxamide 10-oxide and (10R)-10-Ethoxy-14-methoxy-N$^4$,N$^4$,N$^{24}$-trimethyl-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-4,24-dicarboxamide 10-oxide Prepared analogously to Example 40 using dimethylamine (1.58 mg, 35.0 mmol) to afford 15.4 mg of the desired title compound (99%). $^1$H NMR (400 MHz, CD$_3$OD) δ 8.33 (s, 1H), 8.15 (d, J=8.8 Hz, 1H), 7.75 (d, J=8.8 Hz, 1H), 7.67-7.72 (m, 2H), 7.35 (d, J=1.8 Hz, 1H), 6.91 (t, J=1.8 Hz, 1H), 6.68 (td, J=2.2, 8.2 Hz, 1H), 4.44 (q, J=5.8 Hz, 2H), 3.84-4.00 (m, 5H), 3.74 (dd, J=5.9, 9.0 Hz, 2H), 3.33-3.42 (m, 2H), 3.14-3.28 (m, 6H), 2.95 (s, 3H), 2.05-2.13 (m, 2H), 1.10 (t, J=7.1 Hz, 3H). MS (ESI): m/z=717.57 [M+H]$^+$. UPLC: $t_R$=1.38 min (UPLC-TOF: polar_2 min).

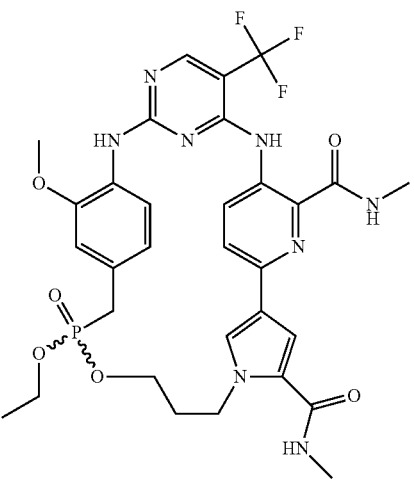

Example 42

(10S)-10-Ethoxy-14-methoxy-N,N'-dimethyl-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-4,24-dicarboxamide 10-oxide and (10R)-10-Ethoxy-14-methoxy-N,N'-dimethyl-20-(trifluoromethyl)-9-oxa-5,16,18,22,25,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-4,24-dicarboxamide 10-oxide Prepared analogously to Example 40 using methylamine (1.09 mg, 35.0 mmol) to afford 10.9 mg of the desired title compound (71%). $^1$H NMR (400 MHz, CD$_3$OD) δ 8.33 (s, 1H), 8.13 (d, J=8.6 Hz, 1H), 7.62-7.74 (m, 3H), 7.53 (d, J=2.0 Hz, 1H), 6.90 (s, 1H), 6.60-6.67 (m, 1H), 4.61-4.69 (m, 1H), 4.52-4.61 (m, J=7.1 Hz, 1H), 3.84-3.99 (m, 5H), 3.63-3.73 (m, 2H), 3.34-3.41 (m, 1H), 3.20-3.27 (m, 1H), 2.96 (s, 3H), 2.88 (s, 3H), 2.13-2.23 (m, 2H), 1.10 (t, J=7.1 Hz, 3H). MS (ESI): m/z=703.57 [M+H]$^+$. UPLC: t$_R$=1.35 min (UPLC-TOF: polar_2 min).

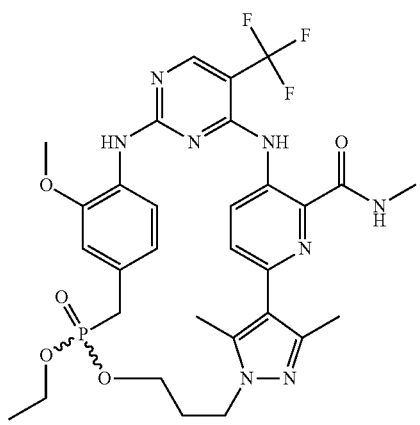

Example 43

(10S)-10-Ethoxy-14-methoxy-N,3,31-trimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-Ethoxy-14-methoxy-N,3,31-trimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 38 using ethyl hydrogen (4-{[4-({6-[1-(3-hydroxypropyl)-3,5-dimethyl-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 43A, 127 mg, 0.183 mmol) to afford 1.7 mg of the desired title compound (1.4%). $^1$H NMR (400 MHz, CD$_3$OD) δ 8.33 (s, 1H), 7.95 (d, J=8.3 Hz, 1H), 7.46 (d, J=8.3 Hz, 1H), 7.27 (d, J=8.1 Hz, 1H), 6.78 (s, 1H), 6.21 (td, J=2.1, 8.3 Hz, 1H), 4.15-4.39 (m, 2H), 3.96-4.12 (m, 2H), 3.73-3.95 (m, 5H), 3.10 (d, J=4.8 Hz, 1H), 3.04 (d, J=4.8 Hz, 1H), 2.90 (s, 3H), 2.43 (s, 3H), 2.38 (s, 3H), 2.30 (d, J=5.1 Hz, 2H), 1.25 (t, J=7.1 Hz, 3H). MS (ESI): m/z=675.52 [M+H]$^+$. UPLC: t$_R$=1.23 min (UPLC-TOF: polar_2 min).

Compound 43A: Ethyl hydrogen (4-{[4-({6-[1-(3-hydroxypropyl)-3,5-dimethyl-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Example 38B using 3-[3,5-dimethyl-4-(4,4,5,5-tetramethyl-1,3,2-dioxaborolan-2-yl)-1H-pyrazol-1-yl]propan-1-ol (Compound 43B, 74.64 mg, 0.2664 mmol) to afford 131 mg of the desired title compound (78%). $^1$H NMR (400 MHz, CD$_3$OD) δ 9.07 (br. s., 1H), 8.33 (s, 1H), 7.73 (d, J=8.1 Hz, 1H), 7.41 (d, J=8.8 Hz, 1H), 7.11 (s, 1H), 6.88 (d, J=8.1 Hz, 1H), 4.20 (t, J=6.9 Hz, 2H), 3.78-3.92 (m, 5H), 3.57 (t, J=5.9 Hz, 2H), 2.93-3.03 (m, 5H), 2.47 (s, 3H), 2.38 (s, 3H), 1.97-2.07 (m, 2H), 1.15 (t, J=6.9 Hz, 3H). MS (ESI): m/z=693.23 [M+H]$^+$. HPLC: t$_R$=1.18 min (UPLC-TOF: polar_3 min).

Compound 43B: 3-[3,5-dimethyl-4-(4,4,5,5-tetramethyl-1,3,2-dioxaborolan-2-yl)-1H-pyrazol-1-yl]propan-1-ol 1-[3-(Benzyloxy)propyl]-3,5-dimethyl-4-(4,4,5,5-tetramethyl-1,3,2-dioxaborolan-2-yl)-1H-pyrazole (Compound 43C, 560 mg, 1.5 mmol) was hydrogenated using the procedure from Compound 38A to afford 421 mg of the desired title compound (99%). $^1$H NMR (400 MHz, CD$_3$OD) δ 4.08 (t, J=7.1 Hz, 2H), 3.50 (t, J=6.1 Hz, 2H), 2.40 (s, 3H), 2.27 (s, 3H), 1.95 (t, J=6.7 Hz, 2H), 1.30 (s, 12H). MS (ESI): m/z=280.37 [M+H]$^+$. UPLC: t$_R$=1.29 min (UPLC-TOF: polar_2 min)

Compound 43C: 1-[3-(benzyloxy)propyl]-3,5-dimethyl-4-(4,4,5,5-tetramethyl-1,3,2-dioxaborolan-2-yl)-1H-pyrazole Prepared analogously to Compound 38E replacing Compound 38F with 3,5-dimethylpyrazole-4-boronic acid, pinacol ester (0.75 g, 3.4 mmol) to afford 560 mg of the desired title compound (45%). $^1$H NMR (400 MHz, CD$_3$OD) δ 7.24-7.36 (m, 5H), 4.45-4.48 (m, 2H), 4.08 (t, J=6.8 Hz, 2H), 3.41 (t, J=5.8 Hz, 2H), 2.36 (s, 3H), 2.26 (s, 3H), 2.04 (t, J=6.3 Hz, 2H), 1.30 (s, 12H). MS (ESI): m/z=370.60 [M+H]$^+$. UPLC: t$_R$=1.79 min (UPLC-TOF: polar_2 min).

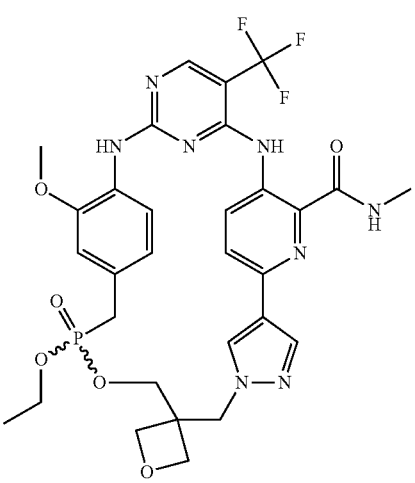

Example 44

(10S)-10-ethoxy-14-methoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide and (10R)-10-ethoxy-14-methoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide

[1,1'-bis(diphenylphosphino)ferrocene]dichloropalladium(II), complex with dichloromethane (1:1) (9.56 mg, 0.012 mmol) and potassium carbonate (45 mg, 0.33 mmol) were added to a stirring suspension of racemic ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 44A, 96.4 mg, 0.108 mmol) in 8 mL of 4:1 dioxane:H$_2$O (1.94 mL). The mixture was evacuated and charged with Argon (3×) and irradiated for 30 min at 100° C. in a CEM microwave reactor. The reaction was concentrated in vacuo and purified using a Teledyne ISCO Combiflash® Rf system [0→100% Acetone/Heptanes] to afford 31.6 mg of racemic Example 44 (43%). $^1$H NMR (400 MHz, CD$_3$OD) δ 8.38 (s, 1H), 8.31-8.36 (m, 2H), 8.15 (d, J=8.6 Hz, 1H), 7.78 (d, J=8.6 Hz, 1H), 7.62 (d, J=8.3 Hz, 1H), 6.89-6.94 (m, 1H), 6.65 (td, J=2.3, 8.1 Hz, 1H), 4.68-4.82 (m, 4H), 4.49 (dd, J=6.8, 9.1 Hz, 2H), 3.72-3.94 (m, 7H), 3.33-3.42 (m, 2H), 2.94 (s, 3H), 1.01 (t, J=6.9 Hz, 3H). MS (ESI): m/z=689.51 [M+H]$^+$. UPLC: t$_R$=1.26 min (UPLC-TOF: polar_2 min).

Compound 44A: Ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-3-methoxybenzyl)phosphonate The mixture resulting from the addition of (Benzotriazol-1-yloxy)tripyrrolidino-phosphonium hexafluorophosphate (840 mg, 1.62 mmol) to a stirring suspension of ethyl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 38C, 500 mg, 0.807 mmol), (3-{[4-(4,4,5,5-tetramethyl-1,3,2-dioxaborolan-2-yl)-1H-pyrazol-1-yl]methyl}oxetan-3-yl)methanol (Compound 44B, 249 mg, 0.848 mmol) and DIPEA (0.8 mL, 4 mmol) in 1,2-dichloroethane (57.3 mL) was allowed to stir at rt for 24 hrs. The reaction mixture was then diluted with EtOAc and washed with brine (2×), dried over sodium sulfate, filtered and concentrated in vacuo and purified using a Teledyne ISCO Combiflash® Rf system [0→60% Acetone/Heptanes] to afford 96.4 mg of racemic Compound 44A (13%). $^1$H NMR (400 MHz, CD$_3$OD) δ 9.00 (br. s., 1H), 8.76 (d, J=4.8 Hz, 1H), 8.33 (s, 1H), 7.73-7.75 (m, 1H), 7.65 (s, 1H), 7.50-7.56 (m, 1H), 7.03 (s, 1H), 6.90 (d, J=8.1 Hz, 1H), 4.55-4.66 (m, 2H), 4.32-4.45 (m, 4H), 3.96-4.19 (m, 4H), 3.88 (s, 3H), 3.35 (s, 2H), 2.93 (d, J=4.8 Hz, 3H), 1.24-1.33 (m, 15H). MS (ESI): m/z=897.21/899.24 [M+H]$^+$. HPLC: t$_R$=1.19 min (UPLC-TOF: polar_2 min).

Compound 44B: (3-{[4-(4,4,5,5-tetramethyl-1,3,2-dioxaborolan-2-yl)-1H-pyrazol-1-yl]methyl}oxetan-3-yl)methanol 1-({3-[(Benzyloxy)methyl]oxetan-3-yl}methyl)-4-(4,4,5,5-tetramethyl-1,3,2-dioxaborolan-2-yl)-1H-pyrazole (Compound 44C, 1.37 mg, 3.56 mmol) was hydrogenated using the procedure from Compound 38A to afford 998 mg of the title compound (95%). $^1$H NMR (400 MHz, CD$_3$OD) δ 7.86 (s, 1H), 7.67 (s, 1H), 4.65 (d, J=6.3 Hz, 2H), 4.49 (s, 2H), 4.42 (d, J=6.3 Hz, 2H), 3.57 (s, 2H), 1.32 (s, 12H).

Compound 44C: 1-({3-[(benzyloxy)methyl]oxetan-3-yl}methyl)-4-(4,4,5,5-tetramethyl-1,3,2-dioxaborolan-2-yl)-1H-pyrazole A mixture of 4-(4,4,5,5-tetramethyl[1,3,2]dioxaborolan-2-yl)-1H-pyrazole (0.825 g, 4.25 mmol) and {3-[(benzyloxy)methyl]oxetan-3-yl}methyl methyl sulfate (Compound 44D, 1.35 g, 4.46 mmol) in DMF (3.90 mL) was charged with potassium carbonate (588 mg, 4.25 mmol) and allowed to stir at rt for 16 hrs. The reaction mixture was diluted with EtOAc and washed with brine (2×), dried over sodium sulfate, filtered and concentrated in vacuo and purified using a Teledyne ISCO Combiflash® Rf system [0→40% Acetone/Heptanes] to afford 1.37 g of the title compound (84%). $^1$H NMR (400 MHz, CD$_3$OD) δ 7.76 (s, 1H), 7.66 (s, 1H), 7.25-7.37 (m, 5H), 4.67 (d, J=6.6 Hz, 2H), 4.48-4.52 (m, 4H), 4.42 (d, J=6.6 Hz, 2H), 3.45 (s, 2H), 1.20 (s, 12H). MS (ESI): m/z=385.20 [M+H]$^+$. HPLC: t$_R$=1.08 min (UPLC-TOF: polar_2 min).

Compound 44D: {3-[(benzyloxy)methyl]oxetan-3-yl}methyl methanesulfonate

An ice cooled solution of (3-(benzyloxymethyl)oxetan-3-yl)methanol (Example 44E, 1.00 g, 4.80 mmol) in DCM (5.14 mL) was treated with triethylamine (1.31 mL, 9.43 mmol) and methanesulfonyl chloride (0.438 mL, 5.66 mmol) and gradually allowed to warm up to rt over 16 hrs. The mixture was diluted with DCM, washed with saturated aqueous NaHCO$_3$ solution (1×), brine (2×), dried over anhydrous sodium sulfate, filtered, concentrated in vacuo to a solid to afford 7.2 g of the title compound (100%). The crude product was used in next step without further purification. $^1$H NMR (400 MHz, CD$_3$OD) δ 7.23-7.38 (m, 5H), 4.58 (s, 2H), 4.46-4.54 (m, 6H), 3.74 (s, 2H), 3.09 (s, 3H).

Compound 44E: {3-[(Benzyloxy)methyl]oxetan-3-yl}methanol

This compound was prepared by selective monobenzylation of oxetane-3,3-diyldimethanol (US 2010/0305113 A1) using the procedure of Maki et al in *Tetrahedron Letters*, 2009, 50, 1466-1468. $^1$H NMR (400 MHz, CDCl$_3$) δ 7.31-7.37 (m, 5H), 4.56 (s, 2H), 4.49 (d, J=3.6 Hz, 2H), 4.42 (d, J=3.9 Hz, 2H), 3.94 (d, J=3.3 Hz, 2H), 3.80 (s, 2H), 2.21 (t, J=3.6 Hz, 1H).

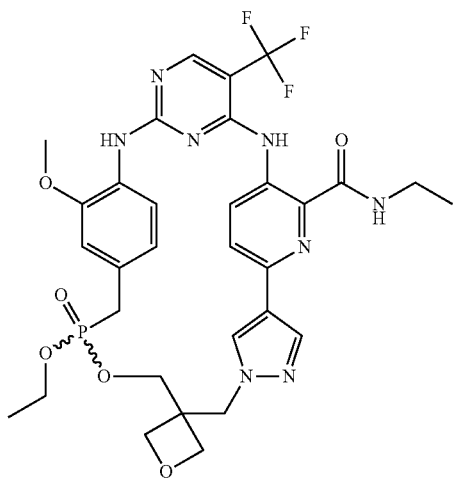

Example 45

(10S)-10-ethoxy-N-ethyl-14-methoxy-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide and (10R)-10-ethoxy-N-ethyl-14-methoxy-20-(trifluoromethyl)spiro[9-oxa-4,5,16,18,22,25,28-heptaaza-10-phosphapentacyclo[21.2.2.2$^{12,15}$1$^{2,5}$.1$^{17,21}$]hentriaconta-1(25),2(31),3,12,14,17(28),18,20,23,26,29-undecaene-7,3'-oxetane]-24-carboxamide 10-oxide Prepared analogously to Example 44 using racemic ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(ethylcarbamoyl)pyridin-3-yl]amino}-5-(trifluoromethyl)pyrimidin-2-yl]amino}-3-methoxybenzyl)phosphonate (Compound 45A, 37.7 mg, 0.0414 mmol) to afford 2.8 mg of the title compound (10%). $^1$H NMR (400 MHz, CD$_3$OD) δ 8.39 (s, 1H), 8.34 (s, 1H), 8.31 (s, 1H), 8.13 (d, J=8.6 Hz, 1H), 7.78 (d, J=8.6 Hz, 1H), 7.62 (d, J=8.1 Hz, 1H), 6.91 (t, J=1.8 Hz, 1H), 6.64 (td, J=2.3, 8.3 Hz, 1H), 4.49 (t, J=6.4 Hz, 2H), 4.03-4.16 (m, 1H), 3.86-3.96 (m, 5H), 3.74-3.85 (m, 3H), 3.62 (br. s., 3H), 3.33-3.42 (m, 3H), 1.17-1.24 (m, 3H), 0.99-1.07 (m, 3H). MS (ESI): m/z=703.39 [M+H]$^+$. UPLC: t$_R$=1.29 min (UPLC-TOF: polar_2 min).

Compound 45A: Ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(ethylcarbamoyl)pyridin-3-yl]amino}-5-(trifluoromethyl)pyrimidin-2-yl]amino}-3-methoxybenzyl)phosphonate Racemic Compound 45A was prepared analogously to Compound 44A using ethyl hydrogen (4-{[4-{[6-bromo-2-(ethylcarbamoyl)pyridin-3-yl]amino}-5-(trifluoromethyl)pyrimidin-2-yl]amino}-3-methoxybenzyl)phosphonate (Compound 45B, 78.1 mg, 0.123 mmol) to afford 37.7 mg of the title compound (34%). MS (ESI): m/z=909.40/991.51 [M+H]$^+$. UPLC: t$_R$=1.60 min (UPLC-TOF: polar_2 min).

Compound 45B: Ethyl hydrogen (4-{[4-{[6-bromo-2-(ethylcarbamoyl)pyridin-3-yl]amino}-5-(trifluoromethyl)pyrimidin-2-yl]amino}-3-methoxybenzyl) phosphonate Prepared analogously to Compound 38C with ethyl hydrogen (4-{[4-{[6-bromo-2-(ethylcarbamoyl)pyridin-3-yl]amino}-5-(trifluoromethyl)pyrimidin-2-yl]amino}-3-methoxybenzyl)phosphonate (Compound 45C) to afford 78.1 mg of the title compound (40%). $^1$H NMR (400 MHz, CD$_3$OD) δ 8.92-9.10 (m, 1H), 8.33 (s, 1H), 7.59-7.71 (m, 1H), 7.54 (d, J=9.1 Hz, 1H), 7.10 (s, 1H), 6.83-6.92 (m, 1H), 3.84-3.93 (m, 5H), 3.43 (q, J=7.1 Hz, 2H), 2.95-3.06 (m, 2H), 1.22 (dt, J=4.9, 7.1 Hz, 6H). MS (ESI): m/z=633.16/635.17 [M+H]$^+$. UPLC: t$_R$=1.45 min (UPLC-TOF: polar_2 min).

Compound 45C: Diethyl (4-{[4-{[6-bromo-2-(ethylcarbamoyl)pyridin-3-yl]amino}-5-(trifluoromethyl)pyrimidin-2-yl]amino}-3-methoxybenzyl)phosphonate Prepared analogously to Compound 1B replacing Compound 1C with Compound 45D (300.0 mg, 1.229 mmol) to afford 647 mg of the title compound. (80%). $^1$H NMR (400 MHz, CDCl$_3$) δ 12.32 (br. s., 1H), 9.03 (d, J=8.8 Hz, 1H), 8.41 (s, 1H), 7.88-8.16 (m, 2H), 7.73 (br. s., 1H), 7.52 (d, J=8.8 Hz, 1H), 6.94 (t, J=2.0 Hz, 1H), 6.86 (dt, J=8.3, 2.1 Hz, 1H), 4.01-4.13 (m, 4H), 3.91 (s, 3H), 3.46-3.57 (m, 2H), 3.12-3.23 (m, 2H), 1.29 (t, J=6.9 Hz, 9H). MS (ESI): m/z=661.10/663.11 [M+H]$^+$; UPLC: t$_R$=1.17 min (UPLC-TOF, polar_2 min).

Compound 45D: 3-Amino-6-bromo-N-ethylpyridine-2-carboxamide

A stirred suspension of ethyl 3-amino-6-bromopyridine-2-carboxylate (5 g, 20.3 mmol) in ethanol (40 mL) in a steel bomb was treated with a 2M solution of ethylamine in THF (220 mL, 440 mmol) and heated to 120° C. for 2 days. The reaction mixture was cooled to RT, the solvents were evaporated under reduced pressure and the residue was purified by column chromatography (SiO$_2$, 0.5% methanol in dichloromethane) to give 3.5 g (70%) of the required material as white solid $^1$H NMR (400 MHz, CDCl$_3$) δ 7.77 (brs, 1H), 7.21 (d, J=8.8 Hz, 1H), 6.85 (d, J=8.8 Hz, 1H), 5.99 (brs, 2H), 3.4 (q, J=7.2 Hz, 2H), 1.24 (t, J=7.2 Hz, 3H).

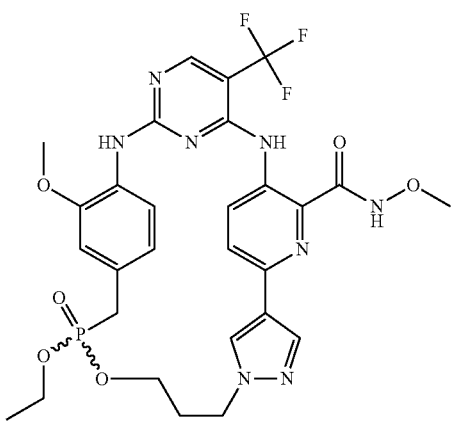

Example 46

(10S)-10-ethoxy-N,14-dimethoxy-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-N,14-dimethoxy-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 44 using racemic ethyl 3-[4-(4,4,5,5-tetramethyl-1,3,2-dioxaborolan-2-yl)-1H-pyrazol-1-yl]propyl (4-{[4-{[6-bromo-2-(methoxycarbamoyl)pyridin-3-yl]amino}-5-(trifluoromethyl)pyrimidin-2-yl]amino}-3-methoxybenzyl)phosphonate (Compound 46A, 45.0 mg, 0.0518 mmol) to afford 3.6 mg of racemic Example 46 (10%). $^1$H NMR (400 MHz, CD$_3$OD) δ 8.45-8.53 (m, 1H), 8.30-8.39 (m, 2H), 8.06-8.17 (m, 1H), 7.78-7.84 (m, 1H), 7.51-7.62 (m, 1H), 6.86-6.92 (m, 1H), 6.52-6.65 (m, 1H), 4.46 (t, J=5.9 Hz, 2H), 3.82-3.91 (m, 5H), 3.79 (br. s., 5H), 3.19-3.29 (m, 2H), 2.23-2.32 (m, 2H), 1.01-1.13 (m, 3H). MS (ESI): m/z=663.33 [M+H]$^+$. UPLC: t$_R$=1.14 min (UPLC-TOF: polar_2 min).

Compound 46A: Ethyl 3-[4-(4,4,5,5-tetramethyl-1,3,2-dioxaborolan-2-yl)-1H-pyrazol-1-yl]propyl (4-{[4-{[6-bromo-2-(methoxycarbamoyl)pyridin-3-yl]amino}-5-(trifluoromethyl)pyrimidin-2-yl]amino}-3-methoxybenzyl)phosphonate Racemic Compound 46A was prepared analogously to Compound 44A using ethyl hydrogen (4-{[4-{[6-bromo-2-(methoxycarbamoyl)pyridin-3-yl]amino}-5-(trifluoromethyl)pyrimidin-2-yl]amino}-3-methoxybenzyl)phosphonate (Compound KS11B, 50.0 mg, 0.0787 mmol) and 3-[4-(4,4,5,5-tetramethyl-1,3,2-dioxaborolan-2-yl)-1H-pyrazol-1-yl]propan-1-ol (Compound 3E, 20.8 mg, 0.0826 mmol) to afford 45 mg of the desired material (28%). MS (ESI): m/z=869.25/871.23 [M+H]$^+$. UPLC: t$_R$=1.48 min (UPLC-TOF: polar_2 min).

Compound 46B: Ethyl hydrogen (4-{[4-{[6-bromo-2-(methoxycarbamoyl)pyridin-3-yl]amino}-5-(trifluoromethyl)pyrimidin-2-yl]amino}-3-methoxybenzyl)phosphonate Prepared analogously to Compound 38C using ethyl hydrogen (4-{[4-{[6-bromo-2-(methoxycarbamoyl)pyridin-3-yl]amino}-5-(trifluoromethyl)pyrimidin-2-yl]amino}-3-methoxybenzyl)phosphonate to afford 107.1 mg of the title compound (28%). $^1$H NMR (400 MHz, CD$_3$OD) δ 8.90-9.16 (m, 1H), 8.32-8.40 (m, 1H), 7.54-7.75 (m, 2H), 7.03-7.11 (m, 1H), 6.86-6.95 (m, 1H), 3.98-4.07 (m, 2H), 3.88 (s, 3H), 3.82 (s, 3H), 3.09-3.21 (m, 2H), 1.27 (s, 3H). MS (ESI): m/z=635.16/637.12 [M+H]$^+$. UPLC: t$_R$=1.21 min (UPLC-TOF: polar_2 min).

Compound 46C: Diethyl (4-{[4-{[6-bromo-2-(methoxycarbamoyl)pyridin-3-yl]amino}-5-(trifluoromethyl)pyrimidin-2-yl]amino}-3-methoxybenzyl) phosphonate This material was prepared analogously to compound 1B using 3-Amino-6-bromo-N-methoxypyridine-2-carboxamide (Compound 46D, 302.0 mg, 1.227 mmol) and diethyl (4-{[4-chloro-5-(trifluoromethyl)pyrimidin-2-yl]amino}-3-methoxybenzyl)phosphonate (Compound 1 E, 612.6 mg, 1.350 mmol) to isolate 189 mg of the title compound (23%). $^1$H NMR (400 MHz, DMSO-d$_6$) δ 12.18 (s, 1H), 11.88 (s, 1H), 9.21 (br. s., 1H), 8.87 (br. s., 1H), 8.44 (s, 1H), 7.65 (d, J=8.8 Hz, 1H), 7.38 (br. s., 1H), 7.06 (s, 1H), 6.90 (d, J=8.1 Hz, 1H), 3.96-4.05 (m, 4H), 3.74 (s, 3H), 3.70 (s, 3H), 3.29 (d, J=21.2 Hz, 2H), 1.20 (t, J=7.0 Hz, 6H)

Compound 46D: 3-Amino-6-bromo-N-methoxypyridine-2-carboxamide

A suspension of 3-amino-N-methoxypyridine-2-carboxamide (Compound 46E, 0.275 g, 1.64 mmol) in H$_2$O (4.5 mL) was treated with a drop of Sulfuric acid and 0.6 mL of AcOH. After about 10 min of vigorous stirring, a solution of Bromine (84.7 uL, 1.64 mmol) in 0.4 mL of AcOH was cautiously added. After an additional 15-20 min of stirring the texture of the reaction mixture/suspension changed to become a more coarse orange ppt. This material was collected by filtration and dried to afford 240 mg of the title compound as an orange solid (59%). $^1$H NMR (400 MHz, DMSO-d$_6$) δ 11.51 (s, 1H), 7.40 (d, J=8.8 Hz, 1H), 7.14 (d, J=8.8 Hz, 1H), 6.91 (br. s., 2H), 3.66 (s, 3H); MS (ESI): m/z=245.98, 247.98 [M+H]$^+$; UPLC: t$_R$=0.67 min (UPLC-TOF: polar_2 min)

Compound 46E: 3-amino-N-methoxypyridine-2-carboxamide

A solution of Methoxylamine hydrochloride (1.02 g, 12.2 mmol) in H$_2$O (5.0 mL) was treated with Potassium carbonate (0.421 g, 3.05 mmol) followed by 1H-pyrido[3,2-d][1,3]oxazine-2,4-dione (*J. Med. Chem.*, 1996, 39, 4962-4703, 1.0 g, 6.1 mmol). This mixture was allowed to stir at 50° C. for ~1 hour forming a suspension. The ppt was collected via filtration and the filtrate was stored in the freezer O/N allowing an additional 35 mg to be collected. The solids were combined to afford 257 mg of the title compound (22%). 1H NMR (400 MHz, DMSO-d$_6$) d 11.62 (s, 1H), 7.75 (dd, J=1.4, 4.2 Hz, 1H), 7.23 (dd, J=4.2, 8.5 Hz, 1H), 7.15 (dd, J=1.4, 8.5 Hz, 1H), 6.74 (br. s., 2H), 3.65 (s, 3H).

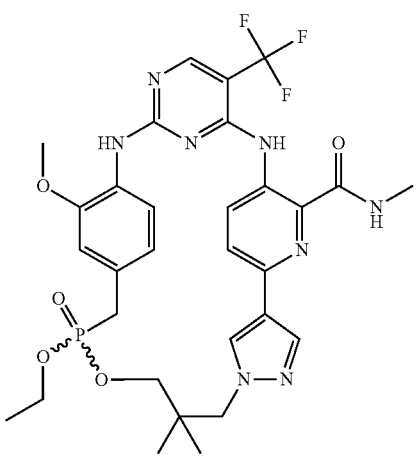

Example 47

(10S)-10-ethoxy-14-methoxy-N,7,7-trimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-14-methoxy-N,7,7-trimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 44 using racemic 2,2-dimethyl-3-[4-(4,4,5,5-tetramethyl-1,3,2-dioxaborolan-2-yl)-1H-pyrazol-1-yl]propylethyl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 47A, 2.59 g, 1.76 mmol) to afford 462 mg of racemic Example 47 (39%). MS (ESI): m/z=675.76 [M+H]$^+$. UPLC: t$_R$=1.33 min (UPLC-TOF: polar__2 min).

Compound 47A: 2,2-dimethyl-3-[4-(4,4,5,5-tetramethyl-1,3,2-dioxaborolan-2-yl)-1H-pyrazol-1-yl]propylethyl (4-{[4-{[6-bromo-2-(methylcarbamoyl)pyridin-3-yl]amino}-5-(trifluoromethyl)pyrimidin-2-yl]amino}-3-methoxybenzyl)phosphonate Racemic Compound 47A was prepared analogously to Compound 44A using ethyl hydrogen 2,2-dimethyl-3-[4-(4,4,5,5-tetramethyl-1,3,2-dioxaborolan-2-yl)-1H-pyrazol-1-yl]propan-1-ol (Compound 47B, 955 mg, 3.41 mmol) and Compound 38C to afford the title compound. MS (ESI): m/z=883.93/885.93 [M+H]$^+$. HPLC: t$_R$=2.71 min (ZQ3: polar__5 min).

Compound 47B: 2,2-dimethyl-3-[4-(4,4,5,5-tetramethyl-1,3,2-dioxaborolan-2-yl)-1H-pyrazol-1-yl]propan-1-ol 1-[2,2-dimethyl-3-(tetrahydro-2H-pyran-2-yloxy)propyl]-4-(4,4,5,5-tetramethyl-1,3,2-dioxaborolan-2-yl)-1H-pyrazole (Compound 47C, 539 mg, 1.48 mmol) was dissolved in EtOH (2.64 mL) and p-TsOH.H$_2$O (56.3 mg, 0.296 mmol) was added to the reaction mixture. The reaction was left to stir at rt for 16 hrs. Solid NaHCO$_3$ (1.24 g, 14.8 mmol) was added to the reaction mixture and left to stir at rt for an additional 30 min. The reaction mixture was quenched with water and then extracted with EtOAc. The organic layer was washed with sat. NaHCO$_3$ (1×), brine (2×), extracted, dried over sodium sulfate, filtered, concentrated in vacuo and purified using a Teledyne ISCO Combiflash® Rf system [0-30% Acetone/Heptanes] to afford 237 mg of the title compound (57%). MS (ESI): m/z=281.38 [M+H]$^+$. UPLC: t$_R$=1.12 min (UPLC-TOF: polar__2 min).

Compound 47C: 1-[2,2-dimethyl-3-(tetrahydro-2H-pyran-2-yloxy)propyl]-4-(4,4,5,5-tetramethyl-1,3,2-dioxaborolan-2-yl)-1H-pyrazole To a solution of 1-[2,2-dimethyl-3-(tetrahydro-2H-pyran-2-yloxy)propyl]-4-iodo-1H-pyrazole (Compound 47D, 539 mg, 1.48 mmol) in THF (20 mL) was added 1.3 M of i-PrMgCl.LiCl in THF (2.28 mL, 2.96 mmol) at 0° C. The reaction was allowed to warm gradually to rt over 20 min. 2-Methoxy-4,4,5,5-tetramethyl-1,3,2-dioxaborolane (0.73 mL, 4.44 mmol) was added and the mixture was stirred at rt for 16 hrs. The reaction mixture was quenched with water and then extracted with EtOAc. The organic layer was washed with water, brine (2×), dried over sodium sulfate, filtered, concentrated in vacuo and purified using a Teledyne ISCO Combiflash® Rf system [0-40% Acetone/Heptanes] to afford 500 mg the desired product (100%). $^1$H NMR (400 MHz, CD$_3$OD) δ 7.81 (s, 1H), 7.65 (s, 1H), 4.58 (d, J=2.8 Hz, 1H), 4.14 (s, 2H), 3.80-3.91 (m, 1H), 3.46-3.54 (m, 1H), 3.44 (d, J=9.6 Hz, 1H), 3.02 (d, J=9.3 Hz, 1H), 1.80-1.97 (m, 1H), 1.68-1.79 (m, 1H), 1.49-1.67 (m, 5H), 1.31 (s, 10H), 0.87-0.98 (m, 6H), 0.84-1.01 (m, 1H). MS (ESI): m/z=365.51 [M+H]$^+$. UPLC: t$_R$=1.54 min (UPLC-TOF: polar__2 min).

Compound 47D: 1-[2,2-dimethyl-3-(tetrahydro-2H-pyran-2-yloxy)propyl]-4-iodo-1H-pyrazole p-Toluenesulfonic acid (44 mg, 0.26 mmol) was added to a stirring solution of 3-(4-iodopyrazol-1-yl)-2,2-dimethyl-propan-1-ol (Compound 47E, 500 mg, 1.79 mmol) in DCM (2.58 mL). The mixture was stirred under argon, chilled in an ice-bath, then dihydropyran (0.261 mL, 2.86 mmol) was added, stirred and gradually warmed to rt over 16 hrs. The reaction mixture was diluted with EtOAc and washed with brine (2×), dried over sodium sulfate, filtered and concentrated in vacuo and purified using a Teledyne ISCO Combiflash® Rf system [0→10% EtOAc/Heptanes] to afford 597 mg of the title compound (92%). $^1$H NMR (400 MHz, CD$_3$OD) δ 7.71 (s, 1H), 7.48 (s, 1H), 4.57 (t, J=3.5 Hz, 1H), 4.04-4.12 (m, 2H), 3.86 (d, J=3.0 Hz, 1H), 3.48-3.56 (m, 1H), 3.45 (d, J=9.3 Hz, 1H), 3.03 (d, J=9.6 Hz, 1H), 1.81-1.91 (m, 1H), 1.67-1.78 (m, 1H), 1.51-1.66 (m, 4H), 0.93 (d, J=4.8 Hz, 6H).

Compound 47E: 3-(4-Iodopyrazol-1-yl)-2,2-dimethylpropan-1-ol

A cold (−20° C.) solution of 3-(4-Iodopyrazol-1-yl)-2,2-dimethylpropionic acid methyl ester (Compound 47F, 6.0 g, 19.48 mmol) in THF (80 mL) was treated with DIBAL (42.85 mL, 42.85 mmol, 1M solution in toluene) and allowed to warm to RT over a period of 2 h. The reaction mixture was treated with aq. ammonium hydroxide (20 mL) and the solids were filtered through celite. The filtrate was diluted with ethyl acetate (50 mL) and washed with brine (2×50 mL). The organic layer was dried over Na$_2$SO$_4$, filtered and concentrated to give 4.9 g (90%) as an oil which crystallized upon standing. ¹H NMR (500 MHz, CDCl₃) δ 7.50 (s, 1H), 7.41 (s, 1H), 4.0 (s, 2H), 3.17 (s, 3H), 0.9 (s, 6H).

Compound 47F:
3-(4-Iodopyrazol-1-yl)-2,2-dimethylpropionic acid methyl ester

A solution of 4-iodo-1H-pyrazole (194 mg, 1 mmol), 3-hydroxy-2,2-dimethylpropionic acid methyl ester (200 mg, 1.5 mmol) and triphenylphosphine (393 mg, 1.5 mmol) in THF (5 mL) was treated with DIAD (0.3 mL, 1.5 mmol) at room temperature. After 2 h, the reaction mixture was concentrated and the crude residue was purified by column chromatography (SiO₂, 10% ethyl acetate/hexanes) to give 249 mg (81%) of desired product as an oil. ¹H NMR (500 MHz, CDCl₃) δ 7.59 (s, 1H), 7.46 (s, 1H), 3.69 (s, 2H), 3.55 (s, 3H), 1.18 (s, 6H).

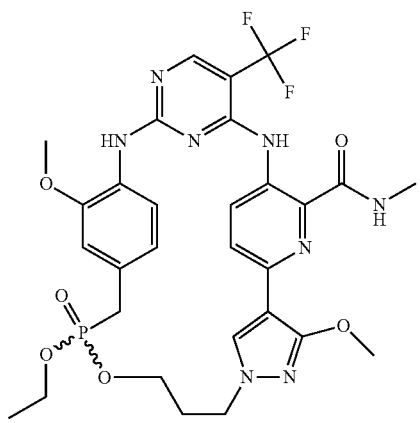

Example 48

(10S)-10-ethoxy-3,14-dimethoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-3,14-dimethoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(3-hydroxypropyl)-3-methoxy-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 48A, 132 mg, 0.189 mmol) to afford 22.2 mg of racemic Example 48 (17%). ¹H NMR (400 MHz, CD₃OD) δ 8.39 (s, 1H), 8.28 (br. s., 1H), 7.79-7.89 (m, 2H), 7.35 (d, J=8.1 Hz, 1H), 6.80 (t, J=1.9 Hz, 1H), 6.36 (td, J=2.3, 8.3 Hz, 1H), 4.26 (t, J=5.8 Hz, 2H), 4.07 (s, 3H), 3.90-4.02 (m, 2H), 3.80-3.89 (m, 5H), 3.11-3.23 (m, 2H), 2.81 (s, 3H), 2.21-2.30 (m, 2H), 1.16 (t, J=7.1 Hz, 3H). MS (ESI): m/z=677.47 [M+H]⁺. UPLC: t$_R$=1.24 min (UPLC-TOF: polar_2 min).

Compound 48A: Ethyl hydrogen (4-{[4-({6-[1-(3-hydroxypropyl)-3-methoxy-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 3A using diethyl (4-{[4-({6-[1-(3-hydroxypropyl)-3-methoxy-1H-pyrazol-4-yl]-2-(methylcarbamoyl)pyridin-3-yl}amino)-5-(trifluoromethyl)pyrimidin-2-yl]amino}-3-methoxybenzyl) phosphonate (Compound 48B, 286 mg, 0.395 mmol) affording 132 mg of the title compound (48%). ¹H NMR (400 MHz, CD₃OD) δ 8.86 (br. s., 1H), 8.29 (br. s., 2H), 7.63-7.77 (m, 2H), 7.12 (s, 1H), 6.88 (d, J=8.1 Hz, 1H), 4.14 (t, J=6.7 Hz, 2H), 4.07 (s, 3H), 3.80-3.90 (m, 5H), 3.59 (t, J=6.1 Hz, 2H), 2.99-3.08 (m, 2H), 2.96 (s, 3H), 2.07 (quin, J=6.4 Hz, 2H), 1.17 (t, J=7.1 Hz, 3H). MS (ESI): m/z=695.56 [M+H]⁺. UPLC: t$_R$=1.15 min (UPLC-TOF: polar_2 min).

Compound 48B: Diethyl (4-{[4-({6-[1-(3-hydroxypropyl)-3-methoxy-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 1B using diethyl (4-{[4-chloro-5-(trifluoromethyl)pyrimidin-2-yl]amino}-3-methoxybenzyl)phosphonate (Compound 1E, 251 mg, 0.553 mmol) and 3-amino-6-[1-(3-hydroxypropyl)-3-methoxy-1H-pyrazol-4-yl]-N-methylpyridine-2-carboxamide (Compound 48C, 177 mg, 0.580 mmol) to afford 139 mg of the title compound (35%). ¹H NMR (400 MHz, CD₃OD) δ 8.90 (br. s., 1H), 8.33 (s, 2H), 7.85 (d, J=8.1 Hz, 1H), 7.79 (d, J=8.6 Hz, 1H), 7.02-7.07 (m, 1H), 6.90 (td, J=2.4, 8.1 Hz, 1H), 4.15 (t, J=6.7 Hz, 2H), 4.00-4.10 (m, 7H), 3.90 (s, 3H), 3.59 (t, J=6.2 Hz, 2H), 3.26 (s, 2H), 2.98 (s, 3H), 2.08 (quin, J=6.5 Hz, 2H), 1.20-1.27 (m, 6H). MS (ESI): m/z=723.42 [M+H]⁺. UPLC: t$_R$=1.31 min (UPLC-TOF: polar_2 min).

Compound 48C: 3-amino-6-[1-(3-hydroxypropyl)-3-methoxy-1H-pyrazol-4-yl]-N-methylpyridine-2-carboxamide Prepared analogously to Compound 3C using 3-amino-N-methyl-6-(4,4,5,5-tetramethyl-1,3,2-dioxaborolan-2-yl)pyridine-2-carboxamide (Compound 48D, 500 mg, 2 mmol) and 3-(4-iodo-3-methoxy-pyrazol-1-yl)-propan-1-ol (Compound 48E, 600 mg, 2.18 mmol) to afford 177 mg of the title compound (30%). ¹H NMR (400 MHz, CD₃OD) δ 8.13 (s, 1H), 7.67 (d, J=8.8 Hz, 1H), 7.11 (d, J=8.8 Hz, 1H), 4.11 (t, J=6.8 Hz, 2H), 3.98 (s, 3H), 3.57 (t, J=6.2 Hz, 2H), 2.93 (s, 3H), 2.05 (t, J=6.4 Hz, 2H). MS (ESI): m/z=306.24 [M+H]⁺. UPLC: t$_R$=0.75 min (UPLC-TOF: polar_2 min).

Compound 48D: 3-Amino-N-methyl-6-(4,4,5,5-tetramethyl-1,3,2-dioxaborolan-2-yl)pyridine-2-carboxamide A solution of 3-amino-6-bromo-N-methylpyridine-2-carboxamide (Compound 6D, 1.15 g, 5.00 mmol), bis(pinacolato)diboron (1.27 g, 5.00 mmol), AcOK (1.47 g, 15.0 mmol), tricyclohexylphosphine (0.105 g, 0.375 mmol) and tris(dibenzylideneacetone)dipalladium (0.229 g, 0.250 mmol) in 1,4-dioxane (30 mL) was evacuated and refilled with argon (3×), then heated at 90° C. for 3 h. The mixture was cooled to rt, then diluted with EtOAc (50 mL) and water (10 mL). The insoluble material was filtered off through a pad of celite. The organic phase was washed with brine (20 mL), and dried over anhydrous sodium sulfate. The crude product was crystallized with EtOAc, affording the desired boronate as a yellow solid (0.72 g, 52% yield). $^1$H NMR (400 MHz, CDCl$_3$): δ 8.37 (br s, 1H), 7.67 (d, J=8.3 Hz, 1H), 6.94 (d, J=8.3 Hz, 1H), 6.40 (br s, 2H), 2.99 (d, J=5.0 Hz, 3H), 1.37 (s, 12H). MS (ESI): m/z 195.86 [M+H]$^+$ for the corresponding boronic acid. HPLC: $t_R$=0.63 min (ZQ3: polar__5 min).

Compound 48E: 3-(4-Iodo-3-methoxy-1H-pyrazol-1-yl)propan-1-ol

A solution of 4-iodo-3(5)-methoxypyrazole (Compound 48F, 2 g, 8.92 mmol) in DMF (5.0 mL) was cooled to 0° C. and NaH (386 mg) was added. After 45 minutes 3-bromopropanol (1.24 g, 8.92 mmol) was added. The reaction mixture was stirred at 0° C. for 1.5 h and then at RT for 1 h. It was then poured into water (30 mL) and extracted with EtOAc (3×20 mL). The combined organic layers were dried over Na$_2$SO$_4$, filtered, concentrated and purified by column chromatography (SiO$_2$, ethyl acetate/hexanes, 1:4) to yield 1.4 g (56%) of the desired product. $^1$H NMR (300 MHz, CDCl$_3$) δ 7.24 (s, 1H), 4.12 (t, J=6.3 Hz, 2H), 3.92 (s, 3H), 3.64 (q, J=5.7 Hz, 2H), 2.63 (t, J=6 Hz, 1H), 1.95-2.03 (m, 2H).

Compound 48F: 4-iodo-3(5)-methoxypyrazole

A solution of 3-methoxy-1H-pyrazole (Compound 48G, 1.6 g, 16.32 mmol) in DMF (25 mL) was cooled to −30° C. and charged with NIS (3.67 g, 16.31 mmol). The reaction mixture was stirred at −30° C. for 1.5 h, and then H$_2$O (30 mL) and EtOAc (40 mL) were added at −30° C. Organic layer was separated and the aqueous layer was re-extracted with EtOAc (3×20 mL) and the combined organic fractions were washed with H$_2$O, 1M aqueous Na$_2$S$_2$O$_3$, followed by brine, dried over Na$_2$SO$_4$, filtered and concentrated in vacuo to afford 2.1 g (58%) of the title compound as a light yellow solid. This material was taken on to the next step without further purification. $^1$H NMR (300 MHz, CDCl3) δ 7.41 (s, 1H), 3.96 (s, 3H).

Compound 48G: 3(5)-Methoxypyrazole

A solution of 1-acetyl-1,2-dihydro-3H-pyrazol-3-one (*Molbank*, 2006 pp M464/1-M464/3, 3.0 g, 23.8 mmol), potassium carbonate (3.28 g, 23.8 mmol) in 2-butanone (72 mL) was charged with dimethyl sulfate (2.48 mL, 26.2 mmol) and heated to reflux for 90 min. The reaction mixture was cooled to rt, filtered and concentrated in vacuo to afford a dark yellow oil. The crude oil was taken up in 10 M aqueous NaOH (1.1 mL) and 80 mL of a 1:1 mixture of THF/MeOH and stirred at rt for 30 min and neutralized with 1N HCl. The reaction mixture was concentrated in vacuo and partitioned between EtOAc and brine (150 mL). The organic layer was dried over Na$_2$SO$_4$, filtered and concentrated in vacuo to afford 1.7 g (73%) of the title compound as an orange oil. $^1$H NMR (300 MHz, CDCl$_3$) δ 7.36 (d, J=2.7 Hz, 1H), 5.74 (d, J=2.4 Hz, 1H), 3.91 (s, 3H).

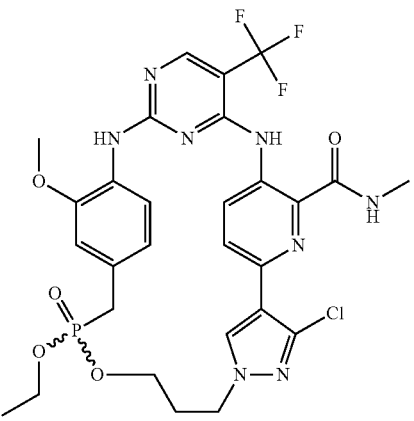

Example 49

(10S)-3-chloro-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-3-chloro-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[3-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 49A, 445.1 mg, 0.6368 mmol) to afford 118 mg of racemic Example 49 (27%). $^1$H NMR (400 MHz, CD$_3$OD) δ 8.49 (s, 1H), 8.34 (s, 1H), 8.12 (d, J=8.6 Hz, 1H), 7.85 (d, J=8.6 Hz, 1H), 7.46 (d, J=8.3 Hz, 1H), 6.88 (s, 1H), 6.55 (d, J=8.3 Hz, 1H), 4.36-4.44 (m, 2H), 3.70-3.95 (m, 7H), 3.25 (d, J=6.6 Hz, 2H), 2.92 (s, 3H), 2.22-2.30 (m, 2H), 1.05 (t, J=7.1 Hz, 3H). MS (ESI): m/z=681.43/683.36 [M+H]$^+$. UPLC: $t_R$=1.32 min (UPLC-TOF: polar__2 min).

Compound 49A: Ethyl hydrogen (4-{[4-({6-[3-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 3A using diethyl (4-{[4-({6-[3-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 49B, 480 mg, 0.661 mmol) to afford 445 mg of the desired product (96%). $^1$H NMR (400 MHz, CD$_3$OD) δ 8.93-9.09 (m, 1H), 8.59 (s, 1H), 8.32 (s, 1H), 7.88 (d, J=9.1 Hz, 1H), 7.62 (d, J=6.6 Hz, 1H), 7.12 (s, 1H), 6.93 (d, J=8.1 Hz, 1H), 4.27 (t, J=6.8 Hz, 2H), 3.82-3.92 (m, 5H), 3.60 (t, J=6.1 Hz, 2H), 3.05 (s, 1H), 2.97-3.02 (m, 4H), 2.11 (quin, J=6.4 Hz, 2H), 1.16 (t, J=6.9 Hz, 3H). MS (ESI): m/z=699.54/701.48 [M+H]$^+$. UPLC: $t_R$=1.21 min (UPLC-TOF: polar__2 min).

Compound 49B: diethyl (4-{[4-({6-[3-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using 3-amino-6-[3-chloro-1-(3-hydroxypropyl)-1H-pyrazol-4-yl]-N-methylpyridine-2-carboxamide (Compound 49C, 365 mg, 1.18 mmol) to afford 480 mg of the title compound (59%). $^1$H NMR (400 MHz, CD$_3$OD) δ 9.06 (br. s., 1H), 8.51 (s, 1H), 8.35 (s, 1H), 7.89 (d, J=9.1 Hz, 1H), 7.82 (d, J=8.1 Hz, 1H), 7.04 (t, J=2.0 Hz, 1H), 6.91 (td, J=2.3, 8.1 Hz, 1H), 4.26 (t, J=6.9 Hz, 2H), 4.00-4.11 (m, 4H), 3.89 (s, 3H), 3.59 (t, J=6.1 Hz, 2H), 3.35 (s, 1H), 3.23 (s, 1H), 2.98 (s, 3H), 2.11 (quin, J=6.5 Hz, 2H), 1.22-1.29 (m, 6H). MS (ESI): m/z=727.38/729.32 [M+H]$^+$. UPLC: $t_R$=1.35 min (UPLC-TOF: polar_2 min).

Compound 49C: 3-amino-6-[3-chloro-1-(3-hydroxypropyl)-1H-pyrazol-4-yl]-N-methylpyridine-2-carboxamide Prepared analogously to Compound 3C using 3-amino-N-methyl-6-(4,4,5,5-tetramethyl-1,3,2-dioxaborolan-2-yl)pyridine-2-carboxamide (Compound 48D, 631.2 mg, 2.28 mmol) and 3-(4-bromo-3-chloro-pyrazol-1-yl)-propan-1-ol (Compound 49E, 600 mg, 2.51 mmol) to afford 365 mg of the title compound 52%. $^1$H NMR (400 MHz, CD$_3$OD) δ 8.27 (s, 1H), 7.73 (d, J=8.8 Hz, 1H), 7.18 (d, J=8.8 Hz, 1H), 4.23 (t, J=6.9 Hz, 2H), 3.56 (t, J=6.1 Hz, 2H), 2.94 (s, 3H), 2.07 (t, J=6.4 Hz, 2H). MS (ESI): m/z=310.20/312.23 [M+H]$^+$. UPLC: $t_R$=min (UPLC-TOF: polar_2 min).

Compound 49D and 49E: 3-(4-Bromo-3-chloro-pyrazol-1-yl)-propan-1-ol and 3-(4-bromo-5-chloro-1H-pyrazol-1-yl)propan-1-ol Sodium hydride (60% dispersion in oil, 0.57 g, 14.3 mmol) was added portionwise to a solution of 3-chloro-4-bromopyrazole (*Chem. Ber,* 1970, 103, 1942-1948, 2 g, 11 mmol) in DMF (5 mL). After 30 min, the mixture was cooled to 0° C. and treated with 3-bromopropanol (1.3 mL, 14.3 mmol) via dropwise addition. After stirring an additional 2 hrs at rt., the reaction mixture was concentrated in vacuo. The residue was purified by column chromatography (SiO$_2$, 50% ethyl acetate in hexanes) to isolate Compound 49D as the nonpolar isomer (0.5 g, 18%) and Compound 49E as the polar isomer (1.6 g, 60%). $^1$H NMR (400 MHz, CDCl$_3$) δ: 7.39 (s, 1H), 4.18 (t, J=6.8 Hz, 2H), 4.08 (q, J=6.8 Hz, 2H), 3.60 (t, J=6.8 Hz, 2H). MS (ESI): m/z=239.01/241.08 [M+H]$^+$. UPLC: $t_R$=0.92 min (UPLC-TOF: polar_2 min).

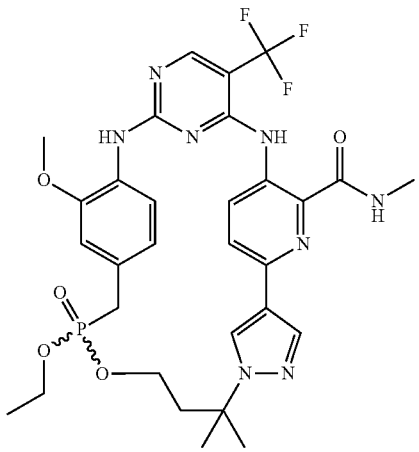

Example 50

(10S)-10-ethoxy-14-methoxy-N,6,6-trimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-14-methoxy-N,6,6-trimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(4-hydroxy-2-methylbutan-2-yl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 50A, 88.6 mg, 0.128 mmol) to afford 17.5 mg of racemic Example 50 (20%). $^1$H NMR (400 MHz, CD$_3$OD) δ 8.77 (s, 1H), 8.36 (s, 2H), 8.12 (d, J=8.6 Hz, 1H), 7.84 (d, J=8.6 Hz, 1H), 7.47-7.52 (m, 1H), 6.86 (s, 1H), 6.50-6.56 (m, 1H), 3.83 (s, 7H), 3.16-3.26 (m, 2H), 2.94 (s, 3H), 2.27-2.46 (m, 2H), 1.77 (d, J=1.0 Hz, 6H), 1.10 (t, J=6.9 Hz, 3H). MS (ESI): m/z=675.53 [M+H]$^+$. UPLC: $t_R$=1.32 min (UPLC-TOF: polar_2 min).

Compound 50A: Ethyl hydrogen (4-{[4-({6-[1-(4-hydroxy-2-methylbutan-2-yl)-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 3A using diethyl (4-{[4-({6-[1-(4-hydroxy-2-methylbutan-2-yl)-1H-pyrazol-4-yl]-2-(methylcarbamoyl)pyridin-3-yl}amino)-5-(trifluoromethyl)pyrimidin-2-yl]amino}-3-methoxybenzyl) phosphonate (Compound 50B, 117 mg, 0.163 mmol) to afford 88.6 mg of the title compound (79%). $^1$H NMR (400 MHz, CD$_3$OD) δ 8.76 (s, 1H), 8.35 (s, 1H), 8.11 (d, J=8.6 Hz, 1H), 7.83 (d, J=8.6 Hz, 1H), 7.50 (d, J=8.1 Hz, 1H), 6.85 (s, 1H), 6.52 (d, J=8.1 Hz, 2H), 3.72-3.98 (m, 7H), 3.15-3.25 (m, 2H), 2.94 (s, 3H), 2.30-2.43 (m, 2H), 1.77 (s, 6H), 1.11 (t, J=7.1 Hz, 3H). MS (ESI): m/z=693.61 [M+H]$^+$. UPLC: $t_R$=1.18 min (UPLC-TOF: polar_2 min).

Compound 50B: diethyl (4-{[4-({6-[1-(4-hydroxy-2-methylbutan-2-yl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using diethyl (4-{[4-chloro-5-(trifluoromethyl)pyrimidin-2-yl]amino}-3-methoxybenzyl)phosphonate (Compound 1 E, 304 mg, 0.671 mmol) and 2-amino-5-[1-(4-hydroxy-2-methylbutan-2-yl)-1H-pyrazol-4-yl]-N-methylbenzamide (Compound 50C, 213.1 mg, 0.705 mmol) to afford 117 mg of the title compound (24%). $^1$H NMR (400 MHz, CD$_3$OD) δ 9.01 (d, J=8.8 Hz, 1H), 8.62 (s, 1H), 8.34 (s, 1H), 8.27 (s, 1H), 7.70-7.76 (m, 2H), 7.07 (s, 1H), 6.96 (dd, J=2.3, 10.6 Hz, 1H), 4.01-4.12 (m, 5H), 3.88 (s, 3H), 3.42 (t, J=7.1 Hz, 2H), 2.99 (s, 3H), 2.14-2.24 (m, 3H), 1.70 (s, 6H), 1.21-1.30 (m, 6H). MS (ESI): m/z=721.49 [M+H]$^+$. UPLC: $t_R$=1.33 min (UPLC-TOF: polar_2 min).

Compound 50C: 3-amino-6-[1-(4-hydroxy-2-methylbutan-2-yl)-1H-pyrazol-4-yl]-N-methylpyridine-2-carboxamide Prepared analogously to Compound 3C using 3-amino-N-methyl-6-(4,4,5,5-tetramethyl-1,3,2-dioxaborolan-2-yl)pyridine-2-carboxamide (Compound 48D, 649 mg, 2.34 mmol) and 3-(4-bromo-pyrazol-1-yl)-3-methyl-butan-1-ol (Compound 50D, 600 mg, 2.57 mmol) to afford 304 mg of the title compound (43%). $^1$H NMR (400 MHz, CD$_3$OD) δ 8.34 (d, J=0.5 Hz, 1H), 8.01 (s, 1H), 7.51 (d, J=8.6 Hz, 1H), 7.15 (d, J=8.6 Hz, 1H), 3.40 (t, J=7.2 Hz, 2H), 2.94 (s, 3H), 2.17 (t, J=7.3 Hz, 2H), 1.66 (s, 6H). MS (ESI): m/z=304.26 [M+H]$^+$. UPLC: $t_R$=0.77 min (UPLC-TOF: polar_2 min).

Compound 50D: 3-(4-Bromo-1H-pyrazol-1-yl)-3-methylbutan-1-ol

Diisobutylaluminium hydride (1 M in toluene, 10.43 mL) was added dropwise to a solution of ethyl 3-(4-bromo-1H-pyrazol-1-yl)-3-methylbutanoate (Compound 50E, 1.3 g, 4.74 mmol), in THF (30 mL) at −78° C. and allowed to stir for 3 hours eventually warming to −10° C. The reaction mixture was quenched with an aqueous solution of K/Na tartrate tetrahydrate (10 mL) and allowed to stir for 2 hours. The mixture was extracted with ethyl acetate (3×15 mL) and the combined organic extracts were washed with water, followed by brine, dried over sodium sulfate, filtered and concentrated to afford 1.0 g of the desired product (91%). $^1$H NMR (300 MHz, CDCl$_3$) δ 7.51 (s, 1H), 7.46 (s, 1H), 3.54-3.58 (q, J=4.5 Hz, 2H), 2.28 (t, J=4.2 Hz, 1H), 2.09 (t, J=4.5 Hz, 2H), 1.58 (s, 6H).

Compound 50E: Ethyl 3-(4-bromo-1H-pyrazol-1-yl)-3-methylbutanoate

A solution of 4-bromo-1H-pyrazole (3.42 g, 23.43) and 3-methyl-2-butenoic acid ethyl ester (1 g, 7.81 mmol) in DMF (50 mL) was treated with cesium carbonate (10.1 g, 31.07) and allowed to stir for 3 hours at room temperature. The reaction mixture was diluted with water (30 mL) and extracted with EtOAc (3×30 mL). The combined extracts were dried over sodium sulfate and concentrated to afford the desired product, 1.1 g (51%) yield. $^1$H NMR (300 MHz, CDCl$_3$) δ 7.51 (s, 1H), 7.45 (s, 1H), 3.98-4.05 (m, 2H), 2.82 (s, 2H), 1.62 (s, 6H), 1.18-1.10 (t, 3H).

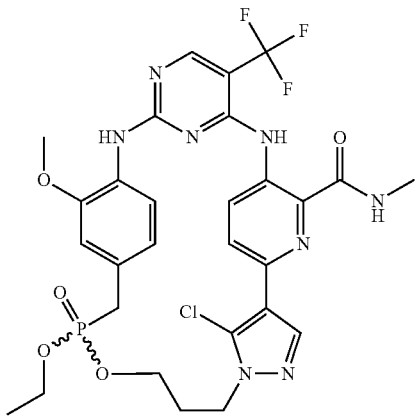

Example 51

(10S)-31-Chloro-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28), 18,20,23, 26,29-undecaene-24-carboxamide 10-oxide and (10R)-31-Chloro-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[5-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 51A, 129 mg, 0.184 mmol) to afford 2.5 mg of the title compound (2%). $^1$H NMR (400 MHz, CD$_3$OD) δ 8.55 (s, 1H), 8.33 (br. s., 1H), 8.16-8.22 (m, 1H), 8.07-8.13 (m, 1H), 7.39 (d, J=8.1 Hz, 1H), 6.81 (s, 1H), 6.56 (d, J=7.1 Hz, 1H), 4.39-4.64 (m, 2H), 3.59-3.87 (m, 7H), 3.11-3.23 (m, 2H), 2.94 (s, 3H), 2.35 (t, J=5.6 Hz, 2H), 0.87 (br. s., 3H). MS (ESI): m/z=681.46/683.47 [M+H]$^+$. UPLC: $t_R$=1.31 min (UPLC-TOF: polar_2 min).

Compound 51A: Ethyl hydrogen (4-{[4-({6-[5-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 3A using diethyl (4-{[4-({6-[5-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 51B, 161 mg, 0.222 mmol) to afford 129 mg of the title compound (83%). $^1$H NMR (400 MHz, CD$_3$OD) δ 9.05 (br. s., 1H), 8.29-8.35 (m, 2H), 7.81 (d, J=8.8 Hz, 1H), 7.69 (d, J=7.3 Hz, 1H), 7.12 (s, 1H), 6.90 (d, J=8.1 Hz, 1H), 4.35 (t, J=7.1 Hz, 2H), 3.79-3.92 (m, 5H), 3.59-3.65 (m, 2H), 3.03 (s, 1H), 2.95 (s, 4H), 2.09 (quin, J=6.6 Hz, 2H), 1.16 (t, J=6.9 Hz, 3H). MS (ESI): m/z=699.54/701.60 [M+H]$^+$. UPLC: $t_R$=1.21 min (UPLC-TOF: polar_2 min).

Compound 51B: diethyl (4-{[4-({6-[15-chloro-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using diethyl (4-{[4-chloro-5-(trifluoromethyl)pyrimidin-2-yl]amino}-3- methoxybenzyl)phosphonate (Compound 1 E, 304 mg, 0.671 mmol) and 3-amino-6-[5-chloro-1-(3-hydroxypropyl)-1H-pyrazol-4-yl]-N-methylpyridine-2-carboxamide (Compound 51C, 218 mg, 0.705 mmol) to afford 161 mg of the title compound (33%). $^1$H NMR (400 MHz, CD$_3$OD) δ 9.09 (br. s., 1H), 8.31-8.39 (m, 2H), 7.76-7.91 (m, 2H), 7.04 (s, 1H), 6.91 (td, J=2.2, 8.1 Hz, 1H), 4.36 (t, J=7.2 Hz, 2H), 4.06 (quin, J=7.3 Hz, 4H), 3.89 (s, 3H), 3.62 (t, J=6.1 Hz, 2H), 3.25 (s, 1H), 2.99 (s, 3H), 2.09 (quin, J=6.6 Hz, 2H), 1.21-1.29 (m, 7H). MS (ESI): m/z=727.38/729.32 [M+H]$^+$. UPLC: $t_R$=1.34 min (UPLC-TOF: polar_2 min).

Compound 51C: 3-amino-6-[5-chloro-1-(3-hydroxypropyl)-1H-pyrazol-4-yl]-N-methylpyridine-2-carboxamide Prepared analogously to Compound 3C using 3-amino-N-methyl-6-(4,4,5,5-tetramethyl-1,3,2-dioxaborolan-2-yl)pyridine-2-carboxamide (Compound 48D, 284 mg, 1.03 mmol) and 3-(4-bromo-5-chloro-1H-pyrazol-1-yl)propan-1-ol (Compound 49D, 270 mg, 1.1 mmol) to afford 151 mg of the title compound (48%). $^1$H NMR (400 MHz, CD$_3$OD) δ 8.12 (s, 1H), 7.67 (d, J=8.6 Hz, 1H), 7.20 (d, J=8.6 Hz, 1H), 4.32 (t, J=7.1 Hz, 2H), 3.60 (t, J=6.1 Hz, 2H), 2.94 (s, 3H), 2.06 (quin, J=6.6 Hz, 2H). MS (ESI): m/z=310.20/312.18 [M+H]$^+$. UPLC: $t_R$=0.77 min (UPLC-TOF: polar_2 min).

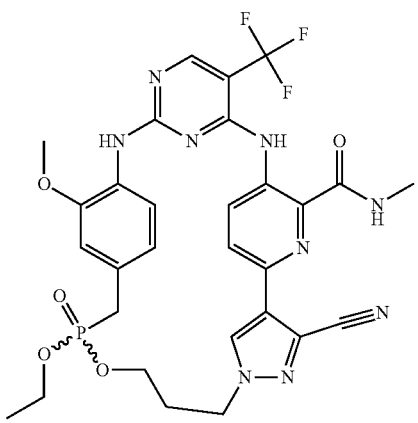

Example 52

(10S)-3-cyano-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-3-cyano-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[3-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 52A, 280 mg, 0.405 mmol) to afford 21.4 mg of the title compound (8%). $^1$H NMR (400 MHz, CD$_3$OD) δ 8.69 (s, 1H), 8.38 (br. s., 1H), 8.30 (d, J=8.8 Hz, 1H), 7.84 (d, J=8.6 Hz, 1H), 7.52 (d, J=8.1 Hz, 1H), 6.93 (s, 1H), 6.67 (d, J=8.3 Hz, 1H), 4.55 (br. s., 2H), 3.86 (s, 3H), 3.74-3.85 (m, 2H), 3.54-3.71 (m, 2H), 3.37 (d, J=9.1 Hz, 1H), 3.15 (d, J=3.3 Hz, 1H), 2.97 (s, 3H), 2.32 (t, J=5.1 Hz, 2H), 0.91 (t, J=7.1 Hz, 3H). MS (ESI): m/z=672.15 [M+H]$^+$. UPLC: $t_R$=1.00 min (UPLC-TOF: polar_2 min).

Compound 52A: ethyl hydrogen (4-{[4-({6-[3-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 3A using diethyl (4-{[4-({6-[3-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 52B, 259 mg, 0.361 mmol) to afford 250 mg of the title compound (100%). $^1$H NMR (400 MHz, CD$_3$OD) δ 9.09 (d, J=7.8 Hz, 1H), 8.88 (br. s., 1H), 8.30 (s, 1H), 7.86 (d, J=9.1 Hz, 1H), 7.51 (br. s., 1H), 7.11 (s, 1H), 6.97 (d, J=7.8 Hz, 1H), 4.39 (t, J=6.8 Hz, 2H), 3.83-3.94 (m, 5H), 3.62 (t, J=5.9 Hz, 2H), 3.00-3.08 (m, 2H), 2.97 (s, 3H), 2.10-2.20 (m, 2H), 1.14 (t, J=7.1 Hz, 3H). MS (ESI): m/z=690.49 [M+H]$^+$. UPLC: $t_R$=1.26 min (UPLC-TOF: polar_2 min).

Compound 52B: diethyl (4-{[4-({6-[3-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using diethyl (4-{[4-chloro-5-(trifluoromethyl)pyrimidin-2-yl]amino}-3-methoxybenzyl)phosphonate (Compound 1 E, 236 mg, 0.520 mmol) and 3-amino-6-[3-cyano-1-(3-hydroxypropyl)-1H-pyrazol-4-yl]-N-methylpyridine-2-carboxamide (Compound 52C, 164 mg, 0.546 mmol) to afford 259 mg of the title compound (69%). $^1$H NMR (400 MHz, CD$_3$OD) δ 9.17 (br. s., 1H), 8.47 (s, 1H), 8.38 (s, 1H), 7.91 (d, J=9.1 Hz, 1H), 7.68 (br. s., 1H), 7.08 (s, 1H), 6.98 (d, J=7.8 Hz, 1H), 4.52 (t, J=6.9 Hz, 2H), 4.08 (quin, J=7.3 Hz, 4H), 3.88 (s, 3H), 3.61 (t, J=6.1 Hz, 2H), 3.33-3.42 (m, 2H), 2.99 (s, 3H), 2.17 (quin, J=6.5 Hz, 2H), 1.26 (t, J=7.1 Hz, 7H). MS (ESI): m/z=718.47 [M+H]$^+$. UPLC: $t_R$=1.39 min (UPLC-TOF: polar_2 min).

Compound 52C: 3-amino-6-[3-cyano-1-(3-hydroxypropyl)-1H-pyrazol-4-yl]-N-methylpyridine-2-carboxamide Prepared analogously to Compound 3C using 3-amino-N-methyl-6-(4,4,5,5-tetramethyl-1,3,2-dioxaborolan-2-yl)pyridine-2-carboxamide (Compound 48D, 657 mg, 2.37 mmol) and 4-bromo-1-(3-hydroxypropyl)-1H-pyrazole-3-carbonitrile (Compound 52E, 600 mg, 2.61 mmol) to afford 164 mg of the title compound (23%). $^1$H NMR (400 MHz, CD$_3$OD) δ 8.29 (s, 1H), 7.57 (d, J=8.6 Hz, 1H), 7.21 (d, J=8.6 Hz, 1H), 4.35 (t, J=6.8 Hz, 2H), 3.57 (t, J=6.1 Hz, 2H), 2.94 (s, 3H), 2.11 (t, J=6.1 Hz, 2H). MS (ESI): m/z=301.24 [M+H]$^+$. UPLC: $t_R$=0.79 min (UPLC-TOF: polar_2 min).

Compound 52D and Compound 52E: 4-bromo-1-(3-hydroxypropyl)-1H-pyrazole-5-carbonitrile and 4-bromo-1-(3-hydroxypropyl)-1H-pyrazole-3-carbonitrile Prepared analogously to 38E using 4-bromo-1H-pyrazole-3-carbonitrile (2.00 g, 11.6 mmol) to afford 434 mg and 2.21 g of the title compounds for Compound 52D and 52E (16% and 83%) respectively. Compound 52E: ¹H NMR (400 MHz, CD₃OD) δ 7.71 (s, 1H), 4.44 (t, J=6.9 Hz, 2H), 3.55 (t, J=6.1 Hz, 2H), 2.02-2.20 (m, 2H). Compound 52E: ¹H NMR (400 MHz, CD₃OD) δ 7.98 (s, 1H), 4.32 (t, J=6.9 Hz, 2H), 3.46-3.59 (m, 2H), 2.05 (quin, J=6.4 Hz, 2H).

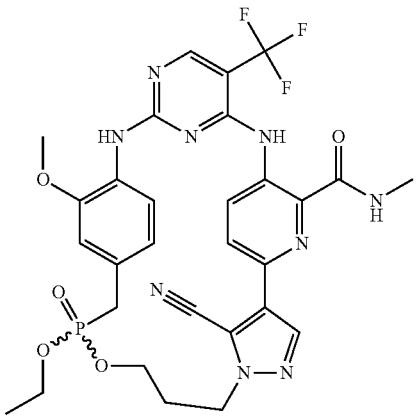

Example 53

(10S)-31-cyano-10-ethoxy-14-methoxy-N-methyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide and (10R)-31-cyano-10-ethoxy-14-methoxy-N-methyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide Prepared analogously to Example 3 using ethyl hydrogen (4-{[4-({6-[5-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 53A, 146 mg, 0.212 mmol) to afford 3.80 mg of the title compound (3%). ¹H NMR (400 MHz, DMSO-d₆) δ 12.42-12.53 (m, 1H), 9.21-9.30 (m, 1H), 8.85-8.95 (m, 1H), 8.39-8.45 (m, 1H), 8.36 (s, 1H), 7.65-7.72 (m, 1H), 7.31-7.40 (m, 1H), 6.98-7.09 (m, 2H), 4.17-4.25 (m, 2H), 4.02-4.14 (m, 4H), 3.71 (s, 3H), 3.37-3.46 (m, 2H), 2.66 (s, 3H), 1.20-1.28 (m, 6H). MS (ESI): m/z=672.65 [M+H]⁺. UPLC: t$_R$=1.61 min (UPLC-TOF: polar_2 min).

Compound 53A: ethyl hydrogen (4-{[4-({6-[5-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 3A using diethyl (4-{[4-({6-[5-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 53B, 191 mg, 0.266 mmol) to afford 146 mg of the title compound (80%). ¹H NMR (400 MHz, CD₃OD) δ 9.15 (br. s., 1H), 8.47 (s, 1H), 8.33 (s, 1H), 7.89 (d, J=9.1 Hz, 1H), 7.61 (br. s., 1H), 7.12 (s, 1H), 6.95 (d, J=8.1 Hz, 1H), 4.49 (t, J=7.1 Hz, 2H), 3.83-3.93 (m, 5H), 3.60 (t, J=6.2 Hz, 2H), 2.99-3.07 (m, 2H), 2.97 (s, 3H), 2.16 (quin, J=6.5 Hz, 2H), 1.16 (t, J=7.1 Hz, 3H). MS (ESI): m/z=690.62 [M+H]⁺. UPLC: t$_R$=1.26 min (UPLC-TOF: polar_2 min).

Compound 53B: diethyl (4-{[4-({6-[5-cyano-1-(3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate Prepared analogously to Compound 1B using diethyl (4-{[4-chloro-5-(trifluoromethyl)pyrimidin-2-yl]amino}-3-methoxybenzyl)phosphonate (Compound 1E, 218 mg, 0.480 mmol) and 3-amino-6-[5-cyano-1-(3-hydroxypropyl)-1H-pyrazol-4-yl]-N-methylpyridine-2-carboxamide (Compound 53C, 151 mg, 0.504 mmol) to afford 191 mg of the title compound (55%). ¹H NMR (400 MHz, CD₃OD) δ 9.19 (br. s., 1H), 8.47 (s, 1H), 8.38 (s, 1H), 7.91 (d, J=8.8 Hz, 1H), 7.69 (br. s., 1H), 7.08 (s, 1H), 6.98 (d, J=7.8 Hz, 1H), 4.52 (t, J=6.9 Hz, 2H), 4.01-4.14 (m, 3H), 3.88 (s, 2H), 3.61 (t, J=6.1 Hz, 2H), 3.36 (s, 2H), 2.99 (s, 3H), 2.17 (quin, J=6.5 Hz, 2H), 1.18-1.31 (m, 8H). MS (ESI): m/z=718.56 [M+H]⁺. UPLC: t$_R$=1.36 min (UPLC-TOF: polar_2 min).

Compound 53C: 3-amino-6-[5-cyano-1-(3-hydroxypropyl)-1H-pyrazol-4-yl]-N-methylpyridine-2-carboxamide Prepared analogously to 3C using 3-amino-N-methyl-6-(4,4,5,5-tetramethyl-1,3,2-dioxaborolan-2-yl)pyridine-2-carboxamide (Compound 48D, 475.3 mg, 1.715 mmol) and 4-bromo-1-(3-hydroxypropyl)-1H-pyrazole-5-carbonitrile (Compound 52D, 434 mg, 1.89 mmol) to afford 151 mg of the title compound (29%). ¹H NMR (400 MHz, CD₃OD) δ 8.08 (s, 1H), 7.63 (d, J=8.6 Hz, 1H), 7.21 (d, J=8.8 Hz, 1H), 4.47 (t, J=7.1 Hz, 2H), 3.60 (t, J=6.1 Hz, 2H), 2.94 (s, 3H), 2.15 (quin, J=6.6 Hz, 2H). MS (ESI): m/z=301.24 [M+H]⁺. UPLC: t$_R$=0.79 min (UPLC-TOF: polar_2 min).

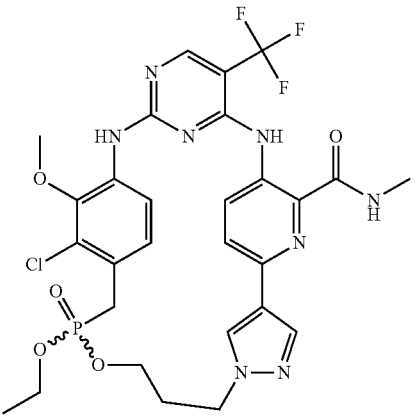

Example 54

(10S)-13-chloro-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$] hentriaconta-1(25),2(31),3,12,14,17(28),18,20,23,26,29-undecaene-24-carboxamide 10-oxide and (10R)-13-chloro-10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 44 using racemic ethyl 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate (Compound 54A, 203 mg, 0.228 mmol) to afford 84.8 mg of Example 54 as a racemic mixture (55%). $^1$H NMR (400 MHz, CD$_3$OD) δ 8.47 (s, 1H), 8.35-8.42 (m, 2H), 8.17 (d, J=8.6 Hz, 1H), 7.82 (d, J=8.8 Hz, 1H), 7.52-7.61 (m, 1H), 6.85 (dd, J=2.8, 8.6 Hz, 1H), 4.42-4.51 (m, 2H), 3.69 (br. s., 7H), 3.43-3.56 (m, 2H), 2.94 (s, 3H), 2.27 (br. s., 2H), 1.03 (t, J=7.1 Hz, 3H). MS (ESI): m/z=681.56 [M+H]$^+$. UPLC: t$_R$=1.36 min (UPLC-TOF: polar_2 min).

Compound 54A: ethyl 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate (203 mg, 74.66%).
Prepared analogously to Compound 44A using ethyl hydrogen (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate (Compound 54B, 200 mg, 0.306 mmol) and 3-[4-(4,4,5,5-tetramethyl-1,3,2-dioxaborolan-2-yl)-1H-pyrazol-1-yl]propan-1-ol (Compound 3E, 81 mg, 0.321 mmol) to afford 203 mg of the title compound as a racemic mixture (75%). MS (ESI): m/z=887.65/889.64 [M+H]$^+$. UPLC: t$_R$=1.68 min (UPLC-TOF: polar_2 min).

Compound 54B: Ethyl hydrogen (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate Prepared analogously to Compound 38C with diethyl (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate (Compound 54C). MS (ESI): m/z 653.03/655.02 [M+H]$^+$. UPLC: t$_R$=0.98 min (UPLC-TOF: polar_2 min).

Compound 54C: Diethyl (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate Prepared analogously to Compound 1B with diethyl (2-chloro-4-{[4-chloro-5-(trifluoromethyl)pyrimidin-2-yl]amino}-3-methoxybenzyl)phosphonate (Compound 54D) and compound 6D. MS (ESI): m/z 681.34/683.34 [M+H]$^+$. UPLC: t$_R$=1.51 min (UPLC-SQD: analytical_2 min).

Compound 54D: Diethyl 2-chloro-4-(4-chloro-5-(trifluoromethyl)pyrimidin-2-ylamino)-3-methoxybenzylphosphonate To a solution of 2,4-dichloro-5-trifluoromethylpyrimidine (2.1 g, 9.77 mmol) in a 1:1 mixture of DCE and t-butanol (20 mL) was added ZnCl$_2$ (1M, 10 mL) and stirred for half an hour at RT. After cooling at 0° C. diethyl 4-amino-2-chloro-3-methoxybenzylphosphonate (3 g, 9.77 mmol) in a 1:1 mixture of DCE and t-butanol (20 mL) was added followed by N-methylimidazole (800 mg, 9.75 mmol) drop wise while stirring was continued for 24 hrs. The solvents were removed under reduced pressure and the residue was purified by column chromatography (SiO$_2$, ethyl acetate and hexanes (1:1)) to yield the desired compound in 1.5 g (32%) yield. $^1$H NMR (300 MHz, CDCl$_3$) δ 8.61 (s, 1H), 8.38 (d, 1H), 8.03 (s, 1H), 4.01-4.18 (q, 4H), 3.98 (s, 3H), 3.29 (d, 2H), 1.24 (t, 6H).

Compound 54E: Diethyl 4-amino-2-chloro-3-methoxybenzylphosphonate

To a solution of diethyl 2-chloro-3-methoxy-4-nitrobenzylphosphonate (Compound 54F, 1 g, 2.96 mmol) in ethanol (15 mL), and iron powder (1.63 g, 29.6 mmol) was added aqueous 2N HCl (5 mL). The reaction mixture was heated to reflux for 1.5 h. The reaction mixture was cooled to RT and saturated solution of Na$_2$CO$_3$ was added until the pH was 9. The reaction mixture was filtered through celite and concentrated to give the residue. It was dissolved in ethyl acetate (25 mL) and washed with water, dried over sodium sulfate, filtered and concentrated to give the required product (89%, 900 mg). $^1$H NMR (300 MHz, CDCl$_3$) δ 7.01 (d, 1H), 6.62 (d, 1H), 4.00-4.19 (m, 4H), 3.83 (s, 3H), 3.25 (d, 2H), 1.23 (t, 6H).

Compound 54F: Diethyl 2-chloro-3-methoxy-4-nitrobenzylphosphonate

To a solution of 1-(bromomethyl)-2-chloro-3-methoxy-4-nitrobenzene (Compound 54G, 900 mg, 3.21 mmol) in toluene (10 mL) was added triethylphosphite (586 mg, 3.53 mmol) and heated to reflux for 24 h. Toluene and triethylphosphite were distilled off under reduced pressure to provide the desired compound, 800 mg (79%). $^1$H NMR (300 MHz, CDCl$_3$) δ 7.77 (d, 1H), 7.35 (d, 1H), 4.19-4.05 (m, 4H), 4.00 (s, 3H), 3.43 (d, 2H), 1.31 (t, 6H).

Compound 54G: 1-(Bromomethyl)-2-chloro-3-methoxy-4-nitrobenzene

To a solution of (2-Chloro-3-methoxy-4-nitrophenyl)methanol (Compound 54H, 1.1 g, 5.06 mmol) in dichloromethane (10 mL) at 0° C. was added phosphorous tribromide (684 mg, 2.53 mmol). After the addition was over, the reaction mixture was allowed to stir at RT overnight. The reaction mixture was neutralized with NaHCO$_3$, extracted with ethyl acetate (30 mL) and the solvent was removed under reduced pressure to get the compound 900 mg (64%). $^1$H NMR (300 MHz, CDCl$_3$) δ 7.72 (d, J=8.4 Hz, 1H), 7.34 (d, J=8.4 Hz, 1H), 4.58 (s, 2H), 4.04 (s, 3H).

Compound 54H: (2-Chloro-3-methoxy-4-nitrophenyl)methanol

To a solution of 2-chloro-3-methoxy-4-nitrobenzaldehyde (Compound 54I, 1.6 g, 7.44 mmol) in methanol (25 mL) at 0°

C. was added sodium borohydride (330 mg, 8.91 mmol). After stirring for 1.5 h, water (15 mL) was added. The solid obtained was filtered and dried to obtain the desired intermediate (1.1 g, 69%). $^1$H NMR (300 MHz, CDCl$_3$) δ 7.78 (d, J=4.8 Hz, 1H), 7.47 (d, J=5.1 Hz, 1H), 4.83 (d, J=3.6 Hz, 2H), 4.02 (s, 3H), 2.25 (t, J=3.6 Hz, 1H).

Compound 54I:
2-Chloro-3-methoxy-4-nitrobenzaldehyde

Potassium nitrate (4 g, 39.6 mmol) was added slowly to a solution of 2-chloro-3-hydroxybenzaldehyde (6 g, 35.2 mmol) in sulfuric acid (28 mL) at 30-40° C. The contents of the flasks were heated to 50-60° C. for 10 minutes and then poured onto ice (60 g). The solid obtained was steam distilled to provide the desired compound (1.6 g, 21%). $^1$H NMR (300 MHz, CDCl$_3$) δ 10.51 (s, 1H), 7.82-7.79 (m, 2H), 4.08 (s, 3H).

3.56 (m, 2H), 2.94 (s, 3H), 1.01 (t, J=7.1 Hz, 3H). MS (ESI):): m/z=723.60/725.57 [M+H]$^+$. UPLC: t$_R$=1.37 min (UPLC-TOF: polar_2 min).

Compound 55A: ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate Prepared analogously to Compound 44A using ethyl hydrogen (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate (Compound 54B, 200 mg, 0.306 mmol) and (3-{[4-(4,4,5,5-tetramethyl-1,3,2-dioxaborolan-2-yl)-1H-pyrazol-1-yl]methyl}oxetan-3-yl)methanol (Compound 44B, 95 mg, 321 mmol) to afford 264 mg of the title compound as a racemic mixture (93%). MS (ESI): m/z=929.64/931.71 [M+H]$^+$. UPLC: t$_R$=1.67 min (UPLC-TOF: polar_2 min).

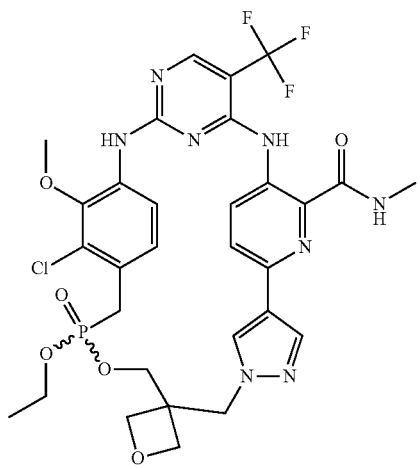

Example 55

(10S)-13-chloro-10-ethoxy-14-methoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28), 18,20,23,26,29-undecaene-7,3'-oxetane]-24-carboxamide 10-oxide and (10R)-13-chloro-10-ethoxy-14-methoxy-N-methyl-20-(trifluoromethyl) spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14, 17(28),18,20,23,26,29-undecaene-7,3'-oxetane]-24-carboxamide 10-oxide Prepared analogously to Example 44 using racemic ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-2-chloro-3-methoxybenzyl)phosphonate (Compound 55A, 264 mg, 0.284 mmol) to afford 80 mg of Example 55 as a racemic mixture (39%). $^1$H NMR (400 MHz, CD$_3$OD) δ 8.39 (d, J=11.6 Hz, 2H), 8.32 (s, 1H), 8.19 (d, J=8.6 Hz, 1H), 7.82 (d, J=8.6 Hz, 1H), 7.61 (d, J=9.1 Hz, 1H), 6.90 (dd, J=2.9, 8.7 Hz, 1H), 4.71-4.82 (m, 4H), 4.49 (dd, J=6.7, 16.8 Hz, 2H), 3.75-3.92 (m, 7H), 3.39-

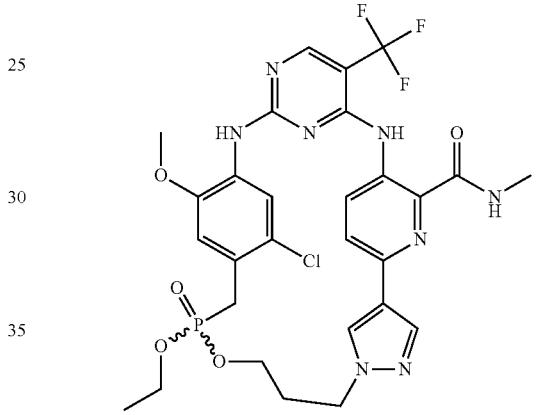

Example 56

(10S)-13-Chloro-10-ethoxy-29-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$] hentriaconta-1(25),2(31),3,12,14,17(28),18,20,23,26, 29-undecaene-24-carboxamide 10-oxide and (10R)-13-chloro-10-ethoxy-29-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17 (28),18,20,23,26,29-undecaene-24-carboxamide 10-oxide Prepared analogously to Compound 44 using ethyl 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate (Compound 56A, 203 mg, 0.228 mmol) to afford 54.7 mg of the title compound as a racemic mixture (35%). $^1$H NMR (400 MHz, CD$_3$OD) δ 8.47 (s, 1H), 8.39 (s, 1H), 8.30 (d, J=0.5 Hz, 1H), 8.12 (d, J=8.8 Hz, 1H), 7.70 (d, J=8.8 Hz, 1H), 7.64 (d, J=1.0 Hz, 1H), 6.96 (d, J=2.5 Hz, 1H), 4.33-4.45 (m, 2H), 4.00-4.11 (m, 2H), 3.86-3.97 (m, 5H), 3.36-3.50 (m, 2H), 2.95 (s, 3H), 2.26-2.37 (m, 2H), 1.21-1.25 (m, 3H). MS (ESI): m/z=681.53/683.56 [M+H]$^+$. UPLC: t$_R$=1.42 min (UPLC-TOF: polar_2 min).

Compound 56A: Ethyl 3-[4-(4,4,5,5-tetramethyl-1,3, 2-dioxaborolan-2-yl)-1H-pyrazol-1-yl]propyl (4-{[4-{[6-bromo-2-(methylcarbamoyl)pyridin-3-yl] amino}-5-(trifluoromethyl)pyrimidin-2-yl]amino}-2-chloro-5-methoxybenzyl)phosphonate Prepared analogously to Compound 44A using ethyl hydrogen (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate (Compound 56B, 200 mg, 0.306 mmol) and 3-[4-(4,4,5,5-tetramethyl-1,3,2-dioxaborolan-2-yl)-1H-pyrazol-1-yl]propan-1-ol (Compound 3E, 81 mg, 0.321 mmol) to afford 181 mg of the title compound as a racemic mixture (67%). MS (ESI): m/z=887.59/889.59 [M+H]$^+$. UPLC: $t_R$=1.74 min (UPLC-TOF: polar_2 min).

Compound 56B: Ethyl hydrogen (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate Prepared analogously to Compound 38C replacing Compound 38B with diethyl (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate (Compound 56C). $^1$H NMR (400 MHz, DMSO-d$_6$) δ=12.39 (br. s., 1H), 9.18 (br. s., 1H), 8.91-8.99 (m, 1H), 8.49 (s, 1H), 7.71 (d, J=9.1 Hz, 1H), 7.64 (br. s., 1H), 7.16 (d, J=2.0 Hz, 1H), 3.95 (quin, J=7.3 Hz, 2H), 3.77 (s, 3H), 3.22-3.27 (m, 2H), 2.81 (d, J=5.1 Hz, 3H), 1.18 (t, J=6.9 Hz, 3H). MS (ESI): m/z 653.02/655.02 [M+H]$^+$. UPLC: $t_R$=0.89 min (polar_2 min).

Compound 56C: Ethyl hydrogen (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate Prepared analogously to Compound 1B replacing Compound 1C with diethyl (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate (Compound 56D). MS (ESI): m/z 681.02/683.27 [M+H]$^+$. UPLC: $t_R$=1.56 min (analytical_2 min).

Compound 56D: 2-Chloro-4-(4-chloro-5-trifluoromethyl-pyrimidin-2-ylamino)-5-methoxy-benzyl]-phosphonic acid diethyl ester A solution of 2,4-dichloro-5-trifluoromethyl-pyrimidine (2.8 g, 13 mmol) in a mixture dichloroethane and t-butanol (1:1, 10 mL) was treated with ZnCl$_2$ (1M solution in ether, 13 mL) and stirred for half an hour at RT. The reaction mixture was cooled to 0° C. and a solution of (4-amino-2-chloro-5-methoxy-benzyl)-phosphonic acid diethylester (Compound 56E, 4 g, 13 mmol) in dichloroethane and t-butanol (1:1, 10 mL) followed by N-methylimidazole were added drop wise while stirring was continued for 24 hrs. The solvents were evaporated under reduced pressure and the residue was purified by column chromatography (SiO$_2$, 1% methanol in dichloromethane) to give the mixture of isomers (3 g containing 20% impurity of the other isomer). Repeated recrystallizations from ethyl acetate gave pure required isomer (1.15 g) as white solid. $^1$H NMR (400 MHz, CDCl$_3$) δ 8.60 (s, 1H), 8.52 (s, 1H), 8.04 (s, 1H), 7.01 (d, J=2.8 Hz, 1H), 4.00-4.08 (m, 4H), 3.89 (s, 3H), 3.28 (d, J=21.50 Hz, 2H), 1.25 (t, J=7.07 Hz, 6H).

Compound 56E: (4-Amino-2-chloro-5-methoxy-benzyl)-phosphonic acid diethylester A suspension of (2-chloro-5-methoxy-4 nitrobenzyl)-phosphonic acid diethylester (Compound 56F, 10.3 g, 30.5 mmol), iron powder (16.8 g, 305 mmol) in 2M aqueous hydrochloric acid (25 mL) and ethanol (150 mL) was heated to reflux for 1 hr. The reaction mixture was cooled to RT and solid Na$_2$CO$_3$ (6 g) was added until the pH was 9. The reaction mixture was filtered through celite, the filter cake was washed with dichloromethane and the filtrate was concentrated to give a residue which was dissolved in ethyl acetate, washed with water, dried over sodium sulfate, filtered and concentrated to give the required material as gum (8 g, 85%). $^1$H NMR (400 MHz, CDCl$_3$) δ: 6.88 (s, 1H), 6.71 (s, 1H), 4.3 (brs, 2H), 4.05-4.13 (m, 4H), 3.85 (s, 3H), 3.26 (d, J=20.50 Hz, 2H), 1.28 (t, J=7.05 Hz, 6H).

Compound 56F: (2-Chloro-5-methoxy-4 nitrobenzyl)-phosphonic acid diethylester A mixture of 1-Bromomethyl-2-chloro-5-methoxy-4-nitro-benzene, 1-Chloro-4-methoxy-2-methyl-5-nitro-benzene and 1-chloro-2-dibromomethyl-4-methoxy-5-nitro-benzene (Compound 56G, 24 g, 1:015:0.5) in toluene (100 mL) were treated with triethylphosphite (15.6 g, 94.2 mmol) and heated to reflux for 24 hrs. Toluene and triethylphosphite were distilled off under reduced pressure. The residue was treated with hot diisopropyl ether to give 10 g of the required compound as dark yellow crystals.

$^1$H NMR (400 MHz, CDCl$_3$) δ: 7.89 (s, 1H), 7.21 (s, 1H), 4.02-4.06 (m, 4H), 3.93 (s, 3H), 3.32 (d, J=20.50 Hz, 2H), 1.26 (t, J=7.05 Hz, 6H).

Compound 56G: 1-Bromomethyl-2-chloro-5-methoxy-4-nitro-benzene

A solution of 1-chloro-4-methoxy-2-methyl-5-nitro-benzene (13.2 g, 65.6 mmol) in dichloroethane (200 mL) was treated with N-bromosuccinimide (12.8 g, 72.2 mmol) and 1,1-azobis cyclohexane carbonitrile (0.5 g, 2 mmol). The reaction mixture was heated to reflux in presence of light for 24 hrs. The reaction mixture was then cooled to RT, washed with sodium thiosulfate (20% aq., 50 mL), water and brine. The organic layer was dried over magnesium sulfate, filtered and concentrated to give a residue (24 g) which by $^1$H NMR was a mixture of desired product, starting material and the dibrominated product (1-chloro-2-dibromomethyl-4-methoxy-5-nitro-benzene) in a ratio of 1:0.5:0.15 and was carried to the next step without further purification. $^1$H NMR (400 MHz, CDCl$_3$) δ: 7.88 (s, 1H), 7.14 (s, 1H), 4.52 (s, 2H), 3.96 (s, 3H).

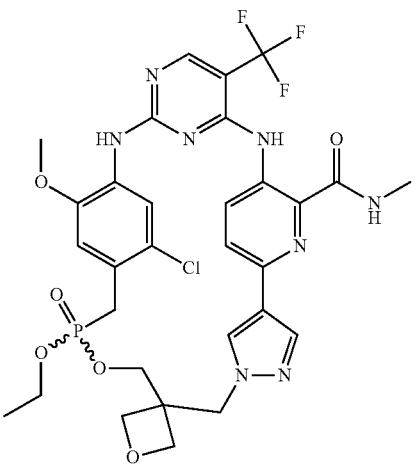

Example 57

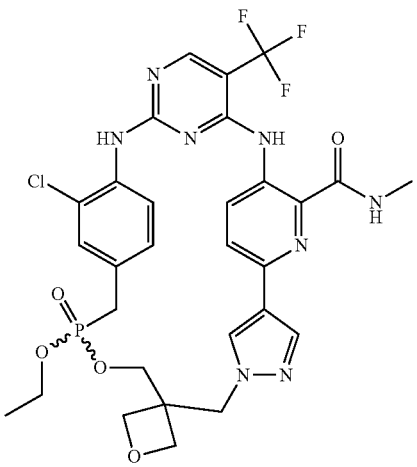

Example 58

(10S)-13-chloro-10-ethoxy-29-methoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide and (10R)-13-chloro-10-ethoxy-29-methoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide Prepared analogously to Compound 44 using ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-2-chloro-5-methoxybenzyl) phosphonate (Compound 57A, 175 mg, 0.188 mmol) to afford 63.6 mg of the title compound as a racemic mixture (47%). $^1$H NMR (400 MHz, CD$_3$OD) δ 8.39 (s, 1H), 8.25 (d, J=1.5 Hz, 2H), 8.09 (d, J=8.8 Hz, 1H), 7.69 (d, J=8.8 Hz, 1H), 7.64 (d, J=1.0 Hz, 1H), 6.98 (d, J=2.5 Hz, 1H), 4.60-4.80 (m, 3H), 4.47-4.57 (m, 2H), 3.92-4.09 (m, 4H), 3.87 (s, 3H), 3.37-3.53 (m, 3H), 2.95 (s, 3H), 1.20 (t, J=7.1 Hz, 3H). MS (ESI): m/z=723.57/725.55 [M+H]$^+$. UPLC: t$_R$=1.40 min (UPLC-TOF: polar_2 min).

Compound 57A: Ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate Prepared analogously to Compound 44A using ethyl hydrogen (4-{[4-{[6-bromo-2-(methylcarbamoyl)pyridin-3-yl]amino}-5-(trifluoromethyl)pyrimidin-2-yl]amino}-2-chloro-5-methoxybenzyl)phosphonate (Compound 56B, 200 mg, 0.306 mmol) and (3-{[4-(4,4,5,5-tetramethyl-1,3,2-dioxaborolan-2-yl)-1H-pyrazol-1-yl]methyl}oxetan-3-yl)methanol (Compound 44B, 94.5 mg, 0.321 mmol) to afford 175 mg of the title compound as a racemic mixture (61%). MS (ESI): m/z=931.68/933.72 [M+H]$^+$. UPLC: t$_R$=1.72 min (UPLC-TOF: polar_2 min).

(10S)-14-Chloro-10-ethoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide and (10R)-14-chloro-10-ethoxy-N-methyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide and Prepared analogously to Example 44 using ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-3-chlorobenzyl)phosphonate (Compound 58A, 170 mg, 0.188 mmol) to afford 27.1 mg of the title compound (21%). $^1$H NMR (400 MHz, CD$_3$OD) δ 8.39 (s, 1H), 8.37 (s, 1H), 8.31 (s, 1H), 8.21 (d, J=8.8 Hz, 1H), 7.70 (d, J=8.6 Hz, 1H), 7.65 (d, J=8.6 Hz, 1H), 7.42 (t, J=2.1 Hz, 1H), 7.09-7.15 (m, 1H), 4.73-4.80 (m, 3H), 4.63-4.70 (m, 1H), 4.42-4.54 (m, 2H), 3.93 (dd, J=5.8, 10.9 Hz, 1H), 3.76 (td, J=7.4, 10.2 Hz, 1H), 3.67 (dd, J=7.7, 10.7 Hz, 1H), 3.58 (dt, J=7.2, 9.7 Hz, 1H), 3.34-3.44 (m, 2H), 2.94 (s, 3H), 0.84 (t, J=7.1 Hz, 3H). MS (ESI): m/z=693.58/695.58 [M+H]$^+$. UPLC: t$_R$=1.38 min (UPLC-TOF: polar_2 min).

Compound 58A: Ethyl (3-{[4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-3-chlorobenzyl)phosphonate Prepared analogously to Compound 44A using (4-{[4-{[6-bromo-2-(methylcarbamoyl)pyridin-3-yl]amino}-5-(trifluoromethyl)pyrimidin-2-yl]amino}-3-chlorobenzyl)phosphonate (Compound 58B, 200 mg, 0.321 mmol) and (3-{[4-(4,4,5,5-tetramethyl-1,3,2-dioxaborolan-2-yl)-1H-pyrazol-1-yl]methyl}oxetan-3-yl)methanol (Compound 44B, 99.0 mg, 0.337 mmol) to afford 160 mg of the title compound as a racemic mixture (56%). MS (ESI): m/z=899.74/901.72 [M+H]$^+$. UPLC: t$_R$=1.64 min (UPLC-TOF: polar_2 min).

Compound 58B: Ethyl hydrogen (4-{[4-{[6-bromo-2-(methylcarbamoyl)pyridin-3-yl]amino}-5-(trifluoromethyl)pyrimidin-2-yl]amino}-3-chlorobenzyl) phosphonate A mixture of diethyl (4-{[4-{[6-bromo-2-(methylcarbamoyl)pyridin-3-yl]amino}-5-(trifluoromethyl)pyrimidin-2-yl]amino}-3-chlorobenzyl)phosphonate (Compound 58C, 4.30 g, 6.60 mmol) and Sodium iodide (1.483 g, 9.896 mmol) in Pyridine (21.4 mL, 265 mmol) was heated to reflux for 18 hours. The pyridine was removed in vacuo and the remaining solids were taken up in water (~50 mL). This was treated with 6N HCl, dropwise with stirring, until pH-2 was reached. A thick ppt formed. This mixture was extracted with DCM twice. The combined organic layers were dried over $Na_2SO_4$, filtered and concentrated to 3.719 g of a tan solid (90%). The material was used without further purification. $^1$H NMR (400 MHz, $CDCl_3$) δ 12.57 (br. s., 1H) 8.81 (d, J=8.8 Hz, 1H) 8.33 (s, 1H) 8.08 (q, J=4.5 Hz, 1H) 7.83 (br. s., 1H) 7.35-7.44 (m, 2H) 7.19 (dt, J=8.3, 2.4 Hz, 1H) 4.06 (quin, J=7.3 Hz, 2H) 3.10 (d, J=22.0 Hz, 2H) 3.02 (d, J=5.1 Hz, 3H) 1.29 (t, J=7.1 Hz, 3H).

Compound 58C: diethyl (4-{[4-{[6-bromo-2-(methylcarbamoyl)pyridin-3-yl]amino}-5-(trifluoromethyl)pyrimidin-2-yl]amino}-3-chlorobenzyl)phosphonate This material was prepared analogously to Compound 1B replacing Compound 1C with Compound 6D and Compound 1 E with Compound 24C. MS (ES+): m/z 651.22/653.22 (MH+). UPLC: $t_R$=1.48 min (UPLC-SQD: analytical_2 min).

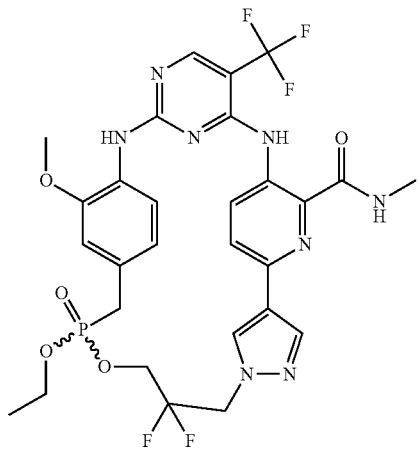

Example 59

(10S)-10-ethoxy-7,7-difluoro-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-10-ethoxy-7,7-difluoro-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Prepared analogously to Example 3 using ethyl hydrogen (4-{[4-({6-[1-(2,2-difluoro-3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl)phosphonate (Compound 59A, 307 mg, 0.438 mmol) and allowing the mixture to stir over a period of 5 days to afford 32 mg of Example 59 as a racemic mixture (11%) %) $^1$H NMR ($CD_3OD$, 400 MHz): δ=8.49 (s, 1H), 8.43 (s, 1H), 8.35 (s, 1H), 8.17 (d, J=8.6 Hz, 1H), 7.76 (d, J=8.6 Hz, 1H), 7.60 (d, J=8.4 Hz, 1H), 6.92 (t, J=1.8 Hz, 1H), 6.63 (dt, J=8.3, 2.3 Hz, 1H), 4.84-4.91 (m, 2H), 3.87 (s, 3H), 3.80-3.96 (m, 4H), 3.35-3.60 (m, 2H), 2.95 (s, 3H), 1.04 (t, J=7.1 Hz, 3H). $^{19}$F NMR ($CD_3OD$, 376 MHz): δ=64.1, 109.4, 109.5. $^{31}$P NMR ($CD_3OD$, 162 MHz): δ=28.0. MS (ESI): m/z 683.57 [M+H]$^+$. UPLC: $t_R$=1.26 min (UPLC-SQD: analytical_2 min).

$^{19}$F NMR ($CD_3OD$, 376 MHz): δ=64.1, 109.4, 109.5. $^{31}$P NMR ($CD_3OD$, 162 MHz): δ=28.0. MS (ESI): m/z 683.57 [M+H]$^+$. UPLC: $t_R$=1.26 min (UPLC-SQD: analytical_2 min).

Compound 59A: Ethyl hydrogen (4-{[4-({6-[1-(2,2-difluoro-3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 3C using diethyl (4-{[4-({6-[1-(2,2-difluoro-3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl) phosphonate (Compound 59B, 388 mg, 0.532 mmol) to afford 348 mg of the title compound (93%). $^1$H NMR (400 MHz, $CD_3OD$) δ 8.96-9.11 (m, 2H), 8.56 (s, 1H), 8.31 (s, 2H), 7.74 (d, J=9.1 Hz, 1H), 7.10 (s, 1H), 6.94 (d, J=8.1 Hz, 1H), 4.66 (d, J=7.6 Hz, 2H), 3.88 (quin, J=6.9 Hz, 5H), 3.65-3.77 (m, 2H), 3.06 (s, 5H), 1.15 (t, J=6.9 Hz, 3H). MS (ESI): m/z=701.68 [M+H]$^+$. UPLC: $t_R$=1.27 min (UPLC-TOF: polar_2 min).

Compound 59B: diethyl (4-{[4-({6-[1-(2,2-difluoro-3-hydroxypropyl)-1H-pyrazol-4-yl]-2-(methylcarbamoyl)pyridin-3-yl}amino)-5-(trifluoromethyl)pyrimidin-2-yl]amino}-3-methoxybenzyl) phosphonate Prepared analogously to Compound 1B using diethyl (4-{[4-chloro-5-(trifluoromethyl)pyrimidin-2-yl]amino}-3-methoxybenzyl)phosphonate (Compound 1 E, 275 mg, 0.606 mmol) and 3-amino-6-[1-(2,2-difluoro-3-hydroxypropyl)-1H-pyrazol-4-yl]-N-methylpyridine-2-carboxamide (Compound 59C, 198 mg, 0.636 mmol) to afford 388 mg of the title compound (84%). MS (ESI): m/z=729.68 [M+H]$^+$. UPLC: $t_R$=1.33 min (UPLC-TOF: polar_2 min).

Compound 59C: 2-amino-5-[1-(2,2-difluoro-3-hydroxypropyl)-1H-pyrazol-4-yl]-N-methylbenzamide Prepared analogously to Example 44C using 2-amino-5-{1-[3-(benzyloxy)-2,2-difluoropropyl]-1H-pyrazol-4-yl}-N-methylbenzamide (Compound 59D, 398 mg, 0.994 mmol) to afford 198 mg of the title compound (64%). $^1$H NMR (400 MHz, $CD_3OD$) δ 8.24 (s, 1H), 8.09 (s, 1H), 7.50 (d, J=8.6 Hz, 1H), 7.16 (d, J=8.6 Hz, 1H), 4.67 (t, J=13.4 Hz, 2H), 3.68 (t, J=12.9 Hz, 3H), 2.94 (s, 2H). MS (ESI): m/z=312.29 [M+H]$^+$. UPLC: $t_R$=0.71 min (UPLC-TOF: polar_2 min).

Compound 59D: 3-amino-6-{1-[3-(benzyloxy)-2,2-difluoropropyl]-1H-pyrazol-4-yl}-N-methylpyridine-2-carboxamide Prepared analogously to Compound 3C using 3-amino-6-bromo-N-methylpyridine-2-carboxamide (Compound 6D, 359 mg, 1.56 mmol) and 1-[3-(benzyloxy)-2,2-difluoropropyl]-4-(4,4,5,5-tetramethyl-1,3,2-dioxaborolan-2-yl)-1H-pyrazole (Compound 59E, 650 mg, 1.72 mmol) to afford 398 mg of the title compound (64%). MS (ESI): m/z=402.16 [M+H]+. UPLC: $t_R$=0.93 min (UPLC-TOF: polar_2 min).

Compound 59E: 1-(3-Benzyloxy-2,2-difluoropropyl)-4-(4,4,5,5-tetramethyl-1,3,2-dioxaborolan-2-yl)-1H-pyrazole A solution of 1-(3-benzyloxy-2,2-difluoropropyl)-4-iodo-1H-pyrazole (Compound 59F, 1.8 g, 4.7 mmol) in THF (40 mL) was cooled to −78° C., treated with iPrMgCl (4.75 mL, 9.5 mmol, 2M) and the temperature was raised to −40° C. After 20 min stirring at −40° C., reaction mixture was cooled to −78° C. and treated with 2-methoxy-4,4,5,5-tetramethyl-1,3,2-dioxaborolane (0.091 mL, 0.56 mmol). The reaction mixture was allowed to warm to RT, treated with sat. aq. ammonium chloride (20 mL) and extracted with ethyl acetate (20 mL). The organic layer was dried over Na$_2$SO$_4$, filtered and concentrated to give 1.56 g (89%) of desired product as an oil. $^1$H NMR (500 MHz, CDCl$_3$) δ 7.81 (s, 1H), 7.78 (s, 1H), 7.36-7.33 (m, 5H), 4.64-4.59 (m, 4H), 3.56 (t, J=12 Hz, 2H), 1.26 (s, 12H).

Compound 59F: 1-(3-Benzyloxy-2,2-difluoropropyl)-4-iodo-1H-pyrazole

A cold (0° C.) solution of 4-iodo-1H-pyrazole (10.1 g, 51.8 mmol) in DMF (20 mL) was treated with NaH (1.56 g, 38.82 mmol, 60%) and allowed to warm to RT. After 1 h, the reaction mixture was treated with methanesulfonic acid 3-benzyloxy-2,2-difluoropropyl ester (Compound 59G, 2.0 g, 6.47 mmol) and was stirred for 24 h at 70° C. The reaction mixture was poured into chilled sat. aq. ammonium chloride (20 mL) and extracted with ethyl acetate (100 mL). The organic layer was washed with water (5×30 mL), dried over Na$_2$SO$_4$, filtered, concentrated and purified by column chromatography (SiO$_2$, 30% ethyl acetate/hexanes) to give 1.8 g (72%) of the title compound as a white solid. $^1$H NMR (500 MHz, CDCl$_3$) δ 7.32-7.38 (m, 7H), 4.63 (s, 2H), 3.89 (s, J=12.5 Hz, 2H), 3.77 (t, J=12.5 Hz, 2H).

Compound 59G: Methanesulfonic acid 3-benzyloxy-2,2-difluoropropyl ester

A solution of 3-benzyloxy-2,2-difluoropropan-1-ol (Compound 59H, 202 mg, 1 mmol) and methanesulfonyl chloride in DCM (3 mL) was cooled to 0° C. and treated with Et$_3$N (0.28 mL, 2 mmol). The reaction mixture was allowed to warm at RT. After 12 h, the reaction mixture was diluted with DCM (5 mL) and washed with aq. K$_2$CO$_3$ (4×5 mL). The organic layer was dried over Na$_2$SO$_4$, filtered and concentrated to give 220 mg (82%) of the title compound as yellow oil. $^1$H NMR (500 MHz, CDCl$_3$) δ 7.37-7.33 (m, 5H), 4.62 (s, 2H), 4.47 (t, J=12.4 Hz, 2H), 3.74 (t, J=12.4 Hz, 2H), 3.05 (s, 3H).

Compound 59H: 3-Benzyloxy-2,2-difluoropropan-1-ol

A suspension of 2,2-difluoropropane-1,3-diol (Compound 59I, 6.0 g, 53.5 mmol), 4-fluorophenylboronic acid (1.5 g, 10.7 mmol) and K$_2$CO$_3$ (11.0 g, 80.3 mmol) in DMF (50 mL) was treated with benzyl bromide (8.9 mL, 74.9 mmol). The reaction mixture was stirred at RT for 72 h, diluted with ethyl acetate (200 mL) and washed with water (5×100 mL). The organic layer was dried over Na$_2$SO$_4$, filtered and concentrated to give yellow oil which was purified by column chromatography (SiO$_2$, 20% ethyl acetate/hexanes) to give 5 g (50%) of the desired product as an oil. $^1$H NMR (500 MHz, CDCl$_3$) δ 7.38-7.34 (m, 5H), 4.70 (s, 2H), 3.89-3.88 (m, 2H), 3.77 (t, J=12.6 Hz, 2H).

Compound 59I: 2,2-Difluoropropane-1,3-diol

A solution of acetic acid 3-acetoxy-2-oxopropyl ester (6.2 g, 35.6 mmol) in DAST (11 mL) was stirred for 48 h. The reaction mixture was added to a mixture of ice and sat. sodium carbonate drop wise. The aq. layer was extracted with ethyl acetate (3×100 mL). The combined organic layers were dried over Na$_2$SO$_4$, filtered and concentrated to give 4.8 g (69%) of acetic acid 3-acetoxy-2,2-difluoro-propyl ester which was dissolved in methanol and treated with NaOMe (3.9 g, 73 mmol). After 6 h, the reaction mixture was neutralized with amberlite IR ion exchange resin (acidic). The resulting mixture was filtered and the filtrate was concentrated to 2.8 g (70%) of desired product as an oil. $^1$H NMR (500 MHz, CDCl$_3$) δ 3.91 (t, J=12.5 Hz, 4H), 1.8 (bs, 2H).

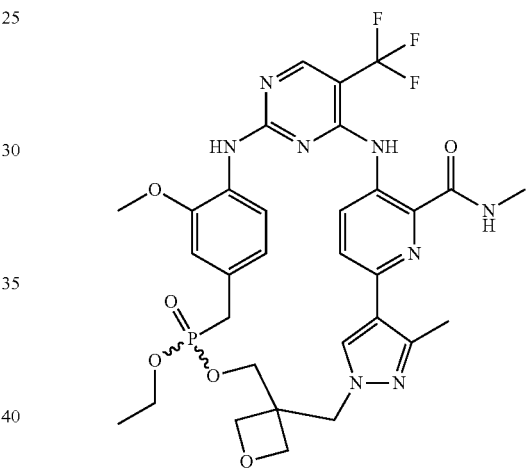

Example 60

(10R)-10-ethoxy-14-methoxy-N,3-dimethyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide and (10S)-10-ethoxy-14-methoxy-N,3-dimethyl-20-(trifluoromethyl)spiro[9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-7,3'-oxetane]-24-carboxamide 10-oxide Prepared analogously to Example 44 using racemic Ethyl (3-{[3-methyl-4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-3-methoxybenzyl) phosphonate (Compound 60A, 259 mg, 0.285 mmol) to give the desired product as a racemic mixture (88 mg, 44%). $^1$H NMR (CD$_3$OD, 400 MHz): δ=8.33 (s, 1H), 8.18 (s, 1H), 8.11 (d, J=8.8 Hz, 1H), 7.69 (d, J=8.6 Hz, 1H), 7.61 (d, J=8.1 Hz, 1H), 6.90 (t, J=1.8 Hz, 1H), 6.63 (dt, J=8.4, 2.2 Hz, 1H), 4.81 (d, J=6.6 Hz, 1H), 4.78 (d, J=6.6 Hz, 1H), 4.62 (d, J=1.3 Hz, 2H), 4.47 (d, J=6.6 Hz, 1H), 4.46 (d, J=6.6 Hz, 1H), 3.85 (s, 3H), 3.81-3.94 (m, 4H), 3.37 (dd, J=21.4, 2.8 Hz, 2H), 2.94 (s, 3H), 2.60 (s, 3H), 1.05 (t, J=7.1 Hz, 3H). $^{19}$F NMR (CD$_3$OD, 376 MHz): δ=64.0. $^{31}$P NMR (CD$_3$OD, 162 MHz): δ=27.9. MS (ESI): m/z 703.60 [M+H]$^+$. UPLC: $t_R$=1.27 min (UPLC-SQD: analytical_2 min).

Compound 60A: Ethyl (3-{[3-methyl-4-(4,4,5,5-tetramethyl-1,3,2-dioxaborolan-2-yl)-1H-pyrazol-1-yl]methyl}oxetan-3-yl)methyl (4-{[4-{[6-bromo-2-(methylcarbamoyl)pyridin-3-yl]amino}-5-(trifluoromethyl)pyrimidin-2-yl]amino}-3-methoxybenzyl)phosphonate Prepared analogously to Compound 44A using ethyl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 38C, 124 mg, 0.200 mmol) and (3-{[3-methyl-4-(4,4,5,5-tetramethyl-1,3,2-dioxaborolan-2-yl)-1H-pyrazol-1-yl]methyl}oxetan-3-yl)methanol (Compound 60B, 75 mg, 0.24 mmol) to give the desired product. MS (ESI): m/z 909.76/911.76 [M+H]$^+$. UPLC: $t_R$=1.63 min (analytical 2 min).

Compound 60B: (3-{[3-Methyl-4-(4,4,5,5-tetramethyl-1,3,2-dioxaborolan-2-yl)-1H-pyrazol-1-yl]methyl}oxetan-3-yl)methanol This material was prepared analogously to Compound 44B using Compound 60C $^1$H NMR (CDCl$_3$, 400 MHz): 1.31 (s, 12H), 2.36 (s, 3H), 3.73 (s, 2H), 4.43 (d, J=6.6 Hz, 2H), 4.47 (s, 2H), 4.48 (d, J=6.6 Hz, 2H), 7.62 (s, 1H). MS (ESI): m/z 309.32 [M+H]$^+$. UPLC: $t_R$=1.01 min (UPLC-SQD: analytical_2 min).

Compound 60C: 1-({3-[(Benzyloxy)methyl]oxetan-3-yl}methyl)-3-methyl-4-(4,4,5,5-tetramethyl-1,3,2-dioxaborolan-2-yl)-1H-pyrazole A solution of (4-(tetramethyl-1,3,2-dioxaborolan-2-yl)-1H-3-methylpyrazole (3.0 g, 14.4 mmol) in DMF (10 mL) was treated with sodium hydride (60% dispersion in oil, 519 mg, 12.98 mmol) and {3-[(benzyloxy)methyl]oxetan-3-yl}methyl methanesulfonate (Compound 44D, 4.15 g, 21.6 mmol) at RT and heated to 80° C. for 12 hrs. The Reaction mixture was cooled to RT, poured into water (100 mL) and extracted twice with ethyl acetate. The combined organic layers were dried over sodium sulfate, filtered, concentrated to give a residue which was purified by column chromatography (SiO$_2$, 0.5% methanol in dichloromethane) to give 1.6 g (36%) of the title compound as the predominant regioisomer. $^1$H NMR (400 MHz, CDCl$_3$) δ: 7.51 (s, 1H), 7.25-7.32 (m, 5H), 4.52 (d, J=5.6 Hz, 2H), 4.36-448 (m, 6H), 3.45 (s, 2H), 2.35 (s, 3H), 1.27 (s, 12H).

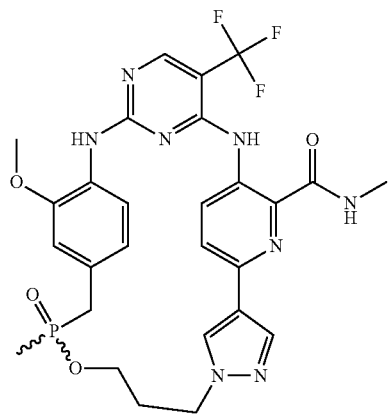

Example 61

(10S)-14-methoxy-N,10-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-14-methoxy-N,10-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Racemic Example 61 was prepared analogously to Example 44 using [1-(3-{[(4-{[4-{[6-bromo-2-(methylcarbamoyl)pyridin-3-yl]amino}-5-(trifluoromethyl)pyrimidin-2-yl]amino}-3-methoxybenzyl)(methyl)phosphoryl]oxy}propyl)-1H-pyrazol-4-yl]boronic acid (Compound 61A, 196 mg, 0.264 mmol) to afford 112 mg of the title compound (69%). $^1$H NMR (400 MHz, CD$_3$OD) δ 8.52 (s, 1H), 8.33-8.40 (m, 2H), 8.07 (d, J=8.6 Hz, 1H), 7.80 (d, J=8.6 Hz, 1H), 7.65 (d, J=8.3 Hz, 1H), 6.83-6.88 (m, 1H), 6.47 (d, J=8.3 Hz, 1H), 4.47 (t, J=5.9 Hz, 2H), 3.87 (s, 4H), 3.47-3.60 (m, 1H), 3.34 (s, 1H), 3.17-3.28 (m, 1H), 2.95 (s, 3H), 2.25 (d, J=5.3 Hz, 2H), 1.39 (d, J=13.9 Hz, 3H). MS (ESI): m/z=617.60 [M+H]$^+$. UPLC: $t_R$=1.14 min (UPLC-TOF: polar_2 min).

Compound 61A: 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)methylphosphinate (Benzotriazol-1-yloxy)tripyrrolidino-phosphonium hexafluorophosphate (2.24 g, 4.30 mmol) was added to stirring suspension of (4-{[4-{[6-bromo-2-(methylcarbamoyl)pyridin-3-yl]amino}-5-(trifluoromethyl)pyrimidin-2-yl]amino}-3-methoxybenzyl)methylphosphinic acid (Compound 61B, 845 mg, 1.43 mmol), 3-[4-(4,4,5,5-tetramethyl-1,3,2-dioxaborolan-2-yl)-1H-pyrazol-1-yl]propan-1-ol (Compound 3E, 362 mg, 1.43 mmol), and 1-methylimidazole (1.37 ml, 17.2 mmol) in 1,2-dichloroethane (31.2 ml) at 60° C. for 16 hrs. The reaction was quenched with water and extracted with EtOAc (3×), dried over sodium sulfate, filtered, and concentrated in vacuo and purified using a Teledyne ISCO Combiflash® Rf system [0→10% MeOH in 1:1 EtOAc/DCM] to afford 194 mg of the title compound as a racemic mixture (16%). MS (ESI): m/z=824.65 [M+H]⁺. UPLC: t_R=1.17 min (UPLC-TOF: polar_2 min).

Compound 61B: (4-{[4-{[6-bromo-2-(methylcarbamoyl)pyridin-3-yl]amino}-5-(trifluoromethyl) pyrimidin-2-yl]amino}-3-methoxybenzyl)methylphosphinic acid (4-{[4-{[6-bromo-2-(methylcarbamoyl)pyridin-3-yl]amino}-5-(trifluoromethyl) pyrimidin-2-yl]amino}-3-methoxybenzyl)methylphosphinate (Compound 61C, 130 mg, 0.215 mmol) in pyridine (10 mL) was charged with bromotrimethylsilane (0.171 mL, 1.29 mmol). The reaction mixture stirred at rt for 16 hrs. The reaction was concentrated in vacuo to solid to afford 100 mg of the title compound (79%). $^1$H NMR (400 MHz, CD$_3$OD) δ 9.04 (br. s., 1H), 8.36 (s, 1H), 7.72 (br. s., 1H), 7.56 (d, J=8.8 Hz, 1H), 7.05 (s, 1H), 6.84-6.95 (m, 1H), 3.86 (s, 3H), 3.20 (d, J=17.7 Hz, 2H), 2.94 (s, 3H), 1.42 (s, 3H). MS (ESI): m/z=589.38/591.37 [M+H]⁺. UPLC: t_R=1.19 min (UPLC-TOF: polar_2 min).

Compound 61C: Ethyl (4-{[4-{[6-bromo-2-(methylcarbamoyl)pyridin-3-yl]amino}-5-(trifluoromethyl) pyrimidin-2-yl]amino}-3-methoxybenzyl)methylphosphinate Prepared analogously to Compound 1B using ethyl (4-{[4-chloro-5-(trifluoromethyl)pyrimidin-2-yl]amino}-3-methoxybenzyl)methylphosphinate (Compound 61 D, 270 mg, 0.64 mmol) and 3-amino-6-bromo-N-methylpyridine-2-carboxamide (Compound 6D, 154 mg, 0.669 mmol) to afford 298 mg of the title compound (76%). $^1$H NMR (400 MHz, CD-$_3$OD) δ 9.00 (br. s., 1H), 8.36 (s, 1H), 7.63-7.73 (m, 1H), 7.51-7.61 (m, 1H), 7.07 (t, J=1.9 Hz, 1H), 6.93 (td, J=2.2, 8.1 Hz, 1H), 4.04-4.16 (m, 2H), 3.89 (s, 3H), 3.33 (s, 1H), 3.29 (s, 1H), 2.93 (s, 3H), 1.51 (s, 3H), 1.33 (t, J=7.1 Hz, 3H). MS (ESI): m/z=617.06/619.06 [M+H]⁺. HPLC: t_R=1.01 min (UPLC-TOF: polar_3 min).

Compound 61 D: Ethyl (4-{[4-chloro-5-(trifluoromethyl)pyrimidin-2-yl]amino}-3-methoxybenzyl)methylphosphinate This material was prepared analogously to Compound 1 E replacing Compound 1F with Compound 61E. After flash column chromatography the material was further purified by HPLC/mass-directed purification to isolate the title compound as 1.09 g of a yellow oil (70%). $^1$H NMR (400 MHz, CD$_3$OD) δ 1.31 (t, J=7.07 Hz, 3H), 1.44-1.50 (m, 3H), 3.27 (d, J=17.68 Hz, 2H), 3.91-3.95 (m, 3H), 4.01-4.12 (m, 2H), 6.89-6.96 (m, 1H), 7.02-7.09 (m, 1H), 8.03 (d, J=8.34 Hz, 1H), 8.62 (s, 1H).

Compound 61E: (4-Amino-3-methoxybenzyl)-methyl phosphonic acid ethyl ester

Pd/C (1.5 g) was added to a solution of (3-methoxy-4-nitrobenzyl)-methyl phosphonic acid ethyl ester (Compound 61F, 8.0 g, 29.09 mmol) in ethanol (70 mL). This mixture was subjected to hydrogenation at RT overnight. The reaction mixture was filtered and the filtrate evaporated under reduced pressure to give a crude oil. The desired product was isolated as 6.3 g (86%) of a clear oil using silica-gel column chromatography (2% MeOH/DCM). $^1$H NMR (CDCl$_3$-300 MHz): δ 1.23 (m, 3H), 1.30 (d, J=13.0 Hz, 3H), 3.0 (d, J=17.4 Hz, 2H), 3.67 (br. s., 2H), 3.79 (s, 3H), 4.02 (m, 2H), 6.60 (s, 2H), 6.69 (s, 1H).

Compound 61F: (3-Methoxy-4-nitrobenzyl)-methyl phosphonic acid ethyl ester

A solution of 4-bromomethyl-2-methoxy-1-nitrobenzene (Compound 61G, 7.5 g, 30.36 mmol) and diethyl methylphosphonite (5.52 g, 40.59 mmol) in toluene (60 mL). was heated to reflux for 16 hr. The reaction mixture was cooled to RT, diluted with ethyl acetate (100 mL), washed with water, dried over anhydrous Na$_2$SO$_4$, filtered and concentrated to give a brown oily material (8.2 g). This crude material was triturated with hexane (6×20 mL) and the oily residue was concentrated on rotary evaporator to remove traces of hexane as well as diethyl methylphosphonite to give the desire product (8.0 g, 96%). $^1$H NMR (CDCl$_3$-300 MHz): δ 1.29 (m, 3H), 1.38 (d, J=13.8 Hz, 3H), 3.17 (dd, J=17, 18 Hz, 2H), 3.94 (s, 3H), 4.05 (m, 2H), 6.88 (d, J=8.1 Hz, 1H), 7.06 (d, J=2.0 Hz, 1H), 7.81 (dd, J=8.1, 8.1 Hz, 1H).

Compound 61F: 4-Bromomethyl-2-methoxy-1-nitrobenzene

N-Bromosuccinimide (58.62 g, 329.34 mmol) was added in portions over a period of 5-10 min to a well stirred solution of 4-methyl-2-methoxy-1-nitro benzene (50.0 g, 299.4 mmol) and 1,1'-Azobis(cyclohexane carbonitrile) (1.0 g, 4.1 mmol) in dichloroethane (600 mL) and the resulting mixture was heated to reflux under a UV light for a maximum 7-8 hr. After cooling to rt, the reaction mixture was diluted with dichloromethane (400 mL) and washed with aqueous Na$_2$S$_2$O$_4$ solution, water and brine. The organic phase was dried over anhydrous Na$_2$SO$_4$, filtered and concentrated to give a crude solid (102.0 g) which was triturated with diisopropyl ether to afford 43.0 g of the desired product. The diisopropyl ether filtrate was concentrated and purified by silica-gel column chromatography (5-40% EtOAc/Hexanes) to obtain an additional 5.5 g of the desired product (48.5 g, 66%). $^1$H NMR (CDCl$_3$-300 MHz): δ=3.98 (s, 3H), 4.46 (s, 2H), 7.05 (dd, J=6.60 Hz, 1H), 7.10 (d, J=1.5 Hz, 1H), 7.82 (d, J=8.4 Hz, 1H).

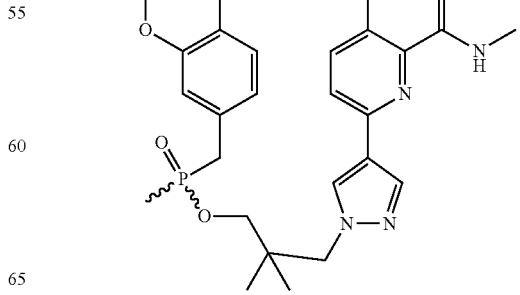

Example 62

(10S)-14-methoxy-N,7,7,10-tetramethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10R)-14-methoxy-N,7,7,10-tetramethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide This material was prepared analogously to Example 44 using 2,2-dimethyl-3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)methylphosphinate (Compound 61B, 66.3 mg, 0.0779 mmol) to afford 32 mg of Example 62 as a racemic mixture (64%). $^1$H NMR (400 MHz, CD$_3$OD) δ 8.36 (s, 2H), 8.31 (s, 1H), 8.14 (d, J=8.8 Hz, 1H), 7.76 (d, J=8.6 Hz, 1H), 7.71 (d, J=8.3 Hz, 1H), 6.91 (s, 1H), 6.47 (d, J=8.3 Hz, 1H), 4.22-4.29 (m, 1H), 4.09-4.18 (m, 1H), 3.90 (s, 3H), 3.69 (t, J=10.4 Hz, 1H), 3.36-3.49 (m, 3H), 2.96 (s, 3H), 1.46 (d, J=13.9 Hz, 3H), 1.14 (s, 6H). MS (ESI): m/z=645.20 [M+H]$^+$. UPLC: t$_R$=0.94 min (UPLC-TOF: polar_2 min).

Compound 62A: 2,2-dimethyl-3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)methylphosphinate This material was prepared analogously to Compound 61A using (4-{[4-{[6-bromo-2-(methylcarbamoyl)pyridin-3-yl]amino}-5-(trifluoromethyl)pyrimidin-2-yl]amino}-3-methoxybenzyl)methylphosphinic acid (Compound 61B, 250 mg, 0.42 mmol) and 2,2-dimethyl-3-[4-(4,4,5,5-tetramethyl-1,3,2-dioxaborolan-2-yl)-1H-pyrazol-1-yl]propan-1-ol (Compound 47B, 119 mg, 0.424 mmol) to afford 70 mg of the title compound (19%). MS (ESI): m/z=851.22/853.23 [M+H]$^+$. UPLC: t$_R$=1.17 min (UPLC-TOF: polar_2 min).

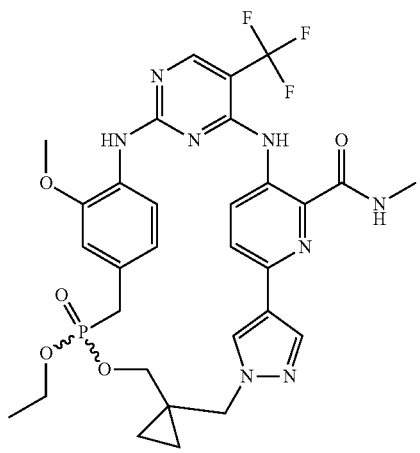

Example 63

(10'S)-10'-ethoxy-1,4'-methoxy-N-methyl-20'-(trifluoromethyl)-9'-oxa-4',5',16',18',22',25',28'-heptaaza-10'-phosphaspiro[cyclopropane-1,7'-pentacyclo[21.2.2.2$^{12,15}$.1$^{2,5}$.1$^{17,21}$]hentriacontane]-1'(25'),2'(31'),3',12',14',17'(28'),18',20',23',26',29'-undecaene-24'-carboxamide 10'-oxide and (10'R)-10'-ethoxy-1,4'-methoxy-N-methyl-20'-(trifluoromethyl)-9'-oxa-4',5',16',18',22',25',28'-heptaaza-10'-phosphaspiro[cyclopropane-1,7'-pentacyclo[21.2.2.2$^{12,15}$.1$^{2,5}$.1$^{17,21}$]hentriacontane]-1'(25'),2'(31'),3',12',14',17'(28'),18',20',23',26',29'-undecaene-24'-carboxamide 10'-oxide This material was prepared analogously to Example 44 using ethyl (1-{[4-(4,4,5,5-tetramethyl-1,3,2-dioxaborolan-2-yl)-1H-pyrazol-1-yl]methyl}cyclopropyl)methyl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 63A, 584 mg, 0.664 mmol) to afford 145 mg of the title compounds (33%). $^1$H NMR (400 MHz, CD$_3$OD) δ 8.51 (s, 1H), 8.36 (d, J=13.6 Hz, 2H), 8.17 (d, J=8.8 Hz, 1H), 7.81 (d, J=8.6 Hz, 1H), 7.62 (d, J=7.8 Hz, 1H), 6.90 (s, 1H), 6.66 (d, J=7.8 Hz, 1H), 4.32-4.38 (m, 1H), 4.17-4.22 (m, 1H), 3.81-3.91 (m, 5H), 3.34-3.61 (m, 7H), 2.95 (s, 3H), 1.04 (t, J=7.1 Hz, 4H). MS (ESI): m/z=673.73 [M+H]$^+$. UPLC: t$_R$=1.26 min (UPLC-TOF: polar_2 min).

Compound 63A: ethyl (1-{[4-(4,4,5,5-tetramethyl-1,3,2-dioxaborolan-2-yl)-1H-pyrazol-1-yl]methyl}cyclopropyl)methyl (4-{[4-{[6-bromo-2-(methylcarbamoyl)pyridin-3-yl]amino}-5-(trifluoromethyl)pyrimidin-2-yl]amino}-3-methoxybenzyl)phosphonate Prepared analogously to Compound 61A using ethyl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 38C, 670 mg, 1.1 mmol) and (1-{[4-(4,4,5,5-tetramethyl-1,3,2-dioxaborolan-2-yl)-1H-pyrazol-1-yl]methyl}cyclopropyl)methanol (Compound 63B, 300 mg, 1.08 mmol) to afford 584 mg of the title compound as a racemic mixture (62%). MS (ESI): m/z=879.92/881.81 [M+H]$^+$. UPLC: t$_R$=1.61 min (UPLC-TOF: polar_2 min).

Compound 63B: (1-{[4-(4,4,5,5-Tetramethyl-1,3,2-dioxaborolan-2-yl)-1H-pyrazol-1-yl]methyl}cyclopropyl)methanol A solution of –({1-[(benzyloxy)methyl]cyclopropyl}methyl)-4-(tetramethyl-1,3,2-dioxaborolan-2-yl)-1H-pyrazole (Compound 63C, 8 g, 21.7 mmol) in ethanol (100 mL) was treated with palladium on charcoal (10%, 6 g) and heated to 50° C. under hydrogen atmosphere for 24 hrs. The catalyst was filtered off and the filtrate was concentrated to a residue under reduced pressure. The residue was triturated with isopropyl ether to give 3.2 g (53%) of the required material as white solid. $^1$H NMR (500 MHz, CDCl$_3$) δ 7.81 (s, 1H), 7.7 (s, 1H), 4.14 (s, 2H), 3.38 (s, 2H), 1.33 (s, 12H), 0.54-0.65 (m, 4H).

Compound 63C: 1-({1-[(benzyloxy)methyl]cyclopropyl}methyl)-4-(4,4,5,5-tetramethyl-1,3,2-dioxaborolan-2-yl)-1H-pyrazole A solution of (4-(4,4,5,5-tetramethyl-1,3,2-dioxaborolan-2-yl)-1H-pyrazole (8.62 g, 44.4 mmol) in DMF (12 mL) was treated with cesium carbonate (14.6 g, 44.4 mmol) and stirred at RT for 10 min. A solution of {1-[(benzyloxy)methyl]cyclopropyl}methyl methanesulfonate (Compound 63D, 12 g, 44.4 mmol) in DMF was added and heated to 70° C. for 24 hrs. The reaction mixture was cooled to RT, poured into water, extracted with ethyl acetate, dried over sodium sulfate, filtered and concentrated to give 12 g (73%) of required compound as a colorless gum which was used without further purification. $^1$H NMR (600 MHz, CDCl$_3$) δ 7.78 (s, 1H), 7.68 (s, 1H), 7.25-7.34 (m, 5H), 4.48 (s, 2H), 4.15 (s, 2H), 3.16 (s, 2H), 1.33 (s, 12H), 0.71 (s, 2H), 0.56 (s, 2H).

Compound 63D
{1-[(benzyloxy)methyl]cyclopropyl}methyl methanesulfonate

Methane sulfonyl chloride (5.2 mL, 68.7 mmol) was added drop wise to an ice cooled solution of {1-[(benzyloxy)methyl]cyclopropyl}methanol (Compound 63E, 11 g, 57.2 mmol) and triethylamine (15.5 mL, 114 mmol) in dichloromethane (50 mL). The reaction mixture warmed to RT and allowed to stir overnight. The reaction mixture was filtered to remove solids. The filtrate was washed with saturated sodium bicarbonate solution followed by brine, dried over magnesium sulfate, filtered and concentrated to give 12 g (77%) of the desired product as light yellow oil which was used without further purification. $^1$H NMR (400 MHz, CDCl$_3$) δ 7.25-7.41 (m, 5H), 4.58 (s, 2H), 4.21 (s, 2H), 3.42 (s, 2H), 2.96 (s, 3H), 0.61-0.75 (m, 4H).

Compound 63E:
(1-Benzyloxymethyl-cyclopropyl)-methanol

This compound was prepared by selective monobenzylation of (1-hydroxymethyl-cyclopropyl)-methanol (30 g, 294 mmol) using the procedure of Maki et al in *Tetrahedron Letters,* 2009, 50, 1466-1468. and purified by column chromatography (SiO$_2$, 100% dichloromethane) to give 32 g (57%) of the title compound. $^1$H NMR (400 MHz, CDCl$_3$) δ 7.23-7.34 (m, 5H), 4.52 (s, 2H), 3.54 (d, J=5.6 Hz, 2H), 3.43 (s, 2H), 2.43-2.44 (m, 1H), 0.44-0.54 (m, 4H).

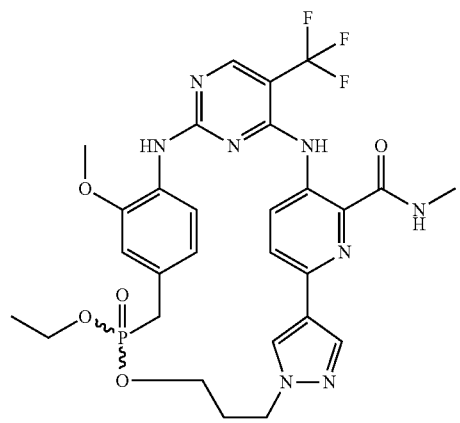

Example 64

(10R)-10-ethoxy-14-methoxy-N-methyl-20-(trifluoromethyl)-9-oxa-3,4,5,16,18,22,25,28-octaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide (10S)-10-ethoxy-14-methoxy-N-methyl-20-(trifluoromethyl)-9-oxa-3,4,5,16,18,22,25,28-octaaza-10-phosphapentacyclo[21.2.2.2$^{12,15}$.1$^{2,5}$.1$^{17,21}$] hentriaconta-1(25),2(31),3,12,14,17(28),18,20,23,26,29-undecaene-24-carboxamide 10-oxide A mixture of ethyl 3-[4-(tributylstannanyl)-1H-1,2,3-triazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 64A, 0.331 mmol assumed) and Pd(PPh$_3$)$_2$Cl$_2$ (11.6 mg, 0.0166 mmol) in 1,4-dioxane (8 mL) was evacuated and refilled with nitrogen (3×), then heated at 100° C. for 5 h. The mixture was concentrated under reduced pressure, the residue was purified by silica gel chromatography (ISCO system: MeOH/DCM-EtOAc (1:1)=0-15%) to give the desired product as a white solid, (51 mg, 24% yield over 2 steps). $^1$H NMR (CDCl$_3$, 400 MHz): δ 10.86 (s, 1H), 8.53 (s, 1H), 8.48 (m, 1H), 8.36 (s, 1H), 8.15 (d, J=8.6 Hz, 1H), 7.80 (d, J=8.6 Hz, 1H), 7.79 (br s, 1H), 7.56 (d, J=7.8 Hz, 1H), 6.66 (s, 1H), 6.25 (d, J=8.4 Hz, 1H), 4.66-4.77 (m, 2H), 4.05-4.11 (m, 2H), 3.89-3.97 (m, 2H), 3.84 (s, 3H), 3.09 (dd, J=21.2, 2.2 Hz, 2H), 3.04 (d, J=5.0 Hz, 3H), 2.36-2.49 (m, 2H), 1.28 (t, J=7.1 Hz, 3H). MS (ESI): m/z 648.69 [M+H]$^+$. UPLC: t$_R$=1.08 min (UPLC-SQD: analytical__2 min).

Compound 64A: Ethyl 3-[4-(tributylstannanyl)-1H-1,2,3-triazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl) phosphonate To a solution of ethyl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 38C, 205 mg, 0.331 mmol), 3-[4-(tributylstannanyl)-1H-1,2,3-triazol-1-yl]propan-1-ol (Compound 64B, 165 mg, 0.397 mmol) and DIPEA (0.17 mL, 0.993 mmol) in 1,2-dichloroethane (8 mL) was added (benzotriazol-1-yloxy) tripyrrolidino-phosphonium hexafluorophosphate (517 mg, 0.993 mmol). The resulting mixture was stirred at rt overnight. The mixture was diluted with DCM (30 mL), washed with sat. aq. NaHCO$_3$ (2×20 mL), brine (20 mL), and dried over anhydrous sodium sulfate. The solvents were evaporated under reduced pressure, and the residue was purified by silica gel chromatography (ISCO system: MeOH/DCM=0-3%) to give the desired product, which was used in the following step. MS (ESI): m/z 1018.86 [M+H]$^+$. UPLC: t$_R$=1.22 min (UPLC-SQD: very non-polar__2 min).

Compound 64B: 3-[4-(tributylstannanyl)-1H-1,2,3-triazol-1-yl]propan-1-ol

A solution of tributylstannylethyne (1.47 g, 4.67 mmol) and 3-azidopropan-1-ol (450 mg, 4.4 mmol) in PhMe (15 mL) was heated at 80° C. under nitrogen for 3 days. Another 0.5 eq. of Tributylstannylethyne was added, and the resulting mixture was heated at 110° C. for 5 h. The solvent was evaporated under reduced pressure, and the residue was purified by silica gel chromatography (ISCO system: acetone/ heptane=0-30%) to give the desired product as a colorless oil, 1.42 g, 77% yield. $^1$H NMR (CDCl$_3$, 400 MHz): δ=7.48 (s, 1H), 4.57 (d, J=6.6 Hz, 2H), 3.63-3.67 (m, 2H), 2.11-2.17 (m, 2H), 1.95 (br s, 1H), 1.54-1.58 (m, 6H), 1.33-1.37 (m, 6H), 1.10-1.14 (m, 6H), 0.89 (t, J=7.3 Hz, 9H).

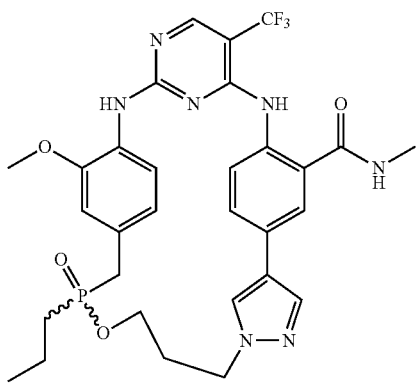

Example 66

(10R)-14-methoxy-N-methyl-10-propyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10S)-14-methoxy-N-methyl-10-propyl-20-(trifluoromethyl)-9-oxa-4,5,16,18,22,28-hexaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide This material was prepared analogously to Example 44 using 3-[4-(4,4,5,5-tetramethyl-1,3,2-dioxaborolan-2-yl)-1H-pyrazol-1-yl]propyl(4-{[4-{[4-bromo-2-(methylcarbamoyl)phenyl]amino}-5-(trifluoromethyl)pyrimidin-2-yl]amino}-3-methoxybenzyl)propylphosphinate (Compound 66A, 0.245 g, 0.288 mmol). After column chromatography, the material was triturated with DCM/heptane. The precipitate was collected and dried to afford the title compounds as 4.5 mg of a white solid (2%). $^1$H NMR (CDCl$_3$, 400 MHz): δ 9.37 (br. s., 1H), 8.30 (br. s., 1H), 8.03 (br. s., 1H), 7.91 (s, 1H), 7.84 (br. s., 1H), 7.70-7.77 (m, 2H), 7.61-7.70 (m, 2H), 6.61 (br. s., 1H), 6.46 (br. s., 1H), 6.21 (d, J=8.1 Hz, 1H), 4.30-4.56 (m, 2H), 4.09 (br. s., 1H), 3.82 (s, 3H), 3.32 (br. s., 1H), 2.82-3.10 (m, 5H), 2.25 (br. s., 2H), 1.61 (d, J=18.9 Hz, 4H), 1.01 (br. s., 3H). MS (ESI): m/z 644.73 [M+H]$^+$. UPLC: t$_R$=1.15 min (UPLC-SQD: analytical_2 min).

Compound 66A: 3-[4-(4,4,5,5-tetramethyl-1,3,2-dioxaborolan-2-yl)-1H-pyrazol-1-yl]propyl (4-{[4-{[4-bromo-2-(methylcarbamoyl)phenyl]amino}-5-(trifluoromethyl)pyrimidin-2-yl]amino}-3-methoxybenzyl)propylphosphinate A solution of 5-bromo-2-{[2-chloro-5-(trifluoromethyl)pyrimidin-4-yl]amino}-N-methylbenzamide (Compound 66B, 150.5 mg, 0.3674 mmol) and 3-[4-(4,4,5,5-tetramethyl-1,3,2-dioxaborolan-2-yl)-1H-pyrazol-1-yl]propyl (4-amino-3-methoxybenzyl)propylphosphinate (Compound 66C, 175.4 mg, 0.3674 mmol) in TFE (5.0 mL) was charged with TFA (0.0602 mL). The reaction mixture was stirred at 50° C. for 24 hours. The reaction mixture was concentrated under reduced pressure to a light yellow oil and purified on a Teledyne ISCO Combiflash® Rf system using DCM/MeOH (100:0→90:10) as eluent to afford the racemic title compound as 0.245 g of a white solid (78%). MS (ESI): m/z 850.91/852.88 [M+H]$^+$. UPLC: t$_R$=1.52 min (UPLC-SQD: analytical_2 min).

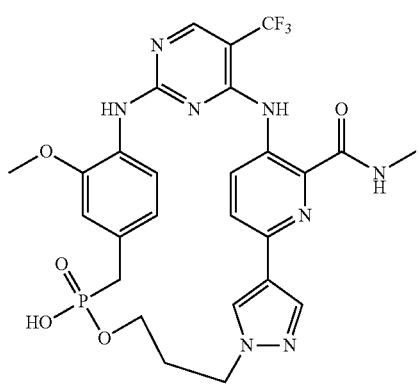

Example 65

10-hydroxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide A solution 10-ethoxy-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide (Example 6, 30.0 mg, 0.0464 mmol) in concentrated HCl (6.0 mL) was stirred at 50° C. for 72 hours. The reaction mixture was concentrated under reduced pressure to a yellow foam. The material was purified on a Teledyne ISCO Combiflash® Rf system using a reverse phase column with Water/MeOH (100:0→0:100) as eluent to afford the title compound as 7.5 mg of a white solid (26%). $^1$H NMR (400 MHz, CD$_3$OD): δ=8.41 (br. s., 1H), 8.31 (s, 1H), 8.27 (br. s., 1H), 7.87 (d, J=6.6 Hz, 1H), 7.59 (d, J=6.6 Hz, 1H), 7.45 (d, J=6.6 Hz, 1H), 6.70 (br. s., 1H), 6.27 (d, J=4.8 Hz, 1H), 4.42 (br. s., 2H), 3.83 (br. s., 3H), 3.52 (br. s., 2H), 2.93 (s, 3H), 2.80 (d, J=17.4 Hz, 2H), 2.16 (br. s., 2H). MS (ESI): m/z 619.17 [M+H]+. UPLC: t$_R$=0.80 min (polar_2 min).

Compound 66B: 5-bromo-2-{[2-chloro-5-(trifluoromethyl)pyrimidin-4-yl]amino}-N-methylbenzamide 2-{[2-chloro-5-(trifluoromethyl)pyrimidin-4-yl]amino}-N-methylbenzamide (WO 2010141406, 4.6 g, 13.9 mmol) and N-bromosuccinimide (2.46 g, 13.9 mmol) were taken up in DMF (8 mL) and stirred for 1 hr. The reaction mixture was poured into water and the resulting precipitate was collected via filtration, air dried and purified by column chromatography (SiO$_2$, 1% methanol in dichloromethane) to give 2.4 g (42%) of the title compound. $^1$H NMR (600 MHz, DMSO-d$_6$) δ: 11.88 (s, 1H), 8.93 (brs, 1H), 8.67 (s, 1H), 8.28 (d, J=9 Hz, 1H), 7.95 (s, 1H), 7.76 (d, J=9 Hz, 1H), 2.75 (d, J=4.2 Hz, 3H).

Compound 66C: 3-[4-(4,4,5,5-tetramethyl-1,3,2-dioxaborolan-2-yl)-1H-pyrazol-1-yl]propyl (4-amino-3-methoxybenzyl)propylphosphinate A solution of 3-[4-(4,4,5,5-tetramethyl-1,3,2-dioxaborolan-2-yl)-1H-pyrazol-1-yl]propyl-(3-methoxy-4-nitrobenzyl)prop-2-en-1-ylphosphinate (Compound 66D, 189.6 mg, 0.38 mmol) in EtOH (5.00 mL, 85.6 mmol) was charged with Palladium 10% wt on activated carbon (40.0 mg, 0.038 mmol). The reaction mixture was evacuated and purged with hydrogen gas (3×). The reaction mixture was allowed to stir under hydrogen at rt for 16 h. The reaction mixture was filtered through a pad of celite. The filtrate was concentrated under reduced pressure to a clear oil, (0.1754 g, 98%). This material was used in successive reactions without further purification. $^1$H NMR (CDCl$_3$, 400 MHz): δ=7.78 (s, 1H), 7.64 (s, 1H), 6.77 (s, 1H), 6.70 (s, 1H), 6.66 (t, J=1.9 Hz, 1H), 4.17 (t, J=7.1 Hz, 2H), 3.87-3.98 (m, 2H), 3.85 (s, 3H), 3.04 (d, J=14.9 Hz, 2H), 2.14 (quin, J=6.3 Hz, 2H), 1.59-1.66 (m, 4H), 1.33 (s, 12H), 1.25 (s, 3H). MS (ESI): m/z 478.26 [M+H]$^+$. UPLC: t$_R$=0.77 min (UPLC-TOF: polar__2 min).

Compound 66D: 3-[4-(4,4,5,5-tetramethyl-1,3,2-dioxaborolan-2-yl)-1H-pyrazol-1-yl]propyl (3-methoxy-4-nitrobenzyl)prop-2-en-1-ylphosphinate A suspension of (3-methoxy-4-nitrobenzyl)prop-2-en-1-ylphosphinic acid (Compound 37E, 241 mg, 0.888 mmol) and 3-[4-(4,4,5,5-tetramethyl-1,3,2-dioxaborolan-2-yl)-1H-pyrazol-1-yl]propan-1-ol (Compound 3E, 224 mg, 0.888 mmol) in 1,2-Dichloroethane (19 mL) and DIPEA (0.928 mL, 5.33 mmol) was charged with (benzotriazol-1-yloxy)tripyrrolidino-phosphonium hexafluorophosphate (1387 mg, 2.665 mmol). The reaction mixture was stirred at rt for 16 hours. The reaction mixture was quenched with water (10 mL) and extracted with DCM (20 mL). The organic layer was washed with NaHCO$_3$ (10 mL), washed with brine (15 mL), dried over anhydrous Na$_2$SO$_4$, filtered, and concentrated under reduced pressure to a yellow oil. The crude material was purified on a Teledyne ISCO Combiflash® Rf system using DCM/MeOH (100:0→95:5) as eluent. The fractions containing product were combined and concentrated under reduced pressure to yield a light yellow oil. The material was re-purified on a Teledyne ISCO Combiflash® Rf system using 1:1 DCM-EtOAc/MeOH (100:0→95:5) as eluent. The fractions containing product were combined and concentrated under reduced pressure to yield a light yellow solid (189.6 mg, 42%). $^1$H NMR (CDCl$_3$, 400 MHz): δ=7.81-7.87 (m, 2H), 7.71 (s, 1H), 7.11 (s, 1H), 6.92 (d, J=7.8 Hz, 1H), 5.73-5.86 (m, 1H), 5.19-5.32 (m, 2H), 4.27 (t, J=6.4 Hz, 2H), 3.90-4.04 (m, 5H), 3.20 (d, J=16.2 Hz, 2H), 2.61 (dd, J=7.6, 17.4 Hz, 2H), 2.15-2.25 (m, 2H), 1.33 (s, 12H). MS (ESI): m/z 506.63 [M+H]$^+$. UPLC: t$_R$=1.23 min (UPLC-SQD: analytical__2 min).

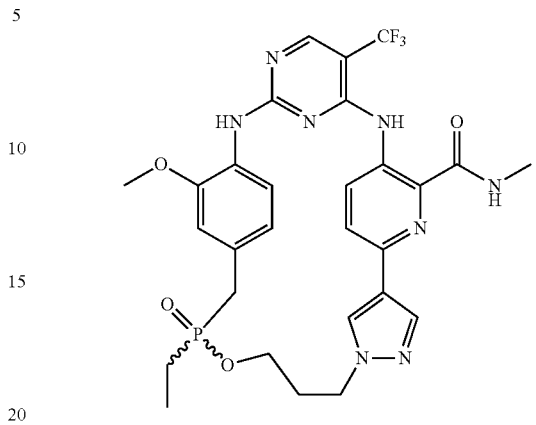

Example 67

(10R)-10-ethyl-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10S)-10-ethyl-14-methoxy-N-methyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide This racemic material was prepared analogously to Example 44 using 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate (Compound 67A, 0.275 g, 0.328 mmol) to afford the title compounds. $^1$H NMR (400 MHz, CD$_3$OD): δ 8.54 (s, 1H), 8.39 (s, 1H), 8.36 (s, 1H), 8.07 (d, J=8.6 Hz, 1H), 7.80 (d, J=8.6 Hz, 1H), 7.65 (d, J=8.3 Hz, 1H), 6.86 (s, 1H), 6.43 (td, J=2.1, 8.3 Hz, 1H), 4.44-4.49 (m, 2H), 3.98-4.07 (m, 1H), 3.87 (s, 3H), 3.48 (dtd, J=4.3, 7.9, 11.7 Hz, 1H), 3.12-3.27 (m, 2H), 2.95 (s, 3H), 2.17-2.32 (m, 2H), 1.66-1.81 (m, 2H), 1.13 (td, J=7.6, 18.6 Hz, 3H). MS (ESI): m/z 631.64 [M+H]$^+$. UPLC: t$_R$=1.18 min (UPLC-SQD: analytical__2 min).

Compound 67A: 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate This material was prepared analogously to Example 44A using (4-{[4-{[6-bromo-2-(methylcarbamoyl)pyridin-3-yl]amino}-5-(trifluoromethyl)pyrimidin-2-yl]amino}-3-methoxybenzyl)ethylphosphinic acid (Compound 67B, 0.220 g, 0.365 mmol) and 3-[4-(4,4,5,5-tetramethyl-1,3,2-dioxaborolan-2-yl)-1H-pyrazol-1-yl]propan-1-ol (Compound 3E, 0.0918 g, 0.364 mmol) to afford the title compound as an off-white foam (275 mg, 90%). MS (ESI): m/z 837.21/839.20 [M+H]$^+$. UPLC: t$_R$=1.14 min (UPLC-TOF: polar__2 min).

Compound 67B: (4-{[4-{[6-bromo-2-(methylcarbamoyl)pyridin-3-yl]amino}-5-(trifluoromethyl)pyrimidin-2-yl]amino}-3-methoxybenzyl)ethylphosphinic acid A solution of ethyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate (Compound 67C, 1.11 g, 1.76 mmol) in pyridine (15.0 mL) was cooled to 0° C. and then charged with bromotrimethylsilane (1.39 mL, 10.6 mmol). The reaction mixture was slowly warmed to rt with stirring for 72 hours. The reaction mixture was quenched with MeOH (2.3 mL, 57 mmol) and then concentrated under reduced pressure to a yellow oil. The material was dissolved in DCM (10 mL) and washed with 3N HCl (10 mL), was washed with brine (10 mL), dried over $Na_2SO_4$, filtered, and concentrated under reduced pressure to a light yellow solid. The acid layer was saturated with solid NaCl and extracted with DCM (10 mL). The organic layer was dried over $Na_2SO_4$, filtered, and concentrated under reduced pressure to a light yellow solid. Both batches of solid were combined (932.5 mg, 88%). $^1$H NMR (CDCl$_3$, 400 MHz): δ=8.91 (d, J=8.3 Hz, 1H), 8.34 (s, 1H), 8.10 (q, J=4.6 Hz, 1H), 7.47 (d, J=8.8 Hz, 1H), 6.89 (s, 1H), 6.82 (d, J=8.1 Hz, 1H), 3.87 (s, 3H), 3.00-3.10 (m, 5H), 1.54-1.68 (m, 2H), 1.13 (td, J=7.5, 18.3 Hz, 3H). MS (ESI): m/z 603.42/605.40 [M+H]$^+$. UPLC: $t_R$=1.24 min (UPLC-SQD: analytical_2 min).

Compound 67C: Ethyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate A mixture of 3-amino-6-bromo-N-methylpyridine-2-carboxamide (Compound 6D, 477.74 mg, 2.0766 mmol) and ethyl (4-{[4-chloro-5-(trifluoromethyl)pyrimidin-2-yl]amino}-3-methoxybenzyl)ethylphosphinate (Compound 67C, 1000.0 mg, 2.2842 mmol) in TFE (8.29 mL) was prepared in a sealable pressure tube equipped with a stir bar and subsequently treated with TFA (319.97 uL, 4.1532 mmol). The tube was sealed and heated to 75° C. overnight. The reaction solution was concentrated directly on to SiO$_2$, loaded into a sample cartridge and purified by column chromatography (Teledyne-ISCO Combiflash, 0-5% MeOH/DCM) to isolate ~800 mg of pure material. The impure fractions were combined, concentrated and re-chromatographed as described to isolate a further 300 mg of desired product for a total of 1.11 g (85%). $^1$H NMR (400 MHz, CD$_3$OD) δ 9.03 (br. s., 1H) 8.38 (s, 1H) 7.72 (d, J=7.6 Hz, 1H) 7.57 (d, J=8.8 Hz, 1H) 7.07 (t, J=1.8 Hz, 1H) 6.93 (dt, J=8.2, 2.2 Hz, 1H) 4.01-4.14 (m, 2H) 3.89 (s, 3H) 2.94 (s, 3H) 1.70-1.84 (m, 2H) 1.31 (t, J=7.1 Hz, 3H) 1.16 (dt, J=18.2, 7.7 Hz, 3H); Benzylic carbon doublet (P coupling) obscured by MeOH. MS (ESI): 631.50, 633.47 [M+H]; UPLC: $t_R$=1.41 (analytical_2 min).

Compound 67D: Ethyl [(4-{[4-chloro-5-(trifluoromethyl)pyrimidin-2-yl]amino}-3-methoxyphenyl)methyl](ethyl) phosphinate A solution of 2,4-dichloro-5-trifluoromethyl-pyrimidine (4.43 g, 20.5 mmol) in dichloroethane and t-butanol (1:1, 10 mL) was treated with ZnCl$_2$ (1M in ether, 20.5 mL) and stirred for half an hour at RT. The reaction mixture was cooled to 0° C. and a solution of ethyl (4-amino-3-methoxyphenyl)methyl-ethyl phosphinate (Compound 67E, 4 g, 13.69 mmol) in dichloroethane and t-butanol (1:1, 10 mL) followed by diisopropylethylamine (3.57 mL, 20.5 mmol) were added drop wise. The mixture was allowed to stir for 24 hrs. A thick residue settled at the bottom of the flask. The solvents were decanted and the residue was purified by column chromatography (SiO$_2$, 1% methanol in dichloromethane) to give 4 g of the pure required isomer. $^1$H NMR (400 MHz, CDCl$_3$) δ 8.55 (s, 1H), 8.32 (d, J=8.4 Hz, 1H), 8.04 (s, 1H), 6.91 (s, 1H), 6.85 (d, J=8 Hz, 1H), 4.04-4.11 (m, 2H), 3.9 (s, 3H), 3.11 (d, J=19.5 Hz, 2H), 1.59-1.66 (m, 2H), 1.25 (t, J=7 Hz, 3H), 1.10 (t, J=7 Hz, 3H).

Compound 67E: Ethyl (4-amino-3-methoxyphenyl)methyl-ethyl phosphinate

A solution of ethyl ethyl [(3-methoxy-4-nitrophenyl)methyl]phosphinate (Compound 67F, 6 g, 20.9 mmol) in ethanol (20 mL) was treated with palladium on carbon (10%, 1 g) and hydrogenated at 45 psi for 24 hrs. The catalyst was filtered off and the filtrate was concentrated to give 5 g of pure amine. $^1$H NMR (400 MHz, CDCl$_3$) δ: 6.72 (s, 1H), 6.6 (s, 2H), 4.05-4.13 (m, 2H), 3.81 (s, 3H), 3.1 (brs, 2H) 3.01 (d, J=16.4 Hz, 2H), 1.55-161(m, 2H), 1.28 (t, 3H), 1.08 (t, 3H).

Compound 67F: Ethyl ethyl [(3-methoxy-4-nitrophenyl) methyl]phosphinate

A mixture of 4-(bromomethyl)-2-methoxy-1-nitrobenzene (Compound 61F, 8 g, 32.5 mmol), diethyl ethyl phosphonite solution in THF (30 mL) (*Synthetic Communications*, 2003, 33, 1665-1674, 9 g, 60.2 mmol) and Toluene (100 mL) were heated to 90° C. for 24 hrs. The solvents were distilled off under reduced pressure and the residue was purified by column chromatography (SiO$_2$, 1% methanol in dichloromethane) to give 6 g of the pure required compound. $^1$H NMR (400 MHz, CDCl$_3$) δ: 7.8 (d, J=8.4 Hz, 1H), 7.06 (s, 1H), 6.85 (d, J=8.5 Hz, 1H), 4.05-4.08 (m, 2H), 3.93 (s, 3H), 3.14 (d, J=16 Hz, 2H), 1.30-1.7 (m, 2H), 1.28 (t, 3H), 1.12 (t, 3H).

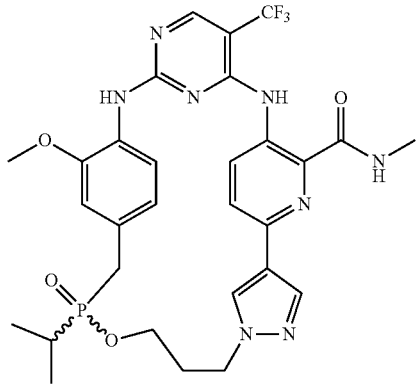

Example 68

(10R)-14-methoxy-N-methyl-10-(propan-2-yl)-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide (10S)-14-methoxy-N-methyl-10-(propan-2-yl)-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide Racemic mixture prepared analogously to Example 67 using 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)propan-2-ylphosphinate (Compound 68A, 0.330 g, 0.388 mmol). $^1$H NMR (CDCl$_3$, 400 MHz): δ 10.97 (br. s., 1H), 8.55 (s, 1H), 8.27-8.38 (m, 2H), 8.17 (s, 1H), 8.14 (d, J=8.6 Hz, 1H), 7.79 (d, J=8.1 Hz, 1H), 7.64 (d, J=8.6 Hz, 1H), 6.62 (s, 1H), 6.36 (d, J=8.6 Hz, 1H), 4.33-4.53 (m, 2H), 4.16 (tt, J=5.2, 10.9 Hz, 1H), 3.87 (s, 3H), 3.50-3.60 (m, 1H), 2.99-3.18 (m, 5H), 2.27 (dd, J=4.5, 9.3 Hz, 2H), 1.99 (tt, J=7.2, 13.8 Hz, 1H), 1.26 (ddd, J=7.2, 17.4, 18.4 Hz, 6H). MS (ESI): m/z 645.75 [M+H]$^+$. UPLC: t$_R$=1.28 min (UPLC-SQD: analytical_2 min).

Compound 68A: 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)propan-2-ylphosphinate A suspension of (4-{[4-{[6-bromo-2-(methylcarbamoyl)pyridin-3-yl]amino}-5-(trifluoromethyl)pyrimidin-2-yl]amino}-3-methoxybenzyl)propan-2-ylphosphinic acid (Compound 68B, 0.240 g, 0.389 mmol) and 3-[4-(4,4,5,5-tetramethyl-1,3,2-dioxaborolan-2-yl)-1H-pyrazol-1-yl]propan-1-ol (Compound 3E, 97.9 g, 0.388 mmol) in 1,2-dichloroethane (8.53 mL) and DIPEA (0.812 mL, 4.66 mmol) was charged with (benzotriazol-1-yloxy)tripyrrolidino-phosphonium hexafluorophosphate (1.21 g, 2.33 mmol). The reaction mixture was stirred at 60° C. for 16 hours. The reaction mixture was quenched with water (10 mL) and extracted with DCM (20 mL). The organic layer was washed with NaHCO$_3$ (10 mL), washed with brine (15 mL), dried over anhydrous Na$_2$SO$_4$, filtered, and concentrated under reduced pressure to a brown oil. The crude material was purified using a Teledyne ISCO Combiflash® Rf system using 1:1 DCM-EtOAc/MeOH (100:0→90:10) as eluent to afford the title compound as an off-white foam. MS (ESI): m/z 851.84/853.82 [M+H]$^+$. UPLC: t$_R$=1.57 min (UPLC-SQD: analytical_2 min).

Compound 68B: (4-{[4-{[6-Bromo-2-(methylcarbamoyl)pyridin-3-yl]amino}-5-(trifluoromethyl)pyrimidin-2-yl]amino}-3-methoxybenzyl)propan-2-ylphosphinic acid Prepared analogously to Compound 67B replacing Compound 67C with ethyl (4-{[4-{[6-bromo-2-(methylcarbamoyl)pyridin-3-yl]amino}-5-(trifluoromethyl)pyrimidin-2-yl]amino}-3-methoxybenzyl)propan-2-ylphosphinate (Compound 68C). MS (ESI): m/z 617.43/619.41 [M+H]$^+$. UPLC: t$_R$=1.30 min (UPLC-SQD: analytical_2 min).

Compound 68C: Ethyl (4-{[4-{[6-bromo-2-(methylcarbamoyl)pyridin-3-yl]amino}-5-(trifluoromethyl)pyrimidin-2-yl]amino}-3-methoxybenzyl)propan-2-ylphosphinate A solution of ethyl (4-{[4-chloro-5-(trifluoromethyl)pyrimidin-2-yl]amino}-3-methoxybenzyl)propan-2-ylphosphinate (Compound 68D, 1.00 g, 2.21 mmol) and 3-amino-6-bromo-N-methylpyridine-2-carboxamide (Compound 6D, 0.516 g, 2.24 mmol) in TFE (11.71 mL) was charged with TFA (0.341 mL, 4.43 mmol). The reaction mixture was heated at 80° C. for 16 hours. The reaction mixture was concentrated under reduced pressure to a light yellow oil. The crude material was purified using a Teledyne ISCO Combiflash® Rf system using DCM/MeOH (100:0→95:5) as eluent to afford the desired product as a white solid (865 mg, 61%). $^1$H NMR (CDCl$_3$, 400 MHz): δ 12.97 (br. s., 1H), 8.85 (d, J=9.3 Hz, 1H), 8.29 (s, 1H), 8.13 (q, J=4.4 Hz, 1H), 7.66 (br. s., 1H), 7.59 (d, J=9.1 Hz, 1H), 7.02 (t, J=1.6 Hz, 1H), 6.88 (td, J=1.8, 8.2 Hz, 1H), 3.92-4.10 (m, 2H), 3.87 (s, 3H), 3.19 (dd, J=2.8, 14.9 Hz, 2H), 3.04 (d, J=5.3 Hz, 3H), 1.87-2.00 (m, 1H), 1.18-1.27 (m, 9H). MS (ESI): m/z 645.55/647.54 [M+H]$^+$. UPLC: t$_R$=1.47 min (UPLC-SQD: analytical_2 min).

Compound 68D: Ethyl (4-{[4-chloro-5-(trifluoromethyl)pyrimidin-2-yl]amino}-3-methoxybenzyl)propan-2-ylphosphinate This material was prepared analogously to Compound 67D replacing Compound 67E with (ethyl (4-amino-3-methoxybenzyl)propan-2-ylphosphinate (Compound 68E, 4 g, 14.7 mmol). The title compound was isolated as a 4 g of a mixture containing 20% of the other regioisomer (ethyl (4-{[2-chloro-5-(trifluoromethyl)pyrimidin-4-yl]amino}-3-methoxybenzyl)propan-2-ylphosphinate after column chromatography purification (SiO$_2$, 1% methanol in dichloromethane). $^1$H NMR (400 MHz, CDCl$_3$) δ 8.60 (s, 1H), 8.3 (d, J=6.8 Hz, 1H), 8.04 (s, 1H), 7.01 (s, 1H), 6.85 (d, J=6.8 Hz, 1H), 4.00-4.08 (m, 2H), 3.89 (s, 3H), 3.14 (m, 2H), 1.9 (m, 1H), 1.05-1.3 (m, 9H).

Compound 68E: Ethyl (4-amino-3-methoxybenzyl)propan-2-ylphosphinate

A solution of ethyl (3-methoxy-4-nitrobenzyl)propan-2-ylphosphinate (Compound 68F, 6 g, 20.9 mmol) in ethanol (20 mL) was treated with palladium on carbon (10%, 1 g) and hydrogenated at 45 psi for 24 hrs. The catalyst was filtered and the filtrate was concentrated to give 5 g of pure amine. $^1$H NMR (400 MHz, CDCl$_3$) δ: 6.77 (s, 1H), 6.59-6.63 (m, 2H), 4.10-4.20 (brs, 2H), 3.81 (s, 3H), 3.65-3.8 (q, 2H),) 2.97-3.02 (m, 2H), 1.80-1.85 (m, 1H), 1.06-1.22 (m, 9H).

Compound 68F: Ethyl (3-methoxy-4-nitrobenzyl)propan-2-ylphosphinate

A mixture of 4-(bromomethyl)-2-methoxy-1-nitrobenzene (Compound 61F, 8 g, 32.5 mmol), diethyl isopropyl phosphonite solution in THF (30 mL) (*Synthetic Communications*, 2003, 33, 1665-1674, 10.1 g, 60.2 mmol) and toluene (100 mL) were heated to 90° C. for 24 hrs. The solvents were distilled off under reduced pressure and the residue was purified by column chromatography (SiO$_2$, 1% methanol in dichloromethane) to give 5 g (51%) of the pure required compound. $^1$H NMR (400 MHz, CDCl$_3$) δ: 7.82 (d, J=8.4 Hz, 1H), 7.14 (s, 1H), 6.91 (d, J=8.5 Hz, 1H), 3.8-4(m, 5H), 3.09-3.18 (m, 2H), 1.86-1.91 (m, 1H), 1.15-1.25 (m, 9H).

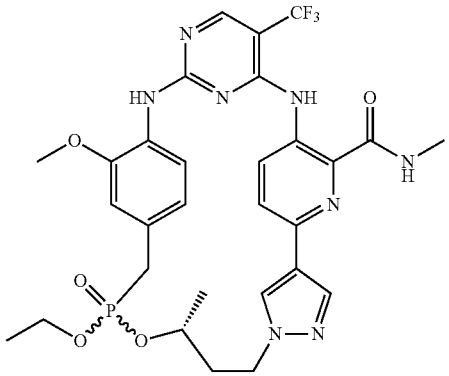

Example 69

(8R,10S)-10-ethoxy-14-methoxy-N,8-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$] hentriaconta-1(25),2(31),3,12,14,17(28),18,20,23,26, 29-undecaene-24-carboxamide 10-oxide and (8R, 10R)-10-ethoxy-14-methoxy-N,8-dimethyl-20-(trifluoromethyl)-9-oxa-4,5,16,18,22,25,28-heptaaza-10-phosphapentacyclo[21.2.2. 2$^{12,15}$.1$^{2,5}$.1$^{17,21}$]hentriaconta-1(25),2(31),3,12,14,17 (28),18,20,23,26,29-undecaene-24-carboxamide 10-oxide Racemic mixture prepared analogously to Example 44 using ethyl (2R)-4-[4-(4,4,5,5-tetramethyl-1,3,2-dioxaborolan-2-yl)-1H-pyrazol-1-yl]butan-2-yl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 69A, 442 mg, 0.510 mmol) to afford 45 mg of the title compound (13%). The diastereomers were separated by SFC on a chiral stationary phase as described in Table 1. Example 69A: $^1$H NMR (400 MHz, CD$_3$OD) δ 8.69 (s, 1H), 8.46 (s, 1H), 8.30 (s, 1H), 8.05 (d, J=8.6 Hz, 1H), 7.79 (d, J=8.6 Hz, 1H), 7.29 (d, J=8.1 Hz, 1H), 6.96 (s, 1H), 6.72 (d, J=8.1 Hz, 1H), 4.43-4.53 (m, 1H), 4.26-4.36 (m, 1H), 4.09-4.19 (m, 1H), 3.82 (s, 3H), 3.68-3.77 (m, 1H), 3.42-3.51 (m, 1H), 3.19-3.28 (m, 2H), 2.88 (s, 3H), 2.27-2.44 (m, 2H), 1.38 (d, J=6.3 Hz, 3H), 0.84 (t, J=7.1 Hz, 3H). MS (ESI): m/z=661.53 [M+H]$^+$. UPLC: t$_R$=1.22 min (UPLC-TOF: polar_2 min). Example 69B: $^1$H NMR (400 MHz, CD$_3$OD) δ 8.52 (s, 1H), 8.26-8.33 (m, 2H), 7.93 (d, J=8.6 Hz, 1H), 7.61 (d, J=8.6 Hz, 1H), 7.34 (d, J=8.3 Hz, 1H), 6.84 (s, 1H), 6.60 (d, J=7.8 Hz, 1H), 4.43-4.54 (m, 1H), 4.24-4.38 (m, 2H), 3.84-3.98 (m, 2H), 3.71-3.78 (m, 3H), 3.08-3.26 (m, 2H), 2.93 (s, 3H), 2.29 (d, J=5.3 Hz, 2H), 1.36 (d, J=6.3 Hz, 3H), 1.12 (t, J=7.1 Hz, 3H). MS (ESI): m/z=661.51 [M+H]$^+$. UPLC: t$_R$=1.19 min (UPLC-TOF: polar_2 min).

Compound 69A: ethyl (2R)-4-[4-(4,4,5,5-tetramethyl-1,3,2-dioxaborolan-2-yl)-1H-pyrazol-1-yl] butan-2-yl (4-{[4-{[6-bromo-2-(methylcarbamoyl) pyridin-3-yl]amino}-5-(trifluoromethyl)pyrimidin-2-yl]amino}-3-methoxybenzyl)phosphonate 1-Methylimidazole (1.91 mL, 24 mmol) was added to a stirring suspension of ethyl hydrogen (4-{[4-{[6-bromo-2-(methylcarbamoyl)pyridin-3-yl]amino}-5-(trifluoromethyl) pyrimidin-2-yl]amino}-3-methoxybenzyl)phosphonate (Compound 38C, 1 g, 2 mmol), (2R)-4-[4-(4,4,5,5-tetramethyl-1,3,2-dioxaborolan-2-yl)-1H-pyrazol-1-yl]butan-2-ol (Compound 69B, 430 mg, 1.6 mmol) and (benzotriazol-1-yloxy)tripyrrolidino-phosphonium hexafluorophosphate (5.04 g, 9.69 mmol) in 1,2-dichloroethane (49.5 mL). The reaction was allowed to stir at 60° C. for 24 hrs, after which, it was concentrated in vacuo to a solid and purified using a Teledyne ISCO Combiflash® RF system [0-5% MeOH in 1:1 EtOAc/DCM] to afford 442 mg of the desired product as mixture of diastereomers (32%). MS (ESI): m/z=867.78/ 869.81 [M+H]$^+$. UPLC: t$_R$=1.69 min (UPLC-TOF: polar_2 min)

Compound 69B: (2R)-4-[4-(4,4,5,5-tetramethyl-1,3, 2-dioxaborolan-2-yl)-1H-pyrazol-1-yl]butan-2-ol A solution of (R)-1-(3-[(tert-butyldimethylsilyl)oxy]butyl]-4-(tetramethyl-1,3,2-dioxaborolan-2-yl)-1H-pyrazole (Compound 69C, 5 g, 13.1 mmol) in THF (20 mL) was treated with tetrabutylammonium fluoride (26 mL, 1M in THF) and stirred for 24 hrs at RT under nitrogen atmosphere. Tetrahydrofuran was evaporated under reduced pressure and the residue was purified by column chromatography (SiO$_2$, 1% methanol in dichloromethane) to give colorless gum (600 mg, 17%). $^1$H NMR (400 MHz, CDCl$_3$) δ 7.74 (s, 1H), 7.64 (s, 1H), 4.15-4.23 (m, 2H), 3.60-3.3.71 (m, 1H), 1.7-1.98 (m, 2H), 1.23 (s, 12H), 1.12 (s, d, 3H).

Compound 69C: 1-[(3R)-3-{[tert-butyl(dimethyl) silyl]oxy}butyl]-4-(4,4,5,5-tetramethyl-1,3,2-dioxaborolan-2-yl)-1H-pyrazole A stirring suspension of (R)-3-(tert-butyldimethylsilyloxy) butyl 4-methylbenzenesulfonate (*J. Org. Chem.* 2009, 74, 2842-2845, 5 g, 13.9 mmol) and cesium carbonate (5 g, 15.2 mmol) in DMF (5 mL) was treated with 4-(tetramethyl-1,3,2-dioxaborolan-2-yl)-1H-pyrazole (2.7 g, 13.9 mmol) and heated at 70° C. overnight. The reaction mixture was cooled to RT and diluted with water (25 mL). The oily layer was separated and the aqueous layer was extracted with hexanes (2×50 mL). The combined organic layers were washed with water and dried over sodium sulfate, filtered, concentrated to give the desired product as light yellow gum. Yield: 5.2 g (quantitative). $^1$H NMR (500 MHz, CDCl$_3$) δ 7.79 (s, 1H), 7.69 (s, 1H), 4.24-4.15 (m, 2H), 3.87-3.85 (m, 1H), 2.05-1.94 (m, 2H), 1.28 (s, 12H), 1.14 (d, J=8 Hz, 3H), 0.86 (s, 9H) 0.01 (s, 6H).

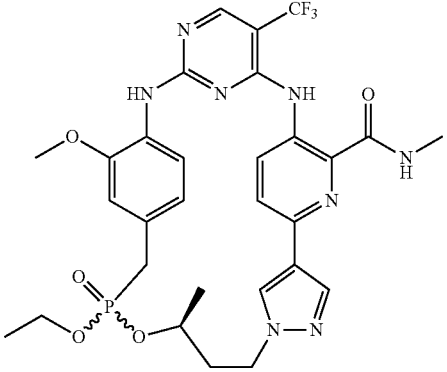

Example 70

(8S,10S)-10-ethoxy-14-methoxy-N,8-dimethyl-20-(trifluoromethyl)-9-oxa-4,5,16,18,22,25,28-heptaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (8S,10R)-10-ethoxy-14-methoxy-N,8-dimethyl-20-(trifluoromethyl)-9-oxa-4,5,16,18,22,25,28-heptaaza-10-phosphapentacyclo[21.2.2.2$^{12,15}$1$^{2,5}$.1$^{17,21}$]hentriaconta-1(25),2(31),3,12,14,17(28),18,20,23,26,29-undecaene-24-carboxamide 10-oxide Racemic mixture prepared analogously to Example 44 using ethyl (2S)-4-[4-(4,4,5,5-tetramethyl-1,3,2-dioxaborolan-2-yl)-1H-pyrazol-1-yl]butan-2-yl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 70A, 453 mg, 0.523 mmol) to afford 72.7 mg of the title compound (21%). The diastereomers were separated by SFC on a chiral stationary phase as described in Table 1. Example 70A: $^1$H NMR (400 MHz, CD$_3$OD) δ 8.57 (s, 1H), 8.32 (d, J=3.5 Hz, 2H), 8.18 (d, J=8.8 Hz, 1H), 7.74 (d, J=8.6 Hz, 1H), 7.45 (d, J=8.1 Hz, 1H), 6.92 (s, 1H), 6.75 (d, J=8.3 Hz, 1H), 4.41-4.52 (m, J=4.8 Hz, 1H), 4.25-4.36 (m, J=19.7 Hz, 1H), 4.03-4.17 (m, 1H), 3.82 (s, 3H), 3.57-3.69 (m, 1H), 3.33-3.39 (m, 2H), 3.25 (d, J=7.8 Hz, 1H), 2.93 (s, 3H), 2.23-2.41 (m, 2H), 1.34 (d, J=6.1 Hz, 3H), 0.73 (t, J=6.9 Hz, 3H). MS (ESI): m/z=661.55 [M+H]$^+$. UPLC: t$_R$=1.22 min (UPLC-TOF: polar_2 min). Example 70B: $^1$H NMR (400 MHz, CD$_3$OD) δ 8.51 (s, 1H), 8.30 (d, J=7.8 Hz, 2H), 7.93 (d, J=8.6 Hz, 1H), 7.61 (d, J=8.6 Hz, 1H), 7.34 (d, J=8.3 Hz, 1H), 6.84 (s, 1H), 6.60 (d, J=8.3 Hz, 1H), 4.43-4.55 (m, 1H), 4.24-4.37 (m, 2H), 3.83-3.98 (m, 2H), 3.75 (s, 3H), 3.04-3.27 (m, 2H), 2.93 (s, 3H), 2.29 (d, J=5.1 Hz, 2H), 1.36 (d, J=6.3 Hz, 3H), 1.12 (t, J=7.1 Hz, 3H). MS (ESI): m/z=661.50 [M+H]$^+$. UPLC: t$_R$=1.19 min (UPLC-TOF: polar_2 min).

Compound 70A: Ethyl (2S)-4-[4-(4,4,5,5-tetramethyl-1,3,2-dioxaborolan-2-yl)-1H-pyrazol-1-yl]butan-2-yl (4-{[4-{[6-bromo-2-(methylcarbamoyl)pyridin-3-yl]amino}-5-(trifluoromethyl)pyrimidin-2-yl]amino}-3-methoxybenzyl)phosphonate Racemic Compound 70A was prepared analogously to Compound 69A using ethyl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 38C, 1 g, 2 mmol) and (2S)-4-[4-(4,4,5,5-tetramethyl-1,3,2-dioxaborolan-2-yl)-1H-pyrazol-1-yl]butan-2-ol (Compound 70B, 400 mg, 2 mmol) to afford 454 mg of the title compound as a mixture of diastereomers (30%). MS (ESI): m/z=867.82/869.81 [M+H]$^+$. UPLC: t$_R$=1.69 min (UPLC-TOF: polar_2 min).

Compound 70B: (2S)-4-[4-(4,4,5,5-tetramethyl-1,3,2-dioxaborolan-2-yl)-1H-pyrazol-1-yl]butan-2-ol A solution of (S)-1-(3-[(tert-butyldimethylsilyl)oxy]butyl]-4-(tetramethyl-1,3,2-dioxaborolan-2-yl)-1H-pyrazole (Compound 70C, 7.7 g, 20.2 mmol) in THF (30 mL) was treated with tetrabutylammonium fluoride (30 mL, 1M solution in THF) and stirred for 24 hrs at RT under nitrogen atmosphere. Tetrahydrofuran was evaporated under reduced pressure and the residue was purified by column chromatography (SiO$_2$, 1% methanol in dichloromethane) to give colorless gum (1 g, 20%). $^1$H NMR (400 MHz, CDCl$_3$) δ 7.74 (s, 1H), 7.64 (s, 1H), 4.15-4.23 (m, 2H), 3.60-3.3.71 (m, 1H), 1.7-1.98 (m, 2H), 1.23 (s, 12H), 1.12 (s, d, 3H).

Compound 70C 1-[(3S)-3-{[tert-butyl(dimethyl)silyl]oxy}butyl]-4-(4,4,5,5-tetramethyl-1,3,2-dioxaborolan-2-yl)-1H-pyrazole A stirred suspension of (S)-3-(tert-butyldimethylsilyloxy)butyl 4-methylbenzenesulfonate (Prepared using the procedure found in J. Org. Chem. 2009, 74, 2842-2845, 7.5 g, 20.8 mmol) and cesium carbonate (7.5 g, 22.8 mmol) in DMF (7.5 mL) was treated with 4-(tetramethyl-1,3,2-dioxaborolan-2-yl)-1H-pyrazole (4 g, 20.8 mmol) and heated at 70° C. overnight. The reaction mixture was cooled to RT and diluted water (25 mL). The oily layer was separated and the aqueous layer was extracted with hexanes (2×50 mL). The combined organic layers were washed with water, dried over sodium sulfate, filtered and concentrated to give the desired product as light yellow gum. Yield: 7.7 g (quantitative). $^1$H NMR (500 MHz, CDCl$_3$) δ 7.79 (s, 1H), 7.69 (s, 1H), 4.24-4.15 (m, 2H), 3.87-3.85 (m, 1H), 2.05-1.94 (m, 2H), 1.28 (s, 12H), 1.14 (d, J=8 Hz, 3H), 0.86 (s, 9H) 0.01 (s, 6H).

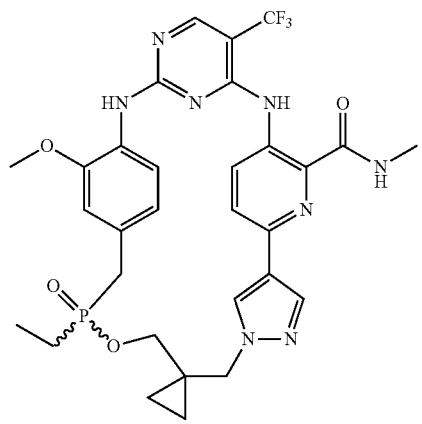

Example 71

(10'R)-10'-Ethyl-1,4'-methoxy-N-methyl-20'-(trifluoromethyl)-9'-oxa-4',5',16',18',22',25',28'-heptaaza-10'-phosphaspiro[cyclopropane-1,7'-pentacyclo[21.2.2.2$^{12',15'}$.1$^{2',5'}$.1$^{17',21'}$]hentriacontane]-1'(25'),2'(31'),3',12',14',17'(28'),18',20',23',26',29'-undecaene-24'-carboxamide 10'-oxide and (10'S)-10'-ethyl-1,4'-methoxy-N-methyl-20'-(trifluoromethyl)-9'-oxa-4',5',16',18',22',25',28'-heptaaza-10'-phosphaspiro[cyclopropane-1,7'-pentacyclo[21.2.2.2$^{12',15'}$.1$^{2',5'}$.1$^{17',21'}$]hentriacontane]-1'(25'),2'(31'),3',12',14',17'(28'),18',20',23',26',29'-undecaene-24'-carboxamide 10'-oxide Racemic mixture prepared analogously to Example 44 using ethyl (1-{[4-(4,4,5,5-tetramethyl-1,3,2-dioxaborolan-2-yl)-1H-pyrazol-1-yl]methyl}cyclopropyl)methyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate (Compound 71A, 129 mg, 0.150 mmol) to afford 23.7 mg of the title compound (24%). $^1$H NMR (400 MHz, CD$_3$OD) δ 8.58 (s, 1H), 8.34-8.40 (m, 2H), 8.11 (d, J=8.6 Hz, 1H), 7.82 (d, J=8.6 Hz, 1H), 7.68 (d, J=8.3 Hz, 1H), 6.86 (s, 1H), 6.49 (d, J=8.3 Hz, 1H), 4.40 (d, J=14.1 Hz, 1H), 4.14 (d, J=14.4 Hz, 1H), 3.87 (s, 3H), 3.56-3.63 (m, 2H), 3.10-3.26 (m, 2H), 2.96 (s, 3H), 1.61-1.73 (m, 2H), 1.10 (td, J=7.7, 18.5 Hz, 3H), 0.69-0.99 (m, 4H). MS (ESI): m/z=657.65 [M+H]⁺. UPLC: $t_R$=1.23 min (UPLC-TOF: polar_2 min).

Compound 71A: (1-{[4-(4,4,5,5-tetramethyl-1,3,2-dioxaborolan-2-yl)-1H-pyrazol-1-yl]methyl}cyclopropyl)methyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate Racemic Compound 71A was prepared analogously to Compound 69A using (4-{[4-{[6-bromo-2-(methylcarbamoyl)pyridin-3-yl]amino}-5-(trifluoromethyl)pyrimidin-2-yl]amino}-3-methoxybenzyl)ethylphosphinic acid (Compound 67B, 206 mg, 0.341 mmol) and (1-{[4-(4,4,5,5-tetramethyl-1,3,2-dioxaborolan-2-yl)-1H-pyrazol-1-yl]methyl}cyclopropyl)methanol (Compound 63B, 400 mg, 2 mmol) to afford 129 mg of the title compound (48%). MS (ESI): m/z=879.92/881.81 [M+H]⁺. UPLC: $t_R$=1.61 min (UPLC-TOF: polar_2 min).

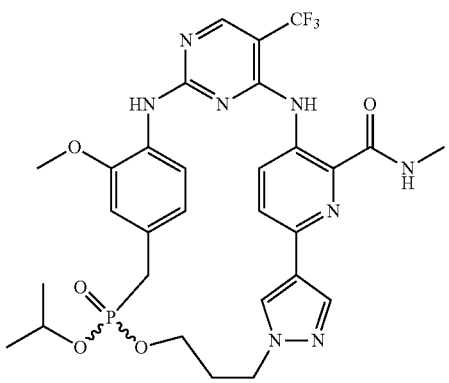

Example 72

(10R)-14-methoxy-N-methyl-10-(propan-2-yloxy)-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide and (10S)-14-methoxy-N-methyl-10-(propan-2-yloxy)-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide Racemic mixture prepared analogously to Example 44 using propan-2-yl 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 72A). ¹H NMR (400 MHz, CD₃OD): δ 8.48 (s, 1H), 8.38 (s, 1H), 8.34 (s, 1H), 8.12 (d, J=8.6 Hz, 1H), 7.78 (d, J=8.6 Hz, 1H), 7.58 (d, J=8.3 Hz, 1H), 6.88 (t, J=1.8 Hz, 1H), 6.60 (td, J=2.1, 8.3 Hz, 1H), 4.51-4.59 (m, 1H), 4.41-4.50 (m, 2H), 3.86 (s, 3H), 3.65-3.76 (m, 2H), 3.33-3.39 (m, 1H), 3.20-3.29 (m, 1H), 2.95 (s, 3H), 2.27 (quin, J=5.8 Hz, 2H), 1.20 (d, J=6.3 Hz, 3H), 0.92 (d, J=6.3 Hz, 3H). MS (ESI): m/z 661.73 [M+H]⁺. UPLC: $t_R$=1.30 min (UPLC-SQD: analytical_2 min).

Compound 72A: Propan-2-yl 3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)phosphonate Prepared analogously to Compound 44A replacing Compound 38C with propan-2-yl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 72B). MS (ESI): m/z 867.90/869.91 [M+H]⁺. UPLC: $t_R$=1.60 min (UPLC-SQD: analytical_2 min).

Compound 72B: Propan-2-yl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate A solution of ethyl propan-2-yl (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 72C, 550.0 mg, 0.83 mmol) in pyridine (5.50 mL) was charged with sodium iodide (748 mg, 4.99 mmol). The reaction was heated at 120° C. for 24 hours.

The reaction mixture was concentrated under reduced pressure to a black solid. The solid residue was dissolved in water (15 mL), then acidified with conc. HCl (pH ~1-2) and extracted with DCM (20 mL). The organic layer was washed with water (15 mL), washed with brine (15 mL), dried over anhydrous Na₂SO₄, filtered and concentrated under reduced pressure to a white solid (0.47 g, 90%). The material was used in successive reactions without any further purification. MS (ESI): m/z 633.50/635.54 [M+H]⁺. UPLC: $t_R$=0.57 min (analytical_1 min).

Compound 72C: Ethyl propan-2-yl (4-{[4-{[6-bromo-2-(methylcarbamoyl)pyridin-3-yl]amino}-5-(trifluoromethyl)pyrimidin-2-yl]amino}-3-methoxybenzyl)phosphonate Prepared analogously to Compound 1B replacing Compound 1C with ethyl propan-2-yl (4-{[4-chloro-5-(trifluoromethyl)pyrimidin-2-yl]amino}-3-methoxybenzyl)phosphonate (Compound 72D). MS (ESI): m/z 661.11/663.09 [M+H]⁺. UPLC: $t_R$=1.14 min (UPLC-TOF: polar_2 min).

Compound 72D: Ethyl propan-2-yl (4-{[4-chloro-5-(trifluoromethyl)pyrimidin-2-yl]amino}-3-methoxybenzyl)phosphonate A solution of 2,4-dichloro-5-trifluoromethyl-pyrimidine (7.5 g, 34.7 mmol) in dichloroethane and t-butanol (1:1, 10 mL) was treated with ZnCl₂ (1M solution in ether, 35 mL) and stirred for half an hour at RT. The reaction mixture was cooled to 0° C. and a solution of ethyl propan-2-yl [(4-amino-3-methoxyphenyl)methyl]phosphonate (Compound 72E, 5 g, 16.28 mmol) in dichloroethane and t-butanol (1:1, 10 mL) followed by diisopropylethylamine (6 mL, 34.7 mmol) were added drop wise while stirring was continued for 24 hrs. The resulting white precipitate was filtered. The solid was dissolved in dichloromethane, washed with water (2×50 mL), dried over magnesium sulfate, filtered and evaporated to give 6.3 g of pure required isomer. ¹H NMR (400 MHz, CDCl₃) δ

8.6 (s, 1H), 8.32 (d, J=8.4 Hz, 1H), 8.04 (s, 1H), 7.04 (s, 1H), 6.89 (d, J=8 Hz, 1H), 4.73-4.76 (m, 1H), 4.08-4.11 (m, 2H), 3.95 (s, 3H), 3.23 (d, J=21 Hz, 2H), 1.24-1.33 (9H).

Compound 72E: Ethyl propan-2-yl (4-amino-3-methoxybenzyl)phosphonate

A solution of ethyl propan-2-yl [(3-methoxy-4-nitrophenyl) methyl]phosphonate (6 g, 20.9 mmol) in ethanol (20 mL) was treated with palladium on carbon (10%, 1 g) and hydrogenated at 45 psi for 24 hrs. The catalyst was filtered and the filtrate was concentrated to give 5 g of pure amine. $^1$H NMR (600 MHz, CDCl$_3$) δ 6.79 (s, 1H), 6.69-6.71 (m, 2H), 4.60-4.61 (m, 1H), 3.95-3.98 (m, 2H), 3.84 (s, 3H), 3.1 (brs, 2H) 3.01 (d, J=16.4 Hz, 2H), 1.18-1.28 (m, 9H).

Compound 72F: Ethyl propan-2-yl (3-methoxy-4-nitrobenzyl)phosphonate

A solution of diethyl (3-methoxy-4-nitrobenzyl)phosphonate (Compound 1G, 5 g, 15.5 mmol) in thionyl chloride (50 mL, 690 mmol) was treated with catalytic amount of DMF and heated to reflux under nitrogen for 6 h. The mixture was concentrated under reduced pressure and co-evaporated with dichloroethane (50 mL) to give crude (ethyl chloro[(3-methoxy-4-nitrophenyl) methyl]phosphinate). This material was taken up in DCM (20 mL) and added to a solution of 2-propanol (4 mL, 52 mmol) and DIPEA (6 mL, 34.5 mmol) in DCM (20 mL). The resulting mixture was stirred at rt for 24 hrs. The solvents were evaporated and the residue was purified by column chromatography (SiO$_2$, 5% methanol in dichloromethane) to give 3 g of the desired product as a light-yellow oil. $^1$H NMR (400 MHz, CDCl$_3$) δ 7.8 2(d, J=8.4 Hz, 1H), 7.1 (s, 1H), 6.92 (d, J=8.5 Hz, 1H), 4.6-4.4.75 (m, 1H), 4.05-4.08 (m, 2H), 3.93 (s, 3H), 3.18 (d, J=20 Hz, 2H), 1.18-1.25 (m, 9H).

aborolan-2-yl)-1H-pyrazol-1-yl]propylpropan-2-yl (4-{[4-{[6-bromo-2-(methylcarbamoyl)pyridin-3-yl]amino}-5-(trifluoromethyl)pyrimidin-2-yl]amino}-3-methoxybenzyl) phosphonate (Compound 73A, 149 mg, 0.167 mmol) to afford 22.4 mg of the title compound (20%). $^1$H NMR (400 MHz, CD$_3$OD) δ 8.58 (s, 1H), 8.34-8.40 (m, 2H), 8.11 (d, J=8.6 Hz, 1H), 7.82 (d, J=8.6 Hz, 1H), 7.68 (d, J=8.3 Hz, 1H), 6.86 (s, 1H), 6.49 (d, J=8.3 Hz, 1H), 4.40 (d, J=14.1 Hz, 1H), 4.14 (d, J=14.4 Hz, 1H), 3.87 (s, 3H), 3.56-3.63 (m, 2H), 3.10-3.26 (m, 2H), 2.96 (s, 3H), 1.61-1.73 (m, 2H), 1.10 (td, J=7.7, 18.5 Hz, 3H), 0.69-0.99 (m, 4H). MS (ESI): m/z=689.71 [M+H]$^+$. UPLC: t$_R$=1.38 min (UPLC-TOF: polar_2 min).

Compound 73A: 2,2-dimethyl-3-[4-(4,4,5,5-tetramethyl-1,3,2-dioxaborolan-2-yl)-1H-pyrazol-1-yl] propyl propan-2-yl (4-{[4-{[6-bromo-2-(methylcarbamoyl)pyridin-3-yl]amino}-5-(trifluoromethyl) pyrimidin-2-yl]amino}-3-methoxybenzyl) phosphonate Racemic Compound 73A was prepared analogously to Compound 69A by using propan-2-yl hydrogen (4-{[4-{[6-bromo-2-(methylcarbamoyl)pyridin-3-yl]amino}-5-(trifluoromethyl)pyrimidin-2-yl]amino}-3-methoxybenzyl)phosphonate (Compound 72B, 265 mg, 0.418 mmol) and 2,2-dimethyl-3-[4-(4,4,5,5-tetramethyl-1,3,2-dioxaborolan-2-yl)-1H-pyrazol-1-yl]propan-1-ol (Compound 47B, 117 mg, 0.418 mmol) to afford 149 mg of the title compound (40%). MS (ESI): m/z=895.81/897.83 [M+H]$^+$. UPLC: t$_R$=1.77 min (UPLC-TOF: polar_2 min).

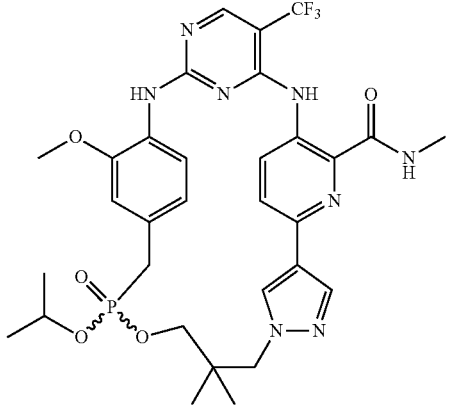

Example 73

(10R)-14-methoxy-N,7,7-trimethyl-10-(propan-2-yloxy)-20-(trifluoromethyl)-9-oxa-4,5,16,18,22,25, 28-heptaaza-10-phosphapentacyclo[21.2.2. 2$^{12,15}$.1$^{2,5}$.1$^{17,21}$]hentriaconta-1(25),2(31),3,12,14,17 (28),18,20,23,26,29-undecaene-24-carboxamide 10-oxide and (10S)-14-methoxy-N,7,7-trimethyl-10- (propan-2-yloxy)-20-(trifluoromethyl)-9-oxa-4,5,16, 18,22,25,28-heptaaza-10-phosphapentacyclo [21.2.2.2$^{12,15}$.1$^{2,5}$.1$^{17,21}$]hentriaconta-1(25),2(31),3, 12,14,17(28),18,20,23,26,29-undecaene-24-carboxamide 10-oxide Racemic mixture prepared analogously to Example 44 using 2,2-dimethyl-3-[4-(4,4,5,5-tetramethyl-1,3,2-diox-

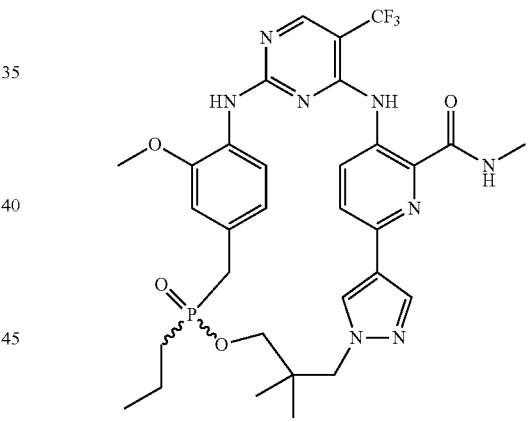

Example 74

(10R)-14-Methoxy-N,7,7-trimethyl-10-propyl-20- (trifluoromethyl)-9-oxa-4,5,16,18,22,25,28-heptaaza-10-phosphapentacyclo[21.2.2.2$^{12,15}$.1$^{2,5}$.1$^{17,21}$] hentriaconta-1(25),2(31),3,12,14,17(28),18,20,23,26, 29-undecaene-24-carboxamide 10-oxide and (10S)- 14-methoxy-N,7,7-trimethyl-10-propyl-20- (trifluoromethyl)-9-oxa-4,5,16,18,22,25,28- heptaaza-10-phosphapentacyclo[21.2.2. 2$^{12,15}$.1$^{2,5}$.1$^{17,21}$]hentriaconta-1(25),2(31),3,12,14,17 (28),18,20,23,26,29-undecaene-24-carboxamide 10-oxide Racemic mixture prepared analogously to Example 44 using 2,2-dimethyl-3-[4-(4,4,5,5-tetramethyl-1,3,2-dioxaborolan-2-yl)-1H-pyrazol-1-yl]propyl (4-{[4-{[6-bromo-2-

(methylcarbamoyl)pyridin-3-yl]amino}-5-(trifluoromethyl)pyrimidin-2-yl]amino}-3-methoxybenzyl)propylphosphinate (Compound 6A, 0.318 g, 0.362 mmol). ¹H NMR (400 MHz, CD₃OD): δ 8.39 (s, 1H), 8.37 (s, 1H), 8.31 (s, 1H), 8.14 (d, J=8.8 Hz, 1H), 7.75 (d, J=8.6 Hz, 1H), 7.69 (d, J=8.3 Hz, 1H), 6.90 (s, 1H), 6.41 (td, J=2.0, 8.3 Hz, 1H), 4.21-4.29 (m, 1H), 4.09-4.16 (m, 1H), 3.90 (s, 3H), 3.81 (t, J=10.6 Hz, 1H), 3.35-3.46 (m, 2H), 3.15-3.25 (m, 1H), 2.96 (s, 3H), 1.58-1.79 (m, 4H), 1.14 (s, 3H), 1.11 (s, 3H), 0.97-1.03 (m, 3H). MS (ESI): m/z 673.76 [M+H]⁺. UPLC: $t_R$=1.44 min (UPLC-SQD: analytical_2 min).

Compound 74A: 2,2-Dimethyl-3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate A suspension of (4-{[4-{[6-bromo-2-(methylcarbamoyl)pyridin-3-yl]amino}-5-(trifluoromethyl)pyrimidin-2-yl]amino}-3-methoxybenzyl)propylphosphinic acid (Compound 74B, 0.500 g, 0.810 mmol) and 2,2-dimethyl-3-[4-(4,4,5,5-tetramethyl-1,3,2-dioxaborolan-2-yl)-1H-pyrazol-1-yl]propan-1-ol (Compound 47B, 227 mg, 0.809 mmol) in 1,2-dichloroethane (24.4 mL) and 1-methylimidazole (0.967 mL, 12.1 mmol) was charged with (benzotriazol-1-yloxy)tripyrrolidino-phosphonium hexafluorophosphate (2530 mg, 4.85 mmol). After stirring at 60° C. for 16 hours, the reaction mixture was quenched with water (10 mL) and extracted with DCM (20 mL). The organic layer was washed with NaHCO₃ (10 mL), washed with brine (15 mL), dried over anhydrous Na₂SO₄, filtered, and concentrated under reduced pressure to a brown oil. The crude material was purified using a Teledyne ISCO Combiflash® Rf system using 1:1 DCM-EtOAc/MeOH (100:0→95:5) as eluent. The fractions containing product were combined and concentrated under reduced pressure to yield an off-white foam (318.1 mg, 45%). MS (ESI): m/z 879.93/881.94 [M+H]⁺. UPLC: $t_R$=1.67 min (UPLC-TOF: polar_2 min).

Compound 74B: (4-{[4-{[6-bromo-2-(methylcarbamoyl)pyridin-3-yl]amino}-5-(trifluoromethyl)pyrimidin-2-yl]amino}-3-methoxybenzyl)propylphosphinic acid Prepared analogously to Compound 67B replacing Compound 67C with ethyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate (Compound 74C). MS (ESI): m/z 617.55/619.52 [M+H]⁺. UPLC: $t_R$=1.31 min (UPLC-SQD: analytical_2 min).

Compound 74C: Ethyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate Prepared analogously to Compound 1B replacing Compound 1C with compound 6D and Compound 1E with ethyl (4-{[4-chloro-5-(trifluoromethyl)pyrimidin-2-yl]amino}-3-methoxybenzyl)propylphosphinate (Compound 37C). ¹H NMR (CDCl₃, 400 MHz): δ 12.25 (s, 1H), 9.05 (d, J=8.8 Hz, 1H), 8.43 (s, 1H), 8.10 (d, J=4.8 Hz, 2H), 7.69 (br. s., 1H), 7.51 (d, J=8.8 Hz, 1H), 6.94 (t, J=1.8 Hz, 1H), 6.82 (td, J=1.8, 8.2 Hz, 1H), 3.98-4.13 (m, 2H), 3.92 (s, 2H), 3.13 (d, J=16.4 Hz, 2H), 3.05 (d, J=5.3 Hz, 3H), 1.62-1.68 (m, 4H), 1.31 (t, J=7.1 Hz, 3H), 0.98-1.04 (m, 3H). MS (ESI): m/z 645.62/647.56 [M+H]⁺. UPLC: $t_R$=1.47 min (UPLC-SQD: analytical_2 min).

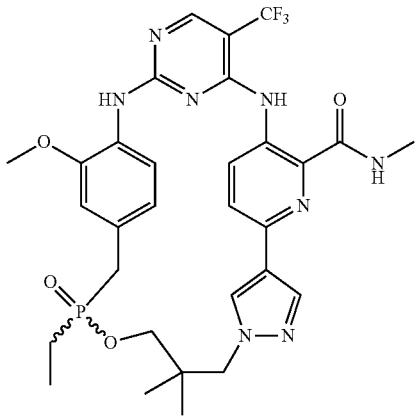

Example 75

(10R)-10-ethyl-14-methoxy-N,7,7-trimethyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide and (10S)-10-ethyl-14-methoxy-N,7,7-trimethyl-20-(trifluoromethyl)-9-oxa-4,5,16,18,22,25,28-heptaaza-10-phosphapentacyclo[21.2.2.2¹²,¹⁵.1²,⁵.1¹⁷,²¹]hentriaconta-1(25),2(31),3,12,14,17(28),18,20,23,26,29-undecaene-24-carboxamide 10-oxide Racemic mixture prepared analogously to Example 44 using 2,2-dimethyl-3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate (Compound 75A, 0.4699 g, 0.5429 mmol). ¹H NMR (400 MHz, CD₃OD): δ 8.39 (s, 1H), 8.37 (s, 1H), 8.31 (s, 1H), 8.13 (d, J=8.6 Hz, 1H), 7.75 (d, J=8.6 Hz, 1H), 7.70 (d, J=8.3 Hz, 1H), 6.90 (s, 1H), 6.41 (td, J=2.0, 8.3 Hz, 1H), 4.23-4.30 (m, 1H), 4.09-4.15 (m, 1H), 3.90 (s, 3H), 3.81 (t, J=10.5 Hz, 1H), 3.35-3.47 (m, 2H), 3.16-3.27 (m, 1H), 2.96 (s, 3H), 1.71-1.87 (m, 2H), 1.13-1.23 (m, 6H), 1.11 (s, 3H). MS (ESI): m/z 659.74 [M+H]⁺. UPLC: $t_R$=1.39 min (UPLC-SQD: analytical_2 min).

Compound 75A: 2,2-dimethyl-3-[4-(4,4,5,5-tetramethyl-1,3,2-dioxaborolan-2-yl)-1H-pyrazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)ethylphosphinate Prepared analogously to Compound 74A replacing Compound 74B with (4-{[4-{[6-bromo-2-(methylcarbamoyl)pyridin-3-yl]amino}-5-(trifluoromethyl)pyrimidin-2-yl]amino}-3-methoxybenzyl)ethylphosphinic acid (Compound 67B). MS (ESI): m/z 865.86/867.92 [M+H]⁺. UPLC: $t_R$=1.61 min (UPLC-SQD: analytical_2 min).

167

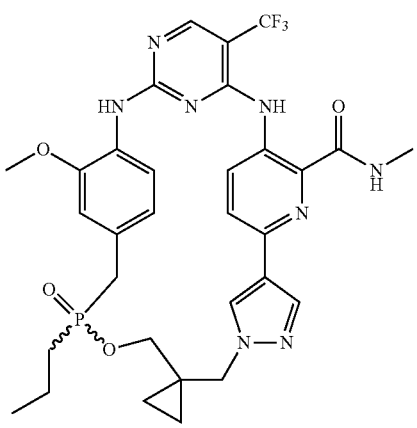

Example 76

(10'R)-14'-methoxy-N-methyl-10'-propyl-20'-(trifluoromethyl)-9'-oxa-4',5',16',18',22',25',28'-heptaaza-10'-phosphaspiro[cyclopropane-1,7'-pentacyclo[21.2.2.2$^{12,15}$1$^{2,5}$.1$^{17,21}$]hentriacontane]-1'(25'),2'(31'),3',12',14',17'(28'),18',20',23',26',29'-undecaene-24'-carboxamide 10'-oxide and (10'S)-14'-methoxy-N-methyl-10'-propyl-20'-(trifluoromethyl)-9'-oxa-4',5',16',18',22',25',28'-heptaaza-10'-phosphaspiro[cyclopropane-1,7'-pentacyclo[21.2.2.2$^{12,15}$.1$^{2,5}$.1$^{17,21}$]hentriacontane]-1'(25'),2'(31'),3',12',14',17'(28'),18',20',23',26',29'-undecaene-24'-carboxamide 10'-oxide Racemic mixture prepared analogously to Example 67 using (1-{[4-(4,4,5,5-tetramethyl-1,3,2-dioxaborolan-2-yl)-1H-pyrazol-1-yl]methyl}cyclopropyl)methyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate (Compound 8A, 0.340 g, 0.388 mmol). $^{1}$H NMR (400 MHz, DMSO-d$_{6}$) δ=10.99 (s, 1H), 9.03 (q, J=4.7 Hz, 1H), 8.77 (s, 1H), 8.55 (s, 1H), 8.42 (s, 1H), 8.32 (s, 1H), 8.15 (d, J=8.6 Hz, 1H), 7.76 (d, J=8.8 Hz, 1H), 7.41 (d, J=8.1 Hz, 1H), 6.93 (s, 1H), 6.63 (d, J=8.3 Hz, 1H), 4.11-4.21 (m, 2H), 3.75 (s, 3H), 3.48-3.62 (m, 2H), 3.05-3.26 (m, 2H), 2.83 (d, J=5.1 Hz, 3H), 1.30-1.54 (m, 4H), 0.76-0.87 (m, 5H), 0.67 (br. s., 2H). MS (ESI): m/z 671.64 [M+H]$^{+}$. UPLC: t$_{R}$=1.28 min (UPLC-SQD: analytical_2 min).

Compound 76A: (1-{[4-(4,4,5,5-tetramethyl-1,3,2-dioxaborolan-2-yl)-1H-pyrazol-1-yl]methyl}cyclopropyl)methyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate Prepared analogously to Compound 74A replacing Compound 47B with (1-{[4-(4,4,5,5-tetramethyl-1,3,2-dioxaborolan-2-yl)-1H-pyrazol-1-yl]methyl}cyclopropyl)methanol (Compound 63B). MS (ESI): m/z 877.90/879.86 [M+H]$^{+}$. UPLC: t$_{R}$=1.60 min (UPLC-SQD: analytical_2 min).

168

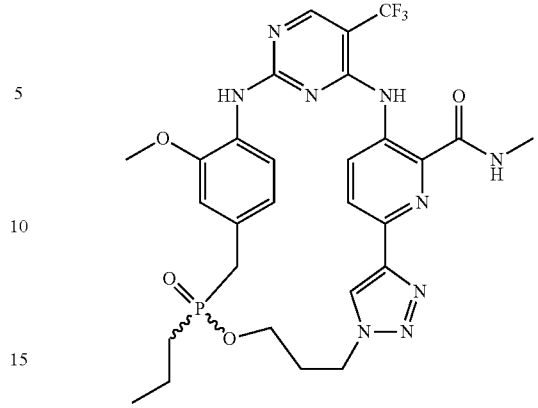

Example 77

(10R)-14-methoxy-N-methyl-10-propyl-20-(trifluoromethyl)-9-oxa-3,4,5,16,18,22,25,28-octaaza-10-phosphapentacyclo[21.2.2.2$^{12,15}$.1$^{2,5}$.1$^{17,21}$]hentriaconta-1(25),2(31),3,12,14,17(28),18,20,23,26,29-undecaene-24-carboxamide 10-oxide and (10S)-14-methoxy-N-methyl-10-propyl-20-(trifluoromethyl)-9-oxa-3,4,5,16,18,22,25,28-octaaza-10-phosphapentacyclo[21.2.2.2$^{12,15}$.1$^{2,5}$.1$^{17,21}$] hentriaconta-1(25),2(31),3,12,14, 17(28),18,20,23, 26,29-undecaene-24-carboxamide 10-oxide A mixture of 3-[4-(tributylstannanyl)-1H-1,2,3-triazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate (Compound 77A, 336 mg, 0.331 mmol) and Pd(PPh$_{3}$)$_{2}$Cl$_{2}$ (11.6 mg, 0.0166 mmol) in 1,4-dioxane (8 mL) was evacuated and purged with nitrogen (3x). The reaction mixture was heated at 100° C. for 24 h. The reaction mixture was concentrated under reduced pressure to a brown oil. The crude material was purified on a Teledyne ISCO Combiflash® Rf system using 1:1 DCM-EtOAc/MeOH (100:0→90:10) as eluent. The fractions containing product were combined and concentrated under reduced pressure to yield a white solid (41.0 mg, 19%). $^{1}$H NMR (400 MHz, CD$_{3}$OD): δ=8.93 (s, 1H), 8.37 (s, 1H), 8.14 (d, J=8.6 Hz, 1H), 7.97 (d, J=8.6 Hz, 1H), 7.45 (d, J=8.3 Hz, 1H), 6.82 (s, 1H), 6.33 (td, J=2.1, 8.3 Hz, 1H), 4.69-4.82 (m, 2H), 4.11-4.17 (m, 1H), 3.84 (s, 3H), 3.75-3.83 (m, 1H), 3.24 (d, J=16.9 Hz, 1H), 3.05-3.16 (m, 1H), 2.94 (s, 3H), 2.32-2.49 (m, 2H), 1.42-1.59 (m, 4H), 0.88-0.95 (m, 3H). MS (ESI): m/z 646.51 [M+H]$^{+}$. UPLC: t$_{R}$=1.10 min (UPLC-SQD: analytical_2 min).

Compound 77A: 3-[4-(Tributylstannanyl)-1H-1,2,3-triazol-1-yl]propyl (4-{[4-{[6-bromo-2-(methylcarbamoyl)pyridin-3-yl]amino}-5-(trifluoromethyl)pyrimidin-2-yl]amino}-3-methoxybenzyl)propylphosphinate A solution of (4-{[4-{[6-bromo-2-(methylcarbamoyl)pyridin-3-yl]amino}-5-(trifluoromethyl)pyrimidin-2-yl]amino}-3-methoxybenzyl)propylphosphinic acid (Compound 74B, 0.370 g, 0.599 mmol), 3-[4-(tributylstannanyl)-1H-1,2,3-triazol-1-yl]propan-1-ol (Compound 64B, 0.299 g, 0.719 mmol) and DIPEA (0.313 mL, 1.80 mmol) in 1,2-dichloroethane (10.0 mL) was charged with (benzotriazol-1- yloxy)tripyrrolidino-phosphonium hexafluorophosphate (0.936 g, 1.80 mmol). The resulting mixture was stirred at rt for 16 hours. The reaction mixture was quenched with sat. aq. NaHCO$_3$ (10 mL) and extracted with DCM (20 mL). The organic layer was washed with sat. aq. NaHCO$_3$ (10 mL), washed with brine (15 mL), dried over anhydrous Na$_2$SO$_4$, filtered, and concentrated under reduced pressure to a brown oil. The crude material was purified using a Teledyne ISCO Combiflash® Rf system using 1:1 DCM-EtOAc/MeOH (100:0→90:10) as eluent. The fractions containing product were combined and concentrated under reduced pressure to yield an off-white solid (352.1 mg, 57.8%). MS (ESI): m/z 1016.90 [M+H]$^+$. UPLC: $t_R$=1.44 min (UPLC-SQD: analytical_non-polar 2 min).

SFC (Supercritical Fluid Chromatography) using a chiral stationary phase can be used to separate the preceding racemic Examples into the individual enantiomers. The following table lists each Example that was separated along with the relevant chiral SFC conditions used. With the exception of Examples 69 and 70, the $^1$H NMR and LC-MS data for the enantiomers was identical to the data obtained for the racemic mixture:

TABLE 1

Chiral SFC conditions used to separate and identify selected Examples

| Racemic Example # | (Semi) Preparative conditions | Analytical Conditions | Enantiomer $t_R$ (min) | Chiral Example # |
|---|---|---|---|---|
| 4 | Chiral column: CHIRALPACK IA 21 × 250 mm, 5μ; Modifier: 50/50 ACN/MeOH Flow Rate: 30 mL/min Gradient/Isocratic(modifier): isocratic 50% $t_R$ (1) = 11.72 $t_R$ (2) = 15.33 | Chiral column: CHIRALPACK IA 4.6 × 100 mm, 5u Modifier: 50/50 ACN/MeOH Flow Rate: 4 mL/min Gradient(modifier): 10 to 60% in 5 min $t_R$ (1) = 4.33 $t_R$ (2) = 4.73 | 4.33 4.73 | 4A 4B |
| 6 | Chiral Column: CHIRALPACK IC 21 × 250 mm, 5μ Modifier: 0.2% IPAmine in MeOH Flow Rate: 30 mL/min Isocratic: 60% $t_R$ (1) = 13.82 minutes $t_R$ (2) = 23.17 minutes | Chiral Column: CHIRALPACK IC 4.6 × 100 mm, 5u Modifier: 0.2% IPAmine in MeOH Flow Rate: 4 mL/min Isocratic: 30% $t_R$ (1) = 2.58 minutes $t_R$ (2) = 5.80 minutes | 2.58 5.80 | 6A 6B |
| 24 | Chiral column: CHIRALPACK AS 20 × 250 mm, 5μ Modifier: 0.2% IPAmine in MeOH Flow Rate: 30 mL/min Gradient(modifier): isocratic 50% $t_R$ (1) = 9.42 $t_R$ (2) = 12.95 | Chiral column: CHIRALPACK AS 4.6 × 100 mm, 5μ Modifier: 0.2% IPAmine in MeOH Flow Rate: 4 mL/min Gradient(modifier): 10-60% in 5 min $t_R$ (1) = 4.20 $t_R$ (2) = 5.17 | 4.20 5.17 | 24A 24B |
| 34 | Chiral column: CHIRALPACK IA 21 × 250 mm, 5μ Modifier: 0.2% IPAmine in MeOH Flow Rate: 30 mL/min Gradient: Start_% End_% Duration (Sec) 35 55 600 55 60 300 60 60 540 60 35 60 35 35 120 $t_R$ (1) = 16.76 min $t_R$ (2) = 20.96 min | Chiral column: CHIRALPACK IA 4.6 × 100 mm, 5μ Modifier: 0.2% IPAmine in MeOH Flow Rate: 4 mL/min Gradient (modifier): 10 to 60% in 5 min $t_R$ (1) = 4.17 $t_R$ (2) = 5.08 | 4.17 5.08 | 34A 34B |
| 35 | Chiral column: CHIRALPACK IA 20 × 250 mm, 5μ Modifier: 0.2% IPAmine in MeOH Flow Rate: 30 mL/min Gradient(modifier): Start % End % Duration (sec) 40 60 120 60 60 1500 60 40 60 40 40 120 $t_R$ (1) = 12.03 $t_R$ (2) = 15.93 | Chiral column: CHIRALPACK IA 4.6 × 100 mm, 5μ Modifier: 0.2% IPAmine in MeOH Flow Rate: 4 mL/min Gradient(modifier) $t_R$ (1) = 3.95 $t_R$ (2) = 4.58 | 3.95 4.58 | 35A 35B |
| 37 | Chiral column: CHIRALPACK IA 21 × 250 mm, 5μ; Modifier: 50/50 ACN/MeOH Flow Rate: 30 mL/min Gradient (modifier): isocratic | Chiral column: CHIRALPACK IA 4.6 × 100 mm, 5μ; Modifier: 50/50 ACN/MeOH Flow Rate: 4 mL/min | 5.01 6.35 | 37A 37B |

TABLE 1-continued

Chiral SFC conditions used to separate and identify selected Examples

| Racemic Example # | (Semi) Preparative conditions | Analytical Conditions | Enantiomer $t_R$ (min) | Chiral Example # |
|---|---|---|---|---|
| | 60%<br>$t_R$ (1) = 11.83<br>$t_R$ (2) = 28.62 | Gradient(modifier): 10 to 60% in 5 min<br>$t_R$ (1) = 5.01<br>$t_R$ (2) = 6.35 | | |
| 44 | Chiral column: CHIRALPACK IA 20 × 250 mm, 5μ<br>Modifier: 0.2% IPAmine in MeOH<br>Flow Rate: 30 mL/min<br>Gradient(modifier): isocratic 60%<br>$t_R$ (1) = 16.77<br>$t_R$ (2) = 32.57 | Chiral column:<br>CHIRALPACK IA 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 5.45<br>$t_R$ (2) = 7.28 | 5.45<br>7.28 | 44A<br>44B |
| 45 | Chiral column: CHIRALPACK IA 20 × 250 mm, 5μ<br>Modifier: 0.2% IPAmine in MeOH<br>Flow Rate: 30 mL/min<br>Gradient(modifier): isocratic 60%<br>$t_R$ (1) = 15.75<br>$t_R$ (2) = 27.32 | Chiral column:<br>CHIRALPACK IA 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 5.05<br>$t_R$ (2) = 6.75 | 5.05<br>6.75 | 45A<br>45B |
| 47 | Chiral column: CHIRALPACK IA 20 × 250 mm, 5μ<br>Modifier: 0.2% IPAmine in MeOH<br>Flow Rate: 30 mL/min<br>Gradient(modifier):<br>Start_%  End_%  Duration (Sec)<br>40       60      120<br>60       60      1500<br>60       40      60<br>40       40      120<br>$t_R$ (1) = 13.77<br>$t_R$ (2) = 17.60 | Chiral column:<br>CHIRALPACK IA 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 4.77<br>$t_R$ (2) = 5.85 | 4.77<br>5.85 | 47A<br>47B |
| 48 | Chiral column: CHIRALPACK IA 20 × 250 mm, 5μ<br>Modifier: 50/50 ACN/MeOH<br>Flow Rate: 30 mL/min<br>Gradient(modifier):<br>Start_%  End_%  Duration (Sec)<br>40       60      120<br>60       60      1800<br>60       40      60<br>40       40      120<br>$t_R$ (1) = 9.32<br>$t_R$ (2) = 23.93 | Chiral column:<br>CHIRALPACK IA 4.6 × 100 mm, 5μ<br>Modifier: 50/50 ACN/MeOH<br>Flow Rate: 4 mL/min<br>Gradient(modifier): 10-60% in 5 min<br>$t_R$ (1) = 4.25<br>$t_R$ (2) = 5.73 | 4.25<br>5.73 | 48A<br>48B |
| 49 | Chiral column: CHIRALPACK IA 20 × 250 mm, 5μ<br>Modifier: 50/50 ACN/MeOH<br>Flow Rate: 30 mL/min<br>Gradient(modifier):<br>Start_%  End_%  Duration (Sec)<br>40       60      120<br>60       60      900<br>60       40      60<br>40       40      120<br>$t_R$ (1) = 9.03<br>$t_R$ (2) = 11.87 | Chiral column:<br>CHIRALPACK IA 4.6 × 100 mm, 5μ<br>Modifier: 50/50 ACN/MeOH<br>Flow Rate: 4 mL/min<br>Gradient(modifier): 10-60% in 5 min<br>$t_R$ (1) = 4.32<br>$t_R$ (2) = 4.97 | 4.32<br>4.97 | 49A<br>49B |
| 50 | Chiral column: CHIRALPACK IA 20 × 250 mm, 5μ<br>Modifier: 50/50 ACN/MeOH<br>Flow Rate: 30 mL/min<br>Gradient(modifier): Start<br>Start_%  End_%  Duration (Sec)<br>40       60      120<br>60       60      1500<br>60       40      60<br>40       40      120<br>$t_R$ (1) = 10.50<br>$t_R$ (2) = 17.35 | Chiral column:<br>CHIRALPACK IA 4.6 × 100 mm, 5μ<br>Modifier: 50/50 ACN/MeOH<br>Flow Rate: 4 mL/min<br>Gradient(modifier): 10-60% in 5 min<br>$t_R$ (1) = 4.70<br>$t_R$ (2) = 5.65 | 4.70<br>5.65 | 50A<br>50B |
| 54 | Chiral column: CHIRALPACK IA 20 × 250 mm, 5μ | Chiral column:<br>CHIRALPACK IA 4.6 × | 4.41<br>4.83 | 54A<br>54B |

TABLE 1-continued

Chiral SFC conditions used to separate and identify selected Examples

| Racemic Example # | (Semi) Preparative conditions | Analytical Conditions | Enantiomer $t_R$ (min) | Chiral Example # |
|---|---|---|---|---|
|  | Modifier: 0.2% IPAmine in MeOH<br>Flow Rate: 30 mL/min<br>Gradient(modifier): isocratic 40%<br>$t_R$ (1) = 28.22<br>$t_R$ (2) = 37.48 | 100 mm, 5μ<br>Modifier: 0.2% IPAmine in MeOH<br>Flow Rate: 4 mL/min<br>Gradient(modifier): 10-60% in 5 min<br>$t_R$ (1) = 4.41<br>$t_R$ (2) = 4.83 | | |
| 55 | Chiral column: CHIRALPACK IC 20 × 250 mm, 5μ<br>Modifier: 0.2% IPAmine in MeOH<br>Flow Rate: 30 mL/min<br>Gradient(modifier): isocratic 60%<br>$t_R$ (1) = 28.83<br>$t_R$ (2) = 37.17 | Chiral column: CHIRALPACK IC 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 6.00<br>$t_R$ (2) = 6.53 | 6.00<br>6.53 | 55A<br>55B |
| 56 | Chiral column: CHIRALPACK AS 20 × 250 mm, 5μ<br>Modifier: 0.2% IPAmine in MeOH<br>Flow Rate: 30 mL/min<br>Gradient(modifier): isocratic 40%<br>$t_R$ (1) = 10.27<br>$t_R$ (2) = 17.18 | Chiral column: CHIRALPACK AS 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 3.50<br>$t_R$ (2) = 4.22 | 3.50<br>4.22 | 56A<br>56B |
| 57 | Chiral column: CHIRALPACK IA 20 × 250 mm, 5μ<br>Modifier: 0.2% IPAmine in MeOH<br>Flow Rate: 30 mL/min<br>Gradient(modifier): isocratic 45%<br>$t_R$ (1) = 23.32<br>$t_R$ (2) = 28.63 | Chiral column: CHIRALPACK IA 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 4.98<br>$t_R$ (2) = 5.50 | 4.98<br>5.50 | 57A<br>57B |
| 58 | Chiral column: CHIRALPACK IA 20 × 250 mm, 5μ<br>Modifier: 0.2% IPAmine in MeOH<br>Flow Rate: 30 mL/min<br>Gradient(modifier): isocratic 60%<br>$t_R$ (1) = 17.75<br>$t_R$ (2) = 25.62 | Chiral column: CHIRALPACK IA 4.6 × 100 mm, 5μ<br>Modifier: 0.2% IPAmine in MeOH<br>Flow Rate: 4 mL/min<br>Gradient(modifier): 10-60% in 5 min<br>$t_R$ (1) = 5.47<br>$t_R$ (2) = 6.32 | 5.47<br>6.32 | 58A<br>58B |
| 59 | Chiral column: CHIRALPACK IA 20 × 250 mm, 5μ;<br>Modifier: 0.2% IPAmine in MeOH<br>Flow Rate: 30 mL/min<br>Gradient (modifier): isocratic 45%<br>$t_R$ (1) = 17.15<br>$t_R$ (2) = 24.20 | Chiral column: CHIRALPACK IA 4.6 × 100 mm, 5μ;<br>Modifier: 0.2% IPAmine in MeOH<br>Flow Rate: 4 mL/min<br>Gradient(modifier): 10 to 60% in 5 min<br>$t_R$ (1) = 4.52<br>$t_R$ (2) = 5.50 | 4.38<br>5.28 | 59A<br>59B |
| 60 | Chiral column: CHIRALPACK IA 20 × 250 mm, 5μ;<br>Modifier: 0.2% IPAmine in MeOH<br>Flow Rate: 30 mL/min<br>Gradient(modifier): isocratic 60%<br>$t_R$ (1) = 16.12<br>$t_R$ (2) = 28.32 | Chiral column: CHIRALPACK IA 4.6 × 100 mm, 5μ;<br>Modifier: 0.2% IPAmine in MeOH<br>Flow Rate: 4 mL/min<br>Gradient(modifier): 20 to 40% in 5 min<br>$t_R$ (1) = 3.31<br>$t_R$ (2) = 3.94 | 3.31<br>3.94 | 60A<br>60B |
| 61 | Chiral column: CHIRALPACK IA 20 × 250 mm, 5μ<br>Modifier: 50/50 ACN/MeOH<br>Flow Rate: 30 mL/min<br>Gradient(modifier): isocratic 60%<br>$t_R$ (1) = 12.72 | Chiral column: CHIRALPACK IA 4.6 × 100 mm, 5μ<br>Modifier: 50/50 ACN/MeOH<br>Flow Rate: 4 mL/min<br>Gradient(modifier): 10-60% in 5 min | 5.05<br>6.18 | 61A<br>61B |

TABLE 1-continued

Chiral SFC conditions used to separate and identify selected Examples

| Racemic Example # | (Semi) Preparative conditions | Analytical Conditions | Enantiomer $t_R$ (min) | Chiral Example # |
|---|---|---|---|---|
| | $t_R$ (2) = 23.89 | $t_R$ (1) = 5.05<br>$t_R$ (2) = 6.18 | | |
| 62 | Chiral column: CHIRALPACK IA 20 × 250 mm, 5μ<br>Modifier: 50/50 ACN/MeOH<br>Flow Rate: 30 mL/min<br>Gradient(modifier): isocratic 60%<br>$t_R$ (1) = 11.37<br>$t_R$ (2) = 28.84 | Chiral column:<br>CHIRALPACK IA 4.6 × 100 mm, 5μ<br>Modifier: 50/50 ACN/MeOH<br>Flow Rate: 4 mL/min<br>Gradient(modifier): 10-60% in 5 min<br>$t_R$ (1) = 4.97<br>$t_R$ (2) = 6.30 | 4.97<br>6.30 | 62A<br>62B |
| 63 | Chiral column: CHIRALPACK IA 20 × 250 mm, 5μ<br>Modifier: 50/50 ACN/MeOH<br>Flow Rate: 30 mL/min<br>Gradient(modifier): isocratic 60%<br>$t_R$ (1) = 11.38<br>$t_R$ (2) = 31.67 | Chiral column:<br>CHIRALPACK IA 4.6 × 100 mm, 5μ<br>Modifier: 50/50 ACN/MeOH<br>Flow Rate: 4 mL/min<br>Gradient(modifier): 10-60% in 5 min<br>$t_R$ (1) = 5.44<br>$t_R$ (2) = 6.73 | 5.44<br>6.73 | 63A<br>63B |
| 64 | Chiral column: CHIRALPACK IA 20 × 250 mm, 5μ;<br>Modifier: 0.2% IPAmine in MeOH<br>Flow Rate: 30 mL/min<br>Gradient(modifier): isocratic 50%<br>$t_R$ (1) = 9.33<br>$t_R$ (2) = 13.13 | Chiral column:<br>CHIRALPACK IA 4.6 × 100 mm, 5μ;<br>Modifier: 50/50 ACN/MeOH<br>Flow Rate: 4 mL/min<br>Gradient(modifier): 10 to 60% in 5 min<br>$t_R$ (1) = 4.08<br>$t_R$ (2) = 4.50 | 4.08<br>4.50 | 64A<br>64B |
| 66 | Chiral column: CHIRALPACK IA 21 × 250 mm, 5μ; Modifier: 0.2% IPA in MeOH<br>Flow Rate: 30 mL/min<br>Gradient(modifier):<br><br>Start % / End % / Total Duration (sec)<br>20 / 40 / 600<br>40 / 40 / 1200<br>40 / 20 / 60<br>20 / 20 / 120<br>$t_R$ (1) = 22.6<br>$t_R$ (2) = 29.71 | Chiral column:<br>CHIRALPACK IA 4.6 × 100 mm, 5μ;<br>Modifier: 0.2% IPA in MeOH<br>Flow Rate: 4 mL/min<br>Gradient(modifier): 10 to 60% in 5 min<br>$t_R$ (1) = 4.15<br>$t_R$ (2) = 4.55 | 4.15<br>4.55 | 66A<br>66B |
| 67 | Chiral column: CHIRALPACK IA 21 × 250 mm, 5μ;<br>Modifier: 0.2% IPA in MeOH<br>Flow Rate: 30 mL/min<br>Gradient/Isocratic(modifier): isocratic 60%<br>$t_R$ (1) = 13.73<br>$t_R$ (2) = 20.35 | Chiral column:<br>CHIRALPACK IA 4.6 × 100 mm, 5μ;<br>Modifier: 0.2% IPA in MeOH<br>Flow Rate: 4 mL/min<br>Gradient(modifier): 10 to 60% in 5 min<br>$t_R$ (1) = 5.37<br>$t_R$ (2) = 6.21 | 5.37<br>6.21 | 67A<br>67B |
| 68 | Chiral column: CHIRALPACK IA 21 × 250 mm, 5μ;<br>Modifier: 0.2% IPA in MeOH<br>Flow Rate: 30 mL/min<br>Gradient/Isocratic(modifier): isocratic 60%<br>$t_R$ (1) = 13.15<br>$t_R$ (2) = 19.60 | Chiral column:<br>CHIRALPACK IA 4.6 × 100 mm, 5μ;<br>Modifier: 0.2% IPA in MeOH<br>Flow Rate: 4 mL/min<br>Gradient(modifier): 10 to 60% in 5 min<br>$t_R$ (1) = 5.27<br>$t_R$ (2) = 6.17 | 5.27<br>6.17 | 68A<br>68B |
| 69 | Chiral column: CHIRALPACK IA 20 × 250 mm, 5u<br>Modifier: 50/50 ACN/MeOH<br>Flow Rate: 30 mL/min<br>Gradient(modifier): ):<br><br>Start % / End % / Total Duration (sec)<br>30 / 40 / 120<br>40 / 40 / 2100<br>40 / 30 / 60<br>30 / 30 / 120<br>$t_R$ (1) = 23.05<br>$t_R$ (2) = 29.25 | Chiral column:<br>CHIRALPACK IA 4.6 × 100 mm, 5μ<br>Modifier: 50/50 ACN/MeOH<br>Flow Rate: 4 mL/min<br>Gradient(modifier): 10-60% in 5 min<br>$t_R$ (1) = 4.45<br>$t_R$ (2) = 4.65 | 4.45<br>4.65 | 69A<br>69B |

TABLE 1-continued

Chiral SFC conditions used to separate and identify selected Examples

| Racemic Example # | (Semi) Preparative conditions | Analytical Conditions | Enantiomer $t_R$ (min) | Chiral Example # |
|---|---|---|---|---|
| 70 | Chiral column: CHIRALPACK IA 20 × 250 mm, 5u<br>Modifier: 50/50 ACN/MeOH<br>Flow Rate: 30 mL/min<br>Gradient(modifier):<br><br>Start %__ End %__ Total Duration (sec)<br>30    40    1200<br>40    40    1500<br>40    30    60<br>30    30    120<br>$t_R$ (1) = 22.37<br>$t_R$ (2) = 26.39 | Chiral column:<br>CHIRALPACK IA 4.6 × 100 mm, 5u<br>Modifier: 50/50 ACN/MeOH<br>Flow Rate: 4 mL/min<br>Gradient(modifier): 10-60% in 5 min<br>$t_R$ (1) = 4.25<br>$t_R$ (2) = 4.50 | 4.25<br>4.50 | 70A<br>70B |
| 71 | Chiral column: CHIRALPACK IA 20 × 250 mm, 5u<br>Modifier: 50/50 ACN/MeOH<br>Flow Rate: 30 mL/min<br>Gradient(modifier): ): isocratic 60%<br>$t_R$ (1) = 16.03<br>$t_R$ (2) = 51.44 | Chiral column:<br>CHIRALPACK IA 4.6 × 100 mm, 5u<br>Modifier: 50/50 ACN/MeOH<br>Flow Rate: 4 mL/min<br>Gradient(modifier): 10-60% in 5 min<br>$t_R$ (1) = 5.48<br>$t_R$ (2) = 7.00 | 5.48<br>7.00 | 71A<br>71B |
| 72 | Chiral column: CHIRALPACK IA 21 × 250 mm, 5μ;<br>Modifier: 50/50 ACN/MeOH<br>Flow Rate: 30 mL/min<br>Gradient (modifier): isocratic 60%<br>$t_R$ (1) = 15.42<br>$t_R$ (2) = 21.10 | Chiral column:<br>CHIRALPACK IA 4.6 × 100 mm, 5μ;<br>Modifier: 50/50 ACN/MeOH<br>Flow Rate: 4 mL/min<br>Gradient(modifier): 10 to 60% in 5 min<br>$t_R$ (1) = 4.52<br>$t_R$ (2) = 5.50 | 4.52<br>5.50 | 72A<br>72B |
| 73 | Chiral column: CHIRALPACK IA 20 × 250 mm, 5u<br>Modifier: 50/50 ACN/MeOH<br>Flow Rate: 30 mL/min<br>Gradient(modifier): ):<br><br>Start %__ End %__ Total Duration (sec)<br>30    40    1200<br>40    40    420<br>40    50    60<br>50    50    1200<br>50    30    60<br>30    30    120<br>$t_R$ (1) = 34.82<br>$t_R$ (2) = 46.07 | Chiral column:<br>CHIRALPACK IA 4.6 × 100 mm, 5u<br>Modifier: 50/50 ACN/MeOH<br>Flow Rate: 4 mL/min<br>Gradient(modifier): 10-60% in 5 min<br>$t_R$ (1) = 4.43<br>$t_R$ (2) = 4.85 | 4.43<br>4.85 | 73A<br>73B |
| 74 | Chiral column: CHIRALPACK IA 21 × 250 mm, 5□<br>Modifier: 50/50 ACN/MeOH<br>Flow Rate: 30 mL/min<br>Gradient(modifier):<br><br>Start %__ End %__ Total Duration (sec)<br>40    60    600<br>60    60    1042<br>60    40    60<br>40    40    120<br>$t_R$ (1) = 11.67<br>$t_R$ (2) = 21.93 | Chiral column:<br>CHIRALPACK IA 4.6 × 100 mm, 5μ;<br>Modifier: 50/50 ACN/MeOH<br>Flow Rate: 4 mL/min<br>Gradient(modifier): 10 to 60% in 5 min<br>$t_R$ (1) = 4.66<br>$t_R$ (2) = 5.86 | 4.66<br>5.86 | 74A<br>74B |
| 75 | Chiral column: CHIRALPACK IA 21 × 250 mm, 5μ;<br>Modifier: 50/50 ACN/MeOH<br>Flow Rate: 30 mL/min<br>Gradient(modifier): isocratic 60%<br>$t_R$ (1) = 11.97<br>$t_R$ (2) = 22.75 | Chiral column:<br>CHIRALPACK IA 4.6 × 100 mm, 5μ;<br>Modifier: 50/50 ACN/MeOH<br>Flow Rate: 4 mL/min<br>Gradient(modifier): 10 to 60% in 5 min<br>$t_R$ (1) = 4.85<br>$t_R$ (2) = 5.74 | 4.85<br>5.74 | 75A<br>75B |
| 76 | Chiral column: CHIRALPACK IA 21 × 250 mm, 5μ;<br>Modifier: 50/50 ACN/MeOH<br>Flow Rate: 30 mL/min | Chiral column:<br>CHIRALPACK IA 4.6 × 100 mm, 5μ;<br>Modifier: 50/50 ACN/MeOH<br>Flow Rate: 4 mL/min | 5.67<br>7.45 | 76A<br>76B |

TABLE 1-continued

Chiral SFC conditions used to separate and identify selected Examples

| Racemic Example # | (Semi) Preparative conditions | Analytical Conditions | Enantiomer $t_R$ (min) | Chiral Example # |
|---|---|---|---|---|
| 77 | Gradient(modifier): isocratic 60% <br> $t_R$ (1) = 14.57 <br> $t_R$ (2) = 61.32 <br> Chiral column: <br> CHIRALPACK IA 21 × 250 mm, 5μ; <br> Modifier: 50/50 ACN/MeOH <br> Flow Rate: 30 mL/min <br> Gradient (modifier): isocratic 50% <br> $t_R$ (1) = 12.75 <br> $t_R$ (2) = 21.82 | Gradient(modifier): 10 to 60% in 5 min <br> $t_R$ (1) = 5.67 <br> $t_R$ (2) = 7.45 <br> Chiral column: <br> CHIRALPACK IA 4.6 × 100 mm, 5μ; <br> Modifier: 50/50 ACN/MeOH <br> Flow Rate: 4 mL/min <br> Gradient(modifier): 10 to 60% in 5 min <br> $t_R$ (1) = 4.42 <br> $t_R$ (2) = 5.07 | 4.42 <br> 5.07 | 77A <br> 77B |

Biological Properties

In some aspects of the invention, compounds of the invention are inhibitors of kinases, including FAK. In some aspects of the invention, compounds of the invention are selective inhibitors of FAK.

The invention includes compounds that exhibit inhibition of FAK in a biochemical assay (such as described herein) with an $IC_{50}$ of about 1 μM or less, or about 100 nM or less, or about 10 nM or less.

The invention includes compounds that exhibit inhibition of FAK in a cellular assay (such as described herein) with an $IC_{50}$ of about 1 μM or less, or about 100 nM or less, or about 10 nM or less.

In some aspects of the invention, compounds of the invention are selective inhibitors of FAK. In some embodiments, a compound is a selective inhibitor of FAK over other kinase targets. In some embodiments, a compound is at least about 50-fold selective for FAK over Aurora B in a cellular assay. In some embodiments, a compound is at least about 1000-fold selective for FAK over Src and/or KDR in a cellular assay.

Compounds of the invention were evaluated in the following biochemical and mechanistic assays, results of which are shown in Table 1.

Biochemical Omnia Assay Protocol

The Omnia Assay (Invitrogen) has been optimized for GST-tagged full-length FAK enzyme (PTK2, Invitrogen PV4085). In this assay system, Omnia Y Peptide 3 (Invitrogen KNZ3031) functions as a substrate for FAK. Phosphorylation of this SOX-containing peptide by FAK results in an increase in fluorescence at 485 nm upon excitation at 360 nm. Assays were carried out in 384-well OptiPlates (Perkin Elmer 6007290) in a total volume of 20 μL containing FAK (25 nM), Omnia Y Peptide 3 (10 μM), ATP (50 μM), and test compound (variable) in assay buffer (50 mM HEPES, pH 7.5, 5 mM $MgCl_2$, 0.15 mM $MnCl_2$, 1% glycerol, 1 mM DTT, 1 mM EGTA, 0.01% BSA) with 1% DMSO.

$IC_{50}$s for test compounds were typically determined using an 11-point three-fold serial dilution with a final assay concentration ranging from 0.17 nM to 10 μM. All compound concentrations were assayed in duplicate. Initial compound dilutions were prepared at 100× concentration in 100% DMSO from a 10 mM stock solution. Compounds were further diluted 1:25 in assay buffer resulting in a 4× concentrated solution.

In running the assay, 5 μL of the above 4× concentrated compound solution (or 4% DMSO for positive controls) was added to the assay plate followed by 5 μL of a solution containing peptide (40 μM) and ATP (200 μM) in assay buffer. The reaction was initiated by the addition of 10 μL of FAK (50 nM) in assay buffer, or assay buffer alone for negative controls. The increase in fluorescence due to peptide phosphorylation was monitored continuously as a function of time using a Spectramax M5 plate reader (Molecular Devices) equipped with SoftMax Pro 5.2 software.

$IC_{50}$ values were determined from the slopes of the linear progress curves by non-linear curve-fitting using GraphPad Prism 5 (GraphPad Software, Inc.). $IC_{50}$'s were determined in duplicate (n=2).

Cell-Based Assays for Inhibition of FAK Autophosphorylation: MiaPaCa2 and U87MG

The ability of compounds to inhibit FAK autophosphorylation was determined in a cell-based capture ELISA assay using U87MG glioblastoma cells (ATCC, Cat # HTB-14) and the FAK [pY397]ELISA kit from Invitrogen (KHO0441). The assay determines the ability of compounds to block endogenous autophosphorylation of FAK stimulated by fibronectin. Cells plated on fibronectin coated 96-well plate were incubated with compounds at various concentrations in the complete growth medium for 2 h. Cell lysates were then prepared and FAK protein was captured onto a FAK antibody-coated 96-well ELISA plate. The phosphotyrosine content of FAK protein was then monitored by quantitation of degree of binding of an antibody that recognizes only the phosphorylated FAK at Y397 within the captured protein. The antibody used has a reporter enzyme (e.g. horse radish peroxidase, HRP) covalently attached, such that binding to phosphorylated FAK can be determined quantitatively by incubation with an appropriate HRP substrate.

Stock Reagents:

Cell Lysis Buffer (Biosource #FNN0011): 10 mM Tris-HCl, pH 7.4; 100 mM NaCl; 1 mM EDTA; 1 mM EGTA; 1 mM NaF; 20 mM $Na_4P_2O_7$; 2 mM $Na_3VO_4$; 1% Triton X-100; 10% glycerol; 0.1% SDS; 0.5% deoxycholate; 1 mM PMSF (stock is 0.1M in ethanol, Sigma #93482); Protease inhibitor cocktail (Sigma, P-2714).

Reagents Provided in Biosource FAK [pY397] Immunoassay Kit (Cat # KHO0441): Standard diluent buffer; FAK antibody-coated wells, 96 wells per plate; Rabbit anti-FAK [pY397] detection antibody; Goat anti-rabbit IgG-Horseradish Peroxidase (HRP) concentrate (100×); HRP diluent; Wash buffer concentrate (25×); Stabilized chromogen (TMB); Stop solution; Plate covers, adhesive strips.

Assay Protocol:

Cultures of U87MG cells growing in MEM (Earles) containing non-essential amino acids, sodium pyruvate (1 mM), L-glutamate (1%) and 10% fetal bovine serum were detached by trypsin-EDTA and suspended in cell growth medium. Cells were then plated onto fibronectin (600 ng/well)-coated 96-well flat bottom plates at $1.7 \times 10^4$ cells per well in 60 uL cell growth medium and incubated overnight at 37° C. in a $CO_2$ incubator.

Compound dilutions were prepared from 10 mM DMSO stocks by dilution in cell growth medium, the final concentration of DMSO in the assay being 0.6%. To compound incubation wells, 60 uL of test compound was added as 2× concentration (compounds were assayed at concentrations between 4 μM-1.3 nM); to positive control wells, 60 μL of cell assay medium containing 1.3% DMSO was added. The cells were then incubated with compounds at 37° C. for 2 h. The medium was removed by aspiration and cells were lysed by addition of 20 uL of ice-cold cell lysis buffer per well. The plates were kept on ice for 20 min and 50 uL of standard diluent was added to each well. 50 uL of cell lysate from each well was transferred to respective wells in an assay plate and 50 uL of detection antibody was added to all wells except H1-H6 which were no antibody control wells. Capture assay plates were incubated overnight in a cold room.

Following incubation of the cell lysates and detection antibodies in the ELISA plate, the wells were washed 4 times with 120 uL of wash buffer (1×), then 100 uL of diluted HRP conjugated antibody (1:100 dil in diluent) was added to each well, and the plate was incubated at RT for 30 min. The wells were then washed for 4 times with 120 uL of wash buffer (1×) and 100 uL of chromogen was added to each well and incubated in the dark at RT for 5-10 min. 100 uL of stop solution was added to each well and the absorbance measured at 450 nm, 0.1 s.

Comparison of the assay signals obtained in the presence of compound with those of positive and negative controls (cells with no compound and no detection antibody being added), allows degree of inhibition of phospho-FAK [Y397] to be determined over a range of compound concentrations. These inhibition vales were fitted to a sigmoidal dose-response inhibition curve to determine the $IC_{50}$ values (i.e. the concentration of the compound that inhibits phosphorylation of FAK by 50%). The assay as described above was modified to determine the effect of inclusion of 50% (v/v) mouse or human plasma. In this assay, the compound plate was prepared as 2× concentration in 100 uL of 100% mouse or human plasma, and 60 uL of this was added to 60 uL of culture medium and incubated at 37° C. incubator for 2 h. The rest of the assay was carried out as described above.

In Table 2, A indicates a mean $IC_{50}$ of less than 0.4 μM; B indicates a mean $IC_{50}$ of 0.4 to 4 μM; and C indicates a mean $IC_{50}$ of greater than 4 μM. HP indicates assay in the presence of human plasma; MP indicates mouse plasma; NP indicates no plasma present.

TABLE 2

| | Biological Data | | | |
|---|---|---|---|---|
| | | FAK Activity | | |
| | Biochemical | Mechanistic (U87MG) | | |
| Ex # | OMNIA; [ATP] = 50uM | NP | MP | HP |
| 1 | A | A | A | A |
| 2 | A | | A | A |
| 3 | A | C | | C |
| 4 | A | A | A | A |
| 4A | A | A | B | B |
| 4B | A | A | A | A |
| 6 | A | A | A | A |
| 6A | A | A | A | A |
| 6B | A | A | A | A |
| 5 | A | A | A | A |
| 7 | A | A | A | A |
| 8 | A | A | A | A |
| 9 | A | A | B | A |
| 10 | A | B | C | C |
| 11 | A | A | B | B |
| 12 | A | A | B | B |
| 13 | A | A | A | A |
| 14 | A | A | A | A |
| 15 | A | A | A | A |
| 16 | A | A | A | A |
| 17 | A | A | A | A |
| 18 | A | A | A | A |
| 19 | A | A | A | A |
| 20 | A | A | A | A |
| 21 | A | A | A | A |
| 22 | A | B | A | A |
| 23 | A | A | A | A |
| 24 | A | B | A | A |
| 24A | A | A | B | C |
| 24B | A | A | B | B |
| 25 | A | A | A | A |
| 26 | A | A | B | A |
| 27 | A | A | B | |
| 28 | A | B | C | |
| 29 | A | B | C | |
| 30 | A | A | B | |
| 31 | A | A | A | |
| 32 | A | A | A | A |
| 33 | A | A | A | A |
| 34 | A | A | A | A |
| 34A | A | A | B | B |
| 34B | A | A | A | A |
| 35 | A | A | A | A |
| 35A | A | A | A | B |
| 35B | A | A | A | A |
| 36 | A | A | B | A |
| 37 | A | A | B | A |
| 37A | A | A | B | B |
| 37B | A | A | A | A |
| 38 | A | A | B | A |
| 39 | A | B | C | |
| 40 | A | A | B | |
| 41 | A | A | A | A |
| 42 | A | A | B | A |
| 43 | A | A | B | B |
| 44 | A | A | A | A |
| 44A | A | A | A | A |
| 44B | A | A | A | A |
| 45 | A | A | A | A |
| 45A | A | A | B | B |
| 45B | A | A | A | A |
| 46 | A | A | B | A |
| 47 | A | A | A | A |
| 47A | A | A | A | A |
| 47B | A | A | A | A |
| 48 | A | A | B | A |
| 48A | A | A | B | C |
| 48B | A | A | A | A |
| 49 | A | A | B | A |
| 49A | A | A | B | C |
| 49B | A | A | B | A |
| 50 | A | A | A | A |
| 50A | A | A | A | B |
| 50B | A | A | A | A |

TABLE 2-continued

Biological Data

| | FAK Activity | | | |
|---|---|---|---|---|
| | Biochemical | Mechanistic (U87MG) | | |
| Ex # | OMNIA; [ATP] = 50uM | NP | MP | HP |
| 51 | A | A | B | A |
| 52 | A | A | | |
| 53 | B | C | | |
| 54 | A | A | B | B |
| 54A | A | B | C | C |
| 54B | A | A | A | B |
| 55 | A | A | B | A |
| 55A | A | A | B | B |
| 55B | A | B | C | C |
| 56 | A | A | B | C |
| 56A | A | A | B | C |
| 56B | A | B | C | C |
| 57 | A | A | B | B |
| 57A | A | A | B | C |
| 57B | A | A | A | A |
| 58 | A | A | A | A |
| 58A | A | A | B | B |
| 58B | A | A | A | A |
| 59A | A | A | B | B |
| 59B | A | B | B | B |
| 60A | A | A | A | A |
| 60B | A | A | A | A |
| 61 | A | A | A | A |
| 61A | A | A | A | A |
| 61B | A | A | A | A |
| 62 | A | A | A | A |
| 62A | | A | B | A |
| 62B | | A | A | A |
| 63 | | A | A | A |
| 64 | A | A | A | A |
| 64A | A | A | A | A |
| 64B | A | A | A | A |
| 65 | A | C | C | C |
| 66 | A | A | A | A |
| 66A | A | A | B | B |
| 66B | A | A | A | A |
| 67 | A | A | A | A |
| 67A | A | A | B | B |
| 67B | A | A | A | A |
| 68 | A | A | A | A |
| 68A | A | A | B | B |
| 68B | A | A | A | A |
| 69 | | A | A | A |
| 70 | | A | B | A |
| 71 | | A | A | A |
| 72 | | A | A | A |
| 72A | | A | A | B |
| 72B | | A | A | A |

Compositions

The invention includes pharmaceutical compositions comprising a compound or pharmaceutically acceptable salt thereof of the invention, which is formulated for a desired mode of administration with or without one or more pharmaceutically acceptable and useful carriers. The compounds can also be included in pharmaceutical compositions in combination with one or more other therapeutically active compounds.

The pharmaceutical compositions of the present invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Uses and Methods

Compounds of the invention inhibit tyrosine kinase enzymes in animals, including humans, and may be useful in the treatment and/or prevention of various diseases and conditions such as hyperproliferative disorders, such as cancers. In particular, compounds of the invention, and compositions thereof, are inhibitors of FAK, and are useful in treating conditions modulated or driven, at least in part, by FAK, or for which inhibition of FAK is beneficial.

In some aspects, the invention includes a method of treating cancer comprising administering to a mammal in need thereof a therapeutically effective amount of a compound or salt of the invention.

A method of treating a cancer for which FAK inhibition is beneficial comprising administering to a mammal in need thereof a therapeutically effective amount of a compound or salt of the invention with or without one or more additional active agents.

In some aspects, the invention includes a method of treating a cancer mediated or driven at least in part by FAK comprising administering to a mammal in need thereof a therapeutically effective amount of a compound or salt of the invention.

In some aspects, the invention includes a method of treating or a method of manufacturing a medicament for treating a cancer, such as those above, which is mediated or driven at least in part by FAK, or for which inhibition of FAK is beneficial comprising administering to a mammal in need thereof a therapeutically effective amount of a compound or salt of the invention.

Compounds of the invention may be useful in the treatment of a variety of cancers, including, but not limited to, solid tumors, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, nonsmall cell lung, breast, or pancreatic cancer. In some aspects, the above methods are used to treat one or more of ovarian, gastric, head and neck, prostate, hepatocellular, renal, glioma, or sarcoma cancer.

In some aspects, the invention includes a method, including the above methods, wherein the compound is used to inhibit cellular epithelial to mesenchymal transition (EMT).

In some embodiments, the method includes treatment with a compound of the invention as part of a regimen that includes administration of one or more additional active agents.

The invention includes practicing the methods of the invention in human patients, and alternatively, in non-human animals.

The invention includes selecting a compound of the invention and a method and treatment regimen according to the invention based on its physicochemical and biological properties.

The dosage strength and regimen will depend upon several variables appreciated by the skilled artisan. Generally, dosage levels on the order of from about 0.01 mg/kg to about 150 mg/kg of body weight per day, or about 0.1 mg/kg to about 10 mg/kg of body weight per day, may be useful or beneficial in the treatment of the above-indicated conditions, or about 0.5 mg to about 7 g per patient per day. For example, cancers may be treated by administration of from about 0.01 to 50 mg of the compound per kg body weight per day, or alternatively about 0.5 mg to about 3.5 g per day per patient.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

As noted above, in some aspects, the method further comprises administering at least on additional active agent. In some aspects, the invention includes a method of treating cancer comprising administering to a mammal in need thereof a therapeutically effective amount of a compound or salt of the invention, wherein at least one additional active anti-cancer agent is used as part of the method. In some aspects, the invention includes a method of treating cancer mediated at least in part by FAK comprising administering to a mammal in need thereof a therapeutically effective regimen comprising a compound or salt of Formula I and at least one additional active agent.

GENERAL DEFINITIONS AND ABBREVIATIONS

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons.

The compounds of the invention and term "compound" in the claims include any pharmaceutically acceptable salts or solvates, and any amorphous or crystal forms, or tautomers, whether or not specifically recited in context.

The term "active agent" of the invention means a compound of the invention in any salt, polymorph, crystal, solvate, or hydrated form.

The term "pharmaceutically acceptable salt(s)" is known in the art and includes salts of acidic or basic groups which can be present in the compounds and prepared or resulting from pharmaceutically acceptable bases or acids.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate. It is also to be understood that in the proper context a moiety may be a diradical or otherwise be multiply substituted. For example, the term "aryl" can include arylene, and "heteroaryl" can include heteroarylene groups, etc, when indicated as such.

In descriptions and claims where subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated. Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

Moreover, a listing of variables need not be mutually exclusive and such is not limiting. For example, "carbocyclic" includes phenyl. A recitation of "carbocyclic or phenyl" does not imply that the meaning of "carbocyclic" is limited or excludes phenyl.

The convention for describing the carbon content of certain moieties is "($C_{a-b}$)" or "$C_a$-$C_b$" meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-12}$alkyl" means alkyl having 0-12 carbons, wherein $C_0$alkyl means a single covalent chemical bond when a linking group and means hydrogen when a terminal group.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "—"), the connections of compound name moieties are at the right-most recited moiety. That is, the substituent name starts with a terminal moiety, continues with any bridging moieties, and ends with the connecting moiety. For example, "heteroarylthio$C_{1-4}$alkyl is a heteroaryl group connected through a thio sulfur to a $C_{1-4}$ alkyl, which alkyl connects to the chemical species bearing the substituent.

The term "aliphatic" means any hydrocarbon moiety, and can contain linear, branched, and cyclic parts, and can be saturated or unsaturated.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like.

The term "alkoxy" means —O-alkyl, —O-alkenyl, or —O-alkynyl. "Haloalkoxy" means an —O-(haloalkyl) group. Representative examples include, but are not limited to, trifluoromethoxy, tribromomethoxy, and the like.

"Haloalkyl" means an alkyl, preferably lower alkyl, that is substituted with one or more same or different halo atoms.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or $S(O)_{0-2}$), and which can be saturated or unsaturated. Ring systems can be bridged and can include fused rings. The size of ring systems may be described using terminology such as "$_{x-y}$cyclic," which means a cyclic ring system that can have from x to y ring atoms. For example, the term "$_{9-10}$carbocyclic" means a 5, 6 or 6,6 fused bicyclic carbocyclic ring system which can be satd., unsatd. or aromatic. It also means a phenyl fused to one 5 or 6 membered satd. or unsatd. carbocyclic group. Nonlimiting examples of such groups include naphthyl, 1,2,3,4 tetrahydronaphthyl, indenyl, indanyl, and the like.

The term "carbocyclic" means a cyclic ring moiety containing only carbon atoms in the ring(s) without regard to aromaticity, including monocyclic, fused, and bridged systems. For example, a 3-10 membered carbocyclic means any chemically feasible ring systems having from 3 to 10 ring atoms.

The term "cycloalkyl" means a non-aromatic 3-12 carbocyclic mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spirocyclic" means a structure consisting of two cycloalkyl (optionally containing one or more heteroatoms) moieties that have exactly one atom in common.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means a planar ring moieties containing 4n+2 pi electrons, wherein n is an integer.

The term "aryl" means an aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl, preferably lower alkyl, that is substituted with an aryl group as defined above; e.g., —CH$_2$ phenyl, —(CH$_2$)$_2$phenyl, —(CH$_2$)$_3$ phenyl, CH$_3$CH(CH$_3$)CH$_2$phenyl, and the like and derivatives thereof.

The term "heterocyclic" means a cyclic ring moiety containing at least one heteroatom (N, O, or S(O)$_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-azabicyclo[2.2.1]heptane, 2-oxa-bicyclo[2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl Non-aryl heterocyclic groups include satd. and unsatd. systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsatd. or fully satd. 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo[4,5-b]pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxyquinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, and the like.

"Heteroaralkyl" group means alkyl, preferably lower alkyl, that is substituted with a heteroaryl group; e.g., —CH$_2$ pyridinyl, —(CH$_2$)$_2$pyrimidinyl, —(CH$_2$)$_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The term "9-10 membered heterocyclic" means a fused 5, 6 or 6,6 bicyclic heterocyclic ring moiety, which can be satd., unsatd. or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridazyl, 1,2,3,4,7,8 hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-dihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin4-yl, 4,5,6,7-tetrahydrobenzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

"Aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

One in the art understands that an "oxo" requires a second bond from the atom to which the oxo is attached. Accordingly, it is understood that oxo cannot be substituted onto an aryl or heteroaryl ring.

The term "halo" or "halogen" means fluoro, chloro, bromo, or iodo.

"Acyl" means a —C(O)R group, where R can be selected from the nonlimiting group of hydrogen or optionally substituted lower alkyl, trihalomethyl, unsubstituted cycloalkyl, aryl. "Thioacyl" or "thiocarbonyl" means a —C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

As used herein, the term "pharmaceutically acceptable salt" means those salts which retain the biological effectiveness and properties of the parent compound and do not present insurmountable safety or toxicity issues.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "treat," "treatment," and "treating" means reversing, alleviating, inhibiting the progress of, or partially or completely preventing the disorder or condition to which such term applies, or one or more symptoms of such disorder or condition. "Preventing" means treating before an infection occurs.

"Therapeutically effective amount" means that amount of the compound being administered which will relieve to some extent one or more of the symptoms of the disorder being treated, or result in inhibition of the progress or at least partial reversal of the condition.

The following abbreviations are used:
min. minute(s)
h hour(s)
d day(s)
RT or rt room temperature
$t_R$ retention time
L liter
mL milliliter
mmol millimole
μmol micromole
equiv. or eq. equivalents
NMR nuclear magnetic resonance
SFC supercritical fluid chromatography
MDP(S) mass-directed HPLC purification (system)
LC/MS liquid chromatography mass spectrometry
HPLC high performance liquid chromatography
TLC thin layer chromatography
CDCl$_3$ deuterated chloroform
CV column volume(s)
CD$_3$OD or MeOD deuterated methanol
DMSO-d$_6$ deuterated dimethylsulfoxide
LDA lithium diisopropylamide
DCM dichloromethane
THF tetrahydrofuran
EtOAc ethyl acetate
EtOH ethanol
MeCN acetonitrile
DMSO dimethylsulfoxide
Boc tert-butyloxycarbonyl
DME 1,2-dimethoxyethane
DMF N,N-dimethylformamide
KOAc potassium acetate
DIPEA diisopropylethylamine
MeOH methanol
MS (ESI) mass spectrometry, electrospray ionization
PS-DIEA polymer-supported diisopropylethylamine
PS-PPh$_3$-Pd polymer-supported Pd(PPh$_3$)$_4$
PyBOP (benzotriazol-1-yloxy)tripyrrolidinophosphonium hexafluorophosphate
EDC 1-(3-dimethylaminopropyl)-3-ethylcarbodiimide
HOBt 1-hydroxybenzotriazole
DMAP 4-dimethylaminopyridine
NBS N-bromosuccinimide
NMP N-methylpyrrolidinone
SCX solid cation exchange
TBTU O-(benzotriazol-1-yl)-N,N,N',N'-tetramethyluronium tetrafluoroborate
TEMPO 2,2,6,6-tetramethylpiperidine-1-oxyl
THF tetrahydrofuran
TFA trifluoroacetic acid
TFE 1,1,1-trifluoroethanol
UPLC ultra performance chromatography

The invention claimed is:
1. A compound of Formula I:

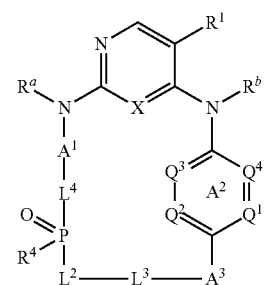

wherein:
X is N or CH;
A$^1$ is optionally substituted phenylene or optionally substituted $_{5-6}$heteroaryl;
A$^3$ is optionally substituted $_{5-6}$heterocyclic;
L$^2$ is —O— or a bond;
L$^3$ is optionally substituted C$_{2-6}$aliphatic;
L$^4$ is optionally substituted C$_{1-2}$aliphatic;
Q$^1$ to Q$^4$ are independently N, N-oxide, or optionally substituted CH;
when Q$^1$ and Q$^4$ are independently CH or N, an optionally substituted $_{5-6}$cyclic containing one or more heteroatoms is optionally fused to Ring A$^2$ at Q$^1$ and Q$^4$;
R$^1$, R$^a$, and R$^b$ are each independently H or an optional substituent; and
R$^4$ is OH, C$_{1-4}$aliphatic, —OC$_{1-3}$aliphatic, $_{3-6}$carbocyclic, or $_{4-6}$heterocyclic;
or a pharmaceutically acceptable salt thereof.

2. The compound or salt of claim 1, wherein:

X is N or CH;

$A^1$ is phenylene or $_{5-6}$heteroaryl either of which is optionally substituted by one or more independent $R^5$;

$A^3$ is $_{5-6}$heterocyclic optionally substituted by one or more independent $R^6$;

$L^2$ is —O— or a bond;

$L^3$ is $C_{2-6}$aliphatic optionally substituted by one or more independent $R^9$;

$L^4$ is $C_{1-3}$aliphatic optionally substituted by one or more independent $R^8$;

$Q^1$ to $Q^3$ are independently N,N-oxide, or $CR^2$;

$Q^4$ is N,N-oxide, or $CR^3$;

wherein an optionally substituted $_{5-6}$cyclic optionally containing one or more heteroatoms is optionally fused to Ring $A^2$ at $Q^1$ and $Q^4$;

$R^a$ and $R^b$ are each independently selected from H, $C_{1-6}$aliphatic, including $C_{3-6}$carbocyclic, or $_{4-6}$heterocyclic, any of which can be substituted by one or more independent $R^{aa}$;

each $R^{aa}$ and $R^8$ is independently selected from H, oxo, halo, $C_{1-6}$aliphatic, $C_{3-6}$carbocyclic, —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$;

$R^1$ is selected from H, halo, —CN, $C_{1-3}$aliphatic (optionally substituted by one or more halo), $C_{3-6}$carbocyclic, —$NO_2$, —$NR^{10}R^{11}$, —$SO_{0-2}R^{12}$, —$C(O)OR^{13}$, —$C(O)R^{12}$, or —$C(O)NR^{10}R^{11}$;

each $R^2$, $R^3$, $R^5$, and $R^6$ is independently selected from H, —$P(O)(OR^{23})_2$, halo, —$CF_3$, —CN, —$NO_2$, —$NR^{20}R^{21}$, —$C(NR^{20}R^{21})$=$NR^{20}$, —$C(R^{22})$=$NR^{20}$, —$NR^{20}C(NR^{20}R^{21})$=$NR^{20}$, —$NR^{20}C(NR^{20}R^{21})$=$N$—$C(O)R^{22}$, —$NR^{20}C(NR^{20}R^{21})$=$CR^{20}R^{21}$, —$NR^{20}C(O)R^{22}$, —$C(O)NR^{20}R^{21}$, —$C(O)R^{22}$, —$C(O)C(O)R^{22}$, —$C(O)OR^{23}$, —$OC(O)R^{22}$, —$OR^{23}$, —$OC(O)OR^{23}$, —$S(O)_{0-2}R^{22}$, —$S(O)(=NR^{20})R^{21}$, $C_{1-6}$aliphatic, or $_{3-10}$cyclic; wherein any substituted or unsubstituted $R^2$, $R^3$, $R^5$, or $R^6$ is optionally substituted by one or more independent $R^7$ groups;

$R^4$ is OH, $C_{1-4}$aliphatic, or —$OC_{1-3}$aliphatic;

each $R^7$ is independently selected from H, —$P(O)(OR^{23})_2$, —$OR^{23}$, —$C(O)R^{24}$, —$C(O)OR^{23}$, —$OC(O)R^{24}$, —$OC(O)OR^{23}$, —$C(O)NR^{24}R^{25}$, —$NR^{24}C(O)$ $NR^{24}R^{25}$, —$NR^{24}R^{25}$, —$NR^{24}C(NR^{24}R^{25})(=NR^{24})$, —$NR^{24}C(NR^{24}R^{25})$=$N$—$C(O)R^{24}$, —$NR^{24}C(O)R^{25}$, —$NR^{24}S(O)_{0-2}R^{24}$, —$S(O)_{0-2}R^{24}$, —$CF_3$, —CN, $C_{1-6}$aliphatic, or $_{3-10}$cyclic; wherein any of the foregoing $R^7$ is optionally substituted by one or more independent -halo, —$CF_3$, —CN, —$NO_2$, —OH, —$O(C_{1-6}$aliphatic), —$C(O)R^{26}$, —$C(O)NR^{26}R^{27}$, —$S(O)_{0-2}R^{26}$, —$S(O)_{0-2}NR^{26}R^{27}$, $_{3-10}$cyclic, —SH, —$S(C_{1-6}$aliphatic), —$NH_2$, —$NH(C_{1-6}$aliphatic), or —$N(C_{1-6}$aliphatic)$_2$ groups;

each $R^9$ is independently selected from H, oxo, halo $C_{1-6}$aliphatic, $C_{3-6}$carbocyclic, $_{3-6}$-spirocyclic (optionally substituted by one or more independent $R^{26}$), —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$;

each $R^{10}$, $R^{11}$, $R^{12}$, and $R^{13}$ is independently selected from H, $C_{1-6}$aliphatic, including $C_{3-6}$-carbocyclic, wherein $R^{10}$ and $R^{11}$ attached to the same atom can be taken together to form a ring containing one or more heteroatoms;

each $R^{20}$ and $R^{21}$ is independently selected from H, —$OR^{23}$, —$S(O)_{0-2}R^{28}$, —$NO_2$, $C_{1-6}$aliphatic, or $_{3-10}$cyclic;

each $R^{22}$ is independently selected from H, halo, —$NR^{24}R^{25}$, $C_{1-6}$aliphatic, or $_{3-10}$cyclic;

each $R^{23}$ is independently selected from H, $C_{1-6}$aliphatic, or $_{3-10}$cyclic;

$R^{24}$ and $R^{25}$ are each independently selected from H, —$NR^{26}C(O)R^{27}$, —$CF_3$, —CN, —$S(O)_{0-2}R^{26}$, $C_{1-6}$aliphatic, or $_{3-10}$cyclic; wherein any of the foregoing is optionally substituted by one or more independent halo, —$CF_3$, —CN, —$NO_2$, —OH, —$O(C_{1-6}$aliphatic), —$C(O)R^{26}$, —$C(O)NR^{26}R^{27}$, —$S(O)_{0-2}R^{26}$, —$S(O)_{0-2}$ $NR^{26}R^{27}$, $_{3-10}$cyclic, —SH, —$S(C_{1-6}$aliphatic), —$NH_2$, —$NH(C_{1-6}$aliphatic), or —$N(C_{1-6}$aliphatic)$_2$ groups;

$R^{26}$ and $R^{27}$ are each independently selected from the group consisting of —H, $C_{1-6}$aliphatic, or $_{3-10}$cyclic; wherein any of the foregoing is optionally substituted by one or more independent halo, —$CF_3$, —CN, —$NO_2$, —OH, —$O(C_{1-6}$aliphatic), —$C(O)C_{1-6}$ aliphatic, $_{3-10}$cyclic, —SH, —$S(C_{1-6}$aliphatic), —$NH_2$, —$NH(C_{1-6}$aliphatic), or —$N(C_{1-6}$aliphatic)$_2$ groups;

each $R^{28}$ is independently selected from H, —$NR^{24}R^{25}$, —$C(O)R^{24}$, —$CF_3$, $C_{1-6}$aliphatic, or $_{3-10}$cyclic;

wherein one or two carbon ring atoms in each of the aforementioned cyclic groups is optionally and independently replaced with C(O) or C(S);

wherein two groups attached to the same tetravalent carbon atom in each of the aforementioned cyclic and aliphatic groups are optionally joined to form a ring system.

3. The compound or salt of claim 1, wherein:

X is N or CH;

$A^1$ is phenylene or $_{5-6}$heteroaryl either of which is optionally substituted by one or more independent $R^5$;

$A^3$ is $_{5-6}$heterocyclic optionally substituted by one or more independent $R^6$;

$L^2$ is —O— or a bond;

$L^3$ is $C_{2-6}$aliphatic optionally substituted by one or more independent $R^9$;

$L^4$ is $C_{1-3}$aliphatic optionally substituted by one or more independent $R^8$;

$Q^1$ to $Q^3$ are independently N,N-oxide, or $CR^2$;

$Q^4$ is N,N-oxide, or $CR^3$;

an optionally substituted $_{5-6}$cyclic containing one or more heteroatoms is optionally fused to Ring $A^2$ at $Q^1$ and $Q^4$;

$R^a$ and $R^b$ are each independently selected from H, $C_{1-6}$aliphatic, $C_{3-6}$carbocyclic, or $_{4-6}$heterocyclic, any of which can be substituted by one or more independent halo or $C_{1-6}$aliphatic;

$R^1$ is selected from H, halo, —CN, $C_{1-3}$aliphatic (optionally substituted by one or more halo), $C_{3-6}$carbocyclic, —$NR^{10}R^{11}$, —$SO_{0-2}R^{12}$, —$C(O)OR^{13}$, —$C(O)R^{12}$, or —$C(O)NR^{10}R^{11}$;

each $R^2$, $R^3$, and $R^5$ is independently selected from H, —$P(O)(OR^{22})_2$, halo, —$CF_3$, —CN, —$NR^{20}R^{21}$, —$NR^{20}C(O)R^{22}$, —$C(O)NR^{20}R^{21}$, —$C(O)R^{22}$, —$C(O)C(O)R^{22}$, —$C(O)OR^{22}$, —$OC(O)R^{22}$, —$OR^{22}$, —$OC(O)OR^{22}$, —$S(O)_{0-2}R^{20}$, —$S(O)(=NR^{20})R^{21}$, $C_{1-6}$aliphatic, or $_{3-10}$cyclic;

$R^4$ is OH, $C_{1-4}$aliphatic, or —$OC_{1-3}$aliphatic;

each $R^6$, $R^{10}$, $R^{11}$, $R^{12}$, $R^{13}$, $R^{20}$, $R^{21}$, and $R^{22}$ is independently selected from H, $C_{1-6}$aliphatic, or $C_{3-6}$carbocyclic, wherein $R^{10}$ and $R^{11}$ or $R^{20}$ and $R^{21}$ attached to the same atom can be taken together to form a ring containing one or more heteroatoms;

each $R^8$ is independently selected from oxo, halo, $C_{1-6}$aliphatic, —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$; and each $R^9$ is independently selected from H, oxo, halo $C_{1-6}$aliphatic, $C_{3-6}$carbocyclic, $_{3-6}$spirocyclic, —$OC_{0-6}$aliphatic, —$NR^{10}R^{11}$, —$S(O)_{0-2}R^{12}$, —$S(O)_2NR^{10}R^{11}$, —$C(O)NR^{10}R^{11}$, —$C(O)OR^{13}$, or —$NR^{10}S(O)_{0-2}R^{12}$.

4. The compound or salt of claim 3, wherein:
X is N.

5. The compound or salt of claim 4, wherein:
$R^1$ is selected from Cl, —CN, —$NO_2$, or —$CF_3$.

6. The compound or salt of claim 4, wherein:
$R^1$ is —$CF_3$.

7. The compound or salt of claim 6, wherein:
$R^a$ and $R^b$ are independently selected from H or $C_{1-3}$aliphatic.

8. The compound or salt of claim 7, wherein:
$R^4$ is selected from OH, $C_{1-4}$aliphatic, or —$OC_{1-3}$aliphatic.

9. The compound or salt of claim 8, wherein:
$A^3$ is a 5-membered heteroaryl ring that is optionally substituted by one or more independent halo, —$CF_3$, —CN, —$NO_2$, —OH, —$O(C_{1-6}$aliphatic), —$C(O)R^{26}$, —$C(O)NR^{26}R^{27}$, —$S(O)_{0-2}R^{26}$, —$S(O)_{0-2}NR^{26}R^{27}$, $_{3-10}$cyclic, —SH, —$S(C_{1-6}$aliphatic), —$NH_2$, —$NH(C_{1-6}$aliphatic), or —$N(C_{1-6}$aliphatic)$_2$ groups.

10. The compound or salt of claim 8, wherein:
$A^3$ is a 5-membered heteroaryl ring that is optionally substituted by one or more $C_{1-3}$aliphatic.

11. The compound or salt of claim 10, wherein:
$L^3$ is $C_{2-4}$aliphatic that is optionally interrupted by one or more heteroatoms and is optionally substituted by one or more oxo, $C_{1-6}$aliphatic, $C_{3-6}$carbocyclic, —$OC_{0-6}$aliphatic, —$S(O)_2R^{12}$, —$S(O)_2NR^{10}R^{11}$, —$C(O)NR^{10}R^{11}$, —$C(O)OR^{13}$; —$NR^{10}S(O)_2R^{12}$, or —$NR^{10}R^{11}$.

12. The compound or salt of claim 10, wherein:
$L^3$ is $C_{3-4}$aliphatic that is optionally substituted by one or more oxo, $C_{1-6}$aliphatic, $C_{3-6}$carbocyclic, —$OC_{0-6}$aliphatic, —$S(O)_2R^{12}$, —$S(O)_2NR^{10}R^{11}$, —$C(O)NR^{10}R^{11}$, —$C(O)OR^{13}$; —$NR^{10}S(O)_2R^{12}$, or —$NR^{10}R^{11}$.

13. The compound or salt of claim 12, wherein:
$L^4$ is $C_{1-2}$aliphatic.

14. The compound or salt of claim 13, wherein:
$A^1$ is phenylene optionally substituted by one or more halo, $C_{1-3}$aliphatic, or —$OC_{1-3}$aliphatic, either of which is optionally substituted by one or more halo.

15. The compound or salt of claim 14, wherein:
each $R^2$ is independently selected from H, halo, $C_{1-2}$aliphatic or —$OC_{1-2}$aliphatic.

16. The compound or salt of claim 14, wherein:
$Q^4$ is $CR^3$;
$R^3$ is selected from halo, —$OR^{12}$, $R^{12}$, $_{3-6}$cyclic, —$NR^{10}R^{11}$, —$NR^{10}SO_2R^{13}$, —$OSO_2(R^{13})$, —$SO_2(R^{13})$, —$SO_2CF_3$, —$SO_2NR^{10}R^{11}$, —$C(O)NR^{10}R^{11}$, —$C(O)R^{12}$, —$C(O)O(R^{12})$, —$C(O)(R^{12})$—$O(R^{12})$, —$C(O)CF_3$, —$C(O)(_{3-6}$cyclic), or —$C(O)O(_{3-6}$cyclic); wherein any of the foregoing is optionally substituted with one or more, halo, —OH, —$CF_3$, —$NO_2$, —CN, —$C_{1-6}$aliphatic, —$OC_{1-6}$aliphatic, —C═N—OH, —C═N—$OR^{12}$, —$NR^{10}R^{11}$, —$SR^{13}$, —$SOR^{13}$, —$SO_2R^{13}$, —$CO_2R^{12}$, —$CONR^{10}R^{11}$, —$SO_2NR^{10}R^{11}$, —$NHCOR^{12}$, —$NR^{10}CONR^{10}R^{11}$, —$NR^{10}SO_2R^{13}$, or —$P(O)(OR^{10})_2$;
when $R^3$ is —$C(O)NR^{10}R^{11}$, $R^{10}$ may be taken with $R^2$ to form a ring containing one or more heteroatoms and fused to Ring $A^2$.

17. The compound or salt of claim 15, wherein:
$Q^4$ is $CR^3$;
$R^3$ is selected from H, $C_{1-6}$aliphatic, —$S(O)_2R^{13}$, —$S(O)_2NR^{10}R^{11}$, —$C(O)NR^{10}R^{11}$, —$C(O)R^{10}$, —$C(O)OR^{10}$; —$NR^{10}S(O)_2R^{13}$, or —$NR^{10}R^{11}$.

18. The compound or salt of claim 2, wherein:
$A^1$ is phenylene optionally substituted by halo, —$C_{1-3}$aliphatic, or —$OC_{1-3}$aliphatic, either of which is optionally substituted by one or more halo or —$OCF_3$;
$A^3$ is a 5-membered heteroaryl ring that is optionally substituted by one or more $C_{1-3}$aliphatic;
$L^2$ is —O— or a bond;
$L^3$ is $C_{2-4}$aliphatic optionally substituted by one or more $C_{1-6}$aliphatic or $C_{3-6}$carbocyclic;
$L^4$ is —$CH_2$— or —$CH_2CH_2$—;
$Q^1$ to $Q^3$ are independently N or $CR^2$;
$Q^4$ is $CR^3$;
$R^a$ and $R^b$ are independently H or $C_{1-3}$aliphatic;
$R^1$ is selected from H, halo, —CN, $C_{1-3}$aliphatic (optionally substituted by 1 to 3 halo), $C_{3-6}$carbocyclic, —$NO_2$, —$N(C_{0-3}$aliphatic)$_2$, —$SO_{0-2}(C_{1-3}$aliphatic), —$C(O)O(C_{1-3}$aliphatic), —$C(O)C_{0-3}$aliphatic, or —$C(O)N(C_{0-3}$aliphatic)$_2$;
each $R^2$ is independently H, halo, —$OC_{1-3}$aliphatic, or —$C_{1-3}$aliphatic;
wherein $R^2$ and $R^3$ are optionally taken together to define an optionally substituted $_{5-6}$cyclic fused at $Q^1$ and $Q^4$ to Ring $A^2$ and containing one or more heteroatoms;
$R^3$ is selected from halo, —$OR^{12}$, $R^{12}$, $_{3-6}$cyclic, —$NR^{10}R^{11}$, —$NR^{10}SO_2R^{13}$, —$OSO_2(R^{13})$, —$SO_2(R^{13})$, —$SO_2CF_3$, —$SO_2NR^{10}R^{11}$, —$C(O)NR^{10}R^{11}$, —$C(O)R^{12}$, —$C(O)O(R^{12})$, —$C(O)(R^{12})$—$O(R^{12})$, —$C(O)CF_3$, —$C(O)(_{3-6}$cyclic), or —$C(O)O(_{3-6}$cyclic); wherein any of the foregoing is optionally substituted with one or more, halo, —OH, —$CF_3$, —$NO_2$, —CN, —$C_{1-6}$aliphatic, —$OC_{1-6}$aliphatic, —C═N—OH, —C═N—$OR^{12}$, —$NR^{10}R^{11}$, —$SR^{13}$, —$SOR^{13}$, —$SO_2R^{13}$, —$CO_2R^{12}$, —$CONR^{10}R^{11}$, —$SO_2NR^{10}R^{11}$, —$NHCOR^{12}$, —$NR^{10}CONR^{10}R^{11}$, —$NR^{10}SO_2R^{13}$, or —$P(O)(OR^{10})_2$;
$R^4$ is OH, $C_{1-4}$aliphatic, or —$OC_{1-3}$aliphatic;
$R^{10}$, $R^{11}$, $R^{12}$, and $R^{13}$ are independently H, $C_{1-6}$aliphatic, or $C_{3-6}$carbocyclic,
or $R^{10}$ and $R^{11}$ attached to the same atom can be taken together with the atoms to which they are attached to form a ring containing one or more heteroatoms.

19. The compound or salt of claim 18, wherein:
$A^1$ is phenylene optionally substituted by halo, methyl, ethyl, or methoxy;
$L^3$ is $C_{3-4}$aliphatic optionally substituted by one or more of $C_{1-2}$aliphatic, —OH, or —$OCH_3$;
$R^1$ is H, halo, $CF_3$, or CN;
$R^3$ is H, $C_{1-6}$aliphatic, —$S(O)_2R^{10}$, —$S(O)_2NR^{10}R^{11}$, —$C(O)NR^{10}R^{11}$, —$C(O)R^{10}$, —$C(O)OR^{10}$; —$NR^{10}S(O)_2R^{11}$, or —$NR^{10}R^{11}$;
$R^{10}$ and $R^{11}$ are independently $C_{0-6}$aliphatic, which $R^{10}$ and $R^{11}$ of a given substituent can be taken together at any of their atoms to form a ring containing one or more heteroatoms;
or alternatively $R^3$ and $Q^1$ define any optionally substituted $_{5-6}$cyclic containing one or more heteroatoms.

20. The compound or salt of claim 2, having the Formula II:

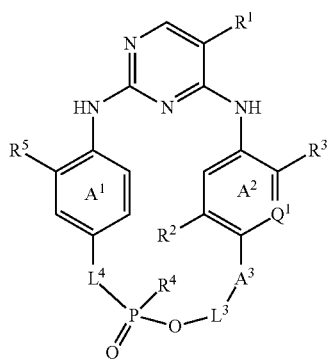

wherein:

A³ is selected from one of:

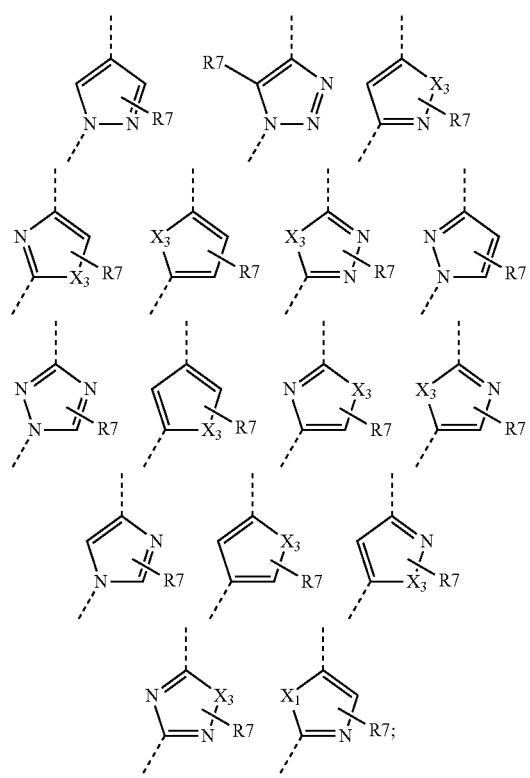

wherein the upper dotted line is a bond to A² and the lower dotted line is a bond to L³, and each X₃ is independently selected from N, O, or S;

L³ is $C_{2-4}$aliphatic that is optionally substituted by one or more $C_{1-2}$aliphatic;

L⁴ is a bond, —CH₂—, or —CH₂CH₂—;

Q¹ is N or CR²;

R¹ is halo, —CF₃, or —CCH;

each R² is independently H, halo, $C_{1-2}$aliphatic, or —OC$_{1-2}$aliphatic;

R³ is H, $C_{1-6}$aliphatic, —C(O)R¹⁰, —S(O)$_{0-2}$NR¹⁰R¹¹ or —C(O)NR¹⁰R¹¹;

and Q¹ and R³ optionally define a $_{5-6}$cyclic fused to ring A² and optionally containing one or more heteroatoms of which each N atom is optionally substituted with an independent $C_{1-2}$aliphatic;

R⁴ is OH, —OC$_{1-3}$aliphatic, or $C_{1-3}$aliphatic;

R⁵ is H, halo, $C_{1-2}$aliphatic, or —OCH₃;

each R7 is independently H or $C_{1-3}$aliphatic;

each R¹⁰ and R¹¹ is independently H, —OCH₃, or $C_{1-3}$aliphatic, and R¹⁰ and R¹¹ can be taken together to form a ring optionally containing one or more additional heteroatoms.

21. The compound or salt of claim 2, having the Formula III:

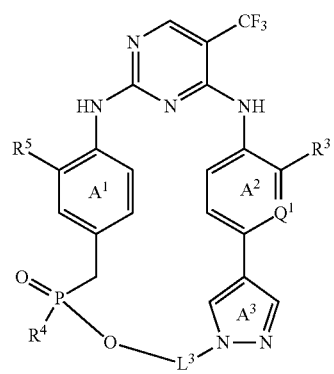

wherein:

Q¹ is N or CR²;

L³ is $C_{2-4}$alkylene optionally substituted by 1-2 independent halo or $C_{1-2}$alkyl;

R² is H, halo, $C_{1-2}$aliphatic, or —OC$_{1-2}$aliphatic;

R³ is —C(O)R¹⁰, —S(O)₂NR¹⁰R¹¹, or —C(O)NR¹⁰R¹¹;

R⁴ is OH or —OC$_{1-3}$aliphatic;

R⁵ is H or —OCH₃;

each R¹⁰ and R¹¹ are independently H, —OCH₃, or $C_{1-3}$aliphatic, and R¹⁰ and R¹¹ can be taken together to form a ring optionally containing one or more additional heteroatoms.

22. The compound or salt of claim 21, having the formula:

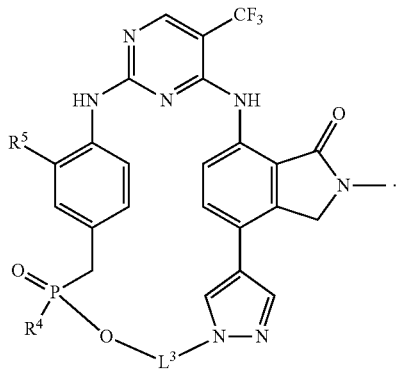

23. The compound or salt of claim 21, wherein:

R³ is —C(O)NR¹⁰R¹¹;

Q¹ is CH, N, or N-oxide;

each R¹⁰ and R¹¹ is independently H, —OCH₃, or $C_{1-2}$aliphatic.

24. The compound or salt of claim 23, wherein $Q^1$ is N.

25. A pharmaceutical composition comprising the compound or salt of claim 1, formulated with or without one or more pharmaceutical carriers.

* * * * *